United States Patent
Mita et al.

(10) Patent No.: US 10,029,986 B2
(45) Date of Patent: Jul. 24, 2018

(54) ALKYNYL PYRIDINE-SUBSTITUTED AMIDE COMPOUND AND PESTICIDE

(71) Applicant: NISSAN CHEMICAL INDUSTRIES, LTD., Chiyoda-ku (JP)

(72) Inventors: Takeshi Mita, Funabashi (JP); Motoyoshi Iwasa, Funabashi (JP); Yusuke Nanjo, Funabashi (JP); Taichi Shimomiya, Funabashi (JP); Hidehito Kuwahara, Shiraoka (JP); Hotaka Imanaka, Shiraoka (JP)

(73) Assignee: Nissan Chemical Industries, Ltd., Chiyoda-ku (JP)

( * ) Notice: Subject to any disclaimer, the term of this patent is extended or adjusted under 35 U.S.C. 154(b) by 0 days.

(21) Appl. No.: 15/119,660

(22) PCT Filed: Feb. 18, 2015

(86) PCT No.: PCT/JP2015/054439
§ 371 (c)(1),
(2) Date: Aug. 17, 2016

(87) PCT Pub. No.: WO2015/125824
PCT Pub. Date: Aug. 27, 2015

(65) Prior Publication Data
US 2017/0008847 A1    Jan. 12, 2017

(30) Foreign Application Priority Data

Feb. 18, 2014  (JP) .................................. 2014-028087
Apr. 11, 2014  (JP) .................................. 2014-082159
(Continued)

(51) Int. Cl.
*C07D 213/61* (2006.01)
*C07D 401/12* (2006.01)
(Continued)

(52) U.S. Cl.
CPC ........... *C07D 213/61* (2013.01); *A01N 43/40* (2013.01); *A01N 43/56* (2013.01); *A01N 43/60* (2013.01);
(Continued)

(58) Field of Classification Search
CPC .................................................. C07D 231/14
(Continued)

(56) References Cited

U.S. PATENT DOCUMENTS

2006/0246102 A1  11/2006 Mansfield et al.
2007/0167491 A1  7/2007 Mansfield et al.
(Continued)

FOREIGN PATENT DOCUMENTS

EP   2 218 717 A1   8/2010
JP   2006-528613 A   12/2006
(Continued)

OTHER PUBLICATIONS

International Search Report dated Apr. 28, 2015 in PCT/JP2015/054439 Filed Feb. 18, 2015.

*Primary Examiner* — Daniel R Carcanague
(74) *Attorney, Agent, or Firm* — Oblon, McClelland, Maier & Neustadt, L.L.P.

(57) ABSTRACT

Provided is a novel pesticide, particularly a fungicide and a nematicide. An alkynyl pyridine-substituted amide compound represented by formula (I), its N-oxide or a salt thereof, and a pesticide containing it. [In the formula, $G^1$ is a structure represented by $G^1$-1a, $G^1$-3a, $G^1$-27a, etc.; $X^1$ is a halogen atom, difluoromethyl, trifluoromethyl, etc.; $Y^1$ is a halogen atom, etc.; $Y^2$, $Y^3$, $R^4$ and $R^5$ independently represent a hydrogen atom, etc.; $R^1$ is a hydrogen atom, a halogen atom, methyl, methoxy, etc.; $R^2$ is a hydrogen atom, a halogen atom, etc., or $R^1$ and $R^2$ together form an alkylene chain thereby to form a cyclopropyl group together with the carbon atom to which $R^1$ and $R^2$ are bonded, or $R^1$ and $R^2$ together form $C_1$-$C_2$ alkylidene or $C_1$-$C_2$ haloalkylidene; $R^3$ is a hydrogen atom, methyl, etc.; and $R^6$ is $C_1$-$C_4$ alkyl, $C_3$-$C_6$ cycloalkyl, $C_1$-$C_4$ alkoxy($C_1$-$C_4$)alkyl, etc.]

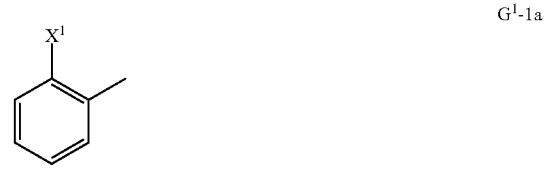

$G^1$-1a

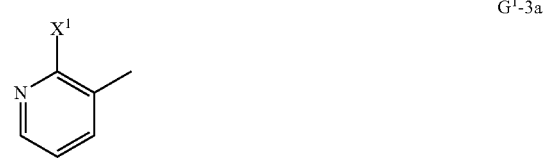

$G^1$-3a

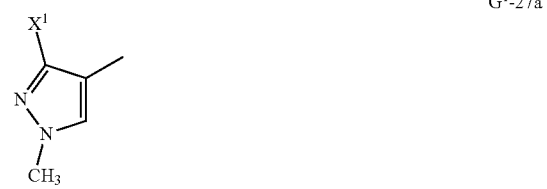

$G^1$-27a

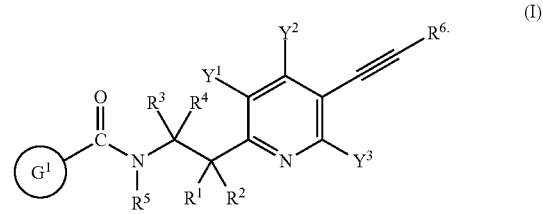

(I)

12 Claims, No Drawings

(30) Foreign Application Priority Data

Apr. 22, 2014 (JP) .................................. 2014-088408
Jun. 25, 2014 (JP) .................................. 2014-130395

(51) Int. Cl.

| | | |
|---|---|---|
| C07D 409/12 | (2006.01) | |
| C07D 411/12 | (2006.01) | |
| C07D 417/12 | (2006.01) | |
| A01N 43/40 | (2006.01) | |
| A01N 43/56 | (2006.01) | |
| A01N 43/60 | (2006.01) | |
| A01N 43/78 | (2006.01) | |
| A61K 45/06 | (2006.01) | |
| C07D 401/06 | (2006.01) | |
| A01N 43/84 | (2006.01) | |
| A01N 55/00 | (2006.01) | |

(52) U.S. Cl.
CPC ............ *A01N 43/78* (2013.01); *A01N 43/84* (2013.01); *A01N 55/00* (2013.01); *A61K 45/06* (2013.01); *C07D 401/06* (2013.01); *C07D 401/12* (2013.01); *C07D 409/12* (2013.01); *C07D 411/12* (2013.01); *C07D 417/12* (2013.01)

(58) Field of Classification Search
USPC ...................................................... 546/275.4
See application file for complete search history.

(56) References Cited

U.S. PATENT DOCUMENTS

| | | |
|---|---|---|
| 2010/0222389 A1 | 9/2010 | Walter et al. |
| 2011/0136831 A1 | 6/2011 | Oda et al. |
| 2011/0207771 A1 | 8/2011 | Stierli et al. |
| 2013/0131119 A1 | 5/2013 | Benting et al. |
| 2014/0088157 A1 | 3/2014 | Kita et al. |
| 2015/0259322 A1 | 9/2015 | Kita et al. |
| 2015/0266853 A1 | 9/2015 | Kita et al. |

FOREIGN PATENT DOCUMENTS

| | | | |
|---|---|---|---|
| JP | 2007-526279 A | | 9/2007 |
| JP | 2009-539791 A | | 11/2009 |
| JP | 2010-529971 A | | 9/2010 |
| JP | 2013-528613 A | | 7/2013 |
| JP | 2017039722 | * | 2/2017 |
| WO | 2004/016088 A2 | | 2/2004 |
| WO | 2004/074280 A1 | | 9/2004 |
| WO | 2005/014545 A2 | | 2/2005 |
| WO | 2005/016876 A2 | | 2/2005 |
| WO | 2005/058828 A1 | | 6/2005 |
| WO | 2005/058833 A1 | | 6/2005 |
| WO | 2005/085238 A1 | | 9/2005 |
| WO | WO 2006/122952 A1 | | 11/2006 |
| WO | WO 2006/122955 A1 | | 11/2006 |
| WO | 2007/108483 A1 | | 9/2007 |
| WO | 2007/141009 A1 | | 12/2007 |
| WO | WO 2007/141473 A1 | | 12/2007 |
| WO | WO 2008/093065 A1 | | 8/2008 |
| WO | 2008/151828 A2 | | 12/2008 |
| WO | 2011/151369 A1 | | 12/2011 |
| WO | WO 2011/151370 A1 | | 12/2011 |
| WO | 2012/028676 A1 | | 3/2012 |
| WO | WO 2012/052489 A1 | | 4/2012 |
| WO | WO 2012/052491 A2 | | 4/2012 |
| WO | WO 2012/118139 A1 | | 9/2012 |
| WO | WO 2013/064460 A1 | | 5/2013 |
| WO | WO 2013/064461 A2 | | 5/2013 |
| WO | WO 2013/120940 A2 | | 8/2013 |
| WO | 2014/010737 A1 | | 1/2014 |
| WO | WO 2014/034750 A1 | | 3/2014 |
| WO | WO 2014/034751 A1 | | 3/2014 |
| WO | 2014/173921 A1 | | 10/2014 |
| WO | WO 2018003924 | * | 1/2018 |

* cited by examiner

ALKYNYL PYRIDINE-SUBSTITUTED AMIDE COMPOUND AND PESTICIDE

TECHNICAL FIELD

The present invention relates to a novel alkynyl pyridine-substituted amide compound, its N-oxide or a salt thereof, and a pesticide containing it as an active ingredient.

BACKGROUND ART

Heretofore, with respect to alkynyl pyridine-substituted amide compounds, for example, N-[[1-[3-chloro-5-(3,3,3-trifluoro-1-propynyl)pyridin-2-yl]cyclopropyl]methyl]-3-fluoropyridine-2-carboxamide, N-[[1-[3-chloro-5-(3,3,3-trifluoro-1-propynyl)pyridin-2-yl]cyclopropyl]methyl]-3-chloropyridine-2-carboxamide, N-[[1-[3-chloro-5-(3,3,3-trifluoro-1-propynyl)pyridin-2-yl]cyclopropyl]methyl]-3-methylpyridine-2-carboxamide and N-[[1-[3-chloro-5-(3,3,3-trifluoro-1-propynyl)pyridin-2-yl]cyclopropyl]methyl]-3-(trifluoromethyl)pyridine-2-carboxamide are known to show nematicidal activities (see Patent Document 1); N-[2-[5-(4-ethoxyphenylethynyl)pyridin-2-yl]ethyl] acetamide is known to have an acetyl CoA carboxylase inhibitory activity (see Patent Document 2); and as an intermediate for producing BACE-1 inhibitors, N-[1-(S)-[(3,5-difluorophenyl)methyl]-2-[5-(3-fluorophenylethynyl)pyridin-2-yl]-2-(hydroxy)ethyl]-3-[N,N-di(normal propyl)carbamoyl]-5-methylbenzamide is known (see Patent Document 3).

Further with respect to pyridine-substituted amide compounds, for example, N-[2-[3-chloro-5-(trifluoromethyl)pyridin-2-yl]ethyl]-2-(trifluoromethyl)benzamide (see Patent Document 4), N-[2-[3-chloro-5-(trifluoromethyl)pyridin-2-yl]ethyl]-3-difluoromethyl-1-methyl-1H-pyrazole-4-carboxamide (see Patent Document 5), N-[2-(3,5-dichloropyridin-2-yl)ethyl]-2-(trifluoromethyl)benzamide (see Patent Document 6), N-[2-[3-chloro-5-(trifluoromethyl)pyridin-2-yl]-1-methylethyl]-2-(trifluoromethyl)benzamide (see Patent Document 7), N-[2-[3-chloro-6-(trifluoromethyl)pyridin-2-yl]butyl]-3-difluoromethyl-1-methyl-1H-pyrazole-4-carboxamide (see Patent Document 8), N-[2-(5-chloropyridin-2-yl)butyl]-3-difluoromethyl-1-methyl-1H-pyrazole-4-carboxamide (see Patent Document 9), N-[2-[3-chloro-5-(trifluoromethyl)pyridin-2-yl]ethyl]-3-trifluoromethyl)pyrazine-2-carboxamide (see Patent Document 10), N-[2-[3-chloro-5-(trifluoromethyl)pyridin-2-yl]-1-methylethyl]-N-cyclopropyl-3-difluoromethyl-1-methyl-1H-pyrazole-4-carboxathioamide (see Patent Document 11), N-[2-[3-chloro-5-(trifluoromethyl)pyridin-2-yl]-1-methylethyl]-N-cyclopropyl-3-difluoromethyl-5-fluoro-1-methyl-1H-pyrazole-4-carboxamide (see Patent Document 12), etc. are known to show bactericidal activities.

However, there has been no patent literature having a disclosure with respect to the alkynyl pyridine-substituted amide compounds of the present invention, and their usefulness as pesticides is not known.

PRIOR ART DOCUMENTS

Patent Documents

Patent Document 1: WO2014/173921
Patent Document 2: WO2012/028676
Patent Document 3: WO2005/016876
Patent Document 4: WO2004/016088
Patent Document 5: WO2004/074280
Patent Document 6: WO2005/014545
Patent Document 7: WO2005/058828
Patent Document 8: WO2005/058833
Patent Document 9: WO2005/085238
Patent Document 10: WO2007/108483
Patent Document 11: EP2218717
Patent Document 12: WO2011/151369

DISCLOSURE OF INVENTION

Technical Problem

Infection or parasitism of pests such as pathogens and parasites causes, in a case where the hosts are plants such as grain, fruits, vegetables or ornamental plants, a decrease in the quality of agricultural crops and a remarkable decrease in the yield, and in some cases, serious damages such as death of the plants, and inflicts heavy economic losses not only on the producers but also on the consumers. Thus, to effectively control such pests is a very important object to achieve efficient and stable production of agricultural crops. Further, in a case where the hosts are animals such as companion creatures/pets or livestock/poultry, to effectively control such pests is an important object also for the purpose of maintaining health of the target animals and further, in a case where the target animals are livestock or poultry, for the purpose of stably producing safe food or high quality general merchandise such as wool, feathers or leathers. From such a viewpoint, heretofore, development of pesticides targeted at pathogens or parasites has advanced, and various effective pesticides have been put into practical use.

However, recently, control of pests with conventional pesticides has become difficult in more and more cases, as pathogens or parasites acquire resistance to them over many years of their use. Problems of the high toxicity of some conventional pesticides and of the disturbance of the ecosystem by some conventional pesticides which remain in the environment for a long period are becoming apparent. Under these circumstances, development of novel pesticides not only having excellent pesticidal activity on pathogens and parasites but also having high pesticidal properties such as low toxicity and low persistence and of an effective controlling method is always expected.

It is an object of the present invention to provide a development of a new pesticide and controlling method, which not only have excellent controlling activities against pathogenic bacteria and parasites, but also have a high level of controlling characteristics such as low toxicity, low residual effects, etc.

Solution to Problem

The present inventors have conducted extensive studies to achieve the above object and as a result, found that a novel alkynyl pyridine-substituted amide compound represented by the following formula (I) is a very useful compound which is excellent in pesticidal activities, especially in antifungal and nematicidal activities, and has little harmful effect on non-target organisms such as plants, mammals, fishes, useful insects and natural enemies, and accomplished the present invention.

That is, the present invention relates to an alkynyl pyridine-substituted amide compound of the formula (I) (hereinafter referred to also as the compound of the present invention), its N-oxide or a salt thereof, all stereoisomers thereof, production intermediates thereof, and to a pesticide containing one or more of them as an active ingredient.

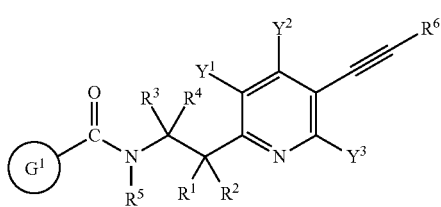
(I)
wherein G¹ is a structure represented by G¹-1 to G¹-51,
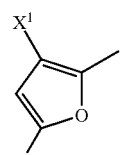
G¹-1
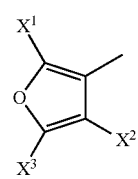
G¹-2
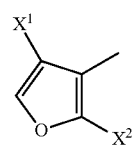
G¹-3
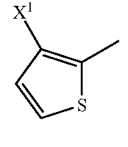
G¹-4
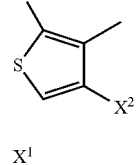
G¹-5
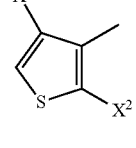
G¹-6
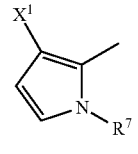
G¹-7
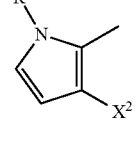
G¹-8
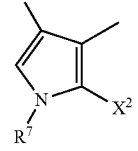
G¹-9
G¹-10
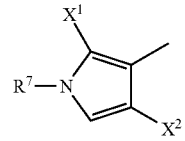
G¹-11
G¹-12
G¹-13
G¹-14
G¹-15
G¹-16
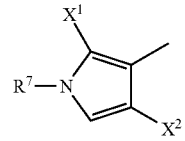
G¹-17

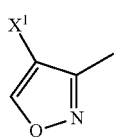 G¹-18
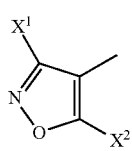 G¹-19
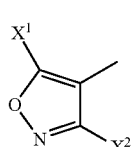 G¹-20
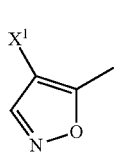 G¹-21
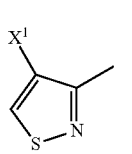 G¹-22
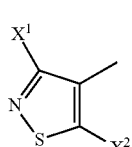 G¹-23
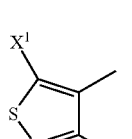 G¹-24
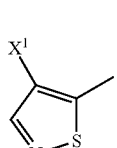 G¹-25
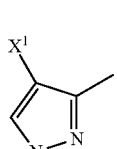 G¹-26
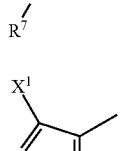 G¹-27
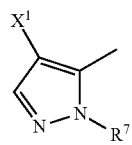 G¹-28
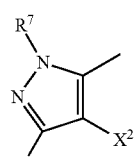 G¹-29
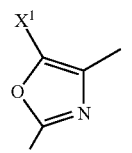 G¹-30
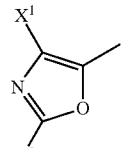 G¹-31
G¹-32
G¹-33
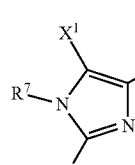 G¹-34
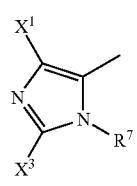 G¹-35
G¹-36

G¹-37 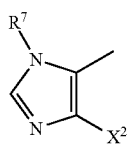

G¹-38 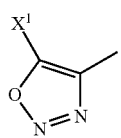

G¹-39 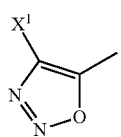

G¹-40 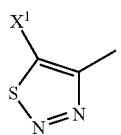

G¹-41 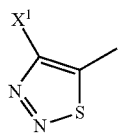

G¹-42 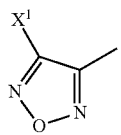

G¹-43 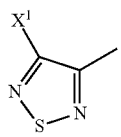

G¹-44 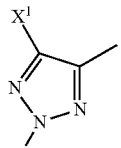

G¹-45 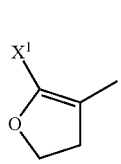

G¹-46 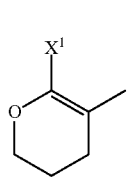

G¹-47 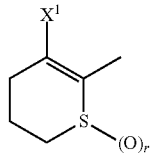

G¹-48 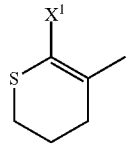

G¹-49 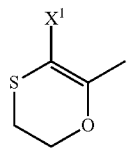

G¹-50 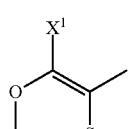

G¹-51 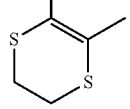

$X^1$ is a halogen atom, nitro, $C_1$-$C_4$ alkyl or $C_1$-$C_4$ haloalkyl, $X^2$ is a hydrogen atom or a halogen atom, provided that when $G^1$ is a structure represented by $G^1$-27, and $X^1$ is dihalomethyl, $X^2$ is a hydrogen atom, $X^3$ is a hydrogen atom or $C_1$-$C_4$ alkyl, $Y^1$ is a hydrogen atom, a halogen atom, nitro, $C_1$-$C_4$ alkyl, $C_1$-$C_4$ haloalkyl, $C_1$-$C_4$ alkoxy, $C_1$-$C_4$ haloalkoxy or $C_1$-$C_4$ alkylthio, $Y^2$ and $Y^3$ are each independently a hydrogen atom, a halogen atom or methyl, $R^1$ and $R^2$ are each independently a hydrogen atom, a halogen atom, cyano, $C_1$-$C_4$ alkyl, $C_1$-$C_4$ haloalkyl, $C_3$-$C_6$ cycloalkyl, phenylmethyl, phenylmethyl substituted by $(Z)_m$, $C_1$-$C_4$ alkoxy, $C_1$-$C_4$ haloalkoxy, cyano $(C_1$-$C_4)$alkoxy, $C_3$-$C_6$ alkenyloxy, $C_3$-$C_6$ haloalkenyloxy, $C_3$-$C_6$ alkynyloxy, $C_3$-$C_6$ haloalkynyloxy, phenyl $(C_1$-$C_4)$alkoxy, $C_1$-$C_4$ alkylthio, $C_1$-$C_4$ alkoxyamino, $C_1$-$C_4$ alkoxycarbonyl, —C(O)NH$_2$ or —C(S)NH$_2$, alternatively, $R^1$ and $R^2$ together form a $C_2$-$C_5$ alkylene chain thereby to form a 3-6 membered ring together with the carbon atom to which $R^1$ and $R^2$ are bonded, wherein the alkylene chain may contain one or two oxygen atoms, sulfur atoms or nitrogen atoms and may optionally be substituted by a $C_1$-$C_3$ alkyl group, a $C_1$-$C_3$ haloalkyl group or an oxo group, or $R^1$ and $R^2$ together form $C_1$-$C_6$ alkylidene, $C_1$-$C_6$ haloalkylidene or $C_1$-$C_4$ alkoxy($C_1$-$C_2$)alkylidene, $R^3$ and $R^4$ are each independently a hydrogen atom, $C_1$-$C_4$ alkyl, $C_1$-$C_4$ haloalkyl, $C_1$-$C_4$ alkoxymethyl, $C_3$-$C_6$ cycloalkyl or phenyl, alternatively, $R^3$ and $R^4$ together form an ethylene chain thereby to form a cyclopropyl ring together with the carbon atom to which $R^3$ and $R^4$ are bonded, further alternatively, $R^1$ or $R^2$, and $R^3$ or $R^4$, together form a $C_1$-$C_4$ alkylene chain thereby to form a 3-6 membered ring together with the carbon atoms to which $R^1$ or $R^2$ and $R^3$ or $R^4$, are bonded, wherein the alkylene chain may contain one oxygen atom or sulfur atom, $R^5$ is a hydrogen atom, $C_1$-$C_4$ alkyl, $C_1$-$C_4$ haloalkyl, ($C_1$-$C_2$) alkyl substituted by $R^8$, $C_3$-$C_6$ cycloalkyl, $C_2$-$C_4$ alkenyl, $C_3$-$C_4$ alkynyl, —OH, $C_1$-$C_4$ alkoxy, $C_1$-$C_4$ haloalkoxy, $C_1$-$C_4$ haloalkylthio, —C(O)$R^9$ or $C_1$-$C_4$ alkoxycarbonyl, $R^6$ is a hydrogen atom, a halogen atom, $C_1$-$C_4$ alkyl, $C_1$-$C_4$ haloalkyl, ($C_1$-$C_4$) alkyl optionally substituted by $R^{10}$, $C_3$-$C_6$ cycloalkyl, $C_3$-$C_6$ halocycloalkyl, hydroxy($C_3$-$C_6$)cycloalkyl, E-9, $C_5$-$C_6$ cycloalkenyl, tri($C_1$-$C_4$ alkyl)silyl, —C($R^{11}$)=NO$R^{12}$, phenyl, phenyl substituted by (Z)$_m$, D-1 to D-4, D-7, D-8, D-10 to D-12, D-22, D-28, D-29 or D-32, provided that when $G^1$ is a structure represented by $G^1$-1 to $G^1$-7, and $R^1$ and $R^2$ together form an ethylene chain thereby to form a cyclopropyl ring together with the carbon atom to which $R^1$ and $R^2$ are bonded, $R^6$ is a hydrogen atom, $C_1$-$C_4$ alkyl, ($C_1$-$C_4$) alkyl optionally substituted by $R^{10}$, $C_3$-$C_6$ cycloalkyl, $C_3$-$C_6$ halocycloalkyl, hydroxy ($C_3$-$C_6$)cycloalkyl, E-9, $C_5$-$C_6$ cycloalkenyl, tri($C_1$-$C_4$ alkyl)silyl, —C($R^{11}$)=NO$R^{12}$, phenyl, phenyl substituted by (Z)$_m$, D-1 to D-4, D-7, D-8, D-10 to D-12, D-22, D-28, D-29 or D-32, D-1 to D-4, D-7, D-8, D-10 to D-12, D-22, D-28, D-29 and D-32 are respectively aromatic heterocyclic rings represented by the following structural formulae, Z is a halogen atom, cyano, nitro, $C_1$-$C_4$ alkyl, trifluoromethyl, methoxy, difluoromethoxy, trifluoromethoxy, methylthio, methylsulfinyl, methylsulfonyl, trifluoromethylthio, trifluoromethylsulfinyl, trifluoromethylsulfonyl or phenyl; when m or n is 2 or more, the respective Z's may be identical with or different from one another; and when there are two Z's, the two neighboring Z's may form —CH=CH—CH=CH— to form a 6-membered ring together with the carbon atoms attached to the two Z's, $R^7$ is $C_1$-$C_4$ alkyl or $C_1$-$C_4$ haloalkyl, $R^8$ is cyano, —O$R^{14}$, $C_1$-$C_4$ alkylthio, $C_1$-$C_4$ alkoxycarbonyl, —C(O)NH$_2$ or —C(S)NH$_2$, $R^9$ is $C_1$-$C_4$ alkyl, $C_1$-$C_4$ alkoxymethyl, $C_3$-$C_4$ cycloalkyl or $C_2$-$C_4$ alkenyl, $R^{10}$ is cyano, —OH, —O$R^{15}$, $C_1$-$C_4$ alkylcarbonyloxy, $C_1$-$C_4$ alkylsulfonyloxy, $C_1$-$C_4$ alkylthio, $C_1$-$C_4$ haloalkylthio, D-3, D-7, D-11, D-22, D-28 or D-29, $R^{11}$ is a hydrogen atom or $C_1$-$C_4$ alkyl, $R^{12}$ is $C_1$-$C_4$ alkyl, $R^{13}$ is $C_1$-$C_4$ alkyl, $R^{14}$ is $C_1$-$C_4$ alkyl, $C_2$-$C_4$ haloalkyl, $C_1$-$C_4$ alkylcarbonyl, $C_3$-$C_6$ cycloalkylcarbonyl or $C_1$-$C_4$ alkoxycarbonyl, $R^{s15}$ is $C_1$-$C_4$ alkyl, $C_1$-$C_4$ haloalkyl, $C_1$-$C_4$ alkoxy($C_1$-$C_2$)alkyl, E-5, E-14, $C_3$-$C_4$ alkenyl, $C_3$-$C_4$ haloalkenyl, $C_3$-$C_4$ alkynyl, $C_3$-$C_4$ haloalkynyl, phenyl or phenyl substituted by (Z)$_m$, E-5, E-9 and E-14 are respectively saturated heterocyclic rings represented by the following structural formulae,

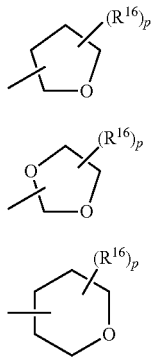

$R^{16}$ is $C_1$-$C_4$ alkyl, and when p is 2, the respective $R^{16}$'s may be identical with or different from one another,
m is 1, 2, 3, 4 or 5,
n is 0, 1, 2, 3 or 4,
p is 0, 1 or 2,
r is 0, 1 or 2.

Advantageous Effects of Invention

The compound of the present invention represented by the formula (I) and a pesticide containing the compound as an active ingredient, exhibit excellent controlling effects against pests in agricultural and horticultural fields or livestock and sanitation fields, especially against fungi and nematodes, and also exhibit sufficient controlling effects against such pests that have acquired resistance to existing drugs. Further, they bring about little adverse effect against non-target organisms such as plants and mammals, fish, useful insects, natural enemies, etc., and the load on the environment is light with low residual effects. Thus, the present invention can provide a useful novel pesticide.

DESCRIPTION OF EMBODIMENTS

In the alkynyl pyridine-substituted amide compounds represented by the formula (I) covered by the present invention, there may sometimes be optically active isomers due to the presence of one or more asymmetric carbon atoms depending upon their substituents, and, the present invention covers all of such optically active isomers or racemates. In the compounds covered by the present invention, there may sometimes be geometric isomers such as E-isomers and Z-isomers depending upon their substituents, and the present invention covers such E-isomers, Z-isomers and mixtures containing E-isomers and Z-isomers in optional proportions.

In this specification, the following terms or expressions are, respectively, used in the following meanings or usage.

As the halogen atom, a fluorine atom, a chlorine atom, a bromine atom and an iodine atom may be mentioned. In this specification, the expression "halo" also represents these halogen atoms.

In the specific description of the substituents, the expression "n-" means "normal", "i-" means "iso", "s-" means "secondary", and "tert-" means "tertiary".

The expression "$C_a$-$C_b$ alkyl" represents a linear or branched hydrocarbon group containing from a to b carbon atoms, and may, for example, be a methyl group, an ethyl group, a n-propyl group, an i-propyl group, a n-butyl group, an i-butyl group, a s-butyl group, a tert-butyl group, a pentyl group, a 1-ethylpropyl group, a 2,2-dimethylpropyl group or a hexyl group, and it is selected in the range of the specified number of carbon atoms.

The expression "$C_a$-$C_b$ haloalkyl" represents a linear or branched hydrocarbon group containing from a to b carbon atoms in which hydrogen atom(s) on carbon atom(s) are optionally substituted with halogen atom(s) which may be identical with or different from one another if two or more halogen atoms are substituted. For example, a fluoromethyl group, a chloromethyl group, a bromomethyl group, an iodomethyl group, a difluoromethyl group, a dichloromethyl group, a trifluoromethyl group, a chlorodifluoromethyl group, a trichloromethyl group, a bromodifluoromethyl group, a 1-fluoroethyl group, a 2-fluoroethyl group, a 2-chloroethyl group, a 2-bromoethyl group, a 2,2-difluoroethyl group, a 2,2,2-trifluoroethyl group, a 2-chloro-2,2-difluoroethyl group, a 2,2,2-trichloroethyl group, a 2-bromo-2,2-difluoroethyl group, a 1,1,2,2-tetrafluoroethyl group, a 2-chloro-1,1,2-trifluoroethyl group, a pentafluoroethyl group, a 2,2-difluoropropyl group, a 3,3,3-trifluoropropyl group, a 3-bromo-3,3-difluoropropyl group, a 2,2,3,3,3-tetrafluoropropyl group, a 2,2,3,3,3-pentafluoropropyl group, a 1,1,2,3,3,3-hexafluoropropyl group, a heptafluoropropyl group, a 2,2,2-trifluoro-1-(methyl)ethyl group, a 2,2,2-trifluoro-1-(trifluoromethyl)ethyl group, a 1,2,2,2-tetrafluoro-1-(trifluoromethyl)ethyl group, a 2,2,3,4,4,4-hexafluorobutyl group, a 2,2,3,3,4,4,4-heptafluorobutyl group or a nonafluorobutyl group, etc. may be mentioned as specific examples, and it is selected within the range of the specified number of carbon atoms.

The expression "$C_a$-$C_b$ cycloalkyl" represents a cyclic hydrocarbon group containing from a to b carbon atoms in the form of a 3- to 10-membered monocyclic or polycyclic ring. Further, each ring may optionally be substituted by an alkyl group within the range of the specified number of carbon atoms. For example, a cyclopropyl group, a cyclobutyl group, a 1-methylcyclopropyl group, a 2-methylcyclopropyl group, a cyclopentyl group, a 2,2-dimethylcyclopropyl group, a 1-methylcyclobutyl group, a cyclohexyl group, etc. may be mentioned as specific examples, and it is selected within the range of the specified number of carbon atoms.

The expression "$C_a$-$C_b$ halocycloalkyl" represents a cyclic hydrocarbon group containing from a to b carbon atoms in which hydrogen atom(s) on carbon atom(s) are optionally substituted with halogen atom(s) and which may be in the form of a 3- to 10-membered monocyclic or polycyclic ring. Further, each ring may optionally be substituted by an alkyl group within the range of the specified number of carbon atoms; the substitution by halogen atom(s) may be in a ring moiety and/or in a side chain; and when substituted by two or more halogen atoms, such halogen atoms may be identical with or different from one another. For example, a 1-fluorocyclopropyl group, a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 2,2,3,3-tetrafluorocyclobutyl group, etc. may be mentioned as specific examples, and it is selected within the range of the specified number of carbon atoms.

The expression "$C_a$-$C_b$ alkenyl" represents a linear or branched unsaturated hydrocarbon group containing from a to b carbon atoms and having one or more double bond(s) in the molecule, and for example, a vinyl group, a 1-propenyl group, a 2-propenyl group, a 1-methylethenyl group, a 1-butenyl group, a 2-butenyl group, a 1-methyl-1-propenyl group, a 2-methyl-1-propenyl group, a 2-methyl-2-propenyl group, a 3-methyl-3-butenyl group, etc. may be mentioned as specific examples, and it is selected within the range of the specified number of carbon atoms.

The expression "$C_a$-$C_b$ haloalkenyl" represents a linear or branched unsaturated hydrocarbon group containing from a to b carbon atoms and having one or more double bond(s) in the molecule, in which hydrogen atom(s) on carbon atom(s) are optionally substituted by halogen atom(s). Here, when substituted by two or more halogen atoms, such halogen atoms may be identical with or different from one another. For example, a 2-fluorovinyl group, a 2-chlorovinyl group, a 1,2-dichlorovinyl group, a 2,2-dichlorovinyl group, a 2,2-dibromovinyl group, a 2-fluoro-2-propenyl group, a 2-chloro-2-propenyl group, a 3-chloro-2-propenyl group, a 3,3-difluoro-2-propenyl group, a 2,3-dichloro-2-propenyl group, a 3,3-dichloro-2-propenyl group, a 2,3,3-trifluoro-2-propenyl group, a 2,3,3-trichloro-2-propenyl group, a 1-(trifluoromethyl)ethenyl group, a 4,4-difluoro-3-butenyl group, a 3,4,4-trifluoro-3-butenyl group, a 2,4,4,4-tetrafluoro-2-butenyl group, a 3-chloro-4,4,4-trifluoro-2-butenyl group, etc. may be mentioned as specific examples, and it is selected within the range of the specified number of carbon atoms.

The expression "$C_a$-$C_b$ cycloalkenyl" represents a cyclic unsaturated hydrocarbon group containing from a to b carbon atoms and containing one or more double bond(s) in the form of a 3- to 10-membered monocyclic or polycyclic ring. Further, each ring may optionally be substituted by an alkyl group within the range of the specified number of carbon atoms, and further, the double bond may be either endo-form or exo-form. For example, a 1-cyclopentenyl group, a 2-cyclopentenyl group, a 1-cyclohexenyl group, a 2-cyclohexenyl group, a bicyclo[2.2.1]-5-hepten-2-yl group, etc. may be mentioned as specific examples, and it is selected within the range of the specified number of carbon atoms.

The expression "$C_a$-$C_b$ alkynyl" represents a linear or branched unsaturated hydrocarbon group containing from a to b carbon atoms and having one or more triple bond(s) in the molecule. For example, an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 1-hexynyl group, a 3-hexynyl group, a 3-methyl-1-petynyl group, a 4-methyl-1-pentynyl group, a 3,3-dimethyl-1-butynyl group, etc. may be mentioned as specific examples, and it is selected within the range of the specified number of carbon atoms.

The expression "$C_a$-$C_b$ haloalkynyl" represents a linear or branched unsaturated hydrocarbon group containing from a to b carbon atoms and having one or more triple bond(s) in the molecule, in which hydrogen atom(s) on carbon atom(s) are optionally substituted by halogen atom(s). Here, when substituted by two or more halogen atoms, such halogen atoms may be identical with or different from one another. For example, a 2-chloroethynyl group, a 2-bromoethynyl group, a 2-iodoethynyl group, a 3-fluoro-1-propynyl group, a 3-chloro-1-propynyl group, a 3-chloro-2-propynyl group, a 3-bromo-1-propynyl group, a 3-bromo-2-propynyl group, a 3-iodo-2-propynyl group, a 3,3-difluoro-1-propynyl group, a 3,3,3-trifluoro-1-propynyl group, a 3-bromo-1-butynyl group, a 3-fluoro-3-methyl-1-butynyl group, a 3-chloro-3-methyl-1-butynyl group, a 3-bromo-3-methyl-1-butynyl group, etc. may be mentioned as specific examples, and it is selected within the range of the specified number of carbon atoms.

The expression "$C_a$-$C_b$ alkoxy" represents an alkyl-O— group in which the alkyl is a previously mentioned alkyl group containing from a to b carbon atoms. For example, a methoxy group, an ethoxy group, a n-propyloxy group, an i-propyloxy group, a n-butyloxy group, an i-butyloxy group, a s-butyloxy group, a tert-butyloxy group, a pentyloxy group, a hexyloxy group, etc. may be mentioned as specific examples, and it is selected within the range of the specified number of carbon atoms.

The expression "$C_a$-$C_b$ haloalkoxy" represents a haloalkyl-O— group in which the haloalkyl is a previously mentioned haloalkyl group containing from a to b carbon atoms; for example, a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a 2-chloro-1,1,2-trifluoroethoxy group, a 1,1,2,3,3,3-hexafluoropropyloxy group, etc. may be mentioned as specific examples, and it is selected within the range of the specified number of carbon atoms.

The expression "$C_a$-$C_b$ alkenyloxy" represents an alkenyl-O— group in which the alkenyl is a previously mentioned alkenyl group containing from a to b carbon atoms; for example, a 2-propenyloxy group, a 2-butenyloxy group, a 1-methyl-2-propenyloxy group, a 2-methyl-2-propenyloxy group, a 3-methyl-2-butenyloxy group, a 1,1-dimethyl-2-propenyloxy group, etc. may be mentioned as specific examples, and it is selected within the range of the specified number of carbon atoms.

The expression "$C_a$-$C_b$ haloalkenyloxy" represents a haloalkenyl-O— group in which the haloalkenyl is a previously mentioned haloalkenyl group containing from a to b carbon atoms; for example, a 2-fluoro-2-propenyloxy group, a 2-chloro-2-propenyloxy group, a 3-chloro-2-propenyloxy group, a 3,3-difluoro-2-propenyloxy group, a 2,3-dichloro-2-propenyloxy group, a 3,3-dichloro-2-propenyloxy group, a 2,3,3-trifluoro-2-propenyloxy group, etc. may be mentioned as specific examples, and it is selected within the range of the specified number of carbon atoms.

The expression "$C_a$-$C_b$ alkynyloxy" represents an alkynyl-O— group in which the alkynyl is a previously mentioned alkynyl group containing from a to b carbon atoms; for example, a 2-propynyloxy group, a 2-butynyloxy group, a 1-methyl-2-propynyloxy group, a 1,1-dimethyl-2-propynyloxy group, etc. may be mentioned as specific examples, and it is selected within the range of the specified number of carbon atoms.

The expression "$C_a$-$C_b$ haloalkynyloxy" represents a haloalkynyl-O— group in which the haloalkynyl is a previously mentioned haloalkynyl group containing from a to b carbon atoms; for example, a 3-chloro-2-propynyloxy group, a 3-bromo-2-propynyloxy group, a 3-iodo-2-propynyloxy group, etc. may be mentioned as specific examples, and it is selected within the range of the specified number of carbon atoms.

The expression "$C_a$-$C_b$ alkylthio" represents an alkyl-S— group in which the alkyl is a previously mentioned alkyl group containing from a to b carbon atoms; for example, a methylthio group, an ethylthio group, a n-propylthio group, an i-propylthio group, a n-butylthio group, an i-butylthio group, a s-butylthio group, a tert-butylthio group, etc. may be mentioned as specific examples, and it is selected within the range of the specified number of carbon atoms.

The expression "$C_a$-$C_b$ haloalkylthio" represents a haloalkyl-S— group in which the haloalkyl is a previously mentioned haloalkyl group containing from a to b carbon atoms; for example, a difluoromethylthio group, a trifluoromethylthio group, a chlorodifluoromethylthio group, a trichloromethylthio group, a bromodifluoromethylthio group, a 2,2,2-trifluoroethylthio group, a 1,1,2,2-tetrafluoroethylthio group, a 2-chloro-1,1,2-trifluoroethylthio group, a pentafluoroethylthio group, a 1,1,2,3,3,3-hexafluoropropylthio group, a heptafluoropropylthio group, a 1,2,2,2-tetrafluoro-1-(trifluoromethyl)ethylthio group, a nonafluorobutylthio group, etc. may be mentioned as specific examples, and it is selected within the range of the specified number of carbon atoms.

The expression "tri($C_a$-$C_b$ alkyl)silyl" represents a silyl group replaced by previously mentioned alkyl groups containing from a to b carbon atoms which may be identical with or different from one another; for example, a trimethylsilyl group, a triethylsilyl group, a tri(n-propyl)silyl group, an ethyldimethylsilyl group, a n-propyldimethylsilyl group, a n-butyldimethylsilyl group, an i-butyldimethylsilyl group, a tert-butyldimethylsilyl group, etc. may be mentioned as specific examples, and it is selected within the range of the specified number of carbon atoms.

The expression "$C_a$-$C_b$ alkylcarbonyl" represents an alkyl-C(O)— group in which the alkyl is a previously mentioned alkyl group containing from a to b carbon atoms; for example, an acetyl group, a propionyl group, a butyryl group, an isobutyryl group, a valeryl group, an isovaleryl group, a 2-methylbutanoyl group, a pivaloyl group, etc. may be mentioned as specific examples, and it is selected within the range of the specified number of carbon atoms.

The expression "$C_a$-$C_b$ cycloalkylcarbonyl" represents a cycloalkyl-C(O)— group in which the cycloalkyl is a previously mentioned cycloalkyl group containing from a to b carbon atoms; for example, a cyclopropylcarbonyl group, a cyclobutylcarbonyl group, a 1-methylcyclopropylcarbonyl group, a 2-methylcyclopropylcarbonyl group, a cyclopentylcarbonyl group, a 2,2-dimethylcyclopropylcarbonyl group, a cyclohexylcarbonyl group, etc. may be mentioned as specific examples, and it is selected within the range of the specified number of carbon atoms.

The expression "$C_a$-$C_b$ alkoxycarbonyl" represents an alkyl-O—C(O)— group in which the alkyl is a previously mentioned alkyl group containing from a to b carbon atoms; for example, a methoxycarbonyl group, an ethoxycarbonyl group, a n-propyloxycarbonyl group, an i-propyloxycarbonyl group, a n-butoxycarbonyl group, an i-butoxycarbonyl group, a tert-butoxycarbonyl group, etc. may be mentioned as specific examples, and it is selected within the range of the specified number of carbon atoms.

The expression "$C_a$-$C_b$ alkylcarbonyloxy" represents an alkyl-C(O)—O— group in which the alkyl is a previously mentioned alkyl group containing from a to b carbon atoms; for example, an acetyloxy group, a propionyloxy group, a butyryloxy group, an isobutyryloxy group, etc. may be mentioned as specific examples, and it is selected within the range of the specified number of carbon atoms.

The expression "$C_a$-$C_b$ alkylsulfonyloxy" represents an alkylsulfonyl-O— group in which the alkylsulfonyl is a previously mentioned alkylsulfonyl group containing from a to b carbon atoms; for example, a methylsulfonyloxy group, an ethylsulfonyloxy group, a n-propylsulfonyloxy group, an i-propylsulfonyloxy group, etc. may be mentioned as specific examples, and it is selected within the range of the specified number of carbon atoms.

The expression "$C_a$-$C_b$ alkoxymethyl" or "$C_a$-$C_b$ alkoxy($C_d$-$C_e$)alkyl", respectively, represents a methyl group or a previously mentioned alkyl group containing from d to e carbon atoms in which hydrogen atom(s) on carbon atom(s) are optionally substituted by previously mentioned optional $C_a$-$C_b$ alkoxy group, and it is selected within the range of the specified number of carbon atoms.

The expression "($C_a$-$C_b$) alkyl substituted by $R^{10}$" represents a previously mentioned alkyl group containing from a to b carbon atoms in which hydrogen atom(s) on carbon atom(s) are substituted by optional $R^8$, and it is selected within the range of the specified number of carbon atoms.

The expression "($C_a$-$C_b$) alkyl optionally substituted by $R^{10}$" represents a previously mentioned alkyl group containing from a to b carbon atoms in which hydrogen atom(s) on carbon atom(s) are optionally substituted by optional $R^{10}$, and it is selected within the range of the specified number of carbon atoms. Here, when two or more substituents $R^{10}$ are present on the $C_a$-$C_b$ alkyl group, the respective $R^{10}$'s may be identical with or different from one another.

The expression "hydroxy($C_d$-$C_e$)cycloalkyl" represents a previously mentioned cycloalkyl group containing from d to e carbon atoms in which hydrogen atom(s) on carbon atom(s) are substituted by hydroxy group(s), and it is selected within the range of the specified number of carbon atoms.

The expression "$C_a$-$C_b$ alkylidene" represents a linear or branched hydrocarbon group containing from a to b carbon atoms, bonded by a double bond; for example, a methylidene group, an ethylidene group, a propylidene group, a 1-methylethylidene group, a butylidene group, a 1-methylpropylidene group, a pentylidene group, a 1-methylbutylidene group, a 1-ethylethylidene group, a hexylidene group, etc. may be mentioned as specific examples, and it is selected within the range of the specified number of carbon atoms.

The expression "$C_a$-$C_b$ haloalkylidene" represents a linear or branched hydrocarbon group containing from a to b carbon atoms, bonded by a double bond, in which hydrogen atom(s) on carbon atoms are optionally substituted by halogen atom(s). Here, when substituted by two or more halogen atoms, such halogen atoms may be identical with or different from one another. For example, a fluoromethylidene group, a chloromethylidene group, a difluoromethylidene group, a dichloromethylidene group, a 2,2,2-trifluoroethylidene group, etc. may be mentioned as specific examples, and it is selected within the range of the specified number of carbon atoms.

The expression "$C_a$-$C_b$ alkoxy($C_d$-$C_e$)alkylidene" represents a previously mentioned alkylidene group containing from d to e carbon atoms in which hydrogen atom(s) on carbon atom(s) are substituted by previously mentioned optional $C_a$-$C_b$ alkoxy group, and it is selected within the range of the specified number of carbon atoms.

A specific example of the expression "$R^1$ and $R^2$ together form a $C_2$-$C_5$ alkylene chain thereby to form a 3-6 membered ring together with the carbon atom to which $R^1$ and $R^2$ are bonded, wherein the alkylene chain may contain one or two oxygen atoms, sulfur atoms or nitrogen atoms", may, for example, be a ring such as cyclopropane, oxirane, thiirane, aziridine, cyclobutane, oxetane, thietane, azetidine, cyclopentane, oxolane, thiolane, pyrrolidine, dioxolane, dithiolane, cyclohexane, tetrahydropyran, tetrahydrothiopyran, piperidine, 1,3-dioxane or 1,3-dithiane, and it is selected within the range of the specified number of carbon atoms.

A specific example of the expression "$R^1$ or $R^2$, and $R^3$ or $R^4$, together form a $C_1$-$C_4$ alkylene chain thereby to form a 3-6 membered ring together with the carbon atoms to which $R^1$ or $R^2$, and $R^3$ or $R^4$, are bonded, wherein the alkylene chain may contain one oxygen atom or sulfur atom", may, for example, be a ring such as cyclopropane, oxirane, thiirane, cyclobutane, oxetane, thietane, cyclopentane, oxolane, thiolane, cyclohexane, tetrahydropyran or tetrahydrothiopyran, and it is selected within the range of the specified number of carbon atoms.

In the present invention, a preferred range of the substituent represented by $G^1$ includes, for example, the following groups $G^1$-I to $G^1$-XXV.

That is, $G^1$-I: $G^1$-1 [wherein, $X^1$ is a halogen atom or trifluoromethyl, and $X^2$ is a hydrogen atom].

$G^1$-II: $G^1$-2 [wherein $X^1$ is a halogen atom or trifluoromethyl].

$G^1$-III: $G^1$-3 [wherein $X^1$ is a halogen atom, difluoromethyl or trifluoromethyl, and $X^2$ is a hydrogen atom].

$G^1$-IV: $G^1$-7 [wherein $X^1$ is trifluoromethyl].

$G^1$-V: $G^1$-11 [wherein $X^1$ is methyl or trifluoromethyl].

$G^1$-VI: $G^1$-12 [wherein $X^1$ is a halogen atom, and $X^2$ is a hydrogen atom].

$G^1$-VII: $G^1$-27 [wherein $X^1$ is difluoromethyl or trifluoromethyl, $X^2$ is a hydrogen atom, and $R^7$ is methyl].

$G^1$-VIII: $G^1$-33 [wherein $X^1$ is difluoromethyl or trifluoromethyl, and $X^3$ is methyl].

$G^1$-IX: $G^1$-50 [wherein $X^1$ is trifluoromethyl, and r is 0].

$G^1$-X: $G^1$-1 [wherein $X^1$ is nitro, methyl or difluoromethyl, and $X^2$ is a hydrogen atom].

$G^1$-XI: $G^1$-1 [wherein $X^1$ and $X^2$ represent each independently a fluorine atom or a chlorine atom].

$G^1$-XII: $G^1$-2 [wherein $X^1$ is difluoromethyl].

$G^1$-XIII: $G^1$-3 [wherein $X^1$ is methyl, and $X^2$ is a hydrogen atom].

$G^1$-XIV: $G^1$-7 [wherein $X^1$ is a halogen atom, methyl or difluoromethyl].

$G^1$-XV: $G^1$-8 [wherein $X^1$ is trifluoromethyl, and $X^3$ is a hydrogen atom or methyl].

$G^1$-XVI: $G^1$-9 [wherein $X^1$ is difluoromethyl or trifluoromethyl, $X^2$ is a hydrogen atom, and $X^3$ is a hydrogen atom or methyl].

$G^1$-XVII: $G^1$-11 [wherein $X^1$ is a halogen atom or difluoromethyl].

$G^1$-XVIII: $G^1$-12 [wherein $X^1$ is difluoromethyl or trifluoromethyl, and $X^2$ is a hydrogen atom].

$G^1$-XIX: $G^1$-13 [wherein $X^1$ is a halogen atom, difluoromethyl or trifluoromethyl, and $X^2$ is a hydrogen atom].

$G^1$-XX: $G^1$-16 [wherein $X^1$ is difluoromethyl or trifluoromethyl, $X^2$ is a hydrogen atom, and $R^7$ is methyl].

$G^1$-XXI: $G^1$-27 [wherein $X^1$ is methyl, ethyl or trifluoromethyl, $X^2$ is a halogen atom, and $R^7$ is methyl].

$G^1$-XXII: $G^1$-32 [wherein $X^1$ is difluoromethyl or trifluoromethyl, and $X^3$ is a hydrogen atom or methyl].

$G^1$-XXIII: $G^1$-33 [wherein $X^1$ is difluoromethyl or trifluoromethyl, and $X^3$ is a hydrogen atom].

$G^1$-XXIV: $G^1$-44 [wherein $X^1$ is difluoromethyl or trifluoromethyl, and $R^7$ is methyl].

$G^1$-XXV: $G^1$-50 [wherein $X^1$ is methyl or trifluoromethyl, and r is 0, 1 or 2].

Among these, as the substituent represented by $G^1$, more preferred is $G^1$-I to $G^1$-IX, $G^1$-XI, $G^1$-XII, $G^1$-XIV, $G^1$-XVII, $G^1$-XVIII or $G^1$-XX to $G^1$-XXII, and particularly preferred is $G^1$-I to $G^1$-V, $G^1$-VII, $G^1$-VIII, $G^1$-XII, $G^1$-XIV, $G^1$-XVII or $G^1$-XVIII.

A preferred range of the combination of substituents represented by $Y^1$, $Y^2$ and $Y^3$ includes, for example, the following groups Y-I to Y-III.

Y-I: $Y^1$ is a halogen atom, and $Y^2$ and $Y^3$ are simultaneously hydrogen atoms.

Y-II: $Y^1$ is methyl, and $Y^2$ and $Y^3$ are simultaneously hydrogen atoms.

Y-III: $Y^1$ is a halogen atom or methyl, $Y^2$ is methyl, and $Y^3$ is a hydrogen atom.

Among these, the combination of substituents represented by $Y^1$, $Y^2$ and $Y^3$, is more preferably Y-I or Y-II, particularly preferably Y-I.

A preferred range of the combination of substituents represented by $R^1$, $R^2$, $R^3$ and $R^4$, includes, for example, the following groups R-I to R-XVIII.

R-I: $R^1$, $R^2$, $R^3$ and $R^4$ are hydrogen atoms.

R-II: $R^1$ is methyl or methoxy, and $R^2$, $R^3$ and $R^4$ are hydrogen atoms.

R-III: $R^1$ is cyano, $C_1$-$C_2$ haloalkyl, cyclopropyl, phenylmethyl substituted by $(Z)_m$ [wherein Z is a halogen atom, and m is 1 or 2, when m is 2, the respective Z's may be identical with or different from one another], $C_1$-$C_2$ alkylthio or $C_1$-$C_2$ alkoxycarbonyl, and $R^2$, $R^3$ and $R^4$ are hydrogen atoms.

R-IV: $R^1$ and $R^2$ are simultaneously fluorine atoms, cyano, methyl or $C_1$-$C_2$ alkoxycarbonyl, and $R^3$ and $R^4$ are hydrogen atoms.

R-V: $R^1$ and $R^2$ together form an ethylene chain thereby to form a cyclopropyl ring together with the carbon atom to which $R^1$ and $R^2$ are bonded, and $R^3$ and $R^4$ are hydrogen atoms.

R-VI: $R^1$ and $R^2$ together form —$CH_2O$— thereby to form an oxirane ring together with the carbon atom to which $R^1$ and $R^2$ are bonded, and $R^3$ and $R^4$ are hydrogen atoms.

R-VII: $R^1$ and $R^2$ together form $C_1$-$C_2$ alkylidene or $C_1$-$C_2$ haloalkylidene, and $R^3$ and $R^4$ are hydrogen atoms.

R-VIII: $R^1$ is methoxy, ethoxy, $C_1$-$C_2$ haloalkoxy, cyano($C_1$-$C_2$)alkoxy, $C_3$-$C_4$ alkenyloxy, $C_3$-$C_4$ alkynyloxy, benzyloxy or $C_1$-$C_2$ haloalkylthio, $R^2$ is a hydrogen atom, $R^3$ is methyl, and $R^4$ is a hydrogen atom.

R-IX: $R^1$ and $R^2$ are hydrogen atoms, $R^3$ is methyl, and $R^4$ is a hydrogen atom.

R-X: $R^1$ and $R^2$ are hydrogen atoms, and $R^3$ and $R^4$ together form an ethylene chain thereby to form a cyclopropyl ring together with the carbon atom to which $R^3$ and $R^4$ are bonded.

R-XI: $R^1$ is a halogen atom, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkoxyamino, $C_1$-$C_4$ alkoxycarbonyl, —C(O)NH$_2$ or —C(S)NH$_2$, and $R^2$, $R^3$ and $R^4$ are hydrogen atoms.

R-XII: $R^1$ is a halogen atom, cyano, $C_1$-$C_4$ alkyl, —C(O)NH$_2$ or —C(S)NH$_2$, $R^2$ is a halogen atom, cyano or methyl, and $R^3$ and $R^4$ are hydrogen atoms.

R-XIII: $R^1$ and $R^2$ together form a $C_2$-$C_5$ alkylene chain thereby to form a 3-6 membered ring together with the carbon atom to which $R^1$ and $R^2$ are bonded, wherein the alkylene chain may contain one oxygen atom or sulfur atom, and $R^3$ and $R^4$ are hydrogen atoms.

R-XIV: $R^1$ and $R^2$ together form $C_1$-$C_6$ alkylidene, $C_1$-$C_6$ haloalkylidene or $C_1$-$C_4$ alkoxy($C_1$-$C_2$)alkylidene, and $R^3$ and $R^4$ are hydrogen atoms.

R-XV: $R^1$ is $C_1$-$C_4$ alkyl, $C_1$-$C_4$ alkoxy, $C_1$-$C_4$ haloalkoxy, cyano($C_1$-$C_4$)alkoxy, $C_3$-$C_6$ alkenyloxy, $C_3$-$C_6$ alkynyloxy, phenyl($C_1$-$C_4$)alkoxy or $C_1$-$C_4$ alkoxyamino, $R^2$ is a hydrogen atom, $R^3$ is methyl, and $R^4$ is a hydrogen atom.

R-XVI: $R^1$ and $R^2$ are hydrogen atoms, $R^3$ is $C_1$-$C_4$ alkyl or $C_1$-$C_4$ haloalkyl, and $R^4$ is a hydrogen atom.

R-XVII: $R^1$ and $R^2$ are hydrogen atoms, and $R^3$ and $R^4$ are methyl.

R-XVIII: $R^1$ and $R^3$ together form a $C_2$-$C_4$ alkylene chain thereby to form a 4-6 membered ring together with the carbon atoms to which $R^1$ and $R^3$ are bonded, wherein the alkylene chain may contain one oxygen atom, and $R^2$ and $R^4$ are hydrogen atoms.

Among these, the combination of substituents represented by $R^1$, $R^2$, $R^3$ and $R^4$, is more preferably R-I to R-V, R-VII to R-IX, R-XI, R-XII, R-XV or R-XVI, particularly preferably R-I, R-II, R-IV, R-V or R-VII to R-IX.

A preferred range of the substituent represented by $R^5$, includes, for example, the following groups $R^5$-I to $R^5$-IV.

$R^5$-I: a hydrogen atom.
$R^5$-II: cyclopropyl.
$R^5$-III: $C_1$-$C_4$ alkoxycarbonyl.
$R^5$-IV: methoxy.

Among these, the substituent represented by $R^5$ is more preferably $R^5$-I or $R^5$-II, particularly preferably $R^5$-I.

The preferred range of the substituent represented by $R^6$, includes, for example, the following groups $R^6$-I to $R^6$-IX.

$R^6$-I: $C_1$-$C_4$ alkyl.
$R^6$-II: $C_3$-$C_6$ cycloalkyl.
$R^6$-III: ($C_1$-$C_4$) alkyl optionally substituted by $R^{10}$ [wherein $R^{10}$ is —OH or —$OR^{15}$, $R^{15}$ is $C_1$-$C_4$ alkyl or $C_1$-$C_4$ haloalkyl].
$R^6$-IV: trimethylsilyl.
$R^6$-V: a halogen atom or $C_1$-$C_4$ haloalkyl.
$R^6$-VI: ($C_1$-$C_4$) alkyl substituted by $R^{10}$ [wherein $R^{10}$ is —$OR^{15}$, and $R^{15}$ is $C_1$-$C_4$ alkoxymethyl].
$R^6$-VII: $C_3$-$C_6$ halocycloalkyl or tri($C_1$-$C_4$ alkyl)silyl.
$R^6$-VIII: —C($R^{11}$)=$NOR^{12}$ [wherein $R^{11}$ is a hydrogen atom or methyl, and $R^{12}$ is methyl or ethyl].
$R^6$-IX: a hydrogen atom.

Among these, the substituent represented by $R^6$, is more preferably $R^6$-I to $R^6$-IV or $R^6$-VII, particularly preferably $R^6$-I, $R^6$-II or $R^6$-III.

In the present invention, the respective groups representing a preferred range of the respective substituents may optionally be combined and represent a preferred range of the present compounds.

For example, the combinations as shown in the following Table 1 may be mentioned as examples of combinations of preferred range with respect to $G^1$, $R^1$-$R^4$ (expressed by R-I to R-XVIII) of the compound of formula (I). However, the combinations in Table 1 are for the purpose of exemplification, and the compound of the present invention represented by the formula (I) is by no means limited thereto.

TABLE 1

| $G^1$ | $R^1$~$R^4$ | $R^6$ |
|---|---|---|
| $G^1$-I | R-I | $R^6$-I |
| $G^1$-I | R-I | $R^6$-II |
| $G^1$-I | R-I | $R^6$-III |
| $G^1$-I | R-I | $R^6$-IV |
| $G^1$-I | R-I | $R^6$-V |
| $G^1$-I | R-I | $R^6$-VI |
| $G^1$-I | R-I | $R^6$-VII |
| $G^1$-I | R-I | $R^6$-VIII |
| $G^1$-I | R-I | $R^6$-IX |
| $G^1$-I | R-II | $R^6$-I |
| $G^1$-I | R-II | $R^6$-II |
| $G^1$-I | R-II | $R^6$-III |
| $G^1$-I | R-II | $R^6$-IV |
| $G^1$-I | R-II | $R^6$-V |
| $G^1$-I | R-II | $R^6$-VI |
| $G^1$-I | R-II | $R^6$-VII |
| $G^1$-I | R-II | $R^6$-VIII |
| $G^1$-I | R-II | $R^6$-IX |
| $G^1$-I | R-III | $R^6$-I |
| $G^1$-I | R-III | $R^6$-II |
| $G^1$-I | R-IV | $R^6$-I |
| $G^1$-I | R-IV | $R^6$-II |
| $G^1$-I | R-IV | $R^6$-III |
| $G^1$-I | R-IV | $R^6$-IV |
| $G^1$-I | R-IV | $R^6$-V |
| $G^1$-I | R-IV | $R^6$-VII |
| $G^1$-I | R-V | $R^6$-I |
| $G^1$-I | R-V | $R^6$-II |
| $G^1$-I | R-V | $R^6$-III |
| $G^1$-I | R-V | $R^6$-IV |
| $G^1$-I | R-V | $R^6$-VI |
| $G^1$-I | R-V | $R^6$-VII |
| $G^1$-I | R-V | $R^6$-VIII |
| $G^1$-I | R-VI | $R^6$-I |
| $G^1$-I | R-VI | $R^6$-II |
| $G^1$-I | R-VII | $R^6$-I |
| $G^1$-I | R-VII | $R^6$-II |
| $G^1$-I | R-VII | $R^6$-III |
| $G^1$-I | R-VII | $R^6$-IV |
| $G^1$-I | R-VII | $R^6$-V |
| $G^1$-I | R-VII | $R^6$-VII |
| $G^1$-I | R-VIII | $R^6$-I |
| $G^1$-I | R-VIII | $R^6$-II |
| $G^1$-I | R-VIII | $R^6$-III |
| $G^1$-I | R-VIII | $R^6$-IV |
| $G^1$-I | R-VIII | $R^6$-V |
| $G^1$-I | R-VIII | $R^6$-VI |
| $G^1$-I | R-VIII | $R^6$-VII |
| $G^1$-I | R-VIII | $R^6$-VIII |
| $G^1$-I | R-VIII | $R^6$-IX |
| $G^1$-I | R-IX | $R^6$-I |
| $G^1$-I | R-IX | $R^6$-II |
| $G^1$-I | R-IX | $R^6$-III |
| $G^1$-I | R-IX | $R^6$-IV |
| $G^1$-I | R-IX | $R^6$-V |
| $G^1$-I | R-IX | $R^6$-VI |
| $G^1$-I | R-IX | $R^6$-VII |
| $G^1$-I | R-IX | $R^6$-VIII |
| $G^1$-I | R-IX | $R^6$-IX |
| $G^1$-I | R-X | $R^6$-I |
| $G^1$-I | R-X | $R^6$-II |
| $G^1$-I | R-XI | $R^6$-I |
| $G^1$-I | R-XI | $R^6$-II |
| $G^1$-I | R-XII | $R^6$-I |
| $G^1$-I | R-XII | $R^6$-II |
| $G^1$-I | R-XIII | $R^6$-I |
| $G^1$-I | R-XIII | $R^6$-II |
| $G^1$-I | R-XIV | $R^6$-I |
| $G^1$-I | R-XIV | $R^6$-II |
| $G^1$-I | R-XV | $R^6$-I |
| $G^1$-I | R-XV | $R^6$-II |
| $G^1$-I | R-XVI | $R^6$-I |
| $G^1$-I | R-XVI | $R^6$-II |
| $G^1$-I | R-XVII | $R^6$-I |
| $G^1$-I | R-XVII | $R^6$-II |
| $G^1$-I | R-XVIII | $R^6$-I |
| $G^1$-I | R-XVIII | $R^6$-II |
| $G^1$-II | R-I | $R^6$-I |
| $G^1$-II | R-I | $R^6$-II |
| $G^1$-II | R-II | $R^6$-I |
| $G^1$-II | R-II | $R^6$-II |
| $G^1$-II | R-IV | $R^6$-I |
| $G^1$-II | R-IV | $R^6$-II |
| $G^1$-II | R-V | $R^6$-I |
| $G^1$-II | R-V | $R^6$-II |
| $G^1$-II | R-VII | $R^6$-I |
| $G^1$-II | R-VII | $R^6$-II |
| $G^1$-II | R-VIII | $R^6$-I |
| $G^1$-II | R-VIII | $R^6$-II |
| $G^1$-II | R-IX | $R^6$-I |
| $G^1$-II | R-IX | $R^6$-II |
| $G^1$-II | R-XI | $R^6$-I |
| $G^1$-II | R-XI | $R^6$-II |
| $G^1$-II | R-XV | $R^6$-I |
| $G^1$-II | R-XV | $R^6$-II |
| $G^1$-III | R-I | $R^6$-I |
| $G^1$-III | R-I | $R^6$-II |

TABLE 1-continued

| $G^1$ | $R^1\sim R^4$ | $R^6$ |
|---|---|---|
| $G^1$-III | R-I | $R^6$-III |
| $G^1$-III | R-I | $R^6$-IV |
| $G^1$-III | R-I | $R^6$-V |
| $G^1$-III | R-I | $R^6$-VI |
| $G^1$-III | R-I | $R^6$-VII |
| $G^1$-III | R-I | $R^6$-VIII |
| $G^1$-III | R-I | $R^6$-IX |
| $G^1$-III | R-II | $R^6$-I |
| $G^1$-III | R-II | $R^6$-II |
| $G^1$-III | R-II | $R^6$-III |
| $G^1$-III | R-II | $R^6$-IV |
| $G^1$-III | R-II | $R^6$-V |
| $G^1$-III | R-II | $R^6$-VI |
| $G^1$-III | R-II | $R^6$-VII |
| $G^1$-III | R-II | $R^6$-VIII |
| $G^1$-III | R-II | $R^6$-IX |
| $G^1$-III | R-III | $R^6$-I |
| $G^1$-III | R-III | $R^6$-II |
| $G^1$-III | R-IV | $R^6$-I |
| $G^1$-III | R-IV | $R^6$-II |
| $G^1$-III | R-IV | $R^6$-III |
| $G^1$-III | R-IV | $R^6$-IV |
| $G^1$-III | R-IV | $R^6$-V |
| $G^1$-III | R-IV | $R^6$-VII |
| $G^1$-III | R-V | $R^6$-I |
| $G^1$-III | R-V | $R^6$-II |
| $G^1$-III | R-V | $R^6$-III |
| $G^1$-III | R-V | $R^6$-IV |
| $G^1$-III | R-V | $R^6$-VI |
| $G^1$-III | R-V | $R^6$-VII |
| $G^1$-III | R-V | $R^6$-VIII |
| $G^1$-III | R-V | $R^6$-IX |
| $G^1$-III | R-VI | $R^6$-I |
| $G^1$-III | R-VI | $R^6$-II |
| $G^1$-III | R-VII | $R^6$-I |
| $G^1$-III | R-VII | $R^6$-II |
| $G^1$-III | R-VII | $R^6$-III |
| $G^1$-III | R-VII | $R^6$-IV |
| $G^1$-III | R-VII | $R^6$-V |
| $G^1$-III | R-VII | $R^6$-VI |
| $G^1$-III | R-VIII | $R^6$-I |
| $G^1$-III | R-VIII | $R^6$-II |
| $G^1$-III | R-VIII | $R^6$-III |
| $G^1$-III | R-VIII | $R^6$-IV |
| $G^1$-III | R-VIII | $R^6$-V |
| $G^1$-III | R-VIII | $R^6$-VI |
| $G^1$-III | R-VIII | $R^6$-VII |
| $G^1$-III | R-VIII | $R^6$-VIII |
| $G^1$-III | R-VIII | $R^6$-IX |
| $G^1$-III | R-IX | $R^6$-I |
| $G^1$-III | R-IX | $R^6$-II |
| $G^1$-III | R-IX | $R^6$-III |
| $G^1$-III | R-IX | $R^6$-IV |
| $G^1$-III | R-IX | $R^6$-V |
| $G^1$-III | R-IX | $R^6$-VI |
| $G^1$-III | R-IX | $R^6$-VII |
| $G^1$-III | R-IX | $R^6$-VIII |
| $G^1$-III | R-IX | $R^6$-IX |
| $G^1$-III | R-X | $R^6$-I |
| $G^1$-III | R-X | $R^6$-II |
| $G^1$-III | R-XI | $R^6$-I |
| $G^1$-III | R-XI | $R^6$-II |
| $G^1$-III | R-XII | $R^6$-I |
| $G^1$-III | R-XII | $R^6$-II |
| $G^1$-III | R-XIII | $R^6$-I |
| $G^1$-III | R-XIII | $R^6$-II |
| $G^1$-III | R-XIV | $R^6$-I |
| $G^1$-III | R-XIV | $R^6$-II |
| $G^1$-III | R-XV | $R^6$-I |
| $G^1$-III | R-XV | $R^6$-II |
| $G^1$-III | R-XVI | $R^6$-I |
| $G^1$-III | R-XVI | $R^6$-II |
| $G^1$-III | R-XVII | $R^6$-I |
| $G^1$-III | R-XVII | $R^6$-II |
| $G^1$-III | R-XVIII | $R^6$-I |
| $G^1$-III | R-XVIII | $R^6$-II |
| $G^1$-IV | R-I | $R^6$-I |
| $G^1$-IV | R-I | $R^6$-II |
| $G^1$-IV | R-I | $R^6$-III |
| $G^1$-IV | R-I | $R^6$-IV |
| $G^1$-IV | R-I | $R^6$-V |
| $G^1$-IV | R-I | $R^6$-VI |
| $G^1$-IV | R-I | $R^6$-VII |
| $G^1$-IV | R-I | $R^6$-VIII |
| $G^1$-IV | R-I | $R^6$-IX |
| $G^1$-IV | R-II | $R^6$-I |
| $G^1$-IV | R-II | $R^6$-II |
| $G^1$-IV | R-II | $R^6$-III |
| $G^1$-IV | R-II | $R^6$-IV |
| $G^1$-IV | R-II | $R^6$-V |
| $G^1$-IV | R-II | $R^6$-VI |
| $G^1$-IV | R-II | $R^6$-VII |
| $G^1$-IV | R-II | $R^6$-VIII |
| $G^1$-IV | R-II | $R^6$-IX |
| $G^1$-IV | R-III | $R^6$-I |
| $G^1$-IV | R-III | $R^6$-II |
| $G^1$-IV | R-IV | $R^6$-I |
| $G^1$-IV | R-IV | $R^6$-II |
| $G^1$-IV | R-IV | $R^6$-III |
| $G^1$-IV | R-IV | $R^6$-IV |
| $G^1$-IV | R-IV | $R^6$-V |
| $G^1$-IV | R-IV | $R^6$-VII |
| $G^1$-IV | R-V | $R^6$-I |
| $G^1$-IV | R-V | $R^6$-II |
| $G^1$-IV | R-V | $R^6$-III |
| $G^1$-IV | R-V | $R^6$-IV |
| $G^1$-IV | R-V | $R^6$-VI |
| $G^1$-IV | R-V | $R^6$-VII |
| $G^1$-IV | R-V | $R^6$-VIII |
| $G^1$-IV | R-V | $R^6$-IX |
| $G^1$-IV | R-VI | $R^6$-I |
| $G^1$-IV | R-VI | $R^6$-II |
| $G^1$-IV | R-VII | $R^6$-I |
| $G^1$-IV | R-VII | $R^6$-II |
| $G^1$-IV | R-VII | $R^6$-III |
| $G^1$-IV | R-VII | $R^6$-IV |
| $G^1$-IV | R-VII | $R^6$-V |
| $G^1$-IV | R-VII | $R^6$-VI |
| $G^1$-IV | R-VIII | $R^6$-I |
| $G^1$-IV | R-VIII | $R^6$-II |
| $G^1$-IV | R-VIII | $R^6$-III |
| $G^1$-IV | R-VIII | $R^6$-IV |
| $G^1$-IV | R-VIII | $R^6$-V |
| $G^1$-IV | R-VIII | $R^6$-VI |
| $G^1$-IV | R-VIII | $R^6$-VII |
| $G^1$-IV | R-VIII | $R^6$-VIII |
| $G^1$-IV | R-VIII | $R^6$-IX |
| $G^1$-IV | R-IX | $R^6$-I |
| $G^1$-IV | R-IX | $R^6$-II |
| $G^1$-IV | R-IX | $R^6$-III |
| $G^1$-IV | R-IX | $R^6$-IV |
| $G^1$-IV | R-IX | $R^6$-V |
| $G^1$-IV | R-IX | $R^6$-VI |
| $G^1$-IV | R-IX | $R^6$-VII |
| $G^1$-IV | R-IX | $R^6$-VIII |
| $G^1$-IV | R-IX | $R^6$-IX |
| $G^1$-IV | R-X | $R^6$-I |
| $G^1$-IV | R-X | $R^6$-II |
| $G^1$-IV | R-XI | $R^6$-I |
| $G^1$-IV | R-XI | $R^6$-II |
| $G^1$-IV | R-XII | $R^6$-I |
| $G^1$-IV | R-XII | $R^6$-II |
| $G^1$-IV | R-XIII | $R^6$-I |
| $G^1$-IV | R-XIII | $R^6$-II |
| $G^1$-IV | R-XIV | $R^6$-I |
| $G^1$-IV | R-XIV | $R^6$-II |
| $G^1$-IV | R-XV | $R^6$-I |
| $G^1$-IV | R-XV | $R^6$-II |
| $G^1$-IV | R-XVI | $R^6$-I |
| $G^1$-IV | R-XVI | $R^6$-II |
| $G^1$-IV | R-XVII | $R^6$-I |
| $G^1$-IV | R-XVII | $R^6$-II |
| $G^1$-IV | R-XVIII | $R^6$-I |
| $G^1$-IV | R-XVIII | $R^6$-II |
| $G^1$-V | R-I | $R^6$-I |
| $G^1$-V | R-I | $R^6$-II |

TABLE 1-continued

| $G^1$ | $R^1\sim R^4$ | $R^6$ |
|---|---|---|
| $G^1$-V | R-II | $R^6$-I |
| $G^1$-V | R-II | $R^6$-II |
| $G^1$-V | R-IV | $R^6$-I |
| $G^1$-V | R-IV | $R^6$-II |
| $G^1$-V | R-V | $R^6$-I |
| $G^1$-V | R-V | $R^6$-II |
| $G^1$-V | R-VII | $R^6$-I |
| $G^1$-V | R-VII | $R^6$-II |
| $G^1$-V | R-VIII | $R^6$-I |
| $G^1$-V | R-VIII | $R^6$-II |
| $G^1$-V | R-IX | $R^6$-I |
| $G^1$-V | R-IX | $R^6$-II |
| $G^1$-V | R-XI | $R^6$-I |
| $G^1$-V | R-XI | $R^6$-II |
| $G^1$-V | R-XV | $R^6$-I |
| $G^1$-V | R-XV | $R^6$-II |
| $G^1$-VI | R-I | $R^6$-I |
| $G^1$-VI | R-I | $R^6$-II |
| $G^1$-VI | R-II | $R^6$-I |
| $G^1$-VI | R-II | $R^6$-II |
| $G^1$-VI | R-IV | $R^6$-I |
| $G^1$-VI | R-IV | $R^6$-II |
| $G^1$-VI | R-V | $R^6$-I |
| $G^1$-VI | R-V | $R^6$-II |
| $G^1$-VI | R-VII | $R^6$-I |
| $G^1$-VI | R-VII | $R^6$-II |
| $G^1$-VI | R-VIII | $R^6$-I |
| $G^1$-VI | R-VIII | $R^6$-II |
| $G^1$-VI | R-IX | $R^6$-I |
| $G^1$-VI | R-IX | $R^6$-II |
| $G^1$-VI | R-XI | $R^6$-I |
| $G^1$-VI | R-XI | $R^6$-II |
| $G^1$-VI | R-XV | $R^6$-I |
| $G^1$-VI | R-XV | $R^6$-II |
| $G^1$-VII | R-I | $R^6$-I |
| $G^1$-VII | R-I | $R^6$-II |
| $G^1$-VII | R-I | $R^6$-III |
| $G^1$-VII | R-I | $R^6$-IV |
| $G^1$-VII | R-I | $R^6$-V |
| $G^1$-VII | R-I | $R^6$-VI |
| $G^1$-VII | R-I | $R^6$-VII |
| $G^1$-VII | R-I | $R^6$-VIII |
| $G^1$-VII | R-I | $R^6$-IX |
| $G^1$-VII | R-II | $R^6$-I |
| $G^1$-VII | R-II | $R^6$-II |
| $G^1$-VII | R-II | $R^6$-III |
| $G^1$-VII | R-II | $R^6$-IV |
| $G^1$-VII | R-II | $R^6$-V |
| $G^1$-VII | R-II | $R^6$-VI |
| $G^1$-VII | R-II | $R^6$-VII |
| $G^1$-VII | R-II | $R^6$-VIII |
| $G^1$-VII | R-II | $R^6$-IX |
| $G^1$-VII | R-III | $R^6$-I |
| $G^1$-VII | R-III | $R^6$-II |
| $G^1$-VII | R-IV | $R^6$-I |
| $G^1$-VII | R-IV | $R^6$-II |
| $G^1$-VII | R-IV | $R^6$-III |
| $G^1$-VII | R-IV | $R^6$-IV |
| $G^1$-VII | R-IV | $R^6$-V |
| $G^1$-VII | R-IV | $R^6$-VII |
| $G^1$-VII | R-V | $R^6$-I |
| $G^1$-VII | R-V | $R^6$-II |
| $G^1$-VII | R-V | $R^6$-III |
| $G^1$-VII | R-V | $R^6$-IV |
| $G^1$-VII | R-V | $R^6$-V |
| $G^1$-VII | R-V | $R^6$-VI |
| $G^1$-VII | R-V | $R^6$-VII |
| $G^1$-VII | R-V | $R^6$-VIII |
| $G^1$-VII | R-V | $R^6$-IX |
| $G^1$-VII | R-VI | $R^6$-I |
| $G^1$-VII | R-VI | $R^6$-II |
| $G^1$-VII | R-VII | $R^6$-I |
| $G^1$-VII | R-VII | $R^6$-II |
| $G^1$-VII | R-VII | $R^6$-III |
| $G^1$-VII | R-VII | $R^6$-IV |
| $G^1$-VII | R-VII | $R^6$-V |
| $G^1$-VII | R-VII | $R^6$-VII |
| $G^1$-VII | R-VIII | $R^6$-I |
| $G^1$-VII | R-VIII | $R^6$-II |
| $G^1$-VII | R-VIII | $R^6$-III |
| $G^1$-VII | R-VIII | $R^6$-IV |
| $G^1$-VII | R-VIII | $R^6$-V |
| $G^1$-VII | R-VIII | $R^6$-VI |
| $G^1$-VII | R-VIII | $R^6$-VII |
| $G^1$-VII | R-VIII | $R^6$-VIII |
| $G^1$-VII | R-VIII | $R^6$-IX |
| $G^1$-VII | R-IX | $R^6$-I |
| $G^1$-VII | R-IX | $R^6$-II |
| $G^1$-VII | R-IX | $R^6$-III |
| $G^1$-VII | R-IX | $R^6$-IV |
| $G^1$-VII | R-IX | $R^6$-V |
| $G^1$-VII | R-IX | $R^6$-VI |
| $G^1$-VII | R-IX | $R^6$-VII |
| $G^1$-VII | R-IX | $R^6$-VIII |
| $G^1$-VII | R-IX | $R^6$-IX |
| $G^1$-VII | R-X | $R^6$-I |
| $G^1$-VII | R-X | $R^6$-II |
| $G^1$-VII | R-XI | $R^6$-I |
| $G^1$-VII | R-XI | $R^6$-II |
| $G^1$-VII | R-XII | $R^6$-I |
| $G^1$-VII | R-XII | $R^6$-II |
| $G^1$-VII | R-XIII | $R^6$-I |
| $G^1$-VII | R-XIII | $R^6$-II |
| $G^1$-VII | R-XIV | $R^6$-I |
| $G^1$-VII | R-XIV | $R^6$-II |
| $G^1$-VII | R-XV | $R^6$-I |
| $G^1$-VII | R-XV | $R^6$-II |
| $G^1$-VII | R-XVI | $R^6$-I |
| $G^1$-VII | R-XVI | $R^6$-II |
| $G^1$-VII | R-XVII | $R^6$-I |
| $G^1$-VII | R-XVII | $R^6$-II |
| $G^1$-VII | R-XVIII | $R^6$-I |
| $G^1$-VII | R-XVIII | $R^6$-II |
| $G^1$-VIII | R-I | $R^6$-I |
| $G^1$-VIII | R-I | $R^6$-II |
| $G^1$-VIII | R-I | $R^6$-III |
| $G^1$-VIII | R-I | $R^6$-IV |
| $G^1$-VIII | R-I | $R^6$-V |
| $G^1$-VIII | R-I | $R^6$-VI |
| $G^1$-VIII | R-I | $R^6$-VII |
| $G^1$-VIII | R-I | $R^6$-VIII |
| $G^1$-VIII | R-I | $R^6$-IX |
| $G^1$-VIII | R-II | $R^6$-I |
| $G^1$-VIII | R-II | $R^6$-II |
| $G^1$-VIII | R-II | $R^6$-III |
| $G^1$-VIII | R-II | $R^6$-IV |
| $G^1$-VIII | R-II | $R^6$-V |
| $G^1$-VIII | R-II | $R^6$-VI |
| $G^1$-VIII | R-II | $R^6$-VII |
| $G^1$-VIII | R-II | $R^6$-VIII |
| $G^1$-VIII | R-II | $R^6$-IX |
| $G^1$-VIII | R-III | $R^6$-I |
| $G^1$-VIII | R-III | $R^6$-II |
| $G^1$-VIII | R-IV | $R^6$-I |
| $G^1$-VIII | R-IV | $R^6$-II |
| $G^1$-VIII | R-IV | $R^6$-III |
| $G^1$-VIII | R-IV | $R^6$-IV |
| $G^1$-VIII | R-IV | $R^6$-V |
| $G^1$-VIII | R-IV | $R^6$-VII |
| $G^1$-VIII | R-V | $R^6$-I |
| $G^1$-VIII | R-V | $R^6$-II |
| $G^1$-VIII | R-V | $R^6$-III |
| $G^1$-VIII | R-V | $R^6$-IV |
| $G^1$-VIII | R-V | $R^6$-V |
| $G^1$-VIII | R-V | $R^6$-VI |
| $G^1$-VIII | R-V | $R^6$-VII |
| $G^1$-VIII | R-V | $R^6$-VIII |
| $G^1$-VIII | R-V | $R^6$-IX |
| $G^1$-VIII | R-VI | $R^6$-I |
| $G^1$-VIII | R-VI | $R^6$-II |
| $G^1$-VIII | R-VII | $R^6$-I |
| $G^1$-VIII | R-VII | $R^6$-II |
| $G^1$-VIII | R-VII | $R^6$-III |
| $G^1$-VIII | R-VII | $R^6$-IV |
| $G^1$-VIII | R-VII | $R^6$-V |
| $G^1$-VIII | R-VII | $R^6$-VII |

TABLE 1-continued

| $G^1$ | $R^1 \sim R^4$ | $R^6$ |
|---|---|---|
| $G^1$-VIII | R-VIII | $R^6$-I |
| $G^1$-VIII | R-VIII | $R^6$-II |
| $G^1$-VIII | R-VIII | $R^6$-III |
| $G^1$-VIII | R-VIII | $R^6$-IV |
| $G^1$-VIII | R-VIII | $R^6$-V |
| $G^1$-VIII | R-VIII | $R^6$-VI |
| $G^1$-VIII | R-VIII | $R^6$-VII |
| $G^1$-VIII | R-VIII | $R^6$-VIII |
| $G^1$-VIII | R-VIII | $R^6$-IX |
| $G^1$-VIII | R-IX | $R^6$-I |
| $G^1$-VIII | R-IX | $R^6$-II |
| $G^1$-VIII | R-IX | $R^6$-III |
| $G^1$-VIII | R-IX | $R^6$-IV |
| $G^1$-VIII | R-IX | $R^6$-V |
| $G^1$-VIII | R-IX | $R^6$-VI |
| $G^1$-VIII | R-IX | $R^6$-VII |
| $G^1$-VIII | R-IX | $R^6$-VIII |
| $G^1$-VIII | R-IX | $R^6$-IX |
| $G^1$-VIII | R-X | $R^6$-I |
| $G^1$-VIII | R-X | $R^6$-II |
| $G^1$-VIII | R-XI | $R^6$-I |
| $G^1$-VIII | R-XI | $R^6$-II |
| $G^1$-VIII | R-XII | $R^6$-I |
| $G^1$-VIII | R-XII | $R^6$-II |
| $G^1$-VIII | R-XIII | $R^6$-I |
| $G^1$-VIII | R-XIII | $R^6$-II |
| $G^1$-VIII | R-XIV | $R^6$-I |
| $G^1$-VIII | R-XIV | $R^6$-II |
| $G^1$-VIII | R-XV | $R^6$-I |
| $G^1$-VIII | R-XV | $R^6$-II |
| $G^1$-VIII | R-XVI | $R^6$-I |
| $G^1$-VIII | R-XVI | $R^6$-II |
| $G^1$-VIII | R-XVII | $R^6$-I |
| $G^1$-VIII | R-XVII | $R^6$-II |
| $G^1$-VIII | R-XVIII | $R^6$-I |
| $G^1$-VIII | R-XVIII | $R^6$-II |
| $G^1$-IX | R-I | $R^6$-I |
| $G^1$-IX | R-I | $R^6$-II |
| $G^1$-IX | R-II | $R^6$-I |
| $G^1$-IX | R-II | $R^6$-II |
| $G^1$-IX | R-IV | $R^6$-I |
| $G^1$-IX | R-IV | $R^6$-II |
| $G^1$-IX | R-V | $R^6$-I |
| $G^1$-IX | R-V | $R^6$-II |
| $G^1$-IX | R-VII | $R^6$-I |
| $G^1$-IX | R-VII | $R^6$-II |
| $G^1$-IX | R-VIII | $R^6$-I |
| $G^1$-IX | R-VIII | $R^6$-II |
| $G^1$-IX | R-IX | $R^6$-I |
| $G^1$-IX | R-IX | $R^6$-II |
| $G^1$-X | R-I | $R^6$-I |
| $G^1$-X | R-I | $R^6$-II |
| $G^1$-X | R-II | $R^6$-II |
| $G^1$-X | R-IV | $R^6$-II |
| $G^1$-X | R-V | $R^6$-I |
| $G^1$-X | R-V | $R^6$-II |
| $G^1$-X | R-VII | $R^6$-II |
| $G^1$-X | R-VIII | $R^6$-I |
| $G^1$-X | R-VIII | $R^6$-II |
| $G^1$-X | R-IX | $R^6$-I |
| $G^1$-X | R-IX | $R^6$-II |
| $G^1$-XI | R-I | $R^6$-I |
| $G^1$-XI | R-I | $R^6$-II |
| $G^1$-XI | R-II | $R^6$-I |
| $G^1$-XI | R-II | $R^6$-II |
| $G^1$-XI | R-IV | $R^6$-I |
| $G^1$-XI | R-IV | $R^6$-II |
| $G^1$-XI | R-V | $R^6$-I |
| $G^1$-XI | R-V | $R^6$-II |
| $G^1$-XI | R-VII | $R^6$-I |
| $G^1$-XI | R-VII | $R^6$-II |
| $G^1$-XI | R-VIII | $R^6$-I |
| $G^1$-XI | R-VIII | $R^6$-II |
| $G^1$-XI | R-IX | $R^6$-I |
| $G^1$-XI | R-IX | $R^6$-II |
| $G^1$-XI | R-XI | $R^6$-I |
| $G^1$-XI | R-XI | $R^6$-II |
| $G^1$-XI | R-XV | $R^6$-I |
| $G^1$-XI | R-XV | $R^6$-II |
| $G^1$-XII | R-I | $R^6$-I |
| $G^1$-XII | R-II | $R^6$-I |
| $G^1$-XII | R-II | $R^6$-II |
| $G^1$-XII | R-IV | $R^6$-I |
| $G^1$-XII | R-IV | $R^6$-II |
| $G^1$-XII | R-V | $R^6$-I |
| $G^1$-XII | R-V | $R^6$-II |
| $G^1$-XII | R-VIII | $R^6$-I |
| $G^1$-XII | R-VIII | $R^6$-II |
| $G^1$-XII | R-IX | $R^6$-I |
| $G^1$-XII | R-IX | $R^6$-II |
| $G^1$-XIII | R-I | $R^6$-I |
| $G^1$-XIII | R-I | $R^6$-II |
| $G^1$-XIII | R-II | $R^6$-II |
| $G^1$-XIII | R-IV | $R^6$-II |
| $G^1$-XIII | R-V | $R^6$-I |
| $G^1$-XIII | R-V | $R^6$-II |
| $G^1$-XIII | R-VIII | $R^6$-I |
| $G^1$-XIII | R-VIII | $R^6$-II |
| $G^1$-XIII | R-IX | $R^6$-I |
| $G^1$-XIII | R-IX | R-II |
| $G^1$-XIV | R-I | $R^6$-I |
| $G^1$-XIV | R-I | $R^6$-II |
| $G^1$-XIV | R-II | $R^6$-I |
| $G^1$-XIV | R-II | $R^6$-II |
| $G^1$-XIV | R-IV | $R^6$-I |
| $G^1$-XIV | R-IV | $R^6$-II |
| $G^1$-XIV | R-V | $R^6$-I |
| $G^1$-XIV | R-V | $R^6$-II |
| $G^1$-XIV | R-VII | $R^6$-I |
| $G^1$-XIV | R-VII | $R^6$-II |
| $G^1$-XIV | R-VIII | $R^6$-I |
| $G^1$-XIV | R-VIII | $R^6$-II |
| $G^1$-XIV | R-IX | $R^6$-I |
| $G^1$-XIV | R-IX | $R^6$-II |
| $G^1$-XV | R-I | $R^6$-I |
| $G^1$-XV | R-I | $R^6$-II |
| $G^1$-XV | R-II | $R^6$-I |
| $G^1$-XV | R-II | $R^6$-II |
| $G^1$-XV | R-IV | $R^6$-I |
| $G^1$-XV | R-IV | $R^6$-II |
| $G^1$-XV | R-V | $R^6$-I |
| $G^1$-XV | R-V | $R^6$-II |
| $G^1$-XV | R-VIII | $R^6$-I |
| $G^1$-XV | R-VIII | $R^6$-II |
| $G^1$-XV | R-IX | $R^6$-I |
| $G^1$-XV | R-IX | $R^6$-II |
| $G^1$-XVI | R-I | $R^6$-I |
| $G^1$-XVI | R-I | $R^6$-II |
| $G^1$-XVI | R-II | $R^6$-I |
| $G^1$-XVI | R-II | $R^6$-II |
| $G^1$-XVI | R-IV | $R^6$-I |
| $G^1$-XVI | R-IV | $R^6$-II |
| $G^1$-XVI | R-V | $R^6$-I |
| $G^1$-XVI | R-V | $R^6$-II |
| $G^1$-XVI | R-VIII | $R^6$-I |
| $G^1$-XVI | R-VIII | $R^6$-II |
| $G^1$-XVI | R-IX | $R^6$-I |
| $G^1$-XVI | R-IX | $R^6$-II |
| $G^1$-XVII | R-I | $R^6$-I |
| $G^1$-XVII | R-I | $R^6$-II |
| $G^1$-XVII | R-II | $R^6$-I |
| $G^1$-XVII | R-II | $R^6$-II |
| $G^1$-XVII | R-IV | $R^6$-I |
| $G^1$-XVII | R-IV | $R^6$-II |
| $G^1$-XVII | R-V | $R^6$-I |
| $G^1$-XVII | R-V | $R^6$-II |
| $G^1$-XVII | R-VIII | $R^6$-I |
| $G^1$-XVII | R-VIII | $R^6$-II |
| $G^1$-XVII | R-IX | $R^6$-I |
| $G^1$-XVII | R-IX | $R^6$-II |
| $G^1$-XVIII | R-I | $R^6$-I |
| $G^1$-XVIII | R-I | $R^6$-II |
| $G^1$-XVIII | R-II | $R^6$-I |
| $G^1$-XVIII | R-II | $R^6$-II |
| $G^1$-XVIII | R-IV | $R^6$-I |

TABLE 1-continued

| $G^1$ | $R^1$~$R^4$ | $R^6$ |
|---|---|---|
| $G^1$-XVIII | R-IV | $R^6$-II |
| $G^1$-XVIII | R-V | $R^6$-I |
| $G^1$-XVIII | R-V | $R^6$-II |
| $G^1$-XVIII | R-VII | $R^6$-I |
| $G^1$-XVIII | R-VII | $R^6$-II |
| $G^1$-XVIII | R-VIII | $R^6$-I |
| $G^1$-XVIII | R-VIII | $R^6$-II |
| $G^1$-XVIII | R-IX | $R^6$-I |
| $G^1$-XVIII | R-IX | $R^6$-II |
| $G^1$-XVIII | R-XI | $R^6$-I |
| $G^1$-XVIII | R-XI | $R^6$-II |
| $G^1$-XVIII | R-XV | $R^6$-I |
| $G^1$-XVIII | R-XV | $R^6$-II |
| $G^1$-XIX | R-I | $R^6$-I |
| $G^1$-XIX | R-I | $R^6$-II |
| $G^1$-XIX | R-II | $R^6$-I |
| $G^1$-XIX | R-II | $R^6$-II |
| $G^1$-XIX | R-IV | $R^6$-I |
| $G^1$-XIX | R-IV | $R^6$-II |
| $G^1$-XIX | R-V | $R^6$-I |
| $G^1$-XIX | R-V | $R^6$-II |
| $G^1$-XIX | R-VIII | $R^6$-I |
| $G^1$-XIX | R-VIII | $R^6$-II |
| $G^1$-XIX | R-IX | $R^6$-I |
| $G^1$-XIX | R-IX | $R^6$-II |
| $G^1$-XX | R-I | $R^6$-I |
| $G^1$-XX | R-I | $R^6$-II |
| $G^1$-XX | R-II | $R^6$-I |
| $G^1$-XX | R-II | $R^6$-II |
| $G^1$-XX | R-IV | $R^6$-I |
| $G^1$-XX | R-IV | $R^6$-II |
| $G^1$-XX | R-V | $R^6$-I |
| $G^1$-XX | R-V | $R^6$-II |
| $G^1$-XX | R-VII | $R^6$-I |
| $G^1$-XX | R-VII | $R^6$-II |
| $G^1$-XX | R-VIII | $R^6$-I |
| $G^1$-XX | R-VIII | $R^6$-II |
| $G^1$-XX | R-IX | $R^6$-I |
| $G^1$-XX | R-IX | $R^6$-II |
| $G^1$-XXI | R-I | $R^6$-I |
| $G^1$-XXI | R-I | $R^6$-II |
| $G^1$-XXI | R-II | $R^6$-I |
| $G^1$-XXI | R-II | $R^6$-II |
| $G^1$-XXI | R-IV | $R^6$-I |
| $G^1$-XXI | R-IV | $R^6$-II |
| $G^1$-XXI | R-V | $R^6$-I |
| $G^1$-XXI | R-V | $R^6$-II |
| $G^1$-XXI | R-VIII | $R^6$-I |
| $G^1$-XXI | R-VIII | $R^6$-II |
| $G^1$-XXI | R-IX | $R^6$-I |
| $G^1$-XXI | R-IX | $R^6$-II |
| $G^1$-XXII | R-I | $R^6$-I |
| $G^1$-XXII | R-I | $R^6$-II |
| $G^1$-XXII | R-II | $R^6$-I |
| $G^1$-XXII | R-II | $R^6$-II |
| $G^1$-XXII | R-IV | $R^6$-I |
| $G^1$-XXII | R-IV | $R^6$-II |
| $G^1$-XXII | R-V | $R^6$-I |
| $G^1$-XXII | R-V | $R^6$-II |
| $G^1$-XXII | R-VII | $R^6$-I |
| $G^1$-XXII | R-VII | $R^6$-II |
| $G^1$-XXII | R-VIII | $R^6$-I |
| $G^1$-XXII | R-VIII | $R^6$-II |
| $G^1$-XXII | R-IX | $R^6$-I |
| $G^1$-XXIII | R-X | $R^6$-II |
| $G^1$-XXIII | R-I | $R^6$-I |
| $G^1$-XXIII | R-I | $R^6$-II |
| $G^1$-XXIII | R-II | $R^6$-I |
| $G^1$-XXIII | R-II | $R^6$-II |
| $G^1$-XXIII | R-IV | $R^6$-I |
| $G^1$-XXIII | R-IV | $R^6$-II |
| $G^1$-XXIII | R-V | $R^6$-I |
| $G^1$-XXIII | R-V | $R^6$-II |
| $G^1$-XXIII | R-VIII | $R^6$-I |
| $G^1$-XXIII | R-VIII | $R^6$-I |
| $G^1$-XXIII | R-VIII | $R^6$-II |
| $G^1$-XXIII | R-IX | $R^6$-I |
| $G^1$-XXIII | R-IX | $R^6$-II |
| $G^1$-XXIV | R-I | $R^6$-I |
| $G^1$-XXIV | R-I | $R^6$-II |
| $G^1$-XXIV | R-II | $R^6$-I |
| $G^1$-XXIV | R-II | $R^6$-II |
| $G^1$-XXIV | R-IV | $R^6$-I |
| $G^1$-XXIV | R-IV | $R^6$-II |
| $G^1$-XXIV | R-V | $R^6$-I |
| $G^1$-XXIV | R-V | $R^6$-II |
| $G^1$-XXIV | R-VIII | $R^6$-I |
| $G^1$-XXIV | R-VIII | $R^6$-II |
| $G^1$-XXIV | R-IX | $R^6$-I |
| $G^1$-XXIV | R-IX | $R^6$-II |
| $G^1$-XXV | R-I | $R^6$-I |
| $G^1$-XXV | R-I | $R^6$-II |
| $G^1$-XXV | R-II | $R^6$-I |
| $G^1$-XXV | R-II | $R^6$-II |
| $G^1$-XXV | R-IV | $R^6$-I |
| $G^1$-XXV | R-IV | $R^6$-II |
| $G^1$-XXV | R-V | $R^6$-I |
| $G^1$-XXV | R-V | $R^6$-II |
| $G^1$-XXV | R-VIII | $R^6$-I |
| $G^1$-XXV | R-VIII | $R^6$-II |
| $G^1$-XXV | R-IX | $R^6$-I |
| $G^1$-XXV | R-IX | $R^6$-II |

Among the compounds represented by the formula (I), the acid addition salts may, for example, be salts of hydrohalic acids such as hydrofluoric acid, hydrochloric acid, hydrobromic acid, hydriodic acid, etc., salts of inorganic acids such as nitric acid, sulfuric acid, phosphoric acid, chloric acid, perchloric acid, etc., salts of sulfonic acids such as methanesulfonic acid, ethanesulfonic acid, trifluoromethanesulfonic acid, benzenesulfonic acid, p-toluenesulfonic acid, etc., salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, citric acid, etc., salts of amino acids such as glutamic acid, aspartic acid, etc.

Among the compounds represented by the formula (I), the metal salts may, for example, be salts of alkali metals such as lithium, sodium, potassium, etc., salts of alkaline earth metals such as calcium, barium, magnesium, etc. an aluminum salt, etc.

In this specification, "pesticides" means fungicides and parasiticides for controlling harmful pathogens and parasites which infect/parasitize plants or animals, and more specifically means fungicides and nematicides in agricultural/horticultural fields, or antifungal agents and endoparasite controlling agents for animals.

In this specification, "pathogens" means microorganisms which cause plant diseases and animal infectious diseases. As specific examples, the following microorganisms may be mentioned, but the pathogens are not limited thereto.

Fungi of the phylum Ascomycota, such as *Taphrina* spp. (e.g. *Taphrina deformans, T. pruni*, etc.), *Pneumocystis* spp., *Geotrichum* spp., *Candida* spp. (e.g. *Candida albicans, C. sorbosa*, etc.), *Pichia* spp. (e.g. *Pichia kluyveri*, etc.), *Capnodium* spp., *Fumao* spp., *Hypocapnodium* spp., *Cercospora* spp. (e.g. *Cercospora apii, C. asparagi, C. beticola, C. capsici, C. carotae, C. kaki, C. kikuchii, C. zonata*, etc.), *Cercosporidium* spp., *Cladosporium* spp. (e.g. *Cladosporium colocasiae, C. cucumerinum, C. variabile*, etc.), *Davidiella* spp., *Didymosporium* spp., *Heterosporium* spp. (e.g. *Heterosporium allii*, etc.), *Mycosphaerella* spp. (e.g. *Mycosphaerella arachidis, M. berkeleyi, M. cerasella, M. fijiensis, M. fragariae, M. graminicola, M. nawae, M.*

*pinodes, M. pomi, M. zingiberis*, etc.), *Mycovellosiella* spp. (e.g. *Mycovellosiella fulva, M. nattrassii*, etc.), *Paracercospora* spp. (e.g. *Paracercospora egenula*, etc.), *Phaeoisariopsis* spp., *Phaeoramularia* spp., *Pseudocercospora* spp. (e.g. *Pseudocercospora abelmoschi, P. fuligena, P. vitis*, etc.), *Pseudocercosporella* spp. (e.g. *Pseudocercosporella capsellae*, etc.), *Ramichloridium* spp., *Ramularia* spp., *Septoaloeum* spp., *Septoria* spp. (e.g. *Septoria albopunctata, S. apiicola, S. chrysanthemella, S. helianthi, S. obesa*, etc.), *Sphaerulina* spp., *Aureobasidium* spp., *Kabatiella* spp., *Plowrightia* spp., *Stigmina* spp., *Elsinoe* spp. (e.g. *Elsinoe ampelina, E. araliae, E. fawcettii*, etc.), *Sphaceloma* spp. (e.g. *Sphaceloma caricae*, etc.), *Ascochyta* spp. (e.g. *Ascochyta pisi*, etc.), *Corynespora* spp. (e.g. *Corynespora cassiicola*, etc.), *Leptosphaeria* spp. (e.g. *Leptosphaeria coniothyrium, L. maculans*, etc.), *Saccharicola* spp., *Phaeosphaeria* spp., *Ophiosphaerella* spp., *Setophoma* spp., *Helminthosporium* spp., *Alternaria* spp. (e.g. *Alternaria altemata, A. brassicae, A. brassicicola, A. citr, A. dauci, A. helianthi, A. japonica, A. kikuchiana, A. mali, A. panax, A. porri, A. radicina, A. solani*, etc.), *Bipolaris* spp. (e.g. *Bipolaris sorghicola*, etc.), *Cochliobolus* spp. (e.g. *Cochliobolus heterostrophus, C. lunatus, C. miyabeanus*, etc.), *Curvularia* spp. (e.g. *Curvularia geniculata, C. verruculosa*, etc.), *Drechslera* spp., *Pleospora* spp. (e.g. *Pleospora herbarum*, etc.), *Pyrenophora* spp. (e.g. *Pyrenophora graminea, P. teres*, etc.), *Setosphaeria* spp. (e.g. *Setosphaeria turcica*, etc.), *Stemphylium* spp. (e.g. *Stemphylium botryosum, S. lycopersici, S. solani, S. vesicarium*, etc.), *Fusicladium* spp., *Venturia* spp. (e.g. *Venturia carpophila, V. Inaequalis, V. nashicola, V. Dirina*, etc.), *Didymella* spp. (e.g. *Didymella bryoniae, D. fabae*, etc.), *Hendersonia* spp., *Phoma* spp. (e.g. *Phoma erratica* var. *mikan, P. exigua* var. *exigua, P. wasabiae*, etc.), *Pyrenochaeta* spp. (e.g. *Pyrenochaeta lycopersici*, etc.), *Stagonospora* spp. (e.g. *Stagonospora sacchari*, etc.), *Botryosphaeria* spp. (e.g. *Botryosphaeria berengeriana* f. sp. *piricola, B. dothidea*, etc.), *Dothiorella* spp., *Fusicoccum* spp., *Guignardia* spp., *Lasiodiplodia* spp. (e.g. *Lasiodiplodia theobromae*, etc.), *Macrophoma* spp., *Macrophomina* spp., *Neofusicoccum* spp., *Phyllosticta* spp. (e.g. *Phyllosticta zingiberis*, etc.), *Schizothyrium* spp. (e.g. *Schizothyrium pomi*, etc.), *Acrospermum* spp., *Leptosphaerulina* spp., *Asperillus* spp., *Penicillium* spp. (e.g. *Penicillium digitatum, P. italicum, P. sclerotigenum*, etc.), *Microsporum* spp., *Trichophyton* spp. (e.g. *Trichophton mentagrophytes, T. rubrum*, etc.), *Histoplasma* spp., *Blumeria* spp. (e.g. *Blumeria graminis* f. sp. *hordei, B. g.* f. sp. *tritici*, etc.), *Erysiphe* spp. (e.g. *Erysiphe betae, E. cichoracearum, E. c.* var. *cichoracearum, E. heraclei, E. pisi*, etc.), *Golovinomyces* spp. (e.g. *Golovinomyces cichoracearum* var. *latisporus*, etc.), *Leveillula* spp. (e.g. *Leveillula taurica*, etc.), *Microsphaera* spp., *Oidium* spp. (e.g. *Oidium neolycopersici*, etc.), *Phyllactinia* spp. (e.g. *Phyllactinia kakicola, P. mali, P. moricola*, etc.), *Podosphaera* spp. (e.g. *Podosphaera fusca, P. leucotricha, P. pannosa, P. tridactyla* var. *tridactyla, P. xanthii*, etc.), *Sphaerotheca* spp. (e.g. *Sphaerotheca aphanis* var. *aphanis, S. fuliginea*, etc.), *Uncinula* spp. (e.g. *Uncinula necator, U. n.* var. *necator*, etc.), *Uncinuliella* spp. (e.g. *Uncinuliella simulans* var. *simulans, U. s.* var. *tandae*, etc.), *Blumeriella* spp. (e.g. *Blumeriella jaapii*, etc.), *Cylindrosporium* spp., *Diplocarpon* spp. (e.g. *Diplocarpon mali, D. mespili, D. rosae*, etc.), *Gloeosporium* spp. (e.g. *Gloeosporium minus*, etc.), *Marssonina* spp., *Tapesia* spp. (e.g. *Tapesia acuformis, T. yallundae*, etc.), *Lachnum* spp., *Scleromitrula* spp., *Botryotinia* spp. (e.g. *Botryotinia fuckeliana*, etc.), *Botrytis* spp. (e.g. *Botrytis allii, B. byssoidea, B. cinerea, B. elliptica, B. fabae, B. squamosa*, etc.), *Ciborinia* spp., *Grovesinia* spp., *Monilia mumecola, Monilinia* spp. (e.g. *Monilinia fructicola, M. fructigena, M. laxa, M. mali, M. vaccinii-corymbosi*, etc.), *Sclerotinia* spp. (e.g. *Sclerotinia borealis, S. homoeocarpa, S. minor, S. sclerotiorum*, etc.), *Valdensia* spp. (e.g. *Valdensia heterodoxa*, etc.), *Claviceps* spp. (e.g. *Claviceps sorghi, C. sorghicola*, etc.), *Epichloe* spp., *Ephelis japonica, Villosiclava virens, Hyypomyces* spp. (e.g. *Hypomyces solani* f. sp. *mori, H. s.* f. sp. *pisi*, etc.), *Trichoderma* spp. (e.g. *Trichoderma viride*, etc.), *Calonectria* spp. (e.g. *Calonectria ilicicola*, etc.), *Candelospora* spp., *Cylindrocarpon* spp., *Cylindrocladium* spp., *Fusarium* spp. (e.g. *Fusarium arthrosporioides, F. crookwellense, F. culmorum, F. cuneirostrum, F. oxysporum, F. o.* f. sp. *adzukicola, F. o.* f. sp. *allii, F. o.* f. sp. *asparagi, F. o.* f. sp. *batatas, F. o.* f. sp. *cepae, F. o.* f. sp. *colocasiae, F. o.* f. sp. *conglutinans, F. o.* f. sp. *cubense, F. o.* f. sp. *cucumerinum, F. o.* f. sp. *fabae, F. o.* f. sp. *fragariae, F. o.* f. sp. *lactucae, F. o.* f. sp. *lagenariae, F. o.* f. sp. *lycopersici, F. o.* f. sp. *melongenae, F. o.* f. sp. *melonis, F. o.* f. sp. *nelumbinicola, F. o.* f. sp. *niveum, F. o.* f. sp. *radicis-lycopersici, F. o.* f. sp. *raphani, F. o.* f. sp. *spinaciae, F. sporotrichioides, F. solani, F. s.* f. sp. *cucurbitae, F. s.* f. sp. *eumartii, F. s.* f. sp. i, *F. s.* f. sp. *radicicola*, etc.), *Gibberella* spp. (e.g. *Gibberella avenacea, G. baccata, Q. fuiikuroi, Q. zeae*, etc.), *Haematonectria* spp., *Nectria* spp., *Ophionectria* spp., *Caldariomyces* spp., *Myrothecium* spp., *Trichothecium* spp., *Verticillium* spp. (e.g. *Verticillium albo-atrum, V. dahliae, V. longisporum*, etc.), *Ceratocystis* spp. (e.g. *Ceratocystis ficicola, C. fimbriata*, etc.), *Thielaviopsis* spp. (e.g. *Thielaviopsis basicola*, etc.), *Adisciso* spp., *Monochaetia* spp., *Pestalotia* spp. (e.g. *Pestalotia eriobotrifolia*, etc.), *Pestalotiopsis* spp. (e.g. *Pestalotiopsis funerea, P. lonaiseta, P. neplecta, P. theae*, etc.), *Physalospora* spp., *Nemania* spp., *Nodulisporium* spp., *Rosellinia* spp. (e.g. *Rosellinia necatrix*, etc.), *Monographella* spp. (e.g. *Monographella nivalis*, etc.), *Ophiostoma* spp., *Cryphonectria* spp. (e.g. *Cryphonectria parasitica*, etc.), *Diaporthe* spp. (e.g. *Diaporthe citri, D. kyushuensis, D. nomurai, D. tanakae*, etc.), *Diaporthopsis* spp., *Phomopsis* spp. (e.g. *Phomopsis asparai, P. fukushii, P. obscurans, P. vexans*, etc.), *Cryptosporella* spp., *Discula* spp. (e.g. *Discula theae-sinensis*, etc.), *Gnomonia* spp., *Coniella* spp., *Coryneum* spp., *Greeneria* spp., *Melanconis* spp., *Cytospora* spp., *Leucostoma* spp., *Valsa* spp. (e.g. *Valsa ceratosperma*, etc.), *Tubakia* spp., *Monosporascus* spp., *Clasterosporium* spp., *Gaeumannomyces* spp. (e.g. *Gaeumannomyces graminis*, etc.), *Magnaporthe* spp. (e.g. *Magnaporthe grisea*, etc.), *Pyricularia* spp. (e.g. *Pyricularia zingiberis*, etc.), *Monilochaetes infuscans, Colletotrichum* spp. (e.g. *Colletotrichum acutatum, C. capsici, C. cereale, C. destructivum, C. fragariae, C. lindemuthianum, C. niarum, C. orbiculare, C. spinaciae*, etc.), *Glomerella* spp. (e.g. *Glomerella cingulata*, etc.), *Khuskia oryzae, Phyllachora* spp. (e.g. *Phyllachora pomigena*, etc.), *Ellisembia* spp., *Briosia* spp., *Cephalosporium* spp. (e.g. *Cephalosporium gramineum*, etc.), *Epicoccum* spp., *Gloeocercospora sorghi, Mycocentrospora* spp., *Peltaster* spp. (e.g. *Peltaster fructicola*, etc.), *Phaeocytostroma* spp., *Phialophora* spp. (e.g. *Phialophora gregata*, etc.), *Pseudophloeosporella dioscoreae, Pseudoseptoria* spp., *Rhynchosporium* spp. (e.g. *Rhynchosporium secalis*, etc.), *Sarocladium* spp., *Coleophoma* spp., *Helicoceras orzae*, etc.

Fungi of the phylum Basidiomycota, such as *Septobasidium* spp. (e.g. *Septobasidium boaoriense, S. tanakae*, etc.), *Helicobasidium* spp. (e.g. *Helicobasidium longisporum*, etc.), *Coleosporium* spp. (e.g. *Coleosporium plectranthi*, etc.), *Cronartium* spp., *Phakopsora* spp. (e.g. *Phakop-* sora artemisiae, *P. nishidana*, *P. pachyrhizi*, etc.), *Physopella* spp. (e.g. *Physopella ampelopsidis*, etc.), *Kuehneola* spp. (e.g. *Kuehneola japonica*, etc.), *Phragmidium* spp. (e.g. *Phragmidium fusiforme*, *P. mucronatum*, *P. rosaemultiflorae*, etc.), *Gymnosporangium* spp. (e.g. *Gymnosporangium asiaticum*, *G. yamadae*, etc.), *Puccinia* spp. (e.g. *Puccinia allii*, *P. brachypodii* var. *poae-nemoralis*, *P. coronata*, *P. c.* var. *coronata*, *P. cynodontis*, *P. graminis*, *P. g.* subsp. *graminicola*, *P. hordei*, *P. horiana*, *P. kuehnii*, *P. melanocephala*, *P. recondita*, *P. striiformis* var. *striiformis*, *P. tanaceti* var. *tanaceti*, *P. tokvensis*, *P. zoysiae*, etc.), *Uromyces* spp. (e.g. *Uromyces phaseoli* var. *azukicola*, *U. Q.* var. *phaseoli*, *Uromyces viciae-fabae* var. *viciae-fabae*, etc.), *Naohidemyces vaccinii*, *Nyssopsora* spp., *Leucotelium* spp., *Tranzschelia* spp. (e.g. *Tranzschelia discolor*, etc.), *Aecidium* spp., *Blastospora* spp. (e.g. *Blastospora smilacis*, etc.), *Uredo* spp., *Sphacelotheca* spp., *Urocystis* spp., *Sporisorium* spp. (e.g. *Sporisorium scitamineum*, etc.), *Ustilago* spp. (e.g. *Ustilago maydis*, *U. nuda*, etc.), *Entyloma* spp., *Exobasidium* spp. (e.g. *Exobasidium reticulatum*, *E. vexans*, etc.), *Microstroma* spp., *Tilletia* spp. (e.g. *Tilletia caries*, *T. controversa*, *T. laevis*, etc.), *Itersonilia* spp. (e.g. *Itersonilia perplexans*, etc.), *Cryptococcus* spp., *Bovista* spp. (e.g. *Bovista dermoxantha*, etc.), *Lycoperdon* spp. (e.g. *Lycoperdon curtisii*, *L. perlatum*, etc.), *Conocybe* spp. (e.g. *Conocybe apala*, etc.), *Marasmius* spp. (e.g. *Marasmius oreades*, etc.), *Armillaria* spp., *Helotium* spp., *Lepista* spp. (e.g. *Lepista subnuda*, etc.), *Sclerotium* spp. (e.g. *Sclerotium cepivorum*, etc.), *Typhula* spp. (e.g. *Typhula incarnata*, *T. ishikariensis* var. *ishikariensis*, etc.), *Athelia* spp. (e.g. *Athelia rolfsii*, etc.), *Ceratobasidium* spp. (e.g. *Ceratobasidium cornigerum*, etc.), *Ceratorhiza* spp., *Rhizoctonia* spp. (e.g. *Rhizoctonia solani*, etc.), *Thanatephorus* spp. (e.g. *Thanatephorus cucumeris*, etc.), *Laetisaria* spp., *Waitea* spp., *Fomitiporia* spp., *Ganoderma* spp., *Chondrostereum purpureum*, *Phanerochaete* spp., etc.

Fungi of the phylum Chitridiomycota such as *Olidium* spp., etc.

Fungi of the phylum Blastocladiomycota such as *Physoderma* spp., etc.

Fungi of the phylum Mucoromycotina such as *Choanephora* spp., *Choanephoroidea cucurbitae*, *Mucor* spp. (e.g. *Mucor fragilis*, etc.), *Rhizopus* spp. (e.g. *Rhizopus arrhizus*, *R. chinensis*, *R. oryzae*, *R. stolonifer* var. *stolonifer*, etc.), etc.

Protista of the phylum Cercozoa such as *Plasmodiophora* spp. (e.g. *Plasmodiophora brassicae*, etc.), *Spongospora subterranea* f. sp. *subterranea*, etc.

Microorganisms of the phylum Heterokontophyta class Oomycetes such as *Aphanomyces* spp. (e.g. *Aphanomyces cochlioides*, *A. raphani*, etc.), *Albugo* spp. (e.g. *Albugo macrospora*, *A. wasabiae*, etc.), *Bremia* spp. (e.g. *Bremia lactucae*, etc.), *Hyaloperonospora* spp., *Peronosclerospora* spp., *Peronospora* spp. (e.g. *Peronospora alliariae-wasabi*, *P. chrysanthemi-coronarii*, *P. destructor*, *P. farinosa* f. sp. *spinaciae*, *P. manshurica*, *P. parasitica*, *P. soarsa*, etc.), *Plasmopara* spp. (e.g. *Plasmopara halstedii*, *P. nivea*, *P. viticola*, etc.), *Pseudoperonospora* spp. (e.g. *Pseudoperonospora cubensis*, etc.), *Sclerophthora* spp., *Phytophthora* spp. (e.g. *Phytophthora cactorum*, *P. capsici*, *P. citricola*, *P. citrophthora*, *P. cryotoaea*, *P. fragariae*, *P. infestans*, *P. melonis*, *P. nicotianae*, *P. palmivora*, *P. porni*, *P. soiae*, *P. syringae*, *P. vignae* f. sp. *adzukicola*, etc.), *Pythium* spp. (e.g. *Pythium afertile*, *P. aphanidermatum*, *P. apleroticum*, *P. aristosporum*, *P. arrhenomanes*, *P. buismaniae*, *P. debaryanum*, *P. qraminicola*, *P. horinouchiense*, *P. irregulare*, *P. iwayamai*, *P. myriotylum*, *P. okanoganense*, *P. paddicum*, *P. paroecandrum*, *P. periplocum*, *P. spinosum*, *P. sulcatum*, *P. sylvaticum*, *P. ultimum* var. *ultimum*, *P. vanterpoolii*, *P. vexans*, *P. volutum*, etc.), etc.

Gram-positive bacteria of the phylum Actinobacteria such as *Clavibacter* spp. (e.g. *Clavibacter michiganensis* subsp. *michiganensis*, etc.), *Curtobacterium* spp., *Leifsonia* spp. (e.g. *Leifsonia xyli* subsp. *xyli*, etc.), *Streptomyces* spp. (e.g. *Streptomyces ipomoeae*, etc.), etc.

Gram-positive bacteria of the phylum Firmicutes such as *Clostridium* sp., etc.

Gram-positive bacteria of the phylum Tenericutes such as *Phytoplasma*, etc.

Gram-negative bacteria of the phylum Proteobacteria such as *Rhizobium* spp. (e.g. *Rhizobium radiobacter*, etc.), *Acetobacter* spp., *Burkholderia* spp. (e.g. *Burkholderia andropogonis*, *B. cepacia*, *B. gladioli*, *B. glumae*, *B. plantarii*, etc.), *Acidovorax* spp. (e.g. *Acidovorax avenae* subsp. *avenae*, *A. a.* subsp. *citrulli*, *A. konjaci*, etc.), *Herbaspirillum* spp., *Ralstonia* spp. (e.g. *Ralstonia solanacearum*, etc.), *Xanthomonas* spp. (e.g. *Xanthomonas albilineans*, *X. arboricola* gp. Druni, *X. axonopodis* pv. *vitians*, *X. campestris* pv. *campestris*, *X. c.* pv. *cucurbitae*, *X. c. v. glycines*, *X. c. v. mangiferaeindicae*, *X. c.* pv. *nigromaculans*, *X. c.* pv. *vesicatoria*, *X. citri* subsp. *citri*, *X. oryzae* pv. *oryzae*, etc.), *Pseudomonas* spp. (e.g. *Pseudomonas cichorii*, *P. fluorescens*, *P. marginalis*, *P. m.* pv. *marginalis*, *P. savastanoi* pv. *alvcinea*, *P. syringae*, *P. s.* pv. *actinidiae*, *P. s.* pv. *eriobotryae*, *P. s.* pv. *helianthi*, *P. s.* pv. *lachrymans*, *P. s.* pv. *maculicola*, *P. s.* pv. *mori*, *P. s.* pv. *morsprunorum*, *P. s.* pv. *spinaciae*, *P. s.* pv. *syringae*, *P. s.* Pv. *theae*, *P. viridiflava*, etc.), *Rhizobacter* spp., *Brenneria* spp. (e.g. *Brenneria nigrifluens*, etc.), *Dickeya* spp. (e.g. *Dickeya dianthicola*, *D. zeae*, etc.), *Erwinia* spp. (e.g. *Erwinia amylovora*, *E. rhapontici*, etc.), *Pantoea* spp., *Pectobacterium* spp. (e.g. *Pectobacterium atrosepticum*, *P. carotovorum*, *P. wasabiae*, etc.), etc.

As specific examples the plant diseases and animal infectious diseases caused by infection/proliferation of such pathogens, the following plant diseases and animal infectious diseases may, for example, be mentioned, but the present invention is not restricted thereto.

Plant Diseases:

Leaf curl (*Taphrina deformans*), Plum pockets (*Taphrina pruni*), Leaf spot (*Cercospora asparagi*), Cercospora leaf spot (*Cercospora beticola*), Frogeye leaf spot (*Cercospora capsici*), Angular leaf spot (*Cercospora kaki*), Purple stain (*Cercospora kikuchii*), Brown Leaf spot (*Mycosphaerella arachidis*), Cylindrosporium leaf spot (*Mycosphaerella cerasella*, *Blumeriella jaapii*), Speckled leaf blotch (*Mycosphaerella graminicola*), Circular leaf spot (*Mycosphaerella nawae*), Mycosphaerella blight (*Mycosphaerella pinodes*), Leaf spot (*Mycosphaerella zingiberis*), Leaf mold (*Mycovellosiella fulva*), Leaf mold (*Mycovellosiella nattrassii*), Cercospora leaf mold (*Pseudocercospora fuligena*), Isariopsis leaf spot (*Pseudocercospora vitis*), Leaf spot (*Pseudocercosporella capsellae*), Leaf spot (*Septoria chrysanthemella*), Leaf blight (*Septoria obesa*), Anthracnose (*Elsinoe ampelina*), Spot anthracnose (*Elsinoe araliae*), Scab (*Elsinoe fawcettii*), Leaf spot (*Ascochyta pisi*), Corynespora leaf spot (*Corynespora cassiicola*), Stem canker (*Leptosphaeria coniothyrium*), Leaf spot (*Altemaria alternata*), Leaf blight (*Altemaria dauci*), Black spot (*Altemaria kikuchiana*), Altemaria blotch (*Altemaria mali*), Altemaria leaf spot (*Altemaria porri*), Target spot (*Bipolaris sorghicola*), Southern leaf blight (*Cochliobolus heterostrophus*), Brown spot (*Cochliobolus miyabeanus*), Tip blight (*Pleospora herbarum*), Stripe (*Pyrenophora graminea*), Net blotch (*Pyrenophora teres*), Leaf blight (*Setosphaeria turcica*), Northern leaf blight (*Setosphaeria turcica*), Leaf spot (*Stemphylium botryosum*), Scab (*Venturia carpophila*), Scab (*Venturia lnaequalis*), Scab (*Venturia nashicola*), Gummy stem blight (*Didymella bryoniae*), Leaf spot (*Phoma exigua* var. *exigua*), Streak (*Phoma wasabiae*), Ring rot (*Botryosphaeria berengeriana* f. sp. *piricola*), Soft rot (*Botryosphaeria dothidea, Lasiodiplodia theobromae, Diaporthe* sp.), Common green mold (*Penicillium digitatum*), Blue mold (*Penicillium italicum*), Powdery mildew (*Blumeria graminis* f. sp. *hordei*), Powdery mildew (*Blumeria graminis* f. sp. *tritici*), Powdery mildew (*Erysiphe betae, Leveillula taurica, Oidium* sp., *Podosphaera xanthii*), Powdery mildew (*Erysiphe cichoracearum, Leveillula taurica, Sphaerotheca fuliginea*), Powdery mildew (*Erysiphe heraclei*), Powdery mildew (*Erysiphe pisi*), Powdery mildew (*Leveillula taurica, Oidium neolycopersici, Oidium* sp.), Powdery mildew (*Leveillula taurica*), Powdery mildew (*Oidium* sp., *Podosphaera xanthii*), Powdery mildew (*Oidium* sp.), Powdery mildew (*Phyllactinia kakicola*), Powdery mildew (*Podosphaera fusca*), Powdery mildew (*Podosphaera leucotricha*), Powdery mildew (*Podosphaera pannosa, Uncinuliella simulans* var. *simulans, U. s.* var. *tandae*), Powdery mildew (*Podosphaera xanthii*), Powdery mildew (*Sphaerotheca aphanis* var. *aphanis*), Powdery mildew (*Sphaerotheca fuliginea*), Powdery mildew (*Uncinula necator, U. n.* var. *necator*), Blotch (*Diplocarpon mali*), Black spot (*Diplocarpon rosae*), Gray mold neck rot (*Botrytis allii*), Gray mold, *Botrytis* blight (*Botrytis cinerea*), Leaf blight (*Botrytis cinerea, B. byssoidea, B. squamosa*), Chocolate spot (*Botrytis cinerea, B. elliptical, B. fabae*), Brown rot (*Monilinia fructicola, M. fructigena, M. laxa*), Blossom blight (*Monilinia mali*), Dollar spot (*Sclerotinia homoeocarpa*), Cottony rot, *Sclerotinia* rot, Stem rot (*Sclerotinia sclerotiorum*), False smut (*Villosiclava virens*), Root necrosis (*Calonectria ilicicola*), *Fusarium* blight (*Fusarium crookwellense, F. culmorum, Gibberella avenacea, G. zeae, Monographella nivalis*), *Fusarium* blight (*Fusarium culmorum, Gibberella avenacea, G. zeae*), Dry rot (*Fusarium oxysporum, F. solani* f. sp. *radicicola*), Brown rot (*Fusarium oxysporum, F. solani* f. sp. *pisi, F. s.* f. sp. *radicicola*), *Fusarium* wilt (*Fusarium oxysporum* f. sp. *adzukicola*), *Fusarium* basal rot (*Fusarium oxysporum* f. sp. *allii, F. solani* f. sp. *radicicola*), Stem rot (*Fusarium oxysporum* f. sp. *batatas, F. solani*), Dry rot (*Fusarium oxysporum* f. sp. *colocasiae*), Yellows (*Fusarium oxysporum* f. sp. *conglutinans*), Panama disease (*Fusarium oxysporum* f. sp. *cubense*), *Fusarium* wilt (*Fusarium oxysporum* f. sp. *fragariae*), Root rot (*Fusarium oxysporum* f. sp. *lactucae*), *Fusarium* wilt (*Fusarium oxysporum* f. sp. *lagenariae, F. o.* f. sp. *niveum*), *Fusarium* wilt (*Fusarium oxysporum* f. sp. *lycopersici*), *Fusarium* wilt (*Fusarium oxysporum* f. sp. *melonis*), Yellows (*Fusarium oxysporum* f. sp. *raphani*), *Fusarium* wilt (*Fusarium oxysporum* f. sp. *spinaciae*), "Bakanae" disease (*Gibberella fujikuroi*), *Verticillium* black spot (*Verticillium albo-atrum, V. dahliae*), *Verticillium* wilt (*Verticillium dahliae*), *Ceratocystis* canker (*Ceratocystis ficicola*), Black rot (*Ceratocystis fimbriata*), Gray blight (*Pestalotiopsis longiseta, P. theae*), Endothia canker (*Cryphonectria parasitica*), Melanose (*Diaporthe citri*), Stem blight (*Phomopsis asparagi*), *Phomopsis* canker (*Phomopsis fukushii*), Brown spot (*Phomopsis vexans*), Anthracnose (*Discula theae-sinensis*), Valsa canker (*Valsa ceratosperma*), Blast (*Magnaporthe grisea*), Crown rot (*Colletotrichum acutatum, C. fragariae, Glomerella cingulata*), Bitter rot (*Colletotrichum acutatum, Glomerella cingulata*), Anthracnose (*Colletotrichum acutatum, Glomerella cingulata*), Anthracnose (*Colletotrichum acutatum*), Ripe rot (*Colletotrichum acutatum, Glomerella cingulata*), Anthracnose (*Colletotrichum acutatum*), Anthracnose (*Colletotrichum lindemuthianum*), Anthracnose (*Colletotrichum orbiculare*), Anthracnose on *Dioscorea japonica* (*Glomerella cingulata*), Anthracnose on *Castanea crenata* (*Glomerella cingulata*), Anthracnose on *Diospyros kaki* (*Glomerella cingulata*), Brown stem rot (*Phialophora gregata*), Leaf spot (*Pseudophloeosporella dioscoreae*), Scald (*Rhynchosporium secalis*), Rust (*Phakopsora nishidana*), Rust (*Phakopsora pachyrhizi*), Rust (*Kuehneola japonica, Phragmidium fusiforme, P. mucronatum, P. rosae-multiflorae*), Rust (*Gymnosporangium asiaticum*), Rust (*Gymnosporangium yamadae*), Rust (*Puccinia allii*), Rust (*Puccinia horiana*), Brown rust (*Puccinia recondita*), Rust (*Puccinia tanaceti* var. *tanaceti*), Rust (*Uromyces viciae-fabae* var. *viciae-fabae*), Smut (*Sporisorium scitamineum*), Smut (*Ustilago maydis*), Loose smut (*Ustilago nuda*), Net blister blight (*Exobasidium reticulatum*), Blister blight (*Exobasidium vexans*), Stem rot, Southern blight (*Athelia rolfsii*), Root and stem rot (*Ceratobasidium cornigerum, Rhizoctonia solani*), Damping-off on *Zingiber officinale* (*Rhizoctonia solani*), Damping-off on *Brassica oleracea capitata* (*Rhizoctonia solani*), Damping-off on *Cryptotaenia japonica* (*Rhizoctonia solani*), Bottom rot (*Rhizoctonia solani*), Brown patch, Large patch (*Rhizoctonia solani*), Sheath blight (*Thanatephorus cucumeris*), Root rot/Leaf blight (*Thanatephorus cucumeris*), *Rhizopus* rot (*Rhizopus stolonifer* var. *stolonifer*), Clubroot (*Plasmodiophora brassicae*), *Aphanomyces* root rot (*Aphanomyces cochlioides*), White rust (*Albuo macrospora*), Downy mildew (*Bremia lactucae*), Downy mildew (*Peronospora chrysanthemi-coronarii*), Downy mildew (*Peronospora destructor*), Downy mildew (*Peronospora farinosa* f. sp. *spinaciae*), Downy mildew (*Peronospora manshurica*), Downy mildew (*Peronospora parasitica*), Downy mildew (*Peronospora sparsa*), Downy mildew (*Plasmopara halstedii*), Downy mildew (*Plasmopara nivea*), Downy mildew (*Plasmopara viticola*), Downy mildew (*Pseudoperonospora cubensis*), *Phytophthora* root rot (*Phytophthora cactorum*), Brown rot (*Phytophthora capsici*), *Phytophthora* rot (*Phytophthora capsici*), *Phytophthora* blight (*Phytophthora capsici*), *Phytophthora* rot (*Phytophthora cryotogea*), Late blight (*Phytophthora infestans*), White powdery rot (*Phytophthora palmivora*), Leaf blight (*Phytophthora porri*), *Phytophthora* root and stem rot (*Phytophthora sojae*), *Phytophthora* stem rot (*Phytophthora vignae* f. sp. *adzukicola*), Damping-off (*Pythium aphanidermatum, P. myriotylum, P. paroecandrum, P. ultimum* var. *ultimum*), Root rot (*Pythium aristosporum*), Browning root rot (*Pythium arrhenomanes, P. graminicola*), Damping-off (*Pythium buismaniae, P. myriotylum*), Root rot (*Pythium myriotylum*), Root rot (*Pythium myriotylum, P. ultimum* var. *ultimum*), Brown blotted root rot (*Pythium sulcatum*), Bacterial canker (*Clavibacter michiganensis* subsp. *michiganensis*), Scab (*Streptomyces* spp.), Crown gall (*Rhizobium radiobacter*), Bacterial stripe (*Burkholderia andropogonis*), Soft rot (*Burkholderia cepacia, Pseudomonas marginalis* pv. *marginalis, Erwinia rhapontici*), Bacterial grain rot (*Burkholderia gladioli, B. glumae*), Bacterial fruit blotch (*Acidovorax avenae* subsp. *citrulli*), Bacterial leaf blight (*Acidovorax konjaci*), Bacterial wilt (*Ralstonia solanacearum*), Bacterial shot hole (*Xanthomonas arboricola* pv. *pruni, Pseudomonas syringae* gv. *syringae, Brenneria nigarifluens*), Bacterial leaf spot (*Xanthomonas arboricola* pv. *pruni*), Bacterial spot (*Xanthomonas axonopodis* pv. *vitians*), Black rot (*Xanthomonas campestris* pv. *campestris*), Bacterial pustule (*Xanthomonas campestris* pv. *glycines*), Bacterial spot (*Xanthomonas campestris* pv. *nigromaculans*), Bacterial spot (*Xanthomonas campestris* pv. *vesicatoria*), Citrus canker (*Xanthomonas citri* subsp. *citri*), (*Pseudomonas cichorii*, *P. marginalis* pv. *marginalis, Erwinia* sp.), Bacterial rot (*Pseudomonas cichorii, P. marginalis* pv. *marginalis, P. viridiflava*), Bacterial blossom blight (*Pseudomonas marginalis* pv. *marginalis, P. syringae* pv. *syringae, P. viridiflava*), Bacterial canker (*Pseudomonas syringae* v. *actinidiae*), Canker (*Pseudomonas syringae* pv. *eriobotryae*), Bacterial spot (*Pseudomonas syringae* pv. *lachrymans*), Bacterial black spot (*Pseudomonas syringae* pv. *maculicola*), Bacterial canker (*Pseudomonas syringae* pv. *morsprunorum, Erwinia* sp.), Bacterial shoot blight (*Pseudomonas syringae* pv. *theae*), Bacterial soft rot (*Dickeya* sp., *Pectobacterium carotovorum*), Fire blight (*Erwinia amylovora*), Soft rot (*Pectobacterium carotovorum*), Bacterial soft rot (*Pectobacterium carotovorum*).

Animal Infectious Diseases:

*Pneumocystis* pneumonia (*Pneumocystis jirovecii*), Candidiasis (*Candida albicans*), Aspergillosis (*Asperaillus fumigatus*), Trichophytosis (*Microsporum canis, M. gypseum, Trichophyton mentagrophytes, T. rubrum, T. tonsurans, T. verrucosum*), Histoplasmosis (*Histoplasma capsulatum*), Cryptococcosis (*Cryptococcus neoformans*).

In this specification, "parasites" means Nematoda which includes plant-parasitic nematodes and animal-parasitic nematodes, Acanthocephala, Platyhelminthes, Protozoa and the like, and specifically, the following parasites may, for example, be mentioned, but the parasites are not limited thereto.

Nematodes of the order Enoplida such as Giant kidney worm (*Dioctophyma renale*), Thread worms (*Capillaria annulata*), Cropworm (*Capillaria contorta*), Capillary liver worm (*Capillaria hepatica*), *Capillaria perforans, Capillaria philippinensis, Capillaria suis*, Whipworm (*Trichuris discolor*), Whipworm (*Trichuris ovis*), Pig whipworm (*Trichuris suis*), Human whipworm (*Trichuris trichiura*), Dog whipworm (*Trichuris vulpis*), Pork worm (*Trichinella spiralis*), etc.

Nematodes of the order Rhabditida such as Intestinal threadworm (*Strongyloides papillosus*), *Strongyloides planiceps*, Pig threadworm (*Strongyloides ransomi*), Threadworm (*Strongyloides stercoralis*), *Micronema* spp., etc.

Nematodes of the order Strongylida such as Hookworm (*Ancylostoma braziliense*), Dog hookworm (*Ancylostoma caninum*), Old World hookworm (*Ancylostoma duodenale*), Cat hookworm (*Ancylostoma tubaeforme*), The Northern hookworm of dogs (*Uncinaria stenocephala*), Cattle hookworm (*Bunostomum phlebotomum*), Small ruminant hookworm (*Bunostomum trigonocephalum*), New World hookworm (*Necator americanus*), *Cyathostomum* spp., *Cylicocyclus* spp., *Cylicodontophorus* spp., *Cylicostephanus* spp., *Strongylus asini, Strongylus edentatus*, Blood worm (*Strongylus equinus*), Blood worm (*Strongylus vulgaris*), Large-mouthed bowel worm (*Chabertia ovina*), Nodular worm (*Oesophagostomum brevicaudatum*), Nodule worm (*Oesophagostomum columbianum*), Nodule worm (*Oesophagostomum dentatum*), Nodular worm (*Oesophagostomum georgianum*), Nodular worm (*Oesophagostomum maplestonei*), Nodular worm (*Oesophagostomum quadrispinulatum*), Nodular worm (*Oesophagostomum radiatum*), Nodular worm (*Oesophaostomum venulosum*), *Synagmus skrjabinomorpha*, Gapeworm (*Syngamus trachea*), Swine kidney worm (*Stephanurus dentatus*), Cattle bankrupt worm (*Cooperia oncophora*), Red stomach worm (*Hyostrongylus rubidus*), Stomach hair worm (*Trichostrongylus axei*), *Trichostrongylus colubriformis*, Oriental trichostrongylus (*Trichostronylus orientalis*), Red stomach worm (*Haemonchus contortus*), Cattle stomach worm (*Mecistocirrus digitatus*), Brown stomach worm (*Ostertagia ostertagi*), Common lungworm (*Dictyocaulus filaria*), Bovine lungworm (*Dictyocaulus viviparus*), Thin-necked intestinal worm (*Nematodirus filicollis*), Swine lungworm (*Metastronagylus elongatus*), Lungworm (*Filaroides hirthi*), Lungworm (*Crenosoma aerophila*), Fox lungworm (*Crenosoma vulpis*), Rat lung worm (*Angiostrongylus cantonensis*), French heartworm (*Angiostronagylus vasorum*), *Protostrongylus* spp., etc.

Nematodes of the order Aphelenchida such as Rice white tip nematode (*Aphelenchoides besseyi*), Strawberry foliar nematode (*Aphelenchoides fragariae*), Chrysanthemum foliar nematode (*Aphelenchoides ritzemabosi*), Pine wood nematode (*Bursaphelenchus xylophilus*), etc.

Nematodes of the order Tylenchida such as White potato cyst nematode (*Globodera pallida*), Potato cyst nematode (*Globodera rostochiensis*), Cereal cyst nematode (*Heterodera avenae*), Soybean cyst nematode (*Heterodera glycines*), Sugarbeet cyst nematode (*Heterodera schachtii*), Clover cyst nematode (*Heterodera trifolii*), Peanut root-knot nematode (*Meloidogyne arenaria*), Northern root-knot nematode (*Meloidogyne hapla*), Southern root-knot nematode (*Meloidogyne incognita*), Javanese root-knot nematode (*Meloidogyne javanica*), Apple root-knot nematode (*Meloidogyne mali*), Coffee root-lesion nematode (*Pratylenchus coffeae*), *Pratylenchus* crenatus Loof (*Pratylenchus drenatus*), Tea root-lesion nematode (*Pratylenchus loosi*), California root-lesion nematode (*Pratylenchus neglectus*), Cobb's root-lesion nematode (*Pratylenchus penetrans*), Walnut root-lesion nematode (*Pratylenchus vulnus*), Citrus burrowing nematode (*Radopholus citrophilus*), Banana burrowing nematode (*Radopholus similis*), etc.

Nematodes of the order Oxyurida such as Pinworm (*Enterobius vermicularis*), Equine pinworm (*Oxyuris equi*), Rabbit pinworm (*Passalurus ambiguus*), etc.

Nematodes of the order Ascaridida such as Pig roundworm (*Ascaris suum*), Horse roundworm (*Parascaris equorum*), Dog roundworm (*Toxascaris leonina*), Dog intestinal roundworm (*Toxocara canis*), Feline roundworm (*Toxocara cati*), Large cattle roundworm (*Toxocara vitulorum*), *Anisakis* spp., *Pseudoterranova* spp., Caecal worm (*Heterakis gallinarum*), Chicken roundworm (*Ascaridia galli*), etc.

Nematodes of the order Spirurida such as Guinea worm (*Dracunculus medinensis*), *Gnathostoma doloresi, Gnathostoma hispidum, Gnathostoma nipponicum*, Reddish-coloured worm (*Gnathostoma spinigerum*), Dog stomach worm (*Physaloptera canis*), Cat stomach worm (*Physaloptera felidis, P. praeputialis*), Feline/canine stomach worm (*Physaloptera rara*), Eye worm (*Thelazia callipaeda*), Bovine eyeworm (*Thelazia rhodesi*), Large mouth stomach worm (*Draschia megastoma*), Equine stomach worm (*Habronema microstoma*), Stomach worm (*Habronema muscae*), Gullet worm (*Gonaylonema pulchrum*), Thick stomach worm (*Ascarops strongylina*), Parafilaria (*Parafilaria bovicola*), *Parafilaria multipapillosa, Stephanofilaria okinawaensis*, Bancroft filaria (*Wuchereria bancrofti*), *Brugia malayi*, Neck threadworm (*Onchocerca cervicalis*), *Onchocerca gibsoni*, Cattle filarial worm (*Onchocerca gutturosa*), *Onchocerca volvulus*, Bovine filarial worm (*Setaria digitata*), Peritoneal worm (*Setaria equina*), *Setaria labiatopapillosa, Setaria marshalli*, Dog heartworm (*Dirofilaria immitis*), African eye worm (*Loa loa*), etc.

Microorganisms of the phylum Acanthocephala such as *Moniliformis moniliformis*, Giant thorny-headed worm (*Macracanthorhynchus hirudinaceus*), etc.

Cestodes of the order Pseudophyllidea such as Fish tapeworm (*Diphyllobothrium latum*), *Diphyllobothrium nihonkaiense*, Manson tapeworm (*Spirometra erinaceieuropaei*), *Diploaonoporus grandis*, etc.

Cestodes of the order Cyclophyllidea such as *Mesocestoides lineatus* (*Mesocestoides lineatus*), Chicken tapeworm (*Raillietina cesticillus*), Fowl tapeworm (*Raillietina echinobothrida*), Chicken tapeworm (*Raillietina tetragona*), Canine tapeworm (*Taenia hydatigena*), Canine tapeworm (*Taenia multiceps*), Sheep measles (*Taenia ovis*), Dog tapeworm (*Taenia pisiformis*), Beef tapeworm (*Taenia saginata*), Tapeworm (*Taenia serialis*), Pork tapeworm (*Taenia solium*), Feline tapeworm (*Taenia taeniaeformis*), Hydatid tapeworm (*Echinococcus granulosus*), Small fox tapeworm (*Echincooccus multilocularis*), *Echinococcus oligarthrus*, *Echinococcus vogeli*, Rat tapeworm (*Hymenolepis diminuta*), Dwarf tapeworm (*Hymenolepis nana*), Double-pored dog tapeworm (*Dipylidium caninum*), *Amoebotaenia sphenoides*, *Choanotaenia infundibulum*, *Metroliasthes cotumix*, Equine tapeworm (*Anoplocephala magna*), Cecal tapeworm (*Anoplocephala perfoliata*), Dwarf equine tapeworm (*Paranoplocephala mamillana*), Common tapeworm (*Moniezia benedeni*), Sheep tapeworm (*Moniezia expansa*), *Stilesia* spp., etc.

Trematodes of the order Strigeidida such as *Pharyngostomum cordatum*, Blood fluke (*Schistosoma haematobium*), Blood fluke (*Schistosoma japonicum*), Blood fluke (*Schistosoma mansoni*), etc.

Trematodes of the order Echinostomida such as *Echinostoma cinetorchis*, *Echinostoma hortense*, Giant liver fluke (*Fasciola gigantica*), Common liver fluke (*Fasciola hepatica*), *Fasciolopsis buski*, *Homalogaster paloniae*, etc.

Trematodes of the order Plagiorchiida such as *Dicrocoelium chinensis*, Lancet liver fluke (*Dicrocoelium dendriticum*), African lancet fluke (*Dicrocoelium hospes*), *Eurytrema coelomaticum*, Pancreatic fluke (*Eurytrema pancreaticum*), *Paragonimus miyazakii*, *Paragonimus ohirai*, Lung fluke (*Paragonimus westermani*), etc.

Trematodes of the order Opisthorchiida such as *Amphimerus* spp., Chinese liver fluke (*Clonorchis sinensis*), Cat liver fluke (*Opisthorchis felineus*), Southeast Aasian liver fluke (*Opisthorchis viverrini*), *Pseudamphistomum* spp., *Metorchis* spp., *Parametorchis* spp., Intestinal fluke (*Heterophyes heterophyes*), *Metagonimus yokokawai*, *Pvaidiopsis summa*, etc.

Amebas such as *Entamoeba histolytica*, *E. invadens*, etc.

Piroplasmida sporozoans such as *Babesia bigemina*, *Babesia bovis*, *Babesia caballi*, *Babesia canis*, *Babesia felis*, *Babesia aibsoni*, *Babesia ovata*, *Cytauxzoon felis*, *Theileria annulata*, *Theileria mutans*, *Theileria orientalis*, *Theileria garva*, etc.

Haemosporida sporozoans such as *Haemoproteus mansoni*, *Leucocytozoon caullervi*, *Plasmodium falciparum*, *Plasmodium malariae*, *Plasmodium ovale*, *Plasmodium vivax*, etc.

Eucoccidiorida sporozoans such as *Caryospora* spp., *Eimeria acervulina*, *Eimeria bovis*, *Eimeria brunetti*, *Eimeria maxima*, *Eimeria necatrix*, *Eimeria ovinoidalis*, *Eimeria stiedae*, *Eimeria tenella*, *Isospora canis*, *Isospora felis*, *Isospora suis*, *Tyzzeria alleni*, *Tyzzeria anseris*, *Tyzzeria pemiciosa*, *Wenyonella anatis*, *Wenyonella gagari*, *Cryptosporidium canis*, *Cryptosporidium felis*, *Cryptosporidium hominis*, *Cryptosporidium meleagridis*, *Cryptosporidium muris*, *Cryptosporidium Darvum*, *Sarcocystis canis*, *Sarcocystis cruzi*, *Sarcocystis felis*, *Sarcocystis hominis*, *Sarcocystis miescheriana*, *Sarcocystis neurona*, *Sarcocystis tenella*, *Sarcocystis ovalis*, *Toxoplasma ondii*, *Hepatozoon canis*, *Hepatozoon felis*, etc.

Vestibuliferida ciliata such as *Balantidium coli*, etc.

Trichomonadida flagellata such as *Histomanas meleagridis*, *Pentatrichomonas hominis*, *Trichomonas tenax*, etc.

Diplomonadida flagellata such as *Giardia intestinalis*, *Giardia muris*, *Hexamita meleagridis*, *Hexamita parva*, etc.

Kinetoplastida flagellata such as *Leishmania donovani*, *Leishmania infantum*, *Leishmania major*, *Leishmania tropica*, *Trypanosoma brucei gambiense*, *Trypanosoma brucei rhodesiense*, *Tryanosoma cruzi*, *Trypanosoma eauiperdum*, *Trypanosoma evansi*, etc.

In this specification "plants" means grain, fruits and vegetables cultivated as food for human, feed crop for livestock and poultry, ornamental plants of which appearances are enjoyed, or Tracheophyta such as planting of parks, streets and the like, and specifically, the following plants may, for example, be mentioned, but the plants are not limited thereto.

Plants of the order Pinales belonging to the family Pinaceae such as Japanese Red Pine (*Pinus densiflora*), Scots Pine (*Pinus sylvestris*), Japanese Black Pine (*Pinus thunbergii*), etc.

Plants of the group magnoliids belonging to the family Piperaceae such as pepper (*Piper nigrum*), etc., the family Lauraceae such as Avocado (*Persea americana*), etc.

Plants of the group monocots belonging to the family Araceae such as Konjac (*Amorphophallus konjac*), Eddoe (*Colocasia esculenta*), etc., the family Dioscoreaceae such as Chinese yam (*Dioscorea batatas*), Japanese yam (*Dioscorea japonica*), etc., the family Alliaceae such as Leek (*Allium ampeloprasum* var. *porrum*), Onion (*Allium cepa*), Rakkyo (*Allium chinense*), Welsh onion (*Allium fistulosum*), Garlic (*Allium sativum*), Chives (*Allium schoenoprasum*), Chive (*Allium schoenoprasum* var. *foliosum*), Oriental garlic (*Allium tuberosum*), Scallion (*Allium×wakegi*), etc., the family Asparagaceae such as Asparagus (*Asparagus officinalis*), etc., the family Arecaceae subfamily Arecoideae such as Coconut palm (*Cocos nucifera*), Oil palm (*Elaeis guineensis*), etc., the family Arecaceae the subfamily Coryphoideae such as Date palm (*Phoenix dactylifera*), etc., the family Bromeliaceae such as Pineapple (*Ananas comosus*), etc., the family Poaceae subfamily Ehrhartoideae such as Rice (*Oryz sativa*), etc., the family Poaceae subfamily Pooideae such as Bent grass (*Aarostis* spp.), Blue grass (Poa spp.), Barley (*Hordeum vulgare*), Wheat (*Triticum aestivum*, *T. durum*), Rye (*Secale cereale*), etc., the family Poaceae subfamily Chloridoideae such as Bermuda grass (*Cynodon dactylon*), Grass (*Zoysia* spp.), etc., the family Poaceae subfamily Panicoideae such as Sugarcane (*Saccharum officinarum*), Sorgum (*Sorghum bicolor*), Corn (*Zea mays*), etc., the family Musaceae such as Banana (*Musa* spp.), etc., the family Zingiberaceae such as Myoga (*Zingiber mioga*), Ginger (*Zingiber officinale*), etc.

Plants of the group eudicots belonging to the family Nelumbonaceae such as Lotus root (*Nelumbo nucifera*), etc., the family Fabaceae such as Peanut (*Arachis hypogaea*), Chickpea (*Cicer arietinum*), Lentil (*Lens culinaris*), Pea (*Pisum sativum*), Broad bean (*Vicia faba*), Soybean (*Glycine max*), Common bean (*Phaseolus vulgaris*), Adzuki bean (*Vigna anaularis*), Cowpea (*Vigna unguiculata*), etc., the family Cannabaceae such as Hop (*Humulus lupulus*), etc., the family Moraceae such as Fig Tree (*Ficus carica*), Mulberry (*Morus* spp.), etc., the family Rhamnaceae such as Common jujube (*Ziziphus jujuba*), etc., the family Rosaceae subfamily Rosoideae such as Strawberry (*Fragaria*), Rose (*Rosa* spp.), etc., the family Rosaceae subfamily Maloideae such as Japanese loquat (*Eriobotrya japonica*), Apple (*Malus pumila*), European Pear (*Pyrus communis*), Nashi Pear (*Pyrus pyrifolia* var. *culta*), etc., the family Rosaceae subfamily Prunoideae such as Peach (*Amyydalus persica*), Apricot (*Prunus armeniaca*), Cherry (*Prunus avium*), Prune (*Prunus domestica*), Almond (*Prunus dulcis*), Japanese Apricot (*Prunus mume*), Japanese Plum (*Prunus salicina*), *Cerasus speciosa, Cerasus×yedoensis* 'Somei-yoshino', etc., the family Cucurbitaceae such as Winter melon (*Benincasa hispida*), Watermelon (*Citrullus lanatus*), Bottle gourd (*Lagenaria siceraria* var. *hispida*), Luffa (*Luffa cylindrica*), Pumpkin (*Cucurbita* spp.), Zucchini (*Cucurbita pepo*), Bitter melon (*Momordica charantia* var. *pavel*), Muskmelon (*Cucumis melo*), Oriental pickling melon (*Cucumis melo* var. *conomon*), Oriental melon (*Cucumis melo* var. *makuwa*), Cucumber (*Cucumis sativus*), etc., the family Fagaceae such as Japanese Chestnut (*Castanea crenata*), etc., the family Juglandaceae such as Walnut (*Juglans* spp.), etc., the family Anacardiaceae such as Cashew (*Anacardium occidentale*), Mango (*Mangifera indica*), Pistachio (*Pistacia vera*), etc., the family Rutaceae subfamily Rutoideae such as Japanese pepper (*Zanthoxylum piperitum*), etc., the family Rutaceae subfamily Aurantioideae such as Bitter orange (*Citrus aurantium*), Lime (*Citrus aurantifolia*), Hassaku orange (*Citrus hassaku*), Yuzu (*Citrus junos*), Lemon (*Citrus limon*), Natsumikan (*Citrus natsudaidai*), Grapefruit (*Citrus×paradisi*), Orange (*Citrus sinensis*), Kabosu (*Citrus sphaerocarpa*), Sudachi (*Citrus sudachi*), Mandarin Orange (*Citrus tangerina*), Satsuma (*Citrus unshiu*), Kumquat (*Fortunella* spp.), etc., the family Brassicaceae such as Horseradish (*Armoracia rusticana*), Mustard (*Brassica luncea*), Takana (*Brassica juncea* var. *integrifolia*), Rapeseed (*Brassica napus*), Cauliflower (*Brassica oleracea* var. *botrytis*), Cabbage (*Brassica oleracea* var. *capitata*), Brussels sprout (*Brassica oleracea* var. *gemmifera*), Broccoli (*Brassica oleracea* var. *italica*), Green pak choi (*Brassica rapa* var. *chinensis*), Nozawana (*Brassica rapa* var. *hakabura*), Napa cabbage (*Brassica rapa* var. *nippo-oleifera*), Potherb Mustard (*Brassica rapa* var. *nipposinica*), Napa cabbage (*Brassica rapa* var. *pekinensis*), Turnip leaf (*Brassica rapa* var. *perviridis*), Tumip (*Brassica rapa* var. *rapa*), Garden rocket (*Eruca vesicaria*), Daikon (*Raphanus sativus* var. *longipinnatus*), Wasabi (*Wasabia japonica*), etc., the family Caricaceae such as Papaya (*Carca papaya*), etc., the family Malvaceae such as Okra (*Abelmoschus esculentus*), Cotton plant (*Gossypium* spp.), Cacao (*Theobroma cacao*), etc., the family Vitaceae such as Grape (*Vitis* spp.), etc., the family Amaranthaceae such as Sugar beet (*Beta vulgaris* ssp. *vulgaris* var. *altissima*), Table beet (*Beta vulgaris* ssp. *vulgaris* var. *vulgaris*), Spinach (*Spinacia oleracea*), etc., the family Polygonaceae such as Buckweat (*Fagopyrum esculentum*), etc., the family Ebenaceae such as Kaki Persimmon (*Diospyros kaki*), etc., the family Theaceae scuh as Tea plant (*Camellia sinensis*), etc., the family Actinidiaceae such as Kiwifruit (*Actinidia deliciosa, A. chinensis*), etc., the family Ericaceae such as Blueberry (*Vaccinium* spp.), Cranberry (*Vaccinium* spp.), etc., the family Rubiaceae such as Coffee plants (*Coffea* spp.), etc., the family Lamiaceae such as Lemon balm (*Melissa officinalis*), Mint (*Mentha* spp.), Basil (*Ocimum basilicum*), Shiso (*Perilla frutescens* var. *crispa*), *Perilla frutescens* var. *frutescens*, Common Sage (*Salvia officinalis*), Thyme (*Thymus* spp.), etc., the family Pedaliaceae such as Sesame (*Sesamum indicum*), etc., the family Oleaceae such as Olive (*Olea europaea*), etc. the family Convolvulaceae such as Sweet potato (*Ipomoea batatas*), etc., the family Solanaceae such as Tomato (*Solanum lycopersicum*), Eggplant (*Solanum melongena*), Potato (*Solanum tuberosum*), Chili pepper (*Capsicum annuum*), Bell pepper (*Capsicum annuum* var. '*grossum*'), Tobacco (*Nicotiana tabacum*), etc., the family Apiaceae such as Celery (*Apium graveolens* var. *dulce*), Coriander (*Coriandrum sativum*), Japanese honeywort (*Cryptotaenia Canadensis* subsp. *japonica*), Carrot (*Daucus carota* subsp. *sativus*), Parsley (*Petroselium crispum*), Italian parsley (*Petroselinum neapolitanum*), etc., the family Araliaceae such as Udo (*Aralia cordata*), *Aralia elata*, etc., the family Asteraceae subfamily Carduoideae such as Artichoke (*Cynara scolymus*), etc., the family Asteraceae subfamily Asteraceae such as Chicory (*Cichorium intybus*), Lettuce (*Lactuca sativa*), etc., the family Asteraceae subfamily Asteraceae such as Florists' daisy (*Dendranthema grandiflorum*), Crown daisy (*Glebionis coronaria*), Sunflower (*Helianthus annuus*), Fuki (*Petasites japonicus*), Burdock (*Arctium lappa*), etc.

In this specification "animals" means human, companion creatures/pets, livestock/poultry, and vertebrate such as experimental/laboratory animals, and specifically, the following animals may, for example, be mentioned, but the animals are not limited thereto.

Animals of the class Mammalia belonging to the family Cebidae such as Tufted capuchin (*Cebus apella*), etc., the family Cercopithecidae such as Crab-eating macaque (*Macaca fascicularis*), Rhesus macaque (*Macaca mulatta*), etc., the family Hominidae such as Chimpanzee (*Pan troglodytes*), Human (*Homo sapiens*), etc., the family Leporidae such as European rabbit (*Oryctolagus cuniculus*), etc., the family Chinchillidae such as Long-tailed chinchilla (*Chinchilla lanigera*), etc., the family Caviidae such as Guinea pig (*Cavia porcellus*), etc., the family Cricetidae such as Golden hamster (*Mesocricetus auratus*), Djungarian hamster (*Phodopus sungorus*), Chinese hamster (*Cricetulus griseus*), etc., the family Muridae such as Mongolian gerbil (*Meriones unguiculatus*), House mouse (*Mus musculus*), Black rat (*Rattus rattus*), etc., the family Sciuridae such as Chipmunk (*Tamias sibiricus*), etc., the family Camelidae such as Dromedary (*Camelus dromedarius*), Bactrian camel (*Camelus bactrianus*), Alpaca (*Vicugna pacos*), Llama (*Lama glama*), etc., the family Suidae such as Pig (*Susscrofa domesticus*), etc., the family Cervidae such as Reindeer (*Rangifer tarandus*), Red deer (*Cervus elaphus*), etc., the family Bovidae such as Yak (*Bos grunniens*), Cattle (*Bos taurus*), Water buffalo (*Bubalus amee*), Goat (*Capra hircus*), Sheep (*Ovis aries*), etc., the family Felidae such as Cat (*Felis silvestris catus*), etc., the family Canidae such as Dog (*Canis lupus familiaris*), Red fox (*Vulpes vulpes*), etc., the family Mustelidae such as European mink (*Mustela lutreola*), American mink (*Mustela vison*), Ferret (*Mustela putorius furo*), etc., the family Equidae such as Donkey (*Equus asinus*), Horse (*Equus caballus*), etc., the family Macropodidae such as Red kangaroo (*Macropus rufus*), etc.

Animals of the class Aves belonging to the family Struthionidae such as Ostrich (*Struthio camelus*), etc., the family Rheidae such as American rhea (*Rhea americana*), etc., the family Dromaiidae such as Emu (*Dromaius novaehollandiae*), etc., the family Phasianidae such as Ptarmigan (*Lagopus muta*), Wild turkey (*Meleagris gallopavo*), Japanese quail (*Coturnix japonica*), Chicken (*Gallus gallus domesticus*), Common pheasant (*Phasianus colchicus*), Golden pheasant (*Chrysolophus pictus*), Indian peafowl (*Pavo cristatus*), etc., the family Numididae such as Helmeted guinea-fowl (*Numida meleagris*), etc., the family Anatidae such as Mallard (*Anas platyrhynchos*), Domesticated duck (*Anas platyrhynchos* var. *domesticus*), Spot-billed duck (*Anas poecilorhyncha*), Greylag goose (*Anser anser*), Swan goose (*Anser cyanoides*), Whooper swan (*Cygnus cygnus*), Mute swan (*Cygnus olor*), etc., the family Columbidae such as Rock dove (*Columba livia*), Oriental turtle dove (*Streptopelia orientalis*), European turtle dove (*Streptopelia turtur*), etc., the family Cacatuidae such as Sulphur-crested cockatoo (*Cacatua galerita*), Galah (*Eolophus roseicapilla*), Cockatiel (*Nymphicus hollandicus*), etc., the family Psittacidae such as Rosy-faced lovebird (*Agapornis roseicollis*), Blue-and-yellow macaw (*Ara ararauna*), Scarlet Macaw (*Ara macao*), Budgerigar (*Melopsittacus undulatus*), African grey parrot (*Psittacus erithacus*), etc., the family Sturnidae such as Common hill myna (*Gracula religiosa*), etc., the family Estrildidae such as Red avadavat (*Amandava amandava*), Zebra finch (*Taeniopygia guttata*), Bengalese finch (*Lonchura striata* var. *domestica*), Java sparrow (*Padda oryzivora*), etc., the family Fringillidae such as Domestic canary (*Serinus canaria domestica*), European goldfinch (*Carduelis carduelis*), etc.

Animals of the class Reptilia belonging to the family Chamaeleonidae such as Veiled chameleon (*Chamaeleo calyptratus*), etc., the family Iguanidae such as Green iguana (*Iguana iguana*), Carolina anole (*Anolis carolinensis*), etc., the family Varanidae such as Nile monitor (*Varanus niloticus*), Water monitor (*Varanus salvator*), etc., the family Scincidae such as Solomon islands skink (*Corucia zebrata*), etc., the family Colubridae such as Beauty rat snake (*Elaphe taeniura*), etc., the family Boidae such as Boa constrictor (*Boa constrictor*), etc., the family Pythonidae such as Indian python (*Python molurus*), Reticulated python (*Python reticulatus*), etc., the family Chelydridae such as Common snapping turtle (*Chelydra serpentina*), etc., the family Emydidae such as Diamondback terrapin (*Malaclemys terrapin*), Pond slider (*Trachemys scripta*), etc., the family Geoemydidae such as Japanese pond turtle (*Mauremys japonica*), etc., the family Testudinidae such as Central Asian tortoise (*Agrionemys horsfieldii*), etc., the family Trionychidae such as Soft-shelled turtle (*Pelodiscus sinensis*), etc., the family Alligatoridae such as American alligator (*Alligator mississippiensis*), Black caiman (*Melanosuchus niger*), etc., the family Crocodylidae such as Siamese crocodile (*Crocodylus siamensis*), etc.

Animals of the class Actinopterygii belonging to the family Cyprinidae such as Carp (*Cyprinus carpio*), Goldfish (*Carassius auratus auratus*), Zebrafish (*Danio rerio*), etc., the family Cobitidae such as Kuhli loach (*Pangio kuhlii*), etc., the family Characidae such as Red piranha (*Pygocentrus nattereri*), Neon tetra (*Paracheirodon innesi*), etc., the family Salmonidae such as Maraena whitefish (*Coregonus lavaretus maraena*), Coho salmon (*Oncorhynchus kisutsh*), Rainbow trout (*Oncorhynchus mykiss*), Chinook salmon (*Oncorhynchus tshawytscha*), Atlantic salmon (*Salmo salar*), Brown trout (*Salmo trutta*), etc., the family Percichthyidae such as Spotted sea bass (*Lateolabrax maculatus*), etc., the family Serranidae such as Sea goldie (*Pseudanthias squamipinnis*), Longtooth grouper (*Epinephelus bruneus*), Convict grouper (*Epinephelus septemfasciatus*), etc., the family Centrarchidae such as Bluegill (*Lepomis macrochirus*), etc., the family Carangidae such as White trevally (*Pseudocaranx dentex*), Greater amberjack (*Seriola dumerili*), Japanese amberjack (*Seriola quinqueradiata*), etc., the family Sparidae such as Red sea bream (*Pagrus major*), etc., the family Cichlidae such as Nile tilapia (*Oreochromis niloticus*), Angelfish (*Pterophyllum scalare*), etc., the family Scombridae such as Pacific bluefin tuna (*Thunnus orientalis*), etc., the family Tetraodontidae such as Japanese pufferfish (*Takifugu rubripes*), etc.

In this specification, "useful insects" means insects useful for human life by utilizing their products, or useful to make agricultural work efficient e.g. by using them for pollination of orchards/vegetables, and specifically, Japanese honeybee (*Apis cerana japonica*), Western honey bee (*Apis mellifera*), Bumblebee (*Bombus consobrinus wittenburgi, B. diversus diversus, B. hypocrita hypocrita, B. initus, B. terrestris*), Hornfaced bee (*Osmia cornifrons*), Silkworm (*Bombyx mori*) may, for example, be mentioned, but the useful insects are not limited thereto.

In this specification, "natural enemies" means organisms which kill specific organisms particularly specific organisms damaging agricultural crops by predation or parasitism or which inhibit propagation of such organisms, and specifically, the following organisms may, for example, be mentioned, but the natural enemies are not limited thereto.

Parasitic wasps belonging to the family Braconidae such as *Dacnusa sasakawai, Dacnusa sibirica, Aphidius colemani, Apanteles glomeratus*, etc., the family Aphelinidae such as *Aphelinus albipodus, Aphelinus asychis, Aphelinus gossypii, Aphelinus maculatus, Aphelinus varipes, Encarsia formosa, Eretmocerus eremicus, Eretmocerus mundus*, etc., and the family Eulophidae such as *Chrysocharis pentheus, Neochrysocharis formosa, Diglyphus isaea, Hemiptarsenus varicornis*, etc.; Aphidophagous gall midge (*Aphidoletes aphidimyza*); Seven-spot ladybird (*Coccinella septempunctata*); Asian lady beetle (*Harmonia axyridis*); Predatory beetle (*Proylea japonica*); Anthocorid predatory bugs belonging to the family Anthocoridae such as *Orius minutus, Orius nagaii, Orius sauteri*, Minute pirate bug (*Orius strigicollis*), etc.; Predatory mirids belonging to the family Miridae such as *Pilophorus tyicus, Nesidiocoris tenuis*, etc.; Predatory *thrips* belonging to the family Aeolothripidae such as *Franklinothrips vespiformis*, etc.; Green lacewing belonging to the family Chrysopidae such as *Dichochrysa formosanus, Chrysoperla nipponensis*, etc.; Predatory mites belonging to the family Phytoseiidae such as *Neoseiulus californicus, Amblyseius cucumeris, Amblyseius deneperans, Amblyseius swirskii, Phytoseiulus persimilis*, etc.; Wolf spider (*Pardosa pseudoannulata*); Crab spider (*Misumenops tricuspidatus*).

The compounds of the present invention represented by the formula (I) can be produced, for example, by the following methods.

Production Method A

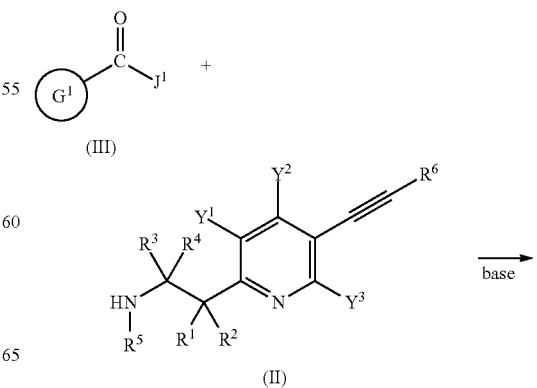

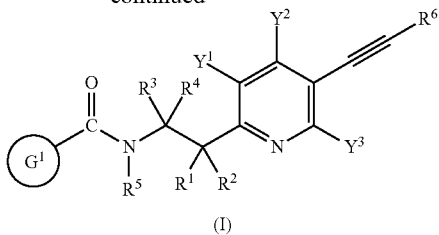

(I)

(In the formula (I) and formula (II), $Y^1$, $Y^2$, $Y^3$, $R^1$, $R^2$, $R^3$, $R^4$, $R^5$ and $R^6$ are as defined above. In the formula (I) and formula (III), $G^1$ is as defined above. In the formula (III), $J^1$ is a chlorine atom, a bromine atom, a $C_1$-$C_4$ alkylcarbonyloxy group (e.g. a pivaloyloxy group), a $C_1$-$C_4$ alkoxycarbonyloxy group (for example, an isobutyloxycarbonyloxy group) or an azolyl group (e.g. an imidazol-1-yl group), etc.)

It is possible to obtain a compound of the present compound represented by the formula (I) by reacting a compound represented by the formula (II) or its salt (e.g. hydrochloride, hydrobromide, trifluoroacetate, p-toluenesulfonate, etc.) and a compound represented by the formula (III), in a temperature range of from 0° C. to the reflux temperature of the reaction mixture, for from 30 minutes to 24 hours, if necessary in the presence of a base such as sodium carbonate, potassium carbonate, sodium bicarbonate, sodium acetate, triethylamine, ethyldiisopropylamine, N-methylmorpholine, pyridine or 4-(dimethylamino)pyridine in an amount of from 1 to 3 equivalents per 1 equivalent of the compound of the formula (II), if necessary by using, as a solvent, benzene, toluene, dichloromethane, chloroform, 1,2-dichloroethane, diethyl ether, tert-butyl methyl ether, tetrahydrofuran, 1,4-dioxane, ethyl acetate, N,N-dimethylformamide, N,N-dimethylacetamide, acetonitrile, water or a mixture of two or more of them in optional proportions.

Some of the compounds represented by the formula (III) to be used here are known compounds, and some of them are commercially available. The rest of them can be synthesized in accordance with known methods disclosed in literatures, for example, by a method in accordance with the method disclosed in Journal of Medicinal Chemistry [J. Med. Chem.], 1991, vol. 34, pp. 1630, etc. (in which a corresponding known carboxylic acid is reacted with a halogenating agent such as thionyl chloride, phosphorus pentachloride or oxalyl chloride), a method in accordance with the method disclosed in Tetrahedron Letters [Tetrahedron Lett.], 2003, vol. 44, pp. 4819, Journal of Medicinal Chemistry [J. Med. Chem.], 1991, vol. 34, pp. 222, etc. (in which a corresponding known carboxylic acid is reacted with an organic acid halide such as pivaloyl chloride or isobutyl chloroformate in the presence of a base if necessary), or a method disclosed in The Journal of Organic Chemistry [J. Org. Chem.], 1989, vol. 54, pp. 5620, etc. (in which a corresponding known carboxylic acid is reacted with carbonyl diimidazole, sulfonyl diimidazole or the like).

Production Method B

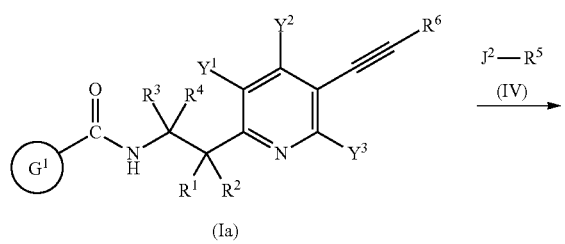

(Ia)

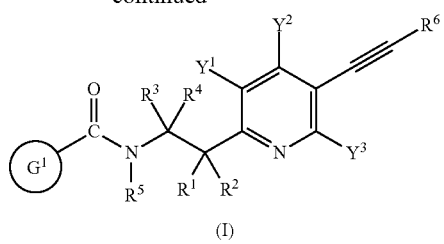

(I)

(In the formula (Ia) and formula (I), $G^1$, $Y^1$, $Y^2$, $Y^3$, $R^1$, $R^2$, $R^3$, $R^4$ and $R^6$ are as defined above. In the formula (IV), $R^5$ is as defined above but excluding a hydrogen atom, —OH, $C_1$-$C_4$ alkoxy and $C_1$-$C_4$ haloalkoxy, and $J^2$ represents a good leaving group such as a chlorine atom, a bromine atom, an iodine atom, a $C_1$-$C_4$ alkylcarbonyloxy group (e.g. a pivaloyloxy group, etc.), a $C_1$-$C_4$ alkyl sulfonate group (e.g. a methanesulfonyloxy group, etc.), a $C_1$-$C_4$ haloalkyl sulfonate group (e.g. a trifluoromethanesulfonyloxy group, etc.), an aryl sulfonate group (e.g. a benzenesulfonyloxy group, a p-toluenesulfonyloxy group, etc.) or an azolyl group (e.g. an imidazol-1-yl group, etc.). In the formula (I), $R^5$ is as defined above.)

It is possible to obtain a compound of the present compound represented by the formula (I) by reacting 1 equivalent of a compound of the present invention represented by the formula (Ia) in which $R^5$ is a hydrogen atom and from 1 to 10 equivalents of a compound represented by the formula (IV), in a temperature range of from 0 to 90° C. for from 10 minutes to 24 hours, if necessary in the presence of a base such as sodium hydride, potassium tert-butoxide, potassium hydroxide, potassium carbonate, triethylamine or pyridine in an amount of from 1 to 3 equivalents per 1 equivalent of the compound represented by the formula (Ia), if necessary by using a polar solvent such as tert-butyl methyl ether, tetrahydrofuran, 1,4-dioxane, acetonitrile or N,N-dimethylformamide.

Some of the compounds represented by the formula (IV) to be used here are known compounds, and some of them are commercially available. The rest of them can be synthesized in accordance with known methods disclosed in literatures, for example, by methods disclosed in Chemical and Pharmaceutical Bulletin [Chem. Pharm. Bull.], 1986, vol. 34, pp. 540 and 2001, vol. 49, pp. 1102, Journal of the American Chemical Society [J. Am. Chem. Soc.], 1964, vol. 86, pp. 4383, The Journal of Organic Chemistry [J. Org. Chem.], 1983, vol. 48, pp. 5280, Organic Synthesis [Org. Synth.], 1988, collective volume 6, pp. 101, Synlett, 2005, pp. 2847, Synthesis, 1990, pp. 1159, Japanese Unexamined patent application publication (JP-A 05/125017), European Patent Publication (EP 0,051,273), British Patent Publication (GB 2,161,802), etc.

Production Method C

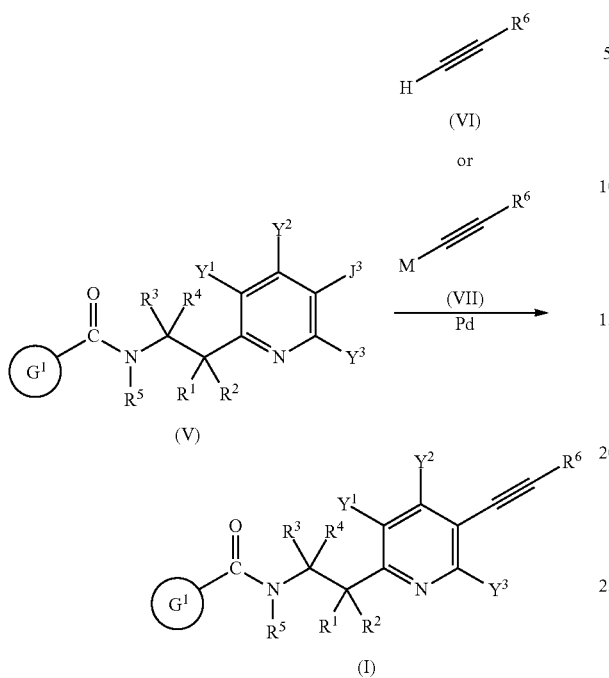

(In the formula (I) and formula (V), $G^1$, $Y^1$, $Y^2$, $Y^3$, $R^1$, $R^2$, $R^3$, $R^4$ and $R^5$ are as defined above. In the formula (V), $J^3$ represents a good leaving group such as a chlorine atom, a bromine atom, an iodine atom or a $C_1$-$C_4$ haloalkyl sulfonate group (e.g. a trifluoromethanesulfonyloxy group, etc.). In the formula (I), formula (VI) and formula (VII), $R^6$ is as defined above. In the formula (VII), M is a —ZnCl group, a —ZnBr group or a —ZnI group.)

It is possible to obtain a compound of the present invention represented by the formula (I) by reacting a compound represented by the formula (V), with a substituted acetylene represented by the formula (VI), for example, under common Sonogashira coupling reaction conditions disclosed e.g. in International Patent Application Publication (WO 2008/093065), or with an alkynyl zinc represented by the formula (VII), for example, under common Negishi coupling reaction conditions described in e.g. Heterocycles, 1997, vol. 46, pp. 209.

Some of the compounds represented by the formula (V) to be used here are known compounds as described in, for example, International Patent Application Publication (WO 2005/014545), International Patent Application Publication (WO 2013/064461), International Patent Application Publication (WO 2013/064521), etc., and the rest of them can also be synthesized in the same manner as known compounds.

Further, some of the compounds represented by the formula (VI) and formula (VII) are known compounds, and some of them are commercially available. The rest of them can also be readily synthesized according to general synthetic methods described in literatures relating to known compounds.

In each of the production methods A to C, the reaction mixture after completion of the reaction, may be subjected to usual post treatment, such as direct concentration, or dissolution in an organic solvent and washing with water, followed by concentration, or pouring into ice water and extraction with an organic solvent, followed by concentra-tion, whereby it is possible to obtain the desired alkynyl pyridine-substituted amide compound. Further, in a case where need for purification arises, separation and purification can be made by an optional purification method, such as recrystallization, column chromatography, thin-layer chromatography or liquid chromatography.

The compound represented by the formula (II) to be used in the production method A can be synthesized, for example, as shown by Reaction Schemes 1 to 9.

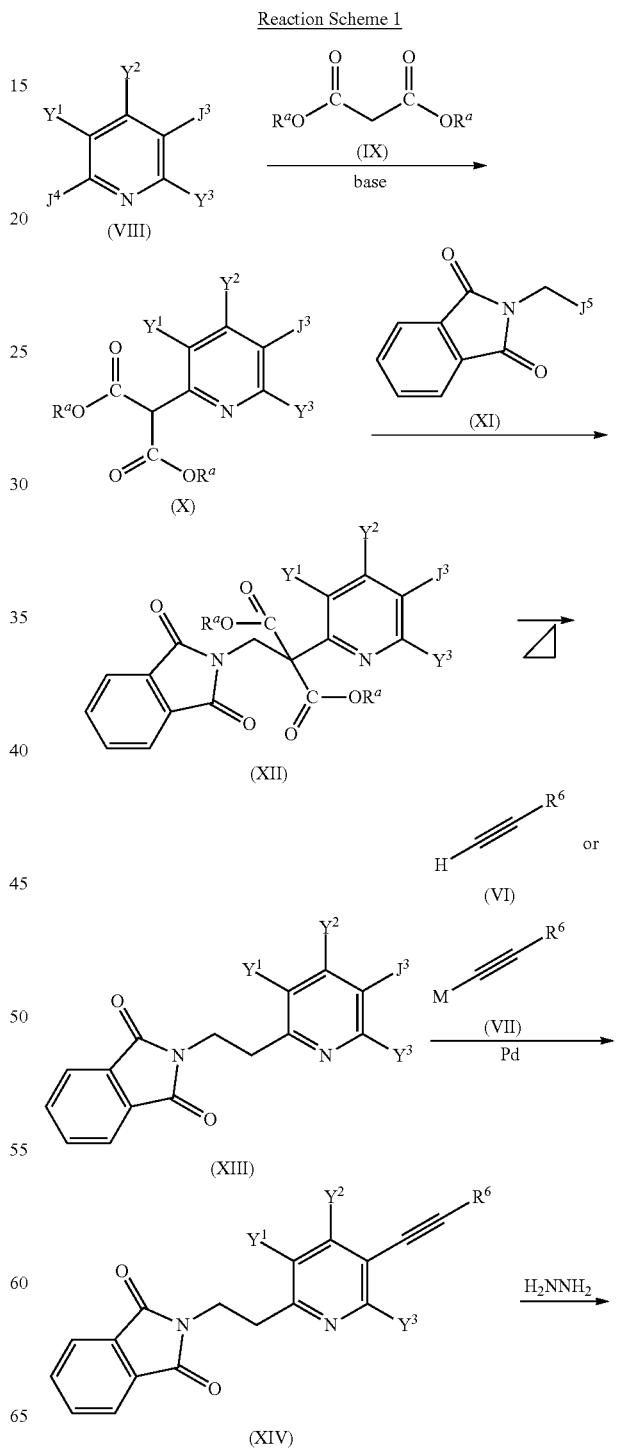

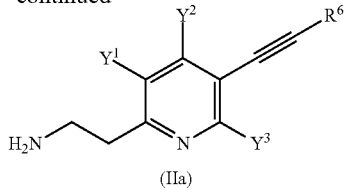

(IIa)

(In the formula (VIII) and formula (XIII), $Y^1$, $Y^2$, $Y^3$ and $J^3$ are as defined above. In the formula (VIII), $J^4$ is a halogen atom. In the formula (IX), $R^a$ is a $C_1$-$C_4$ alkyl group. In the formula (X) and formula (XII), $Y^1$, $Y^2$, $Y^3$, $J^3$ and $R^6$ are as defined above. In the formula (XI), $J^5$ is a chlorine atom, a bromine atom, an iodine atom or a $C_1$-$C_4$ alkylcarbonyloxy group (e.g. an acetoxy group, etc.). In the formula (VI), $R^6$ is as defined above. In the formula (VII), $R^6$ and M are as defined above. In the formula (XIV) and formula (IIa), $Y^1$, $Y^2$, $Y^3$ and $R^6$ are as defined above.)

A compound represented by the formula (VIII) and a known malonic acid ester represented by the formula (IX) are reacted by a method disclosed, for example, in Synthetic Communications [Synth. Commun.], 1990, vol. 20, pp. 2965 to obtain a compound represented by the formula (X), which is then reacted with a known phthalimide derivative represented by the formula (XI) in accordance with a method disclosed, for example, in Journal of Medicinal Chemistry [J. Med. Chem.], 2001, vol. 44, pp. 1217, whereby it is possible to synthesize a compound represented by the formula (XII).

Then, the compound of the formula (XII) is subjected to decarboxylation by heating in accordance with a method disclosed, for example, in Tetrahedron Letters [Tetrahedron Lett.], 2012, vol. 53, pp. 3853, to obtain a compound represented by the formula (XIII), which is then reacted with a substituted acetylene represented by the formula (VI) or an alkynyl zinc represented by the formula (VII) under the same conditions as in the production method C, whereby it is possible to synthesize a compound represented by the formula (XIV).

The compound represented by the formula (XIV) thus obtained, is reacted with an aqueous methylamine, an aqueous hydrazine solution or hydrazine monohydrate in an amount of from 1 to 4 equivalents per 1 equivalent of the compound of the formula (XIV) in a temperature range of from room temperature to the reflux temperature of the reaction mixture, for from 1 to 24 hours, if necessary, by using, as a solvent, toluene, dichloromethane, chloroform, methanol, ethanol, tetrahydrofuran, 1,4-dioxane, water, or a mixture of two or more of them at optional concentrations, if necessary under an inert gas atmosphere such as nitrogen, argon, etc., whereby it is possible to obtain a compound represented by the formula (IIa) which corresponds to the formula (II) wherein $R^1$, $R^2$, $R^3$, $R^4$ and $R^5$ are hydrogen atoms.

Some of the compounds of the formula (VIII) to be used here are known compounds, and some of them are commercially available. The rest of them can also be readily synthesized according to general synthetic methods described in the literatures relating to known compounds.

Reaction Scheme 2

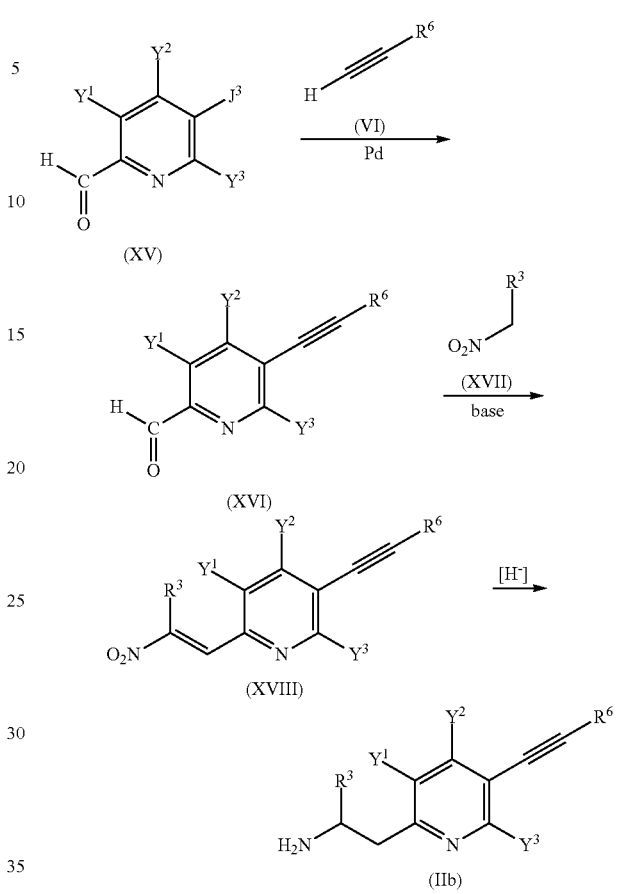

(In the formula (XV), $Y^1$, $Y^2$, $Y^3$ and $J^3$ are as defined above. In the formula (VI), $R^6$ is as defined above. In the formula (XVI), $Y^1$, $Y^2$, $Y^3$ and $R^6$ are as defined above. In the formula (XVII), $R^3$ is as defined above. In the formula (XVIII) and formula (IIb), $Y^1$, $Y^2$, $Y^3$, $R^3$ and $R^6$ are as defined above.)

A compound represented by the formula (XV) and a compound represented by the formula (VI) are reacted under common Sonogashira coupling reaction conditions disclosed, for example, in The Journal of Organic Chemistry [J. Org. Chem.], 2003, vol. 68, pp. 9907, to obtain a compound represented by the formula (XVI), which is then reacted with a known nitro alkane derivative represented by the formula (XVII) in accordance with a method disclosed, for example, in Journal of the Chemical Society, Perkin Transactions 1 [J. Chem. Soc. Perkin Trans. 1], 1979, pp. 643, whereby it is possible to synthesize a compound represented by the formula (XVIII).

The compound of the formula (XVIII) thus obtained, is reduced by using a reducing agent such as lithium aluminum hydride in accordance with a method disclosed, for example, in Journal of Medicinal Chemistry [J. Med. Chem.], 2005, vol. 48, pp. 2407, whereby it is possible to obtain a compound represented by the formula (IIb) which corresponds to the formula (II) wherein $R^1$, $R^2$, $R^4$ and $R^5$ are hydrogen atoms.

Some of the compounds of the formula (XV) to be used here are known compounds, and some of them are commercially available. The rest of them can also be readily synthesized according to general synthetic methods described in literatures relating to known compounds.

& Medicinal Chemistry Letters [Bioorganic & Med. Chem. Lett.], 2009, vol. 19, pp. 6331, whereby it is possible to synthesize a compound represented by the formula (XXI).

The compound of the formula (XXI) thus obtained and a substituted acetylene of the formula (VI) are reacted under common Sonogashira coupling reaction conditions as disclosed, for example, in Tetrahedron Letters [Tetrahedron Lett.], 2012, vol. 53, pp. 4117, to obtain a compound represented by the formula (XXII), which is then reacted with a known amine represented by the formula (XXIII) or its salt (e.g. hydrochloride, acetate, etc.) in the presence of a reducing agent such as sodium cyanoborohydride, in accordance with a method disclosed, for example, in European Journal of Medicinal Chemistry [European J. Med. Chem.], 2009, vol. 44, pp. 4862, whereby it is possible to obtain a compound represented by the formula (IIc) which corresponds to the formula (II) wherein $R^1$, $R^2$ and $R^4$ are hydrogen atoms.

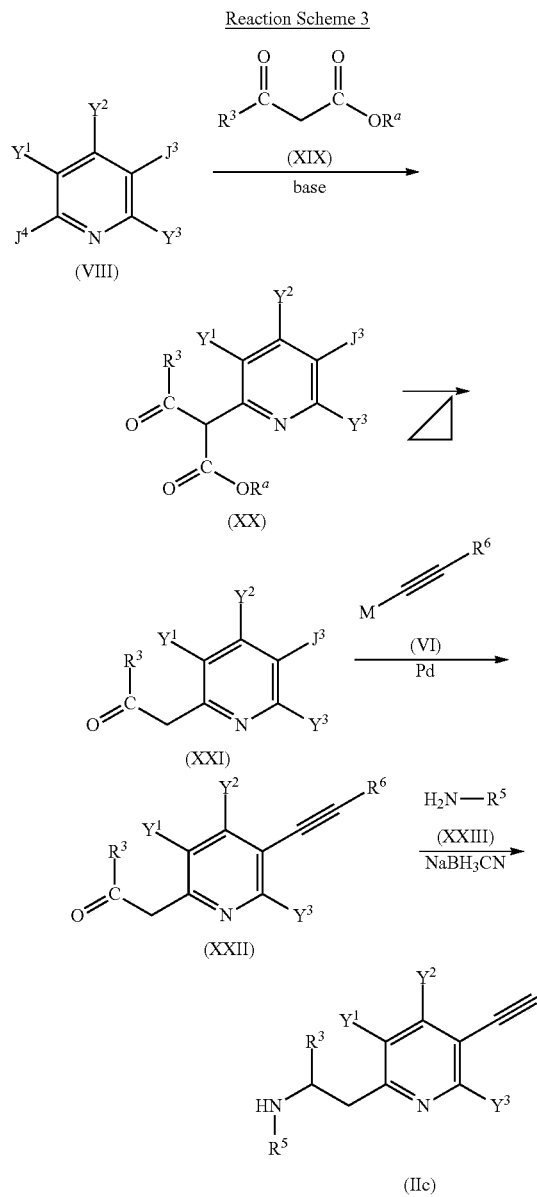

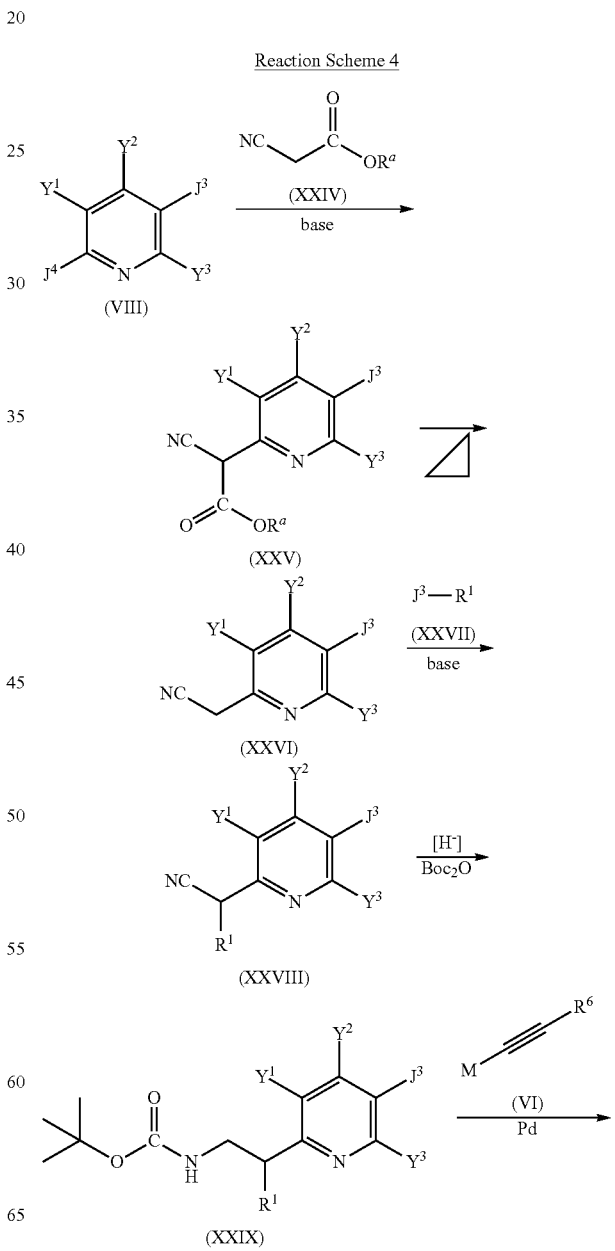

(In the formula (VIII), $Y^1$, $Y^2$, $Y^3$, $J^3$ and $J^4$ are as defined above. In the formula (XIX), $R^3$ is as defined above, and $R^a$ is a $C_1$-$C_4$ alkyl group. In the formula (XX) and formula (XXI), $Y^1$, $Y^2$, $Y^3$, $R^3$ and $J^3$ are as defined above. In the formula (XX), $R^a$ is as defined above. In the formula in (VI), $R^6$ is as defined above. In the formula (XXII), $Y^1$, $Y^2$, $Y^3$, $R^3$ and $R^6$ are as defined above. In the formula (XXIII), $R^5$ is as defined above. In the formula (IIc), $Y^1$, $Y^2$, $Y^3$, $R^3$, $R^5$ and $R^6$ are as defined above.)

A compound represented by the formula (VIII) and a known β-keto ester represented by the formula (XIX) are reacted in accordance with a method disclosed, for example, in Tetrahedron Letters [Tetrahedron Lett.], 2011, vol. 52, pp. 5292, to obtain a compound represented by the formula (XX), which is then subjected to decarboxylation in accordance with a method disclosed, for example, in Bioorganic

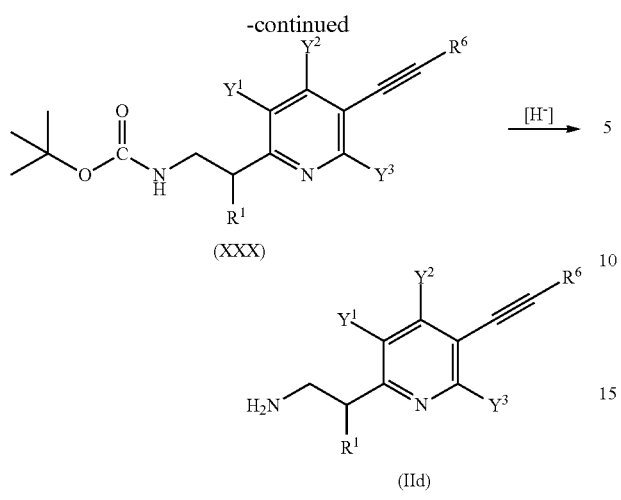

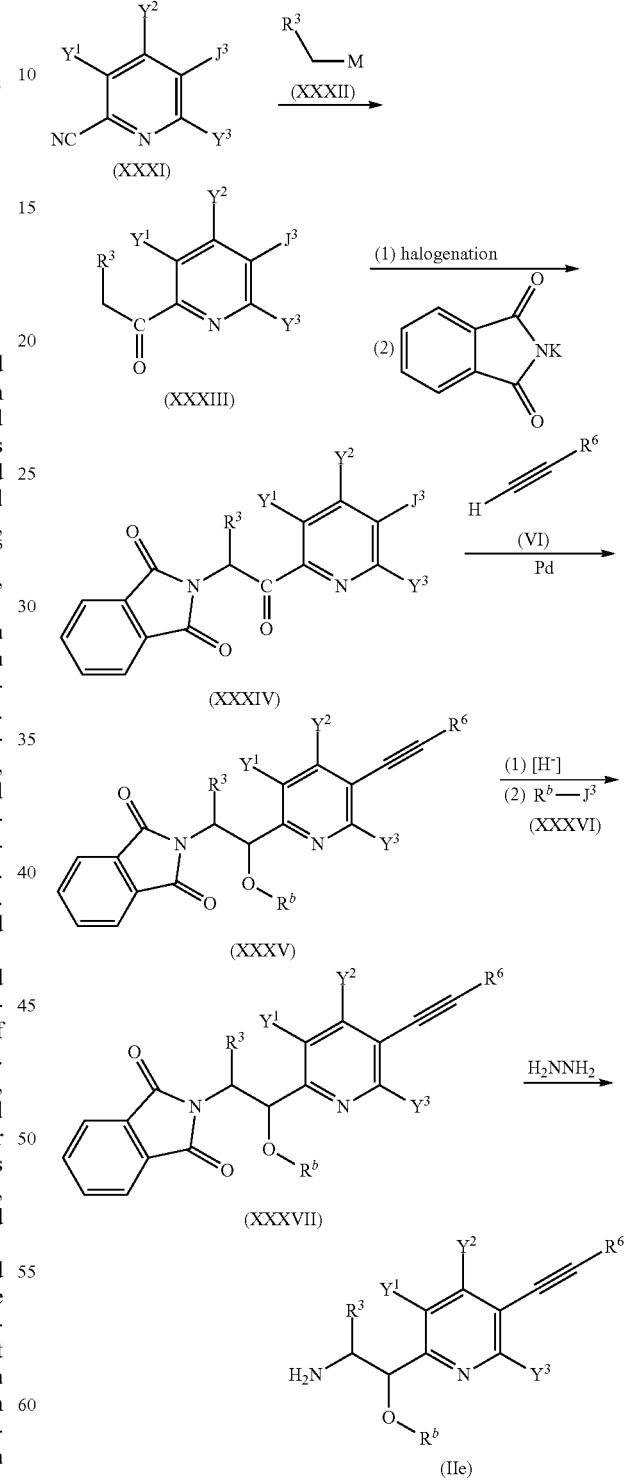

(In the formula (VIII), $Y^1$, $Y^2$, $Y^3$, $J^3$ and $J^4$ are as defined above. In the formula (XXIV), $R^a$ is a $C_1$-$C_4$ alkyl group. In the formula (XXV), $Y^1$, $Y^2$, $Y^3$, $J^3$ and $R^a$ are as defined above. In the formula (XXVI), $Y^1$, $Y^2$, $Y^3$ and $J^3$ are as defined above. In the formula (XXVII), $J^3$ is as defined above, and $R^1$ is a $C_1$-$C_4$ alkyl group or a $C_1$-$C_4$ haloalkyl group. In the formula (XVIII) and formula (XXIX), $Y^1$, $Y^2$, $Y^3$, $R^1$ and $J^3$ are as defined above. In the formula (VI), $R^6$ is as defined above. In the formula (XXX) and formula (IId), $Y^1$, $Y^2$, $Y^3$, $R^1$ and $R^6$ are as defined above.)

A compound represented by the formula (VIII) and a known cyanoacetic acid ester represented by the formula (XXIV) are reacted in accordance with a method as disclosed, for example, in The Journal of Organic Chemistry [J. Org. Chem.], 2008, vol. 73, pp. 1643, Bioorganic & Medicinal Chemistry Letters [Bioorganic & Med. Chem. Lett.], 2009, vol. 19, pp. 4484, to obtain a compound represented by the formula (XXV), which is then subjected to decarboxylation by heating in accordance with a method disclosed, for example, in Journal of Medicinal Chemistry [J. Med. Chem.], 2005, vol. 48, pp. 2167, Synthesis, 2010, pp. 3332, etc., whereby it is possible to synthesize a compound of formula (XXVI).

Then, the compound of the formula (XXVI) is reacted with a known compound of the formula (XXVII) in accordance with a method disclosed, for example, in Journal of Heterocyclic Chemistry [J. Heterocyclic Chem.], 1987, vol. 24, pp. 1061, to obtain a compound of the formula (XXVIII), which is then reduced in the coexistence of di-tert-butyl dicarbonate, in accordance with a method disclosed, for example, in Bioorganic & Medicinal Chemistry Letters [Bioorganic & Med. Chem. Lett.], 2012, vol. 22, pp. 6108, whereby it is possible to synthesize a compound represented by the formula (XXIX).

The compound of the formula (XXIX) thus obtained, and a substituted acetylene represented by the formula (VI), are reacted under common Sonogashira coupling reaction conditions as disclosed, for example, in International Patent Application Publication (WO 2008/093065), to obtain a compound represented by the formula (XXX), which is then reacted with hydrochloric acid, hydrobromic acid, trifluoroacetic acid, etc. for deprotection, in accordance with a method disclosed, for example, in European Patent Publication (EP 1,574,511), International Patent Application Publication (WO 2008/021927), International Patent Application Publication (WO 2010/075200), etc., whereby it is possible to obtain a compound represented by the formula (IId) which corresponds to the formula (II) wherein $R^2$, $R^3$, $R^4$ and $R^5$ are hydrogen atoms, or its salt (e.g. hydrochloride, hydrobromide, trifluoroacetate, etc.).

(In the formula (XXXI), $Y^1$, $Y^2$, $Y^3$ and J are as defined above. In the formula (XXXII), $R^3$ and M are as defined above. In the formula (XXXIII) and formula (XXXIV), $Y^1$, $Y^2$, $Y^3$, $R^3$ and $J^3$ are as defined above. In the formula (VI), $R^6$ is as defined above. In the formula (XXXV), $Y^1$, $Y^2$, $R^3$ and $R^6$ are as defined above. In the formula (XXXVI), $J^3$ is as defined above, and $R^b$ is a $C_1$-$C_4$ alkyl group or a $C_1$-$C_4$ haloalkyl group. In the formula (XXXVII) and formula (IIe), $Y^1$, $Y^2$, $Y^3$, $R^3$, $R^6$ and $R^b$ are as defined above.)

A compound represented by the formula (XXXI) is reacted with a known Grignard reagent of formula (XXXII) in accordance with a method disclosed, for example, in The Journal of Organic Chemistry [J. Org. Chem.], 2009. vol. 74, pp. 4547, Journal of Medicinal Chemistry [J. Med. Chem.], 2006, vol. 49, pp. 6343, whereby it is possible to synthesize a compound represented by the formula (XXXIII).

Then, the compound of the formula (XXXIII) is halogenated and then reacted with potassium phthalimide in accordance with a method disclosed, for example, in International Patent Application Publication (WO 2014/010737), etc., to obtain a compound of the formula (XXXIV), which is then reacted with a substituted acetylene represented by the formula (VI) under common Sonogashira coupling reaction conditions, as disclosed, for example, in Dalton Transactions [Dalton Trans.], 2011, vol. 40, pp. 7534, etc., whereby it is possible to synthesize a compound represented by the formula (XXXV).

The compound of the formula (XXXV) thus obtained, is reduced by using hydrogen or a reducing agent such as sodium borohydride in accordance with a method disclosed, for example, in Bioorganic & Medicinal Chemistry Letters [Bioorganic & Med. Chem. Lett.], 2010, vol. 20, pp. 903, Tetrahedron Letters [Tetrahedron Lett.], 2012, vol. 53, pp. 6761, etc., and then reacted with a known compound represented by the formula (XXXVI) to obtain a compound represented by the formula (XXXVII), which is then reacted with an aqueous methylamine solution, an aqueous hydrazine solution or hydrazine monohydrate, in the same manner as in Reaction Scheme 1, whereby it is possible to obtain a compound represented by the formula (IIe) which corresponds to the formula (II) wherein $R^1$ is —$OR^b$, and $R^2$, $R^4$ and $R^5$ are hydrogen atoms.

Some of the compounds of the formula (XXXI) to be used here are known compounds, and some of them are commercially available. The rest of them can also be readily synthesized according to general synthetic methods described in literatures relating to known compounds.

Reaction Scheme 6

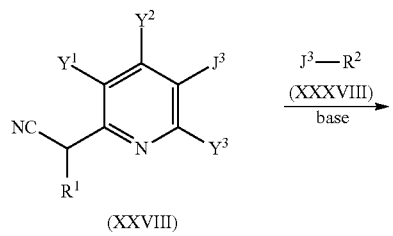

(XXVIII)

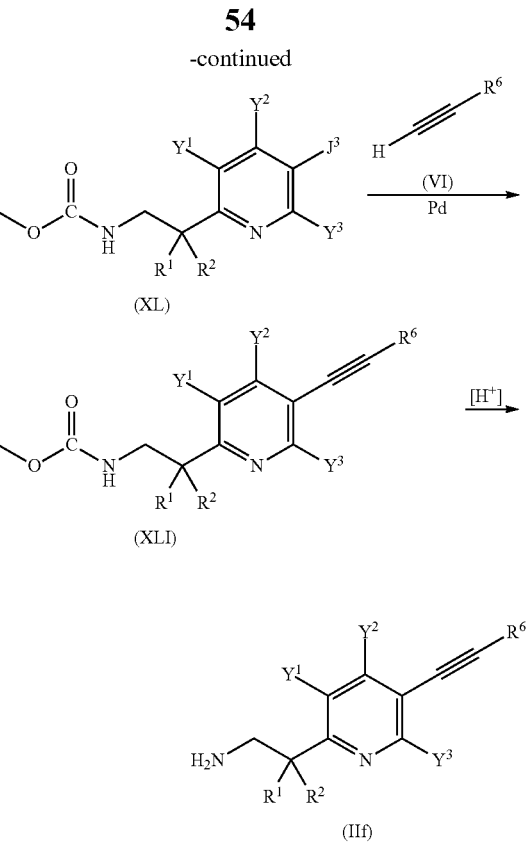

(In the formula (XXVIII) and formula (XXXIX), $Y^1$, $Y^2$, $Y^3$, $J^3$ and $R^1$ are as defined above. In the formula (XXXVIII), $J^3$ is as defined above, and $R^2$ is a $C_1$-$C_4$ alkyl group or a $C_1$-$C_4$ haloalkyl group. In the formula (XXXIX), $R^2$ is as defined above. In the formula (IIf), $Y^1$, $Y^2$, $Y^3$, $R^1$, $R^2$ and $R^6$ are as defined above.)

A compound represented by the formula (XXVIII) being a synthetic intermediate in Reaction Scheme 4, is reacted with a known compound of the formula (XXXVIII) in accordance with a method disclosed, for example, in European Journal of Medicinal Chemistry [Eur. J. Med. Chem.], 2004, vol. 39, pp. 993, etc., whereby it is possible to synthesize a compound represented by the formula (XXXIX).

The compound of the formula (XXXIX) thus obtained, is reacted in the same manner as in Reaction Scheme 4, whereby it is possible to obtain a compound represented by the formula (IIf) which corresponds to the formula (II) wherein $R^3$, $R^4$ and $R^5$ are hydrogen atoms, or its salt (e.g. hydrochloride, hydrobromide, trifluoroacetate, etc.).

Reaction Scheme 7

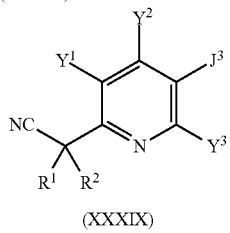 

(XXVI)

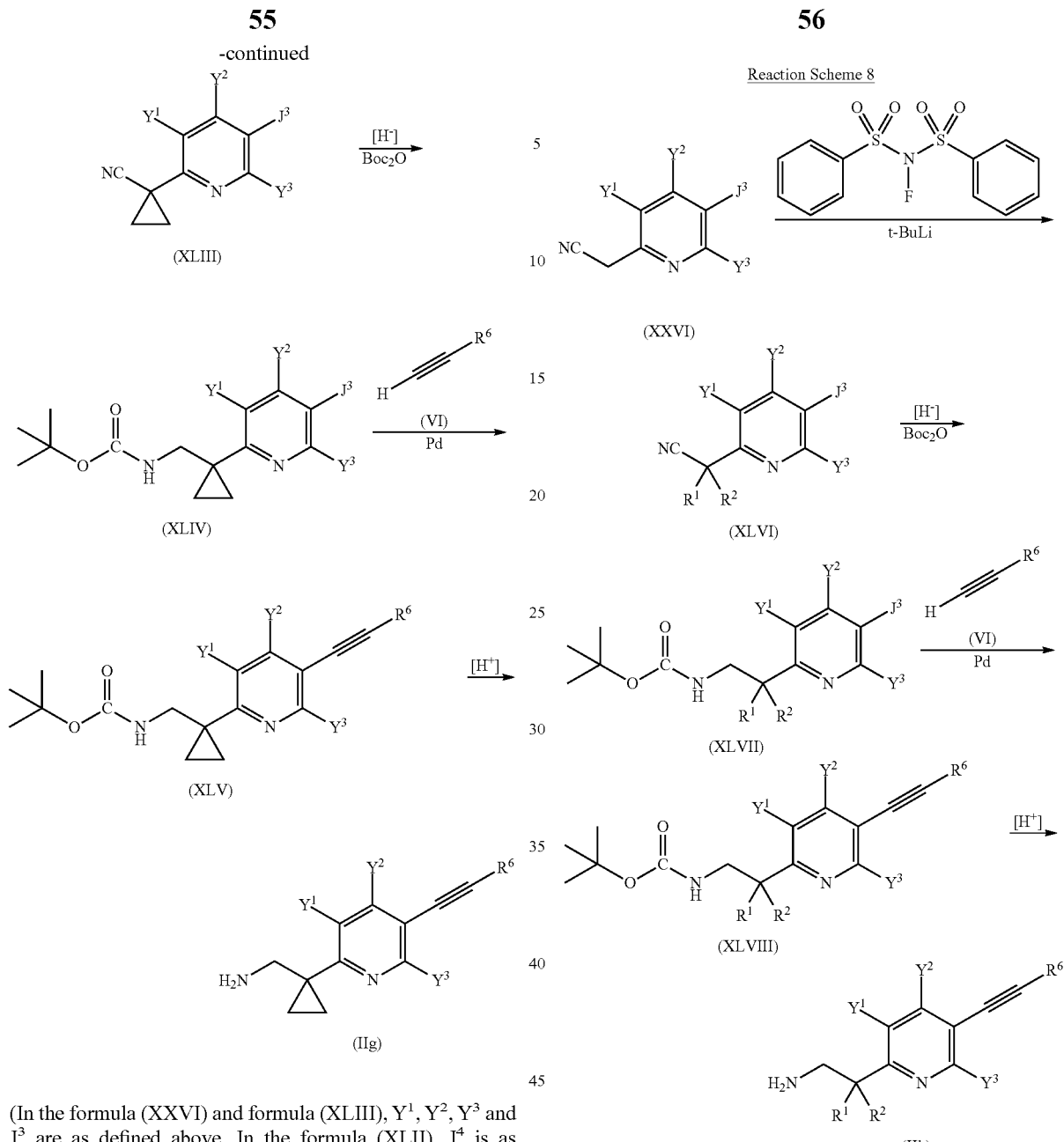

(In the formula (XXVI) and formula (XLIII), $Y^1$, $Y^2$, $Y^3$ and $J^3$ are as defined above. In the formula (XLII), $J^4$ is as defined above. In the formula (IIg), $Y^1$, $Y^2$, $Y^3$ and $R^6$ are as defined above.)

A compound represented by the formula (XXVI) being a synthetic intermediate in Reaction Scheme 4, and a known compound represented by the formula (XLII) are reacted in accordance with a method disclosed, for example, in Journal of Medicinal Chemistry [J. Med. Chem.], 2010, vol. 53, pp. 6003, etc., whereby it is possible to synthesize a compound of the formula (XLIII).

The compound of the formula (XLIII) thus obtained, is reacted in the same manner as in Reaction Scheme 4, whereby it is possible to obtain a compound represented by the formula (IIg) which corresponds to the formula (II) wherein $R^1$ and $R^2$ together form —$CH_2CH_2$— thereby to form a cyclopropyl ring together with the carbon atom to which $R^1$ and $R^2$ are bonded, and $R^3$, $R^4$ and $R^5$ are hydrogen atoms, or its salt (e.g. hydrochloride, hydrobromide, trifluoroacetate, etc.).

(In the formula (XXVI) and formula (XLVI), $Y^1$, $Y^2$, $Y^3$ and $J^3$ are as defined above. In the formula (IIh), $Y^1$, $Y^2$, $Y^3$ and $R^6$ are as defined.)

A compound represented by the formula (XXVI) being a synthetic intermediate in Reaction Scheme 4, is reacted with a fluorinating agent such as N-Fluorobenzenesulfonimide, in accordance with a method disclosed, for example, in The Journal of Organic Chemistry [J. Org. Chem.], 1998, vol. 63, pp. 8052, etc., whereby it is possible to synthesize a compound represented by the formula (XLVI).

The compound of the formula (XLVI) thus obtained, is reacted in the same manner as in Reaction Scheme 4, whereby it is possible to obtain a compound represented by the formula (IIIh) which corresponds to the formula (II) wherein $R^1$ and $R^2$ are fluorine atoms, and $R^3$, $R^4$ and $R^5$ are hydrogen atoms, or its salt (e.g. hydrochloride, hydrobromide, trifluoroacetate, etc.).

Reaction Scheme 9

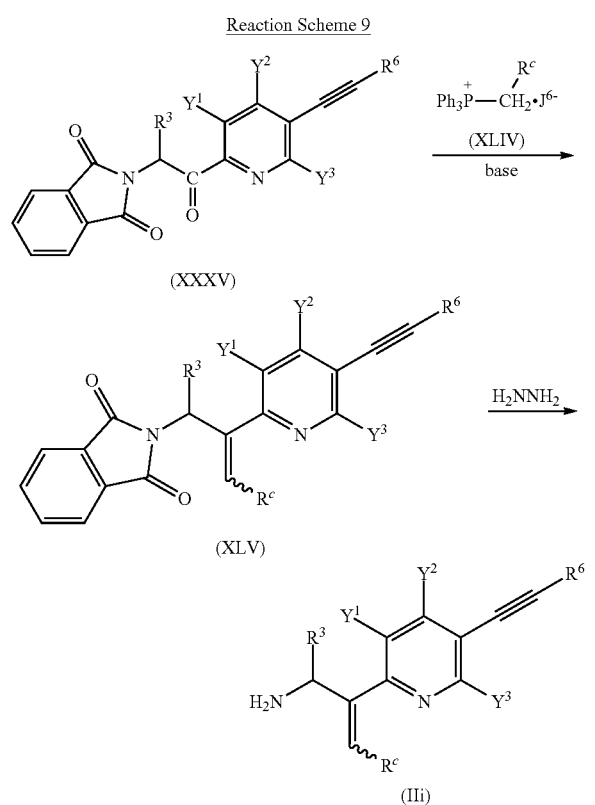

(In the formula (XXXV), $Y^1$, $Y^2$, $Y^3$, $R^3$ and $R^6$ are as defined above. In the formula (XLIV), $R^c$ is a hydrogen atom, a halogen atom, $C_1$-$C_5$ alkyl, $C_1$-$C_5$ haloalkyl or $C_1$-$C_4$ alkoxy, etc., and $J^6$ is a chlorine atom, a bromine atom or an iodine atom. In the formula (XLV) and formula (IIi), $Y^1$, $Y^2$, $Y^3$, $R^3$, $R^6$ and $R^c$ are as defined above.)

A compound represented by the formula (XXXV) being a synthetic intermediate in Reaction Scheme 5, and a compound represented by the formula (XLIV), are reacted in the presence of a strong base such as potassium tert-butoxide, sodium hexamethyldisilazide, lithium diisopropylamide or an alkyl lithium, in accordance with a method disclosed, for example, in Angewandte Chemie International Edition [Angew. Chemie, Int. Ed.], 2011, vol. 50, pp. 2593, Organic Letters [Organic Lett.], 2007, vol. 9, pp. 5219, The Journal of Organic Chemistry [J. Org. Chem.], 1993, vol. 58, pp. 6509, Tetrahedron, 2010, vol. 66, pp. 3499, European Journal of Medicinal Chemistry [European J. Org. Chem.], 2007, pp. 266, etc., whereby it is possible to synthesize a compound represented by the formula (XLV).

Then, the compound of the formula (XLV) is reacted in the same manner as in Reaction Scheme 1, with an aqueous methylamine solution, an aqueous hydrazine solution or hydrazine monohydrate, in a temperature range of from room temperature to the reflux temperature of the reaction mixture, for from 1 to 24 hours, whereby it is possible to obtain a compound represented by the formula (IIi) which corresponds to the formula (II) wherein $R^1$ and $R^2$ together form $C_1$-$C_6$ alkylidene, $C_1$-$C_6$ haloalkylidene or $C_1$-$C_4$ alkoxy($C_1$-$C_2$)alkylidene, and $R^4$ and $R^5$ are hydrogen atoms.

Some of the compounds of the formula (XLIV) to be used here, are known compounds, and some of them are commercially available. The rest of them can also be readily synthesized according to general synthetic methods described in literatures relating to known compounds.

In each of Reaction Schemes as described above, after the completion of the reactions, by performing ordinary post treatment, it is possible to obtain each of the production intermediates to be the starting compound in Production Method A to Production Method C.

The production intermediates respectively produced by these methods, may, respectively, be used for the reaction of the subsequent step as they are, without isolation or purification.

As alkynyl pyridine-substituted amide compounds of the formula (I) in the present invention that can be produced using these methods, specifically compounds represented by the following formulae [I]-1 to [I]-42, may, for example, be mentioned. However, it should be understood that the compounds represented by the following formulae [I]-1 to [I]-42 are for the purpose of exemplification, and alkynyl pyridine-substituted amide compounds encompassed by the present invention are not limited thereto.

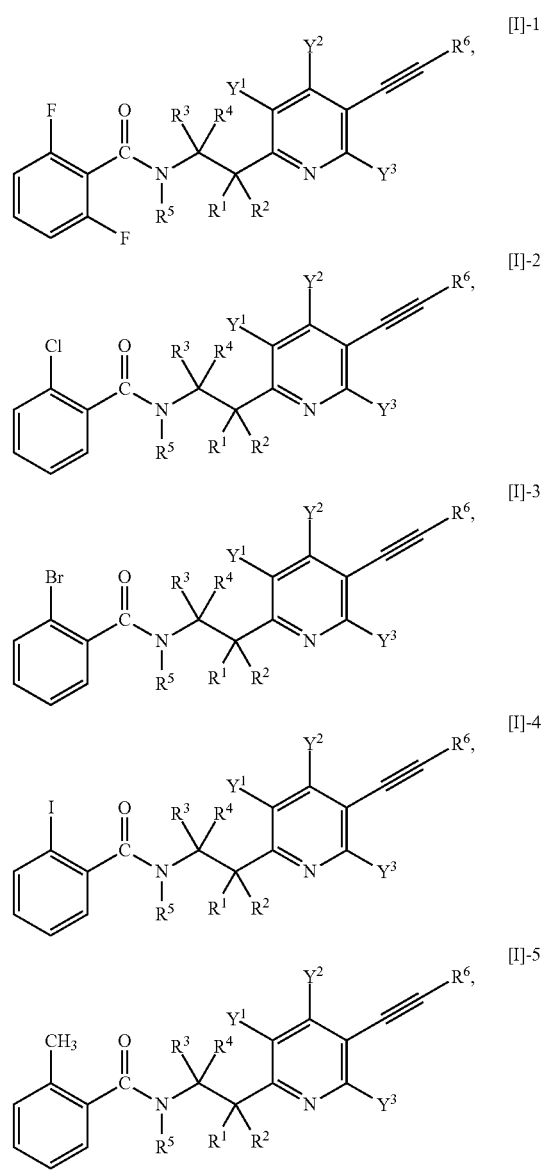

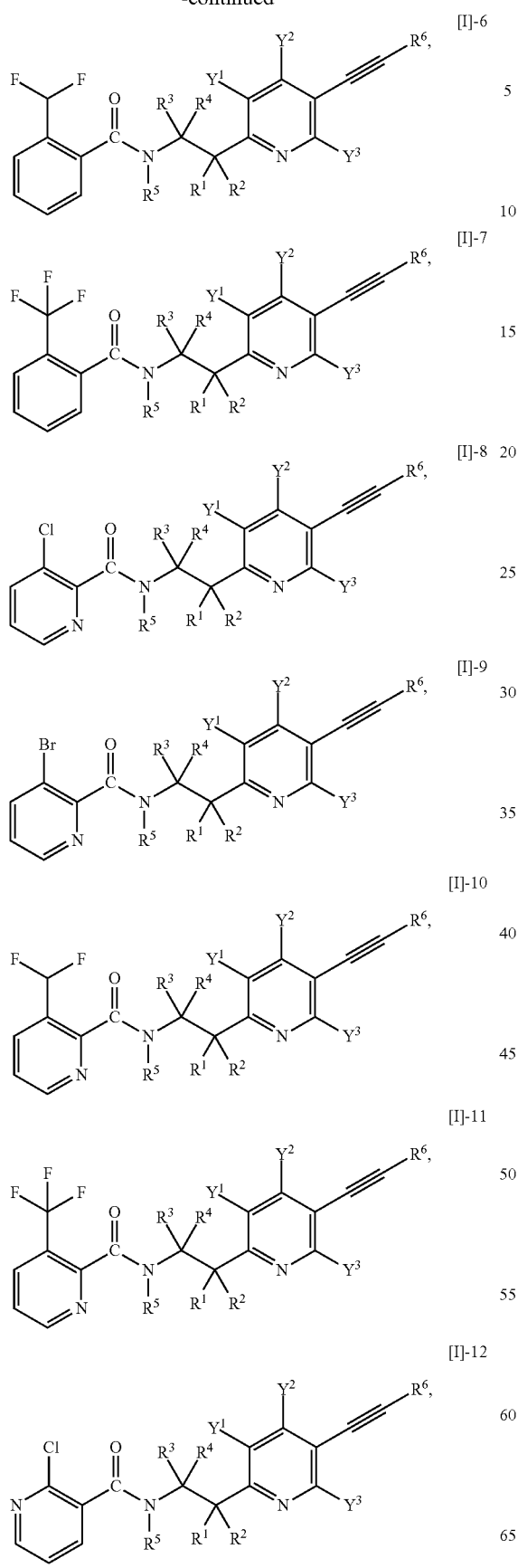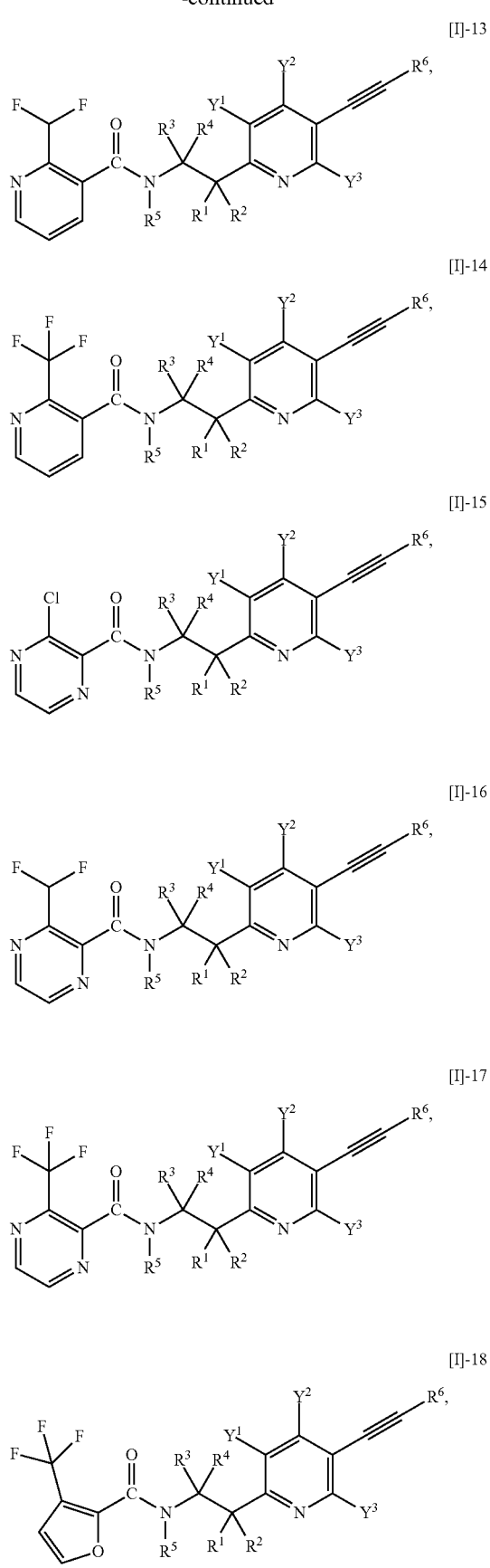

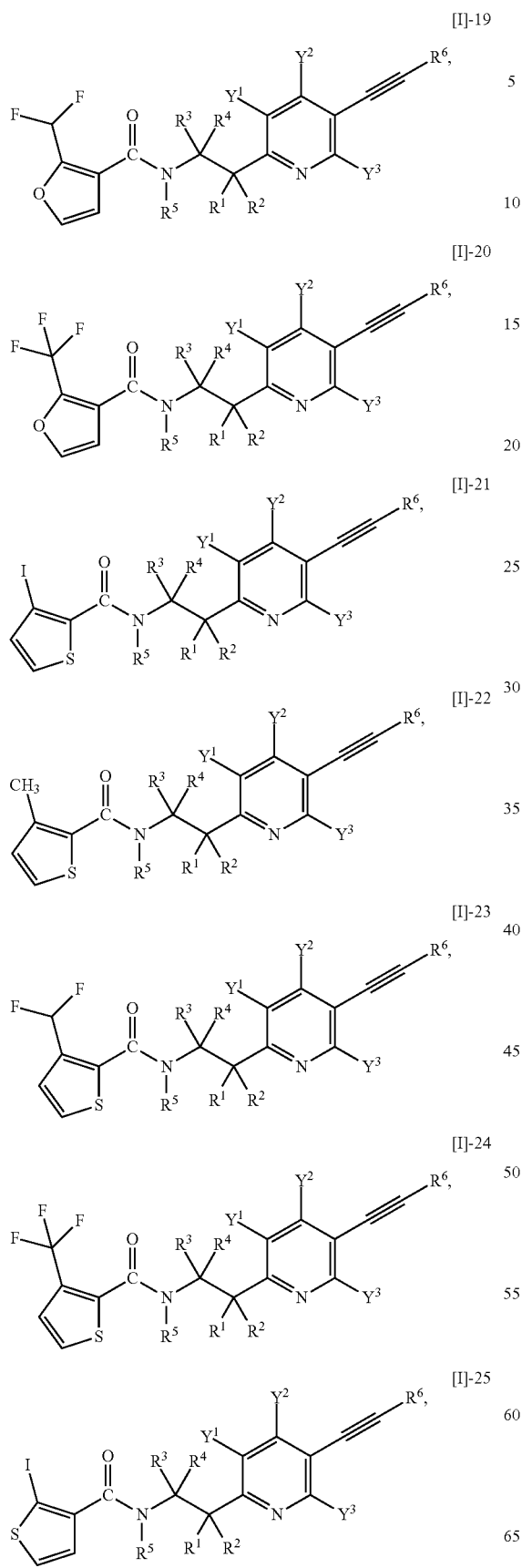
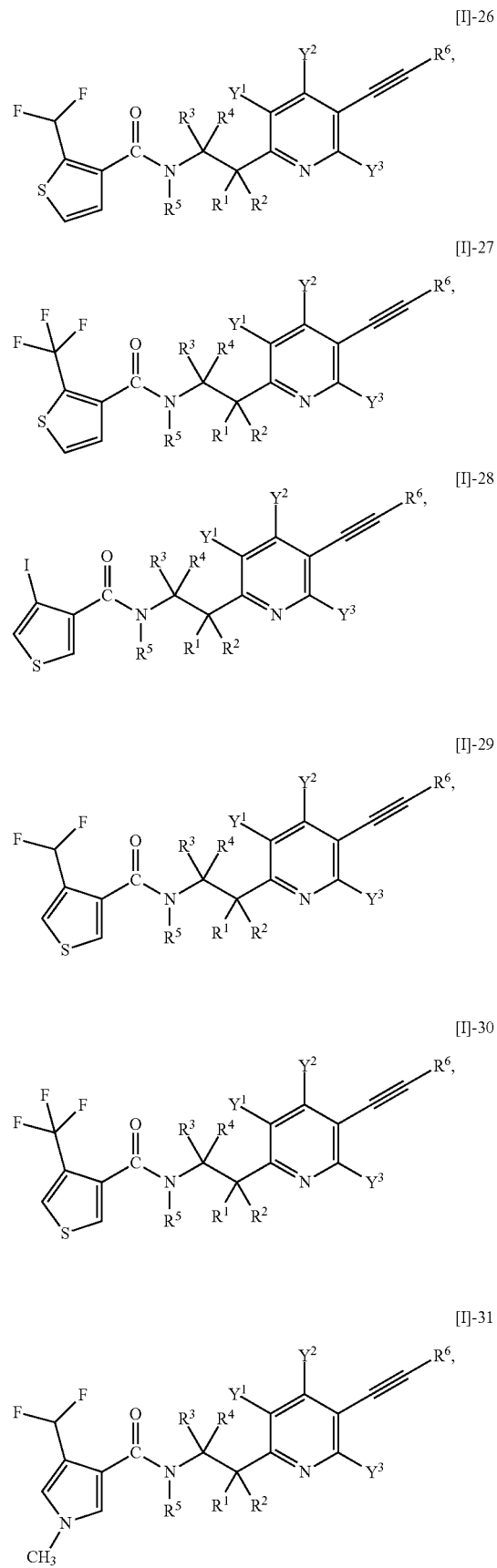

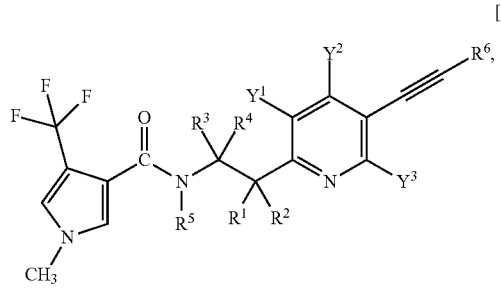
[I]-32
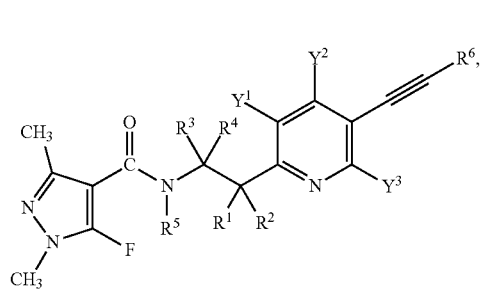
[I]-33
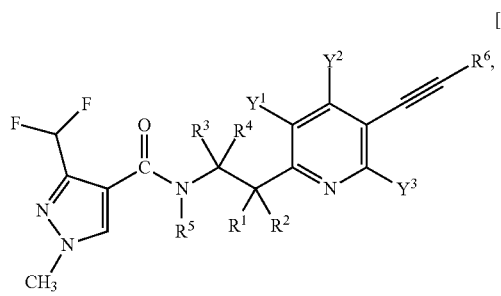
[I]-34
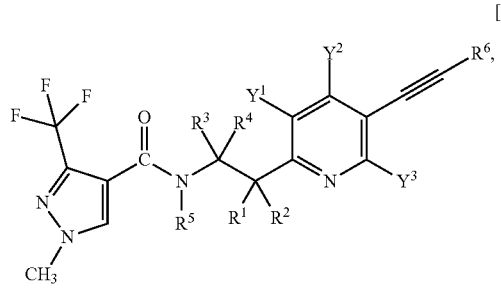
[I]-35
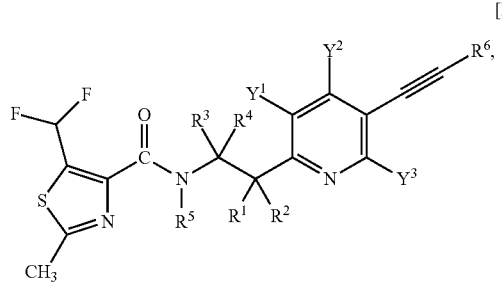
[I]-36
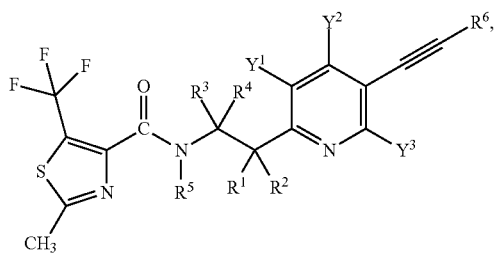
[I]-37
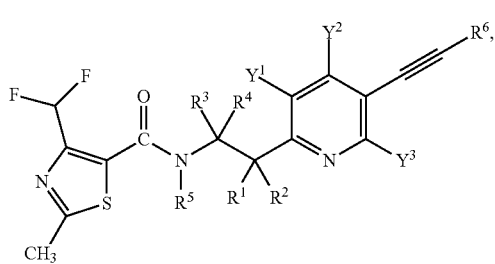
[I]-38
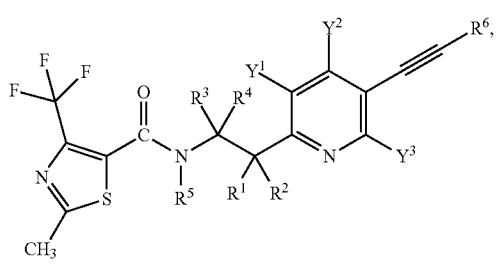
[I]-39
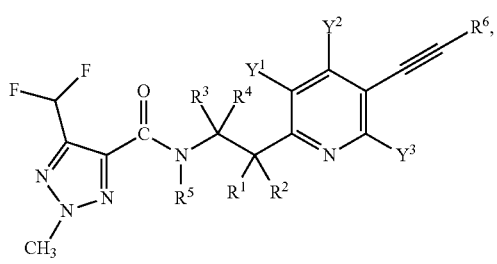
[I]-40
[I]-41
or
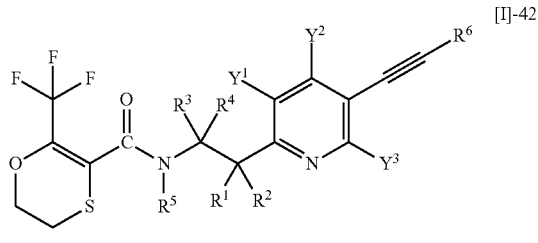
[I]-42

Here, as examples of specific combinations of substituents represented by $Y^1$, $Y^2$, $Y^3$, $R^1$, $R^2$, $R^3$, $R^4$, $R^5$ and $R^6$ in the formulae [I]-1 to [I]-42, combinations as shown in Table 2 may, for example, be mentioned. However, the combinations shown in Table 2 are merely for the purpose of exemplification, and specific combinations of substituents represented by $Y^1$, $Y^2$, $Y^3$, $R^1$, $R^2$, $R^3$, $R^4$, $R^5$ and $R^6$ in the alkynyl pyridine-substituted amide compounds included in the present invention, are not limited thereto.

In the Table, symbol Et represents an ethyl group, and likewise n-Pr represents a normalpropyl group, i-Pr and Pr-i represent an isopropyl group, c-Pr represents a cyclopropyl group, Bu-s represents a secondary butyl group, t-Bu and Bu-t represent a tertiary butyl group, c-Pen represents a cyclopentyl group, and Ph represents a phenyl group.

In the Table, T-1 and T-2 respectively represent the following structures:

T-1

T-2

In the Table, symbol (S) in the column for substituent $R^3$ represents that (S)-isomer is 90% or more, in the mixing ratio of optical isomers with respect to the carbon atom to which $R^3$ is bonded.

In the Table, symbol (E) or (Z) in the columns for substituents $R^1$ and $R^2$ represents that (E) isomer or (Z) isomer is, respectively, 90% or more, in the mixing ratio of geometrical isomers of the alkylidene group, which substituents $R^1$ and $R^2$ form together.

TABLE 2

| $R^5$ | $R^3$ | $R^4$ | $R^1$ | $R^2$ | $Y^1$ | $Y^2$ | $R^6$ | $Y^3$ |
|---|---|---|---|---|---|---|---|---|
| H | H | H | H | H | Cl | H | H | H |
| H | H | H | H | H | Cl | H | Cl | H |
| H | H | H | H | H | Cl | H | Br | H |
| H | H | H | H | H | Cl | H | I | H |
| H | H | H | H | H | Cl | H | $CH_3$ | H |
| H | $CH_3$ | H | H | H | Cl | H | $CH_3$ | H |
| H | Et | H | H | H | Cl | H | $CH_3$ | H |
| H | i-Pr | H | H | H | Cl | H | $CH_3$ | H |
| H | c-Pr | H | H | H | Cl | H | $CH_3$ | H |
| H | c-Bu | H | H | H | Cl | H | $CH_3$ | H |
| H | $CH_2CHF_2$ | H | H | H | Cl | H | $CH_3$ | H |
| H | $CH_2OCH_3$ | H | H | H | Cl | H | $CH_3$ | H |
| H | $CH_2OEt$ | H | H | H | Cl | H | $CH_3$ | H |
| H | $CH_2OC(O)CH_3$ | H | H | H | Cl | H | $CH_3$ | H |
| H | $CH_2OC(O)OCH_3$ | H | H | H | Cl | H | $CH_3$ | H |
| H | $CH_2SCH_3$ | H | H | H | Cl | H | $CH_3$ | H |
| H | $CH_2CN$ | H | H | H | Cl | H | $CH_3$ | H |
| H | $CH_2C(O)OCH_3$ | H | H | H | Cl | H | $CH_3$ | H |
| H | $CH_2C(O)NH_2$ | H | H | H | Cl | H | $CH_3$ | H |
| H | $CH_2C(S)NH_2$ | H | H | H | Cl | H | $CH_3$ | H |
| H | $CH_2CH=CH_2$ | H | H | H | Cl | H | $CH_3$ | H |
| H | $CH_2C\equiv CH$ | H | H | H | Cl | H | $CH_3$ | H |
| H | $OCH_3$ | H | H | H | Cl | H | $CH_3$ | H |
| H | OEt | H | H | H | Cl | H | $CH_3$ | H |
| H | $SCCl_3$ | H | H | H | Cl | H | $CH_3$ | H |
| H | $C(O)CH_3$ | H | H | H | Cl | H | $CH_3$ | H |
| H | $C(O)OCH_3$ | H | H | H | Cl | H | $CH_3$ | H |
| H | H | H | H | H | Cl | H | Et | H |
| H | H | H | H | H | Cl | H | n-Pr | H |
| H | H | H | H | H | Cl | H | i-Pr | H |
| H | H | H | H | H | Cl | H | c-Pr | H |
| H | c-Pr | H | H | H | Cl | H | c-Pr | H |
| H | $OCH_3$ | H | H | H | Cl | H | c-Pr | H |
| H | H | H | H | H | Cl | H | t-Bu | H |
| H | c-Pr | H | H | H | Cl | H | t-Bu | H |
| H | $OCH_3$ | H | H | H | Cl | H | t-Bu | H |
| H | H | H | H | H | Cl | H | T-1 | H |
| H | H | H | H | H | Cl | H | c-Pen | H |
| H | H | H | H | H | Cl | H | $CH_2F$ | H |
| H | H | H | H | H | Cl | H | $CHF_2$ | H |
| H | H | H | H | H | Cl | H | $CF_3$ | H |
| H | H | H | H | H | Cl | H | T-2 | H |
| H | H | H | H | H | Cl | H | $CH_2OCH_3$ | H |
| H | c-Pr | H | H | H | Cl | H | $CH_2OCH_3$ | H |
| H | $OCH_3$ | H | H | H | Cl | H | $CH_2OCH_3$ | H |
| H | H | H | H | H | Cl | H | $CH_2OEt$ | H |
| H | H | H | H | H | Cl | H | $CH_2OBu-t$ | H |

TABLE 2-continued

| R⁵ | R³ | R⁴ | R¹ | R² | Y¹ | Y² | R⁶ | Y³ |
|---|---|---|---|---|---|---|---|---|
| H | H | H | H | H | Cl | H | CH₂OCH₂CF₃ | H |
| H | H | H | H | H | Cl | H | CH₂OCH₂OCH₃ | H |
| H | H | H | H | H | Cl | H | C(CH₃)₂OCH₃ | H |
| H | H | H | H | H | Cl | H | C(CH₃)₂OCH₂CF₃ | H |
| H | H | H | H | H | Cl | H | CH(OCH₃)₂ | H |
| H | H | H | H | H | Cl | H | Si(CH₃)₃ | H |
| H | H | H | H | H | Cl | H | C(CH₃)=NOCH₃ | H |
| H | H | H | H | H | Cl | H | Ph | H |
| H | H | H | H | H | Cl | CH₃ | CH₃ | H |
| H | H | H | H | H | Cl | CH₃ | c-Pr | H |
| H | H | H | H | H | Cl | CH₃ | t-Bu | H |
| H | H | H | H | H | Cl | CH₃ | CH₂OCH₃ | H |
| H | H | H | H | H | Br | H | CH₃ | H |
| H | H | H | H | H | Br | H | c-Pr | H |
| H | H | H | H | H | Br | H | t-Bu | H |
| H | H | H | H | H | Br | H | CH₂OCH₃ | H |
| H | H | H | H | H | CH₃ | H | CH₃ | H |
| H | H | H | H | H | CH₃ | H | c-Pr | H |
| H | H | H | H | H | CH₃ | H | t-Bu | H |
| H | H | H | H | H | CH₃ | H | CH₂OCH₃ | H |
| H | H | H | H | H | CH₃ | CH₃ | CH₃ | H |
| H | H | H | H | H | CH₃ | CH₃ | c-Pr | H |
| H | H | H | H | H | CH₃ | CH₃ | t-Bu | H |
| H | H | H | H | H | CH₃ | CH₃ | CH₂OCH₃ | H |
| H | H | H | H | H | CF₃ | H | CH₃ | H |
| H | H | H | H | H | CF₃ | H | c-Pr | H |
| H | H | H | H | H | CF₃ | H | t-Bu | H |
| H | H | H | H | H | CF₃ | H | CH₂OCH₃ | H |
| H | H | H | H | H | OCH₃ | H | CH₃ | H |
| H | H | H | H | H | OCH₃ | H | c-Pr | H |
| H | H | H | H | H | OCH₃ | H | t-Bu | H |
| H | H | H | H | H | OCH₃ | H | CH₂OCH₃ | H |
| H | H | H | H | H | OCHF₂ | H | CH₃ | H |
| H | H | H | H | H | OCHF₂ | H | c-Pr | H |
| H | H | H | H | H | OCHF₂ | H | t-Bu | H |
| H | H | H | H | H | OCHF₂ | H | CH₂OCH₃ | H |
| H | H | H | H | H | SCH₃ | H | CH₃ | H |
| H | H | H | H | H | SCH₃ | H | c-Pr | H |
| H | H | H | H | H | SCH₃ | H | t-Bu | H |
| H | H | H | H | H | SCH₃ | H | CH₂OCH₃ | H |
| H | H | H | F | H | Cl | H | CH₃ | H |
| H | H | H | F | H | Cl | H | c-Pr | H |
| H | H | H | F | H | Cl | H | t-Bu | H |
| H | H | H | F | H | Cl | H | CH₂OCH₃ | H |
| H | H | H | F | F | Cl | H | CH₃ | H |
| c-Pr | H | H | F | F | Cl | H | CH₃ | H |
| H | H | H | F | F | Cl | H | c-Pr | H |
| c-Pr | H | H | F | F | Cl | H | c-Pr | H |
| H | H | H | F | F | Cl | H | t-Bu | H |
| c-Pr | H | H | F | F | Cl | H | t-Bu | H |
| H | H | H | F | F | Cl | H | CH₂F | H |
| c-Pr | H | H | F | F | Cl | H | CH₂F | H |
| H | H | H | F | F | Cl | H | CH₂OCH₃ | H |
| c-Pr | H | H | F | F | Cl | H | CH₂OCH₃ | H |
| H | H | H | F | F | Cl | H | CH₂OEt | H |
| c-Pr | H | H | F | F | Cl | H | CH₂OEt | H |
| H | H | H | F | F | Cl | H | CH₂OBu-t | H |
| c-Pr | H | H | F | F | Cl | H | CH₂OBu-t | H |
| H | H | H | F | F | Cl | H | CH₂OCH₂CF₃ | H |
| c-Pr | H | H | F | F | Cl | H | CH₂OCH₂CF₃ | H |
| H | H | H | F | F | Cl | H | Si(CH₃)₃ | H |
| c-Pr | H | H | F | F | Cl | H | Si(CH₃)₃ | H |
| H | H | H | F | F | Cl | H | Ph | H |
| c-Pr | H | H | F | F | Cl | H | Ph | H |
| H | H | H | F | F | Br | H | CH₃ | H |
| H | H | H | F | F | Br | H | c-Pr | H |
| H | H | H | F | F | Br | H | t-Bu | H |
| H | H | H | F | F | Br | H | CH₂OCH₃ | H |
| H | H | H | F | F | CH₃ | H | CH₃ | H |
| H | H | H | F | F | CH₃ | H | c-Pr | H |
| H | H | H | F | F | CH₃ | H | t-Bu | H |
| H | H | H | F | F | CH₃ | H | CH₂OCH₃ | H |
| H | H | H | F | F | OCH₃ | H | CH₃ | H |
| H | H | H | F | F | OCH₃ | H | c-Pr | H |
| H | H | H | F | F | OCH₃ | H | t-Bu | H |
| H | H | H | F | F | OCH₃ | H | CH₂OCH₃ | H |
| H | H | H | CH₃ | H | Cl | H | CH₃ | H |
| c-Pr | H | H | CH₃ | H | Cl | H | CH₃ | H |

TABLE 2-continued

| R⁵ | R³ | R⁴ | R¹ | R² | Y¹ | Y² | R⁶ | Y³ |
|---|---|---|---|---|---|---|---|---|
| OCH₃ | H | H | CH₃ | H | Cl | H | CH₃ | H |
| H | H | H | CH₃ | H | Cl | H | c-Pr | H |
| c-Pr | H | H | CH₃ | H | Cl | H | c-Pr | H |
| OCH₃ | H | H | CH₃ | H | Cl | H | c-Pr | H |
| H | H | H | CH₃ | H | Cl | H | t-Bu | H |
| c-Pr | H | H | CH₃ | H | Cl | H | t-Bu | H |
| OCH₃ | H | H | CH₃ | H | Cl | H | t-Bu | H |
| H | H | H | CH₃ | H | Cl | H | CH₂F | H |
| c-Pr | H | H | CH₃ | H | Cl | H | CH₂F | H |
| OCH₃ | H | H | CH₃ | H | Cl | H | CH₂F | H |
| H | H | H | CH₃ | H | Cl | H | CH₂OCH₃ | H |
| c-Pr | H | H | CH₃ | H | Cl | H | CH₂OCH₃ | H |
| OCH₃ | H | H | CH₃ | H | Cl | H | CH₂OCH₃ | H |
| H | H | H | CH₃ | H | Cl | H | CH₂OEt | H |
| c-Pr | H | H | CH₃ | H | Cl | H | CH₂OEt | H |
| OCH₃ | H | H | CH₃ | H | Cl | H | CH₂OEt | H |
| H | H | H | CH₃ | H | Cl | H | CH₂OBu-t | H |
| c-Pr | H | H | CH₃ | H | Cl | H | CH₂OBu-t | H |
| OCH₃ | H | H | CH₃ | H | Cl | H | CH₂OBu-t | H |
| H | H | H | CH₃ | H | Cl | H | CH₂OCH₃CF₃ | H |
| c-Pr | H | H | CH₃ | H | Cl | H | CH₂OCH₂CF₃ | H |
| OCH₃ | H | H | CH₃ | H | Cl | H | CH₂OCH₂CF₃ | H |
| H | H | H | CH₃ | H | Cl | H | Si(CH₃)₃ | H |
| c-Pr | H | H | CH₃ | H | Cl | H | Si(CH₃)₃ | H |
| OCH₃ | H | H | CH₃ | H | Cl | H | Si(CH₃)₃ | H |
| H | H | H | CH₃ | H | Cl | H | Ph | H |
| c-Pr | H | H | CH₃ | H | Cl | H | Ph | H |
| OCH₃ | H | H | CH₃ | H | Cl | H | Ph | H |
| H | H | H | CH₃ | F | Cl | H | CH₃ | H |
| H | H | H | CH₃ | F | Cl | H | c-Pr | H |
| H | H | H | CH₃ | F | Cl | H | t-Bu | H |
| H | H | H | CH₃ | F | Cl | H | CH₂OCH₃ | H |
| H | H | H | CH₃ | CH₃ | Cl | H | CH₃ | H |
| H | H | H | CH₃ | CH₃ | Cl | H | c-Pr | H |
| H | H | H | CH₃ | CH₃ | Cl | H | t-Bu | H |
| H | H | H | CH₃ | CH₃ | Cl | H | CH₂OCH₃ | H |
| H | H | H | Et | H | Cl | H | CH₃ | H |
| H | H | H | Et | H | Cl | H | c-Pr | H |
| H | H | H | Et | H | Cl | H | t-Bu | H |
| H | H | H | Et | H | Cl | H | CH₂OCH₃ | H |
| H | H | H | Et | CH₃ | Cl | H | CH₃ | H |
| H | H | H | Et | CH₃ | Cl | H | c-Pr | H |
| H | H | H | Et | CH₃ | Cl | H | t-Bu | H |
| H | H | H | Et | CH₃ | Cl | H | CH₂OCH₃ | H |
| H | H | H | n-Pr | H | Cl | H | CH₃ | H |
| c-Pr | H | H | n-Pr | H | Cl | H | CH₃ | H |
| OCH₃ | H | H | n-Pr | H | Cl | H | CH₃ | H |
| H | H | H | n-Pr | H | Cl | H | c-Pr | H |
| c-Pr | H | H | n-Pr | H | Cl | H | c-Pr | H |
| OCH₃ | H | H | n-Pr | H | Cl | H | c-Pr | H |
| H | H | H | n-Pr | H | Cl | H | t-Bu | H |
| c-Pr | H | H | n-Pr | H | Cl | H | t-Bu | H |
| OCH₃ | H | H | n-Pr | H | Cl | H | t-Bu | H |
| H | H | H | n-Pr | H | Cl | H | CH₂OCH₃ | H |
| c-Pr | H | H | n-Pr | H | Cl | H | CH₂OCH₃ | H |
| OCH₃ | H | H | n-Pr | H | Cl | H | CH₂OCH₃ | H |
| H | H | H | i-Pr | H | Cl | H | CH₃ | H |
| H | H | H | i-Pr | H | Cl | H | c-Pr | H |
| H | H | H | i-Pr | H | Cl | H | t-Bu | H |
| H | H | H | i-Pr | H | Cl | H | CH₂OCH₃ | H |
| H | H | H | c-Pr | H | Cl | H | CH₃ | H |
| H | H | H | c-Pr | H | Cl | H | c-Pr | H |
| H | H | H | c-Pr | H | Cl | H | t-Bu | H |
| H | H | H | c-Pr | H | Cl | H | CH₂OCH₃ | H |
| H | H | H | CH₂CF₃ | H | Cl | H | CH₃ | H |
| H | H | H | CH₂CF₃ | H | Cl | H | c-Pr | H |
| H | H | H | CH₂CF₃ | H | Cl | H | t-Bu | H |
| H | H | H | CH₂CF₃ | H | Cl | H | CH₂OCH₃ | H |
| H | H | H | —CH₂— | | Cl | H | CH₃ | H |
| H | H | H | —CH₂— | | Cl | H | c-Pr | H |
| H | H | H | —CH₂— | | Cl | H | t-Bu | H |
| H | H | H | —CH₂— | | Cl | H | CH₂OCH₃ | H |
| H | H | H | —CH₂— | | Cl | H | Si(CH₃)₃ | H |
| H | H | H | —CH₂— | | Cl | H | Ph | H |
| H | H | H | —CH₂— | | Br | H | CH₃ | H |
| H | H | H | —CH₂— | | Br | H | c-Pr | H |
| H | H | H | —CH₂— | | Br | H | t-Bu | H |
| H | H | H | —CH₂— | | Br | H | CH₂OCH₃ | H |

TABLE 2-continued

| R⁵ | R³ | R⁴ | R¹ | R² | Y¹ | Y² | R⁶ | Y³ |
|---|---|---|---|---|---|---|---|---|
| H | H | H |  | —CH(F)— | Cl | H | CH₃ | H |
| H | H | H |  | —CH(F)—(E) | Cl | H | CH₃ | H |
| H | H | H |  | —CH(F)—(Z) | Cl | H | CH₃ | H |
| H | H | H |  | —CH(F)— | Cl | H | c-Pr | H |
| H | H | H |  | —CH(F)—(E) | Cl | H | c-Pr | H |
| H | H | H |  | —CH(F)—(Z) | Cl | H | c-Pr | H |
| H | H | H |  | —CH(F)— | Cl | H | t-Bu | H |
| H | H | H |  | —CH(F)—(E) | Cl | H | t-Bu | H |
| H | H | H |  | —CH(F)—(Z) | Cl | H | t-Bu | H |
| H | H | H |  | —CH(F)— | Cl | H | CH₂OCH₃ | H |
| H | H | H |  | —CH(F)—(E) | Cl | H | CH₂OCH₃ | H |
| H | H | H |  | —CH(F)—(Z) | Cl | H | CH₂OCH₃ | H |
| H | H | H |  | —CH(F)— | Cl | H | Si(CH₃)₃ | H |
| H | H | H |  | —CH(F)—(E) | Cl | H | Si(CH₃)₃ | H |
| H | H | H |  | —CH(F)—(Z) | Cl | H | Si(CH₃)₃ | H |
| H | H | H |  | —CH(F)— | Cl | H | Ph | H |
| H | H | H |  | —CH(F)—(E) | Cl | H | Ph | H |
| H | H | H |  | —CH(F)—(Z) | Cl | H | Ph | H |
| H | H | H |  | —CH(Cl)— | Cl | H | CH₃ | H |
| H | H | H |  | —CH(Cl)—(E) | Cl | H | CH₃ | H |
| H | H | H |  | —CH(Cl)—(Z) | Cl | H | CH₃ | H |
| H | H | H |  | —CH(Cl)— | Cl | H | c-Pr | H |
| H | H | H |  | —CH(Cl)—(E) | Cl | H | c-Pr | H |
| H | H | H |  | —CH(Cl)—(Z) | Cl | H | c-Pr | H |
| H | H | H |  | —CH(Cl)— | Cl | H | t-Bu | H |
| H | H | H |  | —CH(Cl)—(E) | Cl | H | t-Bu | H |
| H | H | H |  | —CH(Cl)—(Z) | Cl | H | t-Bu | H |
| H | H | H |  | —CH(Cl)— | Cl | H | CH₂OCH₃ | H |
| H | H | H |  | —CH(Cl)—(E) | Cl | H | CH₂OCH₃ | H |
| H | H | H |  | —CH(Cl)—(Z) | Cl | H | CH₂OCH₃ | H |
| H | H | H |  | —CH(Cl)— | Cl | H | Si(CH₃)₃ | H |
| H | H | H |  | —CH(Cl)—(E) | Cl | H | Si(CH₃)₃ | H |
| H | H | H |  | —CH(Cl)—(Z) | Cl | H | Si(CH₃)₃ | H |
| H | H | H |  | —CH(Cl)— | Cl | H | Ph | H |
| H | H | H |  | —CH(Cl)—(E) | Cl | H | Ph | H |
| H | H | H |  | —CH(Cl)—(Z) | Cl | H | Ph | H |
| H | H | H |  | —CH(CH₃)— | Cl | H | CH₃ | H |
| H | H | H |  | —CH(CH₃)—(E) | Cl | H | CH₃ | H |
| H | H | H |  | —CH(CH₃)—(Z) | Cl | H | CH₃ | H |
| H | H | H |  | —CH(CH₃)— | Cl | H | c-Pr | H |
| H | H | H |  | —CH(CH₃)—(E) | Cl | H | c-Pr | H |
| H | H | H |  | —CH(CH₃)—(Z) | Cl | H | c-Pr | H |
| H | H | H |  | —CH(CH₃)— | Cl | H | t-Bu | H |
| H | H | H |  | —CH(CH₃)—(E) | Cl | H | t-Bu | H |
| H | H | H |  | —CH(CH₃)—(Z) | Cl | H | t-Bu | H |
| H | H | H |  | —CH(CH₃)— | Cl | H | CH₂OCH₃ | H |
| H | H | H |  | —CH(CH₃)—(E) | Cl | H | CH₂OCH₃ | H |
| H | H | H |  | —CH(CH₃)—(Z) | Cl | H | CH₂OCH₃ | H |
| H | H | H |  | —CH(CH₃)— | Cl | H | Si(CH₃)₃ | H |
| H | H | H |  | —CH(CH₃)—(E) | Cl | H | Si(CH₃)₃ | H |
| H | H | H |  | —CH(CH₃)—(Z) | Cl | H | Si(CH₃)₃ | H |
| H | H | H |  | —CH(CH₃)— | Cl | H | Ph | H |
| H | H | H |  | —CH(CH₃)—(E) | Cl | H | Ph | H |
| H | H | H |  | —CH(CH₃)—(Z) | Cl | H | Ph | H |
| H | H | H |  | —CH₂CH₂— | Cl | H | H | H |
| H | H | H |  | —CH₂CH₂— | Cl | H | CH₃ | H |
| H | H | H |  | —CH₂CH₂— | Cl | H | Et | H |
| H | H | H |  | —CH₂CH₂— | Cl | H | n-Pr | H |
| H | H | H |  | —CH₂CH₂— | Cl | H | i-Pr | H |
| H | H | H |  | —CH₂CH₂— | Cl | H | c-Pr | H |
| H | H | H |  | —CH₂CH₂— | Cl | H | t-Bu | H |
| H | H | H |  | —CH₂CH₂— | Cl | H | T-1 | H |
| H | H | H |  | —CH₂CH₂— | Cl | H | c-Pen | H |
| H | H | H |  | —CH₂CH₂— | Cl | H | T-2 | H |
| H | H | H |  | —CH₂CH₂— | Cl | H | CH₂OCH₃ | H |
| H | H | H |  | —CH₂CH₂— | Cl | H | CH₂OEt | H |
| H | H | H |  | —CH₂CH₂— | Cl | H | CH₂OBu-t | H |
| H | H | H |  | —CH₂CH₂— | Cl | H | CH₂OCH₂CF₃ | H |
| H | H | H |  | —CH₂CH₂— | Cl | H | CH₂OCH₂OCH₃ | H |
| H | H | H |  | —CH₂CH₂— | Cl | H | C(CH₃)₂OCH₃ | H |
| H | H | H |  | —CH₂CH₂— | Cl | H | C(CH₃)₂OCH₂CF₃ | H |
| H | H | H |  | —CH₂CH₂— | Cl | H | CH(OCH₃)₂ | H |
| H | H | H |  | —CH₂CH₂— | Cl | H | Si(CH₃)₃ | H |
| H | H | H |  | —CH₂CH₂— | Cl | H | C(CH₃)=NOCH₃ | H |
| H | H | H |  | —CH₂CH₂— | Cl | H | Ph | H |
| H | H | H |  | —CH₂CH₂— | Br | H | CH₃ | H |
| H | H | H |  | —CH₂CH₂— | Br | H | c-Pr | H |
| H | H | H |  | —CH₂CH₂— | Br | H | t-Bu | H |

TABLE 2-continued

| R⁵ | R³ | R⁴ | R¹ | R² | Y¹ | Y² | R⁶ | Y³ |
|---|---|---|---|---|---|---|---|---|
| H | H | H | —CH₂CH₂— | Br | H | CH₂OCH₃ | H |
| H | H | H | —CH₂CH₂— | CH₃ | H | CH₃ | H |
| H | H | H | —CH₂CH₂— | CH₃ | H | c-Pr | H |
| H | H | H | —CH₂CH₂— | CH₃ | H | t-Bu | H |
| H | H | H | —CH₂CH₂— | CH₃ | H | CH₂OCH₃ | H |
| H | H | H | —CH₂CH₂— | OCH₃ | H | CH₃ | H |
| H | H | H | —CH₂CH₂— | OCH₃ | H | c-Pr | H |
| H | H | H | —CH₂CH₂— | OCH₃ | H | t-Bu | H |
| H | H | H | —CH₂CH₂— | OCH₃ | H | CH₂OCH₃ | H |
| H | H | H | —CH₂CH₂CH₂— | Cl | H | CH₃ | H |
| H | H | H | —CH₂CH₂CH₂— | Cl | H | c-Pr | H |
| H | H | H | —CH₂CH₂CH₂— | Cl | H | t-Bu | H |
| H | H | H | —CH₂CH₂CH₂— | Cl | H | CH₂F | H |
| H | H | H | —CH₂CH₂CH₂— | Cl | H | CH₂OCH₃ | H |
| H | H | H | —CH₂CH₂CH₂— | Cl | H | CH₂OEt | H |
| H | H | H | —CH₂CH₂CH₂— | Cl | H | CH₂OBu-t | H |
| H | H | H | —CH₂CH₂CH₂— | Cl | H | CH₂OCH₂CF₃ | H |
| H | H | H | —CH₂CH₂CH₂— | Cl | H | Si(CH₃)₃ | H |
| H | H | H | —CH₂CH₂CH₂— | Cl | H | Ph | H |
| H | H | H | —CH₂OCH₂— | Cl | H | CH₃ | H |
| H | H | H | —CH₂OCH₂— | Cl | H | c-Pr | H |
| H | H | H | —CH₂OCH₂— | Cl | H | t-Bu | H |
| H | H | H | —CH₂OCH₂— | Cl | H | CH₂OCH₃ | H |
| H | H | H | —CH₂SCH₂— | Cl | H | CH₃ | H |
| H | H | H | —CH₂SCH₂— | Cl | H | c-Pr | H |
| H | H | H | —CH₂SCH₂— | Cl | H | t-Bu | H |
| H | H | H | —CH₂SCH₂— | Cl | H | CH₂OCH₃ | H |
| H | H | H | —CH₂S(O)CH₂— | Cl | H | CH₃ | H |
| H | H | H | —CH₂S(O)CH₂— | Cl | H | c-Pr | H |
| H | H | H | —CH₂S(O)CH₂— | Cl | H | t-Bu | H |
| H | H | H | —CH₂S(O)CH₂— | Cl | H | CH₂OCH₃ | H |
| H | H | H | —CH₂SO₂CH₂— | Cl | H | CH₃ | H |
| H | H | H | —CH₂SO₂CH₂— | Cl | H | c-Pr | H |
| H | H | H | —CH₂SO₂CH₂— | Cl | H | t-Bu | H |
| H | H | H | —CH₂SO₂CH₂— | Cl | H | CH₂OCH₃ | H |
| H | H | H | —CH₂CH₂CH₂CH₂— | Cl | H | CH₃ | H |
| H | H | H | —CH₂CH₂CH₂CH₂— | Cl | H | c-Pr | H |
| H | H | H | —CH₂CH₂CH₂CH₂— | Cl | H | t-Bu | H |
| H | H | H | —CH₂CH₂CH₂CH₂— | Cl | H | CH₂OCH₃ | H |
| H | H | H | OCH₃ | H | Cl | H | CH₃ | H |
| H | H | H | OCH₃ | H | Cl | H | c-Pr | H |
| c-Pr | H | H | OCH₃ | H | Cl | H | c-Pr | H |
| H | H | H | OCH₃ | H | Cl | H | t-Bu | H |
| H | H | H | OCH₃ | H | Cl | H | CH₂F | H |
| H | H | H | OCH₃ | H | Cl | H | CH₂OCH₃ | H |
| H | H | H | OCH₃ | H | Cl | H | CH₂OEt | H |
| H | H | H | OCH₃ | H | Cl | H | CH₂OBu-t | H |
| H | H | H | OCH₃ | H | Cl | H | CH₂OCH₂CF₃ | H |
| H | H | H | OCH₃ | H | Cl | H | Si(CH₃)₃ | H |
| H | H | H | OCH₃ | H | Cl | H | Ph | H |
| H | H | H | OEt | H | Cl | H | CH₃ | H |
| H | H | H | OEt | H | Cl | H | c-Pr | H |
| H | H | H | OEt | H | Cl | H | t-Bu | H |
| H | H | H | OEt | H | Cl | H | CH₂F | H |
| H | H | H | OEt | H | Cl | H | CH₂OCH₃ | H |
| H | H | H | OEt | H | Cl | H | CH₂OEt | H |
| H | H | H | OEt | H | Cl | H | CH₂OBu-t | H |
| H | H | H | OEt | H | Cl | H | CH₂OCH₂CF₃ | H |
| H | H | H | OEt | H | Cl | H | Si(CH₃)₃ | H |
| H | H | H | OEt | H | Cl | H | Ph | H |
| H | H | H | OPr-n | H | Cl | H | CH₃ | H |
| H | H | H | OPr-n | H | Cl | H | c-Pr | H |
| H | H | H | OPr-n | H | Cl | H | t-Bu | H |
| H | H | H | OPr-n | H | Cl | H | CH₂OCH₃ | H |
| H | H | H | OPr-i | H | Cl | H | CH₃ | H |
| H | H | H | OPr-i | H | Cl | H | c-Pr | H |
| H | H | H | OPr-i | H | Cl | H | t-Bu | H |
| H | H | H | OPr-i | H | Cl | H | CH₂OCH₃ | H |
| H | H | H | OCH₂CF₃ | H | Cl | H | CH₃ | H |
| H | H | H | OCH₂CF₃ | H | Cl | H | c-Pr | H |
| H | H | H | OCH₂CF₃ | H | Cl | H | t-Bu | H |
| H | H | H | OCH₂CF₃ | H | Cl | H | CH₂OCH₃ | H |
| H | H | H | OCH₂CH=CH₂ | H | Cl | H | CH₃ | H |
| H | H | H | OCH₂CH=CH₂ | H | Cl | H | c-Pr | H |
| H | H | H | OCH₂CH=CH₂ | H | Cl | H | t-Bu | H |
| H | H | H | OCH₂CH=CH₂ | H | Cl | H | CH₂OCH₃ | H |
| H | H | H | OCH₂C≡CH | H | Cl | H | CH₃ | H |
| H | H | H | OCH₂C≡CH | H | Cl | H | c-Pr | H |

TABLE 2-continued

| R⁵ | R³ | R⁴ | R¹ | R² | Y¹ | Y² | R⁶ | Y³ |
|---|---|---|---|---|---|---|---|---|
| H | H | H | OCH₂C≡CH | H | Cl | H | t-Bu | H |
| H | H | H | OCH₂C≡CH | H | Cl | H | CH₂OCH₃ | H |
| H | H | H | —OCH₂— | | Cl | H | CH₃ | H |
| H | H | H | —OCH₂— | | Cl | H | c-Pr | H |
| H | H | H | —OCH₂— | | Cl | H | t-Bu | H |
| H | H | H | —OCH₂— | | Cl | H | CH₂OCH₃ | H |
| H | H | H | —OCH₂CH₂— | | Cl | H | CH₃ | H |
| H | H | H | —OCH₂CH₂— | | Cl | H | c-Pr | H |
| H | H | H | —OCH₂CH₂— | | Cl | H | t-Bu | H |
| H | H | H | —OCH₂CH₂— | | Cl | H | CH₂OCH₃ | H |
| H | H | H | SCH₃ | H | Cl | H | CH₃ | H |
| H | H | H | SCH₃ | H | Cl | H | c-Pr | H |
| H | H | H | SCH₃ | H | Cl | H | t-Bu | H |
| H | H | H | SCH₃ | H | Cl | H | CH₂OCH₃ | H |
| H | H | H | NHOCH₃ | H | Cl | H | CH₃ | H |
| H | H | H | NHOCH₃ | H | Cl | H | c-Pr | H |
| H | H | H | NHOCH₃ | H | Cl | H | t-Bu | H |
| H | H | H | NHOCH₃ | H | Cl | H | CH₂OCH₃ | H |
| H | H | H | NHOEt | H | Cl | H | CH₃ | H |
| H | H | H | NHOEt | H | Cl | H | c-Pr | H |
| H | H | H | NHOEt | H | Cl | H | t-Bu | H |
| H | H | H | NHOEt | H | Cl | H | CH₂OCH₃ | H |
| H | H | H | NHOPr-i | H | Cl | H | CH₃ | H |
| H | H | H | NHOPr-i | H | Cl | H | c-Pr | H |
| H | H | H | NHOPr-i | H | Cl | H | t-Bu | H |
| H | H | H | NHOPr-i | H | Cl | H | CH₂OCH₃ | H |
| H | H | H | NHOBu-s | H | Cl | H | CH₃ | H |
| H | H | H | NHOBu-s | H | Cl | H | c-Pr | H |
| H | H | H | NHOBu-s | H | Cl | H | t-Bu | H |
| H | H | H | NHOBu-s | H | Cl | H | CH₂OCH₃ | H |
| H | H | H | NHOBu-t | H | Cl | H | CH₃ | H |
| H | H | H | NHOBu-t | H | Cl | H | c-Pr | H |
| H | H | H | NHOBu-t | H | Cl | H | t-Bu | H |
| H | H | H | NHOBu-t | H | Cl | H | CH₂OCH₃ | H |
| H | H | H | CN | H | Cl | H | CH₃ | H |
| H | H | H | CN | H | Cl | H | c-Pr | H |
| H | H | H | CN | H | Cl | H | t-Bu | H |
| H | H | H | CN | H | Cl | H | CH₂OCH₃ | H |
| H | H | H | CN | CH₃ | Cl | H | CH₃ | H |
| H | H | H | CN | CH₃ | Cl | H | c-Pr | H |
| H | H | H | CN | CH₃ | Cl | H | t-Bu | H |
| H | H | H | CN | CH₃ | Cl | H | CH₂OCH₃ | H |
| H | H | H | CN | CN | Cl | H | CH₃ | H |
| H | H | H | CN | CN | Cl | H | c-Pr | H |
| H | H | H | CN | CN | Cl | H | t-Bu | H |
| H | H | H | CN | CN | Cl | H | CH₂OCH₃ | H |
| H | H | H | C(O)OCH₃ | H | Cl | H | CH₃ | H |
| H | H | H | C(O)OCH₃ | H | Cl | H | c-Pr | H |
| H | H | H | C(O)OCH₃ | H | Cl | H | t-Bu | H |
| H | H | H | C(O)OCH₃ | H | Cl | H | CH₂OCH₃ | H |
| H | H | H | C(O)NH₂ | H | Cl | H | CH₃ | H |
| H | H | H | C(O)NH₂ | H | Cl | H | c-Pr | H |
| H | H | H | C(O)NH₂ | H | Cl | H | t-Bu | H |
| H | H | H | C(O)NH₂ | H | Cl | H | CH₂OCH₃ | H |
| H | H | H | C(S)NH₂ | H | Cl | H | CH₃ | H |
| H | H | H | C(S)NH₂ | H | Cl | H | c-Pr | H |
| H | H | H | C(S)NH₂ | H | Cl | H | t-Bu | H |
| H | H | H | C(S)NH₂ | H | Cl | H | CH₂OCH₃ | H |
| H | CH₃ | H | H | H | Cl | H | H | H |
| H | CH₃ | H | H | H | Cl | H | Cl | H |
| H | CH₃ | H | H | H | Cl | H | Br | H |
| H | CH₃ | H | H | H | Cl | H | I | H |
| H | CH₃ | H | H | H | Cl | H | CH₃ | H |
| H | CH₃(S) | H | H | H | Cl | H | CH₃ | H |
| c-Pr | CH₃ | H | H | H | Cl | H | CH₃ | H |
| OCH₃ | CH₃ | H | H | H | Cl | H | CH₃ | H |
| OEt | CH₃ | H | H | H | Cl | H | CH₃ | H |
| H | CH₃ | H | H | H | Cl | H | Et | H |
| H | CH₃ | H | H | H | Cl | H | n-Pr | H |
| H | CH₃ | H | H | H | Cl | H | i-Pr | H |
| H | CH₃ | H | H | H | Cl | H | c-Pr | H |
| H | CH₃(S) | H | H | H | Cl | H | c-Pr | H |
| c-Pr | CH₃ | H | H | H | Cl | H | c-Pr | H |
| OCH₃ | CH₃ | H | H | H | Cl | H | c-Pr | H |
| OEt | CH₃ | H | H | H | Cl | H | c-Pr | H |
| H | CH₃ | H | H | H | Cl | H | t-Bu | H |
| H | CH₃(S) | H | H | H | Cl | H | t-Bu | H |
| c-Pr | CH₃ | H | H | H | Cl | H | t-Bu | H |

TABLE 2-continued

| R⁵ | R³ | R⁴ | R¹ | R² | Y¹ | Y² | R⁶ | Y³ |
|---|---|---|---|---|---|---|---|---|
| OCH₃ | CH₃ | H | H | H | Cl | H | t-Bu | H |
| OEt | CH₃ | H | H | H | Cl | H | t-Bu | H |
| H | CH₃ | H | H | H | Cl | H | CH₂F | H |
| H | CH₃(S) | H | H | H | Cl | H | CH₂F | H |
| c-Pr | CH₃ | H | H | H | Cl | H | CH₂F | H |
| OCH₃ | CH₃ | H | H | H | Cl | H | CH₂F | H |
| H | CH₃ | H | H | H | Cl | H | CHF₂ | H |
| H | CH₃ | H | H | H | Cl | H | CH₂OCH₃ | H |
| H | CH₃(S) | H | H | H | Cl | H | CH₂OCH₃ | H |
| c-Pr | CH₃ | H | H | H | Cl | H | CH₂OCH₃ | H |
| OCH₃ | CH₃ | H | H | H | Cl | H | CH₂OCH₃ | H |
| OEt | CH₃ | H | H | H | Cl | H | CH₂OCH₃ | H |
| H | CH₃ | H | H | H | Cl | H | CH₂OEt | H |
| c-Pr | CH₃ | H | H | H | Cl | H | CH₂OEt | H |
| OCH₃ | CH₃ | H | H | H | Cl | H | CH₂OEt | H |
| H | CH₃ | H | H | H | Cl | H | CH₂OBu-t | H |
| c-Pr | CH₃ | H | H | H | Cl | H | CH₂OBu-t | H |
| OCH₃ | CH₃ | H | H | H | Cl | H | CH₂OBu-t | H |
| H | CH₃ | H | H | H | Cl | H | CH₂OCH₂CF₃ | H |
| c-Pr | CH₃ | H | H | H | Cl | H | CH₂OCH₂CF₃ | H |
| OCH₃ | CH₃ | H | H | H | Cl | H | CH₂OCH₂CF₃ | H |
| H | CH₃ | H | H | H | Cl | H | Si(CH₃)₃ | H |
| c-Pr | CH₃ | H | H | H | Cl | H | Si(CH₃)₃ | H |
| OCH₃ | CH₃ | H | H | H | Cl | H | Si(CH₃)₃ | H |
| H | CH₃ | H | H | H | Cl | H | C(CH₃)=NOCH₃ | H |
| H | CH₃ | H | H | H | Cl | H | Ph | H |
| c-Pr | CH₃ | H | H | H | Cl | H | Ph | H |
| OCH₃ | CH₃ | H | H | H | Cl | H | Ph | H |
| H | CH₃ | H | H | H | Cl | CH₃ | CH₃ | H |
| H | CH₃ | H | H | H | Cl | CH₃ | c-Pr | H |
| H | CH₃ | H | H | H | Cl | CH₃ | t-Bu | H |
| H | CH₃ | H | H | H | Cl | CH₃ | CH₂OCH₃ | H |
| H | CH₃ | H | H | H | Br | H | CH₃ | H |
| H | CH₃ | H | H | H | Br | H | c-Pr | H |
| H | CH₃ | H | H | H | Br | H | t-Bu | H |
| H | CH₃ | H | H | H | Br | H | CH₂OCH₃ | H |
| H | CH₃ | H | H | H | CH₃ | H | CH₃ | H |
| H | CH₃ | H | H | H | CH₃ | H | c-Pr | H |
| H | CH₃ | H | H | H | CH₃ | H | t-Bu | H |
| H | CH₃ | H | H | H | CH₃ | H | CH₂OCH₃ | H |
| H | CH₃ | H | F | H | Cl | H | CH₃ | H |
| H | CH₃ | H | F | H | Cl | H | c-Pr | H |
| H | CH₃ | H | F | H | Cl | H | t-Bu | H |
| H | CH₃ | H | F | H | Cl | H | CH₂OCH₃ | H |
| H | CH₃ | H | CH₃ | H | Cl | H | CH₃ | H |
| c-Pr | CH₃ | H | CH₃ | H | Cl | H | CH₃ | H |
| H | CH₃ | H | CH₃ | H | Cl | H | c-Pr | H |
| c-Pr | CH₃ | H | CH₃ | H | Cl | H | c-Pr | H |
| H | CH₃ | H | CH₃ | H | Cl | H | t-Bu | H |
| c-Pr | CH₃ | H | CH₃ | H | Cl | H | t-Bu | H |
| H | CH₃ | H | CH₃ | H | Cl | H | CH₂OCH₃ | H |
| c-Pr | CH₃ | H | CH₃ | H | Cl | H | CH₂OCH₃ | H |
| H | CH₃ | H | —CH₂— | | Cl | H | CH₃ | H |
| H | CH₃(S) | H | —CH₂— | | Cl | H | CH₃ | H |
| H | CH₃ | H | —CH₂— | | Cl | H | c-Pr | H |
| H | CH₃(S) | H | —CH₂— | | Cl | H | c-Pr | H |
| H | CH₃ | H | —CH₂— | | Cl | H | t-Bu | H |
| H | CH₃(S) | H | —CH₂— | | Cl | H | t-Bu | H |
| H | CH₃ | H | —CH₂— | | Cl | H | CH₂OCH₃ | H |
| H | CH₃(S) | H | —CH₂— | | Cl | H | CH₂OCH₃ | H |
| H | CH₃ | H | —CH₂— | | Cl | H | Si(CH₃)₃ | H |
| H | CH₃(S) | H | —CH₂— | | Cl | H | Si(CH₃)₃ | H |
| H | CH₃ | H | —CH₂— | | Cl | H | Ph | H |
| H | CH₃(S) | H | —CH₂— | | Cl | H | Ph | H |
| H | CH₃ | H | —CH₂CH₂— | | Cl | H | CH₃ | H |
| H | CH₃ | H | —CH₂CH₂— | | Cl | H | c-Pr | H |
| H | CH₃ | H | —CH₂CH₂— | | Cl | H | t-Bu | H |
| K | CH₃ | H | —CH₂CH₂— | | Cl | H | CH₂OCH₃ | H |
| H | CH₃ | H | OCH₃ | H | Cl | H | H | H |
| H | CH₃ | H | OCH₃ | H | Cl | H | Cl | H |
| H | CH₃ | H | OCH₃ | H | Cl | H | Br | H |
| H | CH₃ | H | OCH₃ | H | Cl | H | I | H |
| H | CH₃ | H | OCH₃ | H | Cl | H | CH₃ | H |
| c-Pr | CH₃ | H | OCH₃ | H | Cl | H | CH₃ | H |
| OCH₃ | CH₃ | H | OCH₃ | H | Cl | H | CH₃ | H |
| H | CH₃ | H | OCH₃ | H | Cl | H | Et | H |
| H | CH₃ | H | OCH₃ | H | Cl | H | n-Pr | H |
| H | CH₃ | H | OCH₃ | H | Cl | H | i-Pr | H |

TABLE 2-continued

| R⁵ | R³ | R⁴ | R¹ | R² | Y¹ | Y² | R⁶ | Y³ |
|---|---|---|---|---|---|---|---|---|
| H | CH₃ | H | OCH₃ | H | Cl | H | c-Pr | H |
| c-Pr | CH₃ | H | OCH₃ | H | Cl | H | c-Pr | H |
| OCH₃ | CH₃ | H | OCH₃ | H | Cl | H | c-Pr | H |
| H | CH₃ | H | OCH₃ | H | Cl | H | t-Bu | H |
| c-Pr | CH₃ | H | OCH₃ | H | Cl | H | t-Bu | H |
| OCH₃ | CH₃ | H | OCH₃ | H | Cl | H | t-Bu | H |
| H | CH₃ | H | OCH₃ | H | Cl | H | CH₂F | H |
| c-Pr | CH₃ | H | OCH₃ | H | Cl | H | CH₂F | H |
| OCH₃ | CH₃ | H | OCH₃ | H | Cl | H | CH₂F | H |
| H | CH₃ | H | OCH₃ | H | Cl | H | CHF₂ | H |
| H | CH₃ | H | OCH₃ | H | Cl | H | CH₂OCH₃ | H |
| c-Pr | CH₃ | H | OCH₃ | H | Cl | H | CH₂OCH₃ | H |
| OCH₃ | CH₃ | H | OCH₃ | H | Cl | H | CH₂OCH₃ | H |
| H | CH₃ | H | OCH₃ | H | Cl | H | CH₂OEt | H |
| c-Pr | CH₃ | H | OCH₃ | H | Cl | H | CH₂OEt | H |
| OCH₃ | CH₃ | H | OCH₃ | H | Cl | H | CH₂OEt | H |
| H | CH₃ | H | OCH₃ | H | Cl | H | CH₂OBu-t | H |
| c-Pr | CH₃ | H | OCH₃ | H | Cl | H | CH₂OBu-t | H |
| OCH₃ | CH₃ | H | OCH₃ | H | Cl | H | CH₂OBu-t | H |
| H | CH₃ | H | OCH₃ | H | Cl | H | CH₂OCH₂CF₃ | H |
| c-Pr | CH₃ | H | OCH₃ | H | Cl | H | CH₂OCH₂CF₃ | H |
| OCH₃ | CH₃ | H | OCH₃ | H | Cl | H | CH₂OCH₂CF₃ | H |
| H | CH₃ | H | OCH₃ | H | Cl | H | Si(CH₃)₃ | H |
| c-Pr | CH₃ | H | OCH₃ | H | Cl | H | Si(CH₃)₃ | H |
| OCH₃ | CH₃ | H | OCH₃ | H | Cl | H | Si(CH₃)₃ | H |
| H | CH₃ | H | OCH₃ | H | Cl | H | C(CH₃)=NOCH₃ | H |
| H | CH₃ | H | OCH₃ | H | Cl | H | Ph | H |
| c-Pr | CH₃ | H | OCH₃ | H | Cl | H | Ph | H |
| OCH₃ | CH₃ | H | OCH₃ | H | Cl | H | Ph | H |
| H | CH₃ | H | OCH₃ | H | Br | H | CH₃ | H |
| H | CH₃ | H | OCH₃ | H | Br | H | c-Pr | H |
| H | CH₃ | H | OCH₃ | H | Br | H | t-Bu | H |
| H | CH₃ | H | OCH₃ | H | Br | H | CH₂OCH₃ | H |
| H | CH₃ | H | OCH₃ | H | CH₃ | H | CH₃ | H |
| H | CH₃ | H | OCH₃ | H | CH₃ | H | c-Pr | H |
| H | CH₃ | H | OCH₃ | H | CH₃ | H | t-Bu | H |
| H | CH₃ | H | OCH₃ | H | CH₃ | H | CH₂OCH₃ | H |
| H | CH₃ | H | OCH₃ | H | OCH₃ | H | CH₃ | H |
| H | CH₃ | H | OCH₃ | H | OCH₃ | H | c-Pr | H |
| H | CH₃ | H | OCH₃ | H | OCH₃ | H | t-Bu | H |
| H | CH₃ | H | OCH₃ | H | OCH₃ | H | CH₂OCH₃ | H |
| H | CH₃ | H | OEt | H | Cl | H | CH₃ | H |
| H | CH₃ | H | OEt | H | Cl | H | c-Pr | H |
| H | CH₃ | H | OEt | H | Cl | H | t-Bu | H |
| H | CH₃ | H | OEt | H | Cl | H | CH₂F | H |
| H | CH₃ | H | OEt | H | Cl | H | CH₂OCH₃ | H |
| H | CH₃ | H | OEt | H | Cl | H | CH₂OEt | H |
| H | CH₃ | H | OEt | H | Cl | H | CH₂OBu-t | H |
| H | CH₃ | H | OEt | H | Cl | H | CH₂OCH₂CF₃ | H |
| H | CH₃ | H | OEt | H | Cl | H | Si(CH₃)₃ | H |
| H | CH₃ | H | OEt | H | Cl | H | Ph | H |
| H | CH₃ | H | OEt | H | Br | H | CH₃ | H |
| H | CH₃ | H | OEt | H | Br | H | c-Pr | H |
| H | CH₃ | H | OEt | H | Br | H | t-Bu | H |
| H | CH₃ | H | OEt | H | Br | H | CH₂OCH₃ | H |
| H | CH₃ | H | OEt | H | CH₃ | H | CH₃ | H |
| H | CH₃ | H | OEt | H | CH₃ | H | c-Pr | H |
| H | CH₃ | H | OEt | H | CH₃ | H | t-Bu | H |
| H | CH₃ | H | OEt | H | CH₃ | H | CH₂OCH₃ | H |
| H | CH₃ | H | OEt | H | OCH₃ | H | CH₃ | H |
| H | CH₃ | H | OEt | H | OCH₃ | H | c-Pr | H |
| H | CH₃ | H | OEt | H | OCH₃ | H | t-Bu | H |
| H | CH₃ | H | OEt | H | OCH₃ | H | CH₂OCH₃ | H |
| H | CH₃ | H | OPr-n | H | Cl | H | CH₃ | H |
| H | CH₃ | H | OPr-n | H | Cl | H | c-Pr | H |
| H | CH₃ | H | OPr-n | H | Cl | H | t-Bu | H |
| H | CH₃ | H | OPr-n | H | Cl | H | CH₂F | H |
| H | CH₃ | H | OPr-n | H | Cl | H | CH₂OCH₃ | H |
| H | CH₃ | H | OPr-n | H | Cl | H | CH₂OEt | H |
| H | CH₃ | H | OPr-n | H | Cl | H | CH₂OBu-t | H |
| H | CH₃ | H | OPr-n | H | Cl | H | CH₂OCH₂CF₃ | H |
| H | CH₃ | H | OPr-n | H | Cl | H | Si(CH₃)₃ | H |
| H | CH₃ | H | OPr-n | H | Cl | H | Ph | H |
| H | CH₃ | H | OPr-i | H | Cl | H | CH₃ | H |
| H | CH₃ | H | OPr-i | H | Cl | H | c-Pr | H |
| H | CH₃ | H | OPr-i | H | Cl | H | t-Bu | H |
| H | CH₃ | H | OPr-i | H | Cl | H | CH₂F | H |
| H | CH₃ | H | OPr-i | H | Cl | H | CH₂OCH₃ | H |

TABLE 2-continued

| R⁵ | R³ | R⁴ | R¹ | R² | Y¹ | Y² | R⁶ | Y³ |
|---|---|---|---|---|---|---|---|---|
| H | CH₃ | H | OPr-i | H | Cl | H | CH₂OEt | H |
| H | CH₃ | H | OPr-i | H | Cl | H | CH₂OBu-t | H |
| H | CH₃ | H | OPr-i | H | Cl | H | CH₂OCH₂CF₃ | H |
| H | CH₃ | H | OPr-i | H | Cl | H | Si(CH₃)₃ | H |
| H | CH₃ | H | OPr-i | H | Cl | H | Ph | H |
| H | CH₃ | H | OCH₂CF₃ | H | Cl | H | CH₃ | H |
| H | CH₃ | H | OCH₂CF₃ | H | Cl | H | c-Pr | H |
| H | CH₃ | H | OCH₂CF₃ | H | Cl | H | t-Bu | H |
| H | CH₃ | H | OCH₂CF₃ | H | Cl | H | CH₂OCH₃ | H |
| H | CH₃ | H | OCH₂CN | H | Cl | H | CH₃ | H |
| H | CH₃ | H | OCH₂CN | H | Cl | H | c-Pr | H |
| H | CH₃ | H | OCH₂CN | H | Cl | H | t-Bu | H |
| H | CH₃ | H | OCH₂CN | H | Cl | H | CH₂OCH₃ | H |
| H | CH₃ | H | OCH₂CH=CH₂ | H | Cl | H | CH₃ | H |
| H | CH₃ | H | OCH₂CH=CH₂ | H | Cl | H | c-Pr | H |
| H | CH₃ | H | OCH₂CH=CH₂ | H | Cl | H | t-Bu | H |
| H | CH₃ | H | OCH₂CH=CH₂ | H | Cl | H | CH₂OCH₃ | H |
| H | CH₃ | H | OCH₂C≡CH | H | Cl | H | CH₃ | H |
| H | CH₃ | H | OCH₂C≡CH | H | Cl | H | c-Pr | H |
| H | CH₃ | H | OCH₂C≡CH | H | Cl | H | t-Bu | H |
| H | CH₃ | H | OCH₂C≡CH | H | Cl | H | CH₂OCH₃ | H |
| H | CH₃ | H | OCH₂Ph | H | Cl | H | CH₃ | H |
| H | CH₃ | H | OCH₂Ph | H | Cl | H | c-Pr | H |
| H | CH₃ | H | OCH₂Ph | H | Cl | H | t-Bu | H |
| H | CH₃ | H | OCH₂Ph | H | Cl | H | CH₂OCH₃ | H |
| H | CH₃ | H | SCH₂CF₃ | H | Cl | H | CH₃ | H |
| H | CH₃ | H | SCH₂CF₃ | H | Cl | H | c-Pr | H |
| H | CH₃ | H | SCH₂CF₃ | H | Cl | H | t-Bu | H |
| H | CH₃ | H | SCH₂CF₃ | H | Cl | H | CH₂OCH₃ | H |
| H | CH₃ | H | NHOCH₃ | H | Cl | H | CH₃ | H |
| H | CH₃ | H | NHOCH₃ | H | Cl | H | c-Pr | H |
| H | CH₃ | H | NHOCH₃ | H | Cl | H | t-Bu | H |
| H | CH₃ | H | NHOCH₃ | H | Cl | H | CH₂OCH₃ | H |
| H | CH₃ | H | NHOEt | H | Cl | H | CH₃ | H |
| H | CH₃ | H | NHOEt | H | Cl | H | c-Pr | H |
| H | CH₃ | H | NHOEt | H | Cl | H | t-Bu | H |
| H | CH₃ | H | NHOEt | H | Cl | H | CH₂OCH₃ | H |
| H | CH₃ | H | NHOPr-i | H | Cl | H | CH₃ | H |
| H | CH₃ | H | NHOPr-i | H | Cl | H | c-Pr | H |
| H | CH₃ | H | NHOPr-i | H | Cl | H | t-Bu | H |
| H | CH₃ | H | NHOPr-i | H | Cl | H | CH₂OCH₃ | H |
| H | CH₃ | H | NHOBu-s | H | Cl | H | CH₃ | H |
| H | CH₃ | H | NHOBu-s | H | Cl | H | c-Pr | H |
| H | CH₃ | H | NHOBu-s | H | Cl | H | t-Bu | H |
| H | CH₃ | H | NHOBu-s | H | Cl | H | CH₂OCH₃ | H |
| H | CH₃ | H | NHOBu-t | H | Cl | H | CH₃ | H |
| H | CH₃ | H | NHOBu-t | H | Cl | H | c-Pr | H |
| H | CH₃ | H | NHOBu-t | H | Cl | H | t-Bu | H |
| H | CH₃ | H | NHOBu-t | H | Cl | H | CH₂OCH₃ | H |
| H | CH₃ | CH₃ | H | H | Cl | H | CH₃ | H |
| H | CH₃ | CH₃ | H | H | Cl | H | c-Pr | H |
| H | CH₃ | CH₃ | H | H | Cl | H | t-Bu | H |
| H | CH₃ | CH₃ | H | H | Cl | H | CH₂OCH₃ | H |
| H | Et | H | H | H | Cl | H | CH₃ | H |
| H | Et | H | H | H | Cl | H | c-Pr | H |
| H | Et | H | H | H | Cl | H | t-Bu | H |
| H | Et | H | H | H | Cl | H | CH₂OCH₃ | H |
| H | Et | H | OCH₃ | H | Cl | H | CH₃ | H |
| H | Et | H | OCH₃ | H | Cl | H | c-Pr | H |
| H | Et | H | OCH₃ | H | Cl | H | t-Bu | H |
| H | Et | H | OCH₃ | H | Cl | H | CH₂OCH₃ | H |
| H | n-Pr | H | H | H | Cl | H | CH₃ | H |
| H | n-Pr | H | H | H | Cl | H | c-Pr | H |
| H | n-Pr | H | H | H | Cl | H | t-Bu | H |
| H | n-Pr | H | H | H | Cl | H | CH₂OCH₃ | H |
| H | i-Pr | H | H | H | Cl | H | CH₃ | H |
| H | i-Pr | H | H | H | Cl | H | c-Pr | H |
| H | i-Pr | H | H | H | Cl | H | t-Bu | H |
| H | i-Pr | H | H | H | Cl | H | CH₂OCH₃ | H |
| H | —CH₂CH₂— | H | H | H | Cl | H | CH₃ | H |
| H | —CH₂CH₂— | H | H | H | Cl | H | c-Pr | H |
| H | —CH₂CH₂— | H | H | H | Cl | H | t-Bu | H |
| H | —CH₂CH₂— | H | H | H | Cl | H | CH₂OCH₃ | H |
| H | H | —CH₂— | H | H | Cl | H | c-Pr | H |
| H | H | —CH₂CH₂— | H | H | Cl | H | CH₃ | H |
| H | H | —CH₂CH₂— | H | H | Cl | H | c-Pr | H |
| H | H | —CH₂CH₂— | H | H | Cl | H | t-Bu | H |
| H | H | —CH₂CH₂— | H | H | Cl | H | CH₂OCH₃ | H |

TABLE 2-continued

| R⁵ | R³ | R⁴ | R¹ | R² | Y¹ | Y² | R⁶ | Y³ |
|---|---|---|---|---|---|---|---|---|
| H | H | | —CH₂O— | H | Cl | H | CH₃ | H |
| H | H | | —CH₂O— | H | Cl | H | c-Pr | H |
| H | H | | —CH₂O— | H | Cl | H | t-Bu | H |
| H | H | | —CH₂O— | H | Cl | H | CH₂OCH₃ | H |
| H | H | | —CH₂CH₂CH₂— | H | Cl | H | CH₃ | H |
| H | H | | —CH₂CH₂CH₂— | H | Cl | H | c-Pr | H |
| H | H | | —CH₂CH₂CH₂— | H | Cl | H | t-Bu | H |
| H | H | | —CH₂CH₂CH₂— | H | Cl | H | CH₂OCH₃ | H |
| H | H | | —CH₂CH₂CH₂CH₂— | H | Cl | H | CH₃ | H |
| H | H | | —CH₂CH₂CH₂CH₂— | H | Cl | H | c-Pr | H |
| H | H | | —CH₂CH₂CH₂CH₂— | H | Cl | H | t-Bu | H |
| H | H | | —CH₂CH₂CH₂CH₂— | H | Cl | H | CH₂OCH₃ | H |
| H | CH₂F | H | H | H | Cl | H | CH₃ | H |
| c-Pr | CH₂F | H | H | H | Cl | H | CH₃ | H |
| OCH₃ | CH₂F | H | H | H | Cl | H | CH₃ | H |
| H | CH₂F | H | H | H | Cl | H | c-Pr | H |
| c-Pr | CH₂F | H | H | H | Cl | H | c-Pr | H |
| OCH₃ | CH₂F | H | H | H | Cl | H | c-Pr | H |
| H | CH₂F | H | H | H | Cl | H | t-Bu | H |
| c-Pr | CH₂F | H | H | H | Cl | H | t-Bu | H |
| OCH₃ | CH₂F | H | H | H | Cl | H | t-Bu | H |
| H | CH₂F | H | H | H | Cl | H | CH₂OCH₃ | H |
| c-Pr | CH₂F | H | H | H | Cl | H | CH₂OCH₃ | H |
| OCH₃ | CH₂F | H | H | H | Cl | H | CH₂OCH₃ | H |

The compounds of the present invention are capable of controlling pathogens causing plant diseases in Tracheophyta such as plants of the order Pinales, the group magnoliids, the group monocots and the group eudicots, and pathogens causing infections of Vertebrata such as animals of the class Mammalia, the class Aves, the class Reptilia and the class Actinopterygii, and pests such as plant-parasitic or animal-parasitic nematodes, Acanthocephala, Platyhelminthes and Protozoa.

Pests against plants may, for example, be fungi of the phylum Ascomycota, fungi of the phylum Basidiomycota, fungi of the phylum Chitridiomycota, fungi of the phylum Blastocladiomycota, fungi of the phylum Mucoromycotina, protists of the phylum Cercozoa, microorganisms of the phylum Heterokontophyta class Oomycetes, gram-positive bacteria of the phylum Actinobacteria, gram-positive bacteria of the phylum Tenericutes, gram-negative bacteria of the phylum Proteobacteria, nematodes of the order Aphelenchida and nematodes of the order Tylenchida. The compounds of the present invention have excellent controlling effect particularly on plant pathogenic fungi belonging to the phylum Ascomycota and the phylum Basidiomycota, and plant-parasitic nematodes belonging to the order Aphelenchida and the order Tylenchida at low doses.

Pests against animals may, for example, be fungi of the phylum Ascomycota, fungi of the phylum Basidiomycota, gram-positive bacteria of the phylum Actinobacteria, gram-positive bacteria of the phylum Firmicutes, gram-positive bacteria of the phylum Tenericutes, gram-negative bacteria of the phylum Proteobacteria, nematodes of the order Enoplida, nematodes of the order Rhabditida, nematodes of the order Strongylida, nematodes of the order Ascaridida, nematodes of the order Spirurida, microorganisms of the phylum Acanthocephala, cestodes of the order Pseudophyllidea, cestodes of the order Cyclophyllidea, trematodes of the order Strigeidida, trematodes of the order Echinostomida, trematodes of the order Plagiorchiida, trematodes of the order Opisthorchiida, amebas, *Piroplasmida sporozoa, Haemosporida sporozoa, Eucoccidiorida sporozoa, Vestibuliferida ciliata, Trichomonadida flagellata, Diplomonadida flagellata* and *Kinetoplastida flagellata*. Particularly, the compounds of the present invention have excellent effect to control internal parasites parasitizing animals of the class Mammalia belonging to the family Cebidae, the family Cercopithecidae, the family Hominidae, the family Leporidae, the family Chinchillidae, the family Caviidae, the family Cricetidae, the family Muridae, the family Sciuridae, the family Camelidae, the family Suidae, the family Cervidae, the family Bovidae, the family Felidae, the family Canidae, the family Mustelidae, the family Equidae, the family Macropodidae and the like, especially animal-parasitic nematodes belonging to the order Enoplida, the order Rhabditida, the order Strongylida, the order Aphelenchida, the order Tylenchida, the order Ascaridida and the order Spirurida, parasitizing mammals of the family Suidae, the family Bovidae, the family Felidae, the family Canidae and the family Equidae.

The compounds of the present invention are also effective on pests which have acquired resistance to conventional fungicides or nematicides, and the compounds of the present invention have very useful characteristics such that they have little harmful effect on non-target animals such as mammals, fishes, crustaceans, natural enemies and useful insects.

The compounds of the present invention may be used in any dosage form such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet or an emulsifiable gel usually after mixed with an appropriate solid carrier or a liquid carrier, and if necessary, with a surfactant, a penetrant, a spreader, a thickener, an anti-freezing agent, a binder, an anti-caking agent, a disintegrant, an antifoaming agent, a preservative, a stabilizer or the like. A formulation in an arbitrary dosage form may be sealed in water-soluble packaging such as a water-soluble capsule or a water-soluble film, for labor saving or improved safety.

As solid carriers, natural minerals such as quartz, calcite, meerschaum, dolomite, chalk, kaolinite, pyrophyllite, sericite, halloysite, methahalloysite, kibushi clay, gairome clay, pottery stone, zeeklite, allophone, Shirasu, mica, talc, bentonite, activated clay, acid clay, pumice, attapulgite, zeolite and diatomaceous earth, calcined natural minerals such as calcined clay, pearlite, Shirasu-balloons, vermiculite, attapulgus clay and calcined diatomaceous earth, inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride, saccharides such as glucose, fructose, sucrose and lactose, polysaccharides such as starch, cellulose powder and dextrin, organic substances such as urea, urea derivatives, benzoic acid and benzoic acid salts, plants such as wood flour, powdered cork, corncob, walnut shell and tobacco stems, fly ash, white carbon (such as hydrated synthetic silica, anhydrous synthetic silica and hydrous synthetic silicate), fertilizers and the like may be mentioned.

As liquid carriers, aromatic hydrocarbons such as xylene, alkyl ($C_9$ or $C_{10}$ etc.) benzene, phenylxylylethane and alkyl ($C_1$ or $C_3$ etc.)naphthalene, aliphatic hydrocarbons such as machine oil, normalparaffin, isoparaffin and naphthene, mixtures of aromatic hydrocarbons and aliphatic hydrocarbons such as kerosene, alcohols such as ethanol, isopropanol, cyclohexanol, phenoxyethanol and benzyl alcohol, polyhydric alcohols such as ethylene glycol, propylene glycol, diethylene glycol, hexylene glycol, polyethylene glycol and polypropylene glycol, ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether, ketones such as acetophenone, cyclohexanone and γ-butyrolactone, esters such as fatty acid methyl esters, dialkyl succinates, dialkyl glutamate, dialkyl adipates and dialkyl phthalates, acid amides such as N-alkyl ($C_1$, $C_8$ or $C_{12}$ etc.) pyrrolidone, fats and oils such as soybean oil, linseed oil, rapeseed oil, coconut oil, cottonseed oil and castor oil, dimethyl sulfoxide, water and the like may be mentioned.

These solid and liquid carriers may be used alone or in combinations of two or more.

As surfactants, nonionic surfactants such as polyoxyethylene alkyl ether, polyoxyethylene alkyl(mono or di)phenyl ether, polyoxyethylene(mono, di or tri)styrylphenyl ether, polyoxyethylenepolyoxypropylene block copolymers, polyoxyethylene fatty acid (mono or di)ester, sorbitan fatty acid ester, polyoxyethylene sorbitan fatty acid ester, ethylene oxide adducts of castor oil, acetylene glycol, acetylene alcohol, ethylene oxide adducts of acetylene glycol, ethylene oxide adducts of acetylene alcohol and alkyl glycosides, anionic surfactants such as alkyl sulfate salts, alkylbenzenesulfonic acid salts, lignin sulfonate, alkylsulfosuccinic acid salts, naphthalenesulfonic acid salts, alkylnaphthalenesulfonic acid salts, salts of naphthalenesulfonic acid-formalin condensates, salts of alkylnaphthalenesulfonic acid-formalin condensates, polyoxyethylene alkyl ether sulfate or phosphate salts, polyoxyethylene(mono or di) alkylphenyl ether sulfate or phosphate salts, polyoxyethylene(mono, di or tri)styrylphenyl ether sulfate or phosphate salts, polycarboxylic acid salts (such as polyacrylates, polymaleates and copolymers of maleic acid and an olefin) and polystyrenesulfonic acid salts, cationic surfactants such as alkylamine salts and alkyl quaternary ammonium salts, amphoteric surfactants such as amino acid types and betaine types, silicone surfactants and fluorine surfactants may be mentioned.

The amount of these surfactants is usually preferably from 0.05 to 30 parts by weight, more preferably from 0.5 to 20 parts by weight, per 100 parts by weight of the agent of the present invention, though there is no particular restrictions. These surfactants may be used alone or in combination of two or more.

The suitable application dose of the compounds of the present invention is usually from 0.005 to 50 kg per hectare (ha) in terms of the active ingredient, though it varies depending on the application situation, the application season, the application method and the cultivated crop.

When the compounds of the present invention are used to control internal parasites in mammals and birds as farm animals/poultry and companion animals, the compounds of the present invention may be administered in an effective amount together with pharmaceutically acceptable additives orally, parenterally by injection (intramuscular, subcutaneously, intravenously or intraperitoneally); percutaneously by dipping, spraying, bathing, washing, pouring-on and spotting-on and dusting, or intranasally. The compounds of the present invention may be administered through molded articles such as chips, plates, bands, collars, ear marks, limb bands and ID tags. The compounds of the present invention are administered in an arbitrary dosage form suitable for the administration route.

The dosage form may be a solid preparation such as a dust, a granule, a wettable powder, a pellet, a tablet, a ball, a capsule and an molded article containing an active ingredient, a liquid preparation such as an injection fluid, an oral liquid, a liquid preparation applied to the skin or coelom, a pour-on preparation, a spot-on preparation, a flowable, an emulsion, and a semisolid preparation such as an ointment and a gel.

A solid preparation may generally be used by oral administration or by percutaneous or by environmental application after dilution with water or the like. A solid preparation can be prepared by mixing an active ingredient with an appropriate vehicle, and with an adjuvant if necessary, and formulating the mixture into a desired dosage form.

As the vehicle, an inorganic vehicle such as a carbonate, a hydrogen carbonate, a phosphate, aluminum oxide, silica or clay or an organic vehicle such as a saccharide, cellulose, cereal flour or starch may, for example, be mentioned.

An injection fluid may be administered intravenously, intramuscularly or subcutaneously. An injection fluid can be prepared by dissolving an active ingredient in an appropriate solvent and, if necessary, adding additives such as a solubilizer, an acid, a base, a buffering salt, an antioxidant and a protectant.

As solvents, water, ethanol, butanol, benzyl alcohol, glycerin, propylene glycol, polyethylene glycol, N-methylpyrrolidone and mixtures thereof, physiologically acceptable vegetable oils and synthetic oils suitable for injection may be mentioned.

As solubilizers, polyvinylpyrrolidone, polyoxyethylated castor oil, polyoxyethylated sorbitan ester, etc. may be mentioned.

As protectants, benzyl alcohol, trichlorobutanol, p-hydroxybenzoic acid esters, n-butanol, etc. may be mentioned.

An oral liquid may be administered directly or after dilution. Or, it can be prepared in the same manner as an injection fluid.

A flowable, an emulsion or the like may be administered directly or after dilution percutaneously or by environmental application.

A liquid preparation to be applied to the skin is administered by dripping, spreading, rubbing, spraying, sprinkling or dipping (soaking, bathing or washing) and can be prepared in the same manner as an injection fluid.

A pour-on preparation and a spot-on preparation are dripped or sprayed to a limited area of the skin so that they permeate through the skin and act systemically. A pour-on preparation and a spot-on preparation can be prepared by dissolving, suspending or emulsifying an active ingredient in an appropriate skin-friendly solvent or solvent mixture. If necessary, additives such as a surfactant, a colorant, an absorbefacient, an antioxidant, a light stabilizer and an adhesive may be added.

As appropriate solvents, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methylpyrrolidone or 2,2-dimethyl-4-oxy-methylene-1,3-dioxolane may be mentioned.

As absorbefacients, DMSO, isopropyl myristate, pelargonic acid dipropylene glycol, silicone oil, fatty acid esters, triglycerides and aliphatic alcohols may be mentioned.

As antioxidants, sulfites, metabisulfites, ascorbic acid, butylhydroxytoluene, butylhydroxyanisole and tocopherol may be mentioned.

An emulsion may be administered orally, percutaneously or by injection. An emulsion can be prepared by dissolving an active ingredient in a hydrophobic phase or a hydrophilic phase and homogenizing the resulting solution with another liquid phase together with an appropriate emulsifier, and further if necessary with additives such as a colorant, an absorbefacient, a protectant, an antioxidant, a light screen and a thickener.

As hydrophobic phases (oils), paraffin oil, silicone oil, sesame oil, almond oil, castor oil, synthetic triglycerides, ethyl stearate, di-n-butyryl adipate, hexyl laurate, pelargonic acid dipropylene glycol, esters of branched short-chain fatty acids with $C_{16}$-$C_{18}$ saturated fatty acids, isopropyl myristate, isopropyl palmitate, esters of $C_{12}$-$C_{18}$ saturated alcohols with caprylic/capric acid, isopropyl stearate, oleyl oleate, decyl oleate, ethyl oleate, ethyl lactate, fatty acid ester waxes, dibutyl phthalate, diisopropyl adipate, isotridecyl alcohol, 2-octyldodecanol, cetylstearyl alcohol, oleyl alcohol, etc. may be mentioned.

As hydrophilic phases, water, propylene glycol, glycerin, sorbitol, etc. may be mentioned.

As emulsifiers, nonionic surfactants such as polyoxyethylated castor oil, polyoxyethylated sorbitan monoolefinic acid, sorbitan monostearate, glycerin monostearate, polyoxyethyl stearate and alkyl phenol polyglycol ether, amphoteric surfactants such as disodium N-lauryl-β-iminodipropionate and lecithin; anionic surfactants such as sodium lauryl sulfate, aliphatic alcohol sulfate ether, mono/dialkylpolyglycol orthophosphate monoethanolamine salt; and cationic surfactants such as cetyltrimethylammonium chloride may, for example, be mentioned.

As other additives, carboxymethylcellulose, methylcellulose, polyacrylate, alginate, gelatin, gum arabic, polyvinylpyrrolidone, polyvinyl alcohol, methyl vinyl ether, maleic anhydride copolymers, polyethylene glycol, waxes, colloidal silica, etc. may be mentioned.

A semisolid preparation is administered by applying or spreading onto the skin or introducing into the coelom.

A gel can be prepared by adding a thickener to a solution prepared in the same manner as an injection fluid sufficiently to give a transparent viscous substance like an ointment.

Formulation examples of preparations using the compounds of the present invention are given below. However, formulations of the present invention are by no means restricted thereto. In the following formulation examples, "parts" means parts by weight.

[Wettable Powder]

| | |
|---|---|
| Compound of the present invention | 0.1 to 80 parts |
| Solid carrier | 5 to 98.9 parts |
| Surfactant | 1 to 10 parts |
| Others | 0 to 5 parts |

As the others, an anti-caking agent, a stabilizer and the like may be mentioned.

[Emulsifiable Concentrate]

| | |
|---|---|
| Compound of the present invention | 0.1 to 30 parts |
| Organic solvent | 45 to 95 parts |
| Surfactant | 4.9 to 30 parts |
| Water | 0 to 50 parts |
| Others | 0 to 10 parts |

As the others, a spreader, a stabilizer and the like may be mentioned.

[Suspension Concentrate]

| | |
|---|---|
| Compound of the present invention | 0.1 to 70 parts |
| Liquid carrier | 15 to 98.89 parts |
| Surfactant | 1 to 12 parts |
| Others | 0.01 to 30 parts |

As the others, an anti-freezing agent, a thickener and the like may be mentioned.

[Water Dispersible Granule]

| | |
|---|---|
| Compound of the present invention | 0.1 to 90 parts |
| Solid carrier | 0 to 98.9 parts |
| Surfactant | 1 to 20 parts |
| Others | 0 to 10 parts |

As the others, a binder, a stabilizer and the like may be mentioned.

[Soluble Concentrate]

| | |
|---|---|
| Compound of the present invention | 0.01 to 70 parts |
| Liquid carrier | 20 to 99.99 parts |
| Others | 0 to 10 parts |

As the others, an anti-freezing agent, a spreader and the like may be mentioned.

[Granule]

| | |
|---|---|
| Compound of the present invention | 0.01 to 80 parts |
| Solid carrier | 10 to 99.99 parts |
| Others | 0 to 10 parts |

As the others, a binder, a stabilizer and the like may be mentioned.

[Dustable Powder]

| | |
|---|---|
| Compound of the present invention | 0.01 to 30 parts |
| Solid carrier | 65 to 99.99 parts |
| Others | 0 to 5 parts |

As the others, an anti-drift agent, a stabilizer and the like may be mentioned.

Next, more specific examples of preparations containing compounds of the present invention as an active ingredient are given below. However, the present invention is by no means restricted thereto.

In the following Formulation Examples, "parts" means parts by weight.

[Formulation Example 1] Wettable Powder

| | |
|---|---|
| Compound No. 1-002 of the present invention | 20 parts |
| Pyrophyllite | 74 parts |
| Sorpol 5039 | 4 parts |
| (tradename for a mixture of a nonionic surfactant and an anionic surfactant: manufactured by TOHO Chemical Industry Co., Ltd.) | |
| CARPLEX #80D | 2 parts |
| (hydrous synthetic silicic acid: tradename manufactured by Shionogi & Co., Ltd.) | |

The above ingredients are mixed and pulverized homogenously to obtain a wettable powder.

[Formulation Example 2] Emulsifiable Concentrate

| | |
|---|---|
| Compound No. 1-017 of the present invention | 5 parts |
| Xylene | 75 parts |
| N-methylpyrrolidone | 15 parts |
| Sorpol 2680 | 5 parts |
| (tradename for a mixture of a nonionic surfactant and an anionic surfactant: manufactured by TOHO Chemical Industry Co., Ltd.) | |

The above ingredients are mixed homogenously to obtain an emulsifiable concentrate.

[Formulation Example 3] Emulsifiable Concentrate

| | |
|---|---|
| Compound No. 3-001 of the present invention | 4 parts |
| DBE | 36 parts |
| (tradename for a mixture of dimethyl adipate, dimethyl glutarate and dimethyl succinate: manufactured by INVISTA) | |
| Diisobutyl adipate | 30 parts |
| N-methylpyrrolidone | 10 parts |
| Soprofol BSU | 14 parts |
| (tradename for a nonionic surfactant: manufactured by Rhodia Nicca. Ltd.) | |
| Rhodacal 70BC | 6 parts |
| (tradename for an anionic surfactant: manufactured by Rhodia Nicca. Ltd.) | |

The above ingredients are mixed homogenously to obtain an emulsifiable concentrate.

[Formulation Example 4] Emulsifiable Concentrate

| | |
|---|---|
| Compound No. 3-016 of the present invention | 4 parts |
| DBE | 11 parts |
| (tradename for a mixture of dimethyl adipate, dimethyl glutarate and dimethyl succinate: manufactured by INVISTA) | |
| Diisobutyl adipate | 30 parts |
| N-methylpyrrolidone | 5 parts |
| Soprofol BSU | 14 parts |
| (tradename for a nonionic surfactant: manufactured by Rhodia Nicca. Ltd.) | |
| Rhodacal 70BC | 6 parts |
| (tradename for an anionic surfactant: manufactured by Rhodia Nicca. Ltd.) | |
| Propylene glycol | 10 parts |
| Water | 20 parts |

The above ingredients are mixed homogenously to obtain an emulsifiable concentrate.

[Formulation Example 5] Suspension Concentrate

| | |
|---|---|
| Compound No. 3-016 of the present invention | 25 parts |
| AGRISOL S-710 | 10 parts |
| (tradename for a nonionic surfactant: manufactured by Kao Corporation) | |
| Lunox 1000C | 0.5 part |
| (tradename for an anionic surfactant: manufactured by TOHO Chemical Industry Co., Ltd.) | |
| Xanthan gum | 0.2 part |
| Water | 64.3 parts |

The above ingredients are mixed homogenously and wet-pulverized to obtain a suspension concentration.

[Formulation Example 6] Water Soluble Granule

| | |
|---|---|
| Compound No. 3-016 of the present invention | 75 parts |
| HITENOL NE-15 | 5 parts |
| (tradename for an anionic surfactant: manufactured by Dai-ichi Kogyo Seiyaku Co., Ltd.) | |
| VANILLEX N | 10 parts |
| (tradename for an anionic surfactant: manufactured by Nippon Paper Industries Co., Ltd.) | |
| CARPLEX #80D | 10 parts |
| (tradename for hydrous synthetic silicic acid: manufactured by Shionogi & Co., Ltd.) | |

The above ingredients are mixed and pulverized homogenously, then kneaded with a small amount of water, granulated through an extrusion granulator and dried to obtain a water soluble granule.

[Formulation Example 7] Granule

| | |
|---|---|
| Compound No. 8-001 of the present invention | 5 parts |
| Bentonite | 50 parts |
| Talc | 45 parts |

The above ingredients are mixed and pulverized homogenously, then kneaded with a small amount of water, granulated through an extrusion granulator and dried to obtain a granule.

[Formulation Example 8] Dustable Powder

| | |
|---|---|
| Compound No. 9-006b of the present invention | 3 parts |
| CARPLEX #80D | 0.5 part |
| (tradename for a hydrous synthetic silicic acid: manufactured by Shionogi & Co., Ltd.) | |
| Kaolinite | 95 parts |
| Diisopropyl phosphate | 1.5 parts |

The above ingredients are mixed and pulverized homogeneously to obtain a dustable powder.

It is applied after diluted with water by a factor of from 1 to 20000 so as to achieve an active ingredient concentration of from 0.005 to 50 kg/ha.

[Formulation Example 9] Wettable Powder Preparation

| | |
|---|---|
| Compound No. 1-002 of the present invention | 25 parts |
| Sodium diisobutylnaphthalenesulfonate | 1 part |
| Calcium n-dodecylbenzenesulfonate | 10 parts |
| Alkyl aryl polyglycol ether | 12 parts |
| Naphthalenesulfonic acid-formalin condensate sodium salt | 3 parts |
| Silicone emulsion | 1 part |
| Silicon dioxide | 3 parts |
| Kaolin | 45 parts |

[Formulation Example 10] Water-Soluble Concentrate Preparation

| | |
|---|---|
| Compound No. 1-017 of the present invention | 20 parts |
| Polyoxyethylenelauryl ether | 3 parts |
| Sodium dioctylsulfosuccinate | 3.5 parts |
| Dimethyl sulfoxide | 37 parts |
| 2-Propanol | 36.5 parts |

[Formulation Example 11] Liquid Preparation for Spraying

| | |
|---|---|
| Compound No. 3-001 of the present invention | 2 parts |
| Dimethyl sulfoxide | 10 parts |
| 2-Propanol | 35 parts |
| Acetone | 53 parts |

[Formulation Example 12] Liquid Preparation for Percutaneous Administration

| | |
|---|---|
| Compound No. 3-016 of the present invention | 5 parts |
| Hexylene glycol | 50 parts |
| Isopropanol | 45 parts |

[Formulation Example 13] Liquid Preparation for Percutaneous Administration

| | |
|---|---|
| Compound No. 3-021 of the present invention | 5 parts |
| Propylene glycol monomethyl ether | 50 parts |
| Dipropylene glycol | 45 parts |

[Formulation Example 14] Liquid Preparation for Percutaneous Administration (by Dripping)

| | |
|---|---|
| Compound No. 1-002 of the present invention | 2 parts |
| Light liquid paraffin | 98 parts |

[Formulation Example 15] Liquid Preparation for Percutaneous Administration (by Dripping)

| | |
|---|---|
| Compound No. 1-017 of the present invention | 2 parts |
| Light liquid paraffin | 58 parts |
| Olive oil | 30 parts |
| ODO-H | 9 parts |
| Shin-etsu silicone | 1 part |
| (tradename for silicone: manufactured by Shin-etsu Chemical Co., Ltd.) | |

For use as agricultural fungicides or nematicides, the compounds of the present invention in effective amounts may be used alone as active ingredients, or if necessary, the compounds of the present invention may be mixed with other fungicides, other nematicides, insecticides, miticides, plant growth regulators, herbicides, synergists, fertilizers, soil conditioners and the like at the time of formulation or application.

Further, for use as endoparasite, the compounds of the present invention in effective amounts may be applied alone as active ingredients, or if necessary, they may be mixed with other antibiotics, other anthelmintic and the like at the time of formulation or application.

Particularly, the combined use with other fungicides, other nematicides, other antibiotics, other anthelmintic or the like is expected to broaden the pesticidal spectrum by the additive or synergistic effect of the other agrochemicals, to improve the pesticidal effect, to reduce the application cost by enabling control at lower doses, and further, to prolong the pesticidal effect for a long period of time. Particularly, the combined use with other fungicides, nematicides, antibiotics or anthelmintic differing in the mechanism of action is a very useful controlling method with a view to preventing the pests from acquiring resistance to pesticides. In such cases, they may be combined with a plurality of known fungicides, known nematicides, known insecticides, known miticides, known antibiotics or known anthelmintic simultaneously.

The fungicides, nematicides, insecticides, miticides, anthelmintic and antibiotics to be used in combination with the compounds of the present invention include, for example, the compounds disclosed in e.g. The Pesticidal Manual, 16th edition, 2012. Specifically, their common names will be exemplified below, but useful agents are not limited thereto.

Fungicides:
A: Nucleic Acid Biosynthesis Inhibitors
  benalaxyl, benalaxyl-M, furalaxyl, metalaxyl, metalaxyl-M, ofurace, oxadixyl,
  bupirimate, ethirimol,
  hymexazol,
B: Mitosis and Cell Division Inhibitors
  benomyl, carbendazim, fuberidazole, thiabendazole, thiophanate-methyl,
  diethofencarb,
  ethaboxam, zoxamide,
  pencycuron,
  fluopicolide,
C: Respiration Inhibitors
  diflumetorim,
  benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, pyraziflumid, sedaxane, thifluzamide,
  azoxystrobin, coumoxystrobin, dimoxystrobin, enestrobin, enoxastrobin, famoxadone, fenamidone, fenaminstrobin, flufenoxystrobin, fluoxastrobin, kresoxim-methyl, mandestrobin, metominostrobin, orysastrobin, picoxystrobin, pyraclostrobin, pyrametostrobin, pyraoxystrobin, pyribencarb-methyl, pyriminostrobin, triclopyricab, trifloxystrobin,
  amisulbrom, cyazofamid,
  dinocap, fluazinam, meptyldinocap,
  fentin, tributyltin oxide,
  silthiofam,
  ametoctradin,
D: Amino Acid and Protein Biosynthesis Inhibitors
  cyprodinil, mepanipyrim, pyrimethanil,
  blasticidin-S,
  kasugamycin,
E: Drugs acting on the signaling system
  proquinazid, quinoxyfen,
  fenpiclonil, fludioxonil,
  chlozolinate, iprodione, procymidone, vinclozolin,
F: Lipid Synthesis and Cell Membrane Formation Inhibitors
  edifenphos, iprobenfos, isoprothiolane, pyrazophos,
  biphenyl, chloroneb, dicloran, etridiazole, quintozene, tecnazene, tolclofos-methyl,
  propamocarb hydrochloride,
  *Bacillus subtilis*, Strain: D747, FZB24, GBO3, HA10404, MBI600, QST713, Y1336, etc.,
G: Sterol Biosynthesis Inhibitors
  azaconazole, bitertanol, bromuconazole, cyproconazole, difenoconazole, diniconazole, diniconazole-M, epoxiconazole, etaconazole, fenarimol, fenbuconazole, fluquinconazole, flusilazole, flutriafol, hexaconazole, imazalil, imibenconazole, ipconazole, metconazole, myclobutanil, nuarimol, oxpoconazole fumarate, pefurazoate, penconazole, prochloraz, propiconazole, prothioconazole, pyrifenox, pyrisoxazole, simeconazole, tebuconazole, tetraconazole, triadimefon, triadimenol, triflumizole, triforine, triticonazole,
  aldimorph, dodemorph-acetate, fenpropidin, fenpropimorph, piperalin, spiroxamine, tridemorph,
  fenhexamid, fenpyrazamine,
H: Cell Wall Synthesis Inhibitors
  validamycin,
  polyoxins, polyoxorim,
  benthiavalicarb-isopropyl, dimethomorph, flumorph, iprovalicarb, mandipropamid, pyrimorph, valifenalate,
I: Melanin Synthesis Inhibitors
  phthalide, pyroquilon, tricyclazole,
  carpropamid, diclocymet, fenoxanil,
P: Resistance of Plants Inducing Agents
  acibenzolar-S-methyl,
  probenazole,
  isotianil, tiadinil,
  laminarin,
M: Drugs of Multi-Point of Action
  bordeaux mixture, cheshunt mixture, copper carbonate basic, copper hydroxide, copper naphthenate, copper oleate, copper oxychloride, copper sulfate, copper sulfate basic, oxine copper, calcium polysulfide, sulfur, amobam, ferbam, mancozeb, maneb, metiram, polycarbamate, propineb, thiram, ziram, captan, folpet, chlorothalonil, dichlofluanid, tolylfluanid, guazatine, iminoctadine-albesilate, iminoctadine-triacetate, anilazine, dithianon, chinomethionat, fluoroimide,
and
U: Mechanism of Action Unknown and Other Agents
  cyflufenamid, cymoxanil, diclomezine, dipymetitrone, dodine, ferimzone, flusulfamide, flutianil, fosetyl-aluminium, metrafenone, oxathiapiprolin, picarbutrazox, pyriofenone, tebufloquin, tolprocarb, triazoxide, potassium hydrogen carbonate, sodium hydrogen carbonate, shiitake mushroom mycelium extract, shiitake mushroom fruiting body extract, BCF-082 (test name), ZF-9646 (test name), etc.
Insecticides, Acaricides:
1: Acetylcholinesterase (AChE) Inhibitors
  alanycarb, aldicarb, bendiocarb, benfuracarb, butocarboxim, carbaryl, carbofuran, carbosulfan, ethiofencarb, fenobucarb, formetanate, furathiocarb, isoprocarb, methiocarb, methomyl, pirimicarb, thiodicarb, thiofanox, triazamate,
  acephate, azamethiphos, azinphos-ethyl, azinphos-methyl, chlorethoxyfos, chlorfenvinphos, chlormephos, chlorpyrifos, chlorpyrifos-methyl, cyanophos, diazinon, dichlorvos, dimethoate, dimethylvinphos, disulfoton, EPN, fenitrothion, fenthion, isoxathion, malathion, methamidophos, methidathion, omethoate, oxydemeton-methyl, parathion-methyl, phenthoate, phorate, phosalone, phosmet, phoxim, pirimiphos-methyl, profenofos, prothiofos, pyraclofos, sulfotep, terbufos, tetrachlorvinphos, thiometon, trichlorfon,
2: GABA-Gated Chloride Channel Antagonists
  endosulfan, alpha-endosulfan,
  ethiprole, fipronil, flufiprole, pyriprole,
  afoxolaner, fluralaner, lotilaner, sarolaner,
3: Sodium Channel Modulators
  acrinathrin, allethrin, benfluthrin, bifenthrin, kappa-bifenthrin, bioallethrin, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, zeta-cypermethrin, cyphenothrin, deltamethrin, empenthrin, esfenvalerate, etofenprox, fenpropathrin, fenvalerate, flucythrinate, flumethrin, fluvalinate, tau-fluvalinate, halfenprox, heptafluthrin, imiprothrin, meperfluthrin, metofluthrin, permethrin, phenothrin, pyrethrins, resmethrin, silafluofen, tefluthrin, kappa-tefluthrin, tetramethrin, d-tetramethrin, tetramethylfluthrin, tralomethrin, transfluthrin,
  methoxychlor, 4: Nicotinic Acetylcholine Receptor (nAChR) Agonists
  acetamiprid, clothianidin, dinotefuran, imidacloprid, nitenpyram, thiacloprid, thiamethoxam,
  sulfoxaflor,
  flupyradifurone,
5: Nicotinic Acetylcholine Receptor (nAChR) Allosteric Modulators
  spinetoram, spinosad,
6: Chloride Ion Channel Activators
  abamectin, emamectin-benzoate, lepimectin, milbemectin,
7: Juvenile Hormone Similar Agents
  methoprene,
  fenoxycarb,
  pyriproxyfen,
9: Hemiptera Selective Feeding Inhibitors
  pymetrozine,
  flonicamid,
10: Mite Growth Inhibitors
  clofentezine, hexythiazox,
  etoxazole,
11: Microorganism-Derived Insect Intestinal Membrane Disrupting Agents
  *bacillus thuringiensis*, subsp. *israelensis*, subsp. *aizawai*, subsp. *kurstaki*, subsp. *tenebrionis*, etc.,
12: Mitochondrial ATP Synthase Inhibitors
  diafenthiuron,
  azocyclotin, fenbutatin oxide,
  propargite,
13: Oxidative Phosphorylation Uncouplers
  chlorfenapyr,
14: Nicotinic Acetylcholine Receptor (nAChR) Channel Blockers
  bensultap, cartap, thiocyclam,
15: Chitin Biosynthesis Inhibitors (Type 0)
  bistrifluron, chlorfluazuron, diflubenzuron, flucycloxuron, flufenoxuron, hexaflumuron, lufenuron, novaluron, noviflumuron, teflubenzuron, triflumuron,
16: Chitin Biosynthesis Inhibitors (Type 1)
  buprofezin,
17: Molting Inhibitors (Diptera Insect)
  cyromazine,
18: Molting Hormone (Ecdysone) Receptor Agonists
  chromafenozide, halofenozide, methoxyfenozide, tebufenozide,
19: Octopamine Receptor Agonists
  amitraz,
20: Mitochondrial Electron Transport Chain Complex III Inhibitors
  hydramethylnon,
  acequinocyl,
  fluacrypyrim,
21: Mitochondrial Electron Transport Chain Complex I Inhibitors
  fenazaquin, fenpyroximate, pyrimidifen,pyridaben, tebufenpyrad, tolfenpyrad,
  rotenone,
22: Voltage-Dependent Sodium Channel Blockers
  indoxacarb, indoxacarb-MP,
  metaflumizone,
23: Acetyl CoA Carboxylase Inhibitors
  spirodiclofen, spiromesifen, spirotetramat,
25: Mitochondrial Electron Transport System Complex II Inhibitors
  cyenopyrafen, cyflumetofen,
28: Ryanodine Receptor Modulators
  chlorantraniliprole, cyantraniliprole, cyclaniliprole, flubendiamide, tetraniliprole,
  and
UN: Mechanism of Action Unknown and Other Drugs
  azadirachtin, benzoximate, bifenazate, bromopropylate, dicofol, pyridalyl, pyrifluquinazon,
  afidopyropen, broflanilide, dicloromezotiaz, flometoquin, fluhexafon, pyflubumide, triflumezopyrim, ME5382 (test name), NA-89 (test name), NC-515 (test name), ZDI2501 (test name), etc.

Nematicides: cadusafos, dichlofenthion, ethoprophos, fenamiphos, fluensulfone, fosthiazate, fosthietan, imicyafos, isamidofos, isazofos, methyl bromide, methyl isothiocyanate, oxamyl, sodium azide, tioxazafen, BYI-1921 (test name), MAI-08015 (test name), etc.

Anthelmintics: acriflavine, albendazole, atovaguone, azithromycin, bithionol, bromofenofos, cambendazole, camidazole, chloroquine, clazuril, clindamycin hydrochloride, clorsulon, closantel, coumaphos, cymiazol, dichlorophen, diethylcarbamazine, diminazene, disophenol, dithiazanine iodide, doxycycline hydrochloride, doramectin, emodepside, eprinomectin, febantel, fenbendazole, flubendazole, furazolidone, glycalpyramide, imidocarb, ivermectin, levamisole, mebendazole, mefloquine, melarsamine hydrochloride, metronidazole, metyridine, milbemycin oxime, monepantel, morantel tartrate, moxidectin, nicarbazin, niclosamide, nitroscanate, nitroxynil, omphalotin, oxantel pamoate, oxantel tartrate, oxfendazolee, oxibendazole, oxyclozanide, pamaquine, phenothiazine, piperazine adipate, piperazine citrate, piperazine phosphate, PNU-97333 (paraherquamide A), PNU-141962 (2-deoxyparaherquamide), praziquantel, primaquine, propetamphos, propoxur, pyrantel pamoate, pyrimethamine, santonin, selamectin, sulfadimethoxine, sulfadoxine, sulfamerazine, sulfamonomethoxine, sulfamoildapsone, thiabendazole, tinidazole, toltrazuril, tribromsalan, triclabendazole, etc.

Antifungal agents: climbazole, ketoconazole, miconazole nitrate, etc.

Antimicrobials: amoxicillin, ampicillin, bethoxazin, bithionol, bronopol, cefapirin, cefazolin, cefquinome, ceftiofur, chlortetracycline, clavulanic acid, danofloxacin, difloxacin, dinitolmide, enrofloxacin, florfenicol, lincomycin, lomefloxacin, marbofloxacin, miloxacin, mirosamycin, nitrapyrin, norfloxacin, octhilinone, ofloxacin, orbifloxacin, oxolinic acid, oxytetracycline, penicillin, streptomycin, thiamphenicol, tiamulin fumarate, tilmicosin phosphate, acetylisovaleryltylosin, tylosin phosphate, tulathromycin, valnemulin, calcined shell calcium (calcium oxide), *Talaromyces* genus, *Trichoderma*, Koniochiriumu spp., etc.

EXAMPLES

In the following, the present invention will be described in further detail by specifically describing Synthesis Examples and Test Examples of the compounds of the present invention as Examples, but the present invention is by no means limited thereto.

Synthesis Example 1

N-[2-[3-chloro-5-(3,3-dimethyl-1-butynyl)pyridin-2-yl]ethyl]-2-(trifluoromethyl)benzamide (Compound No. 1-003 of the present invention)

Step 1: Production of 2-(5-bromo-3-chloropyridin-2-yl)-2-[[2-(trifluoromethyl)benzamide]methyl]malonic acid diethyl ester To a 30 ml solution of 3.00 g of 2-(5-bromo-3-chloropyridin-2-yl)malonic acid diethyl ester in N,N-dimethylformamide, 1.92 g of potassium tert-butoxide was added under ice-cooling and stirring, followed by stirring for 30 minutes at 0° C. Then, to this reaction mixture, 2.44 g of N-chloromethyl-2-(trifluoromethyl)benzamide was added, and stirring was continued at room temperature for further 30 minutes. After completion of the reaction, 100 ml of water was added to the reaction mixture, followed by extraction with ethyl acetate (50 ml×2), and organic layers were combined and washed with water (50 ml×1), whereupon it was dehydrated and dried in the order of with a saturated sodium chloride solution and then with anhydrous sodium sulfate, and then, the solvent was evaporated under reduced pressure. The residue was purified by silica gel column chromatography wherein it was eluted with ethyl acetate-hexane (gradient of from 5:95 to 30:70 (volume ratio, the same applies hereinafter)), to obtain 1.11 g of the desired product as a colorless oily substance.

$^1$H NMR (CDCl$_3$, Me$_4$Si, 300 MHz) δ8.47 (d, J=1.8 Hz, 1H), 7.91 (d, J=1.8 Hz, 1H), 7.15-7.65 (m, 4H), 6.93 (bs, 1H), 4.56 (d, J=6.6 Hz, 2H), 4.2-4.35 (m, 4H), 1.2-1.35 (m, 6H).

Step 2: Production of N-[2-(5-bromo-3-chloropyridin-2-yl)ethyl]-2-(trifluoromethyl)benzamide To a 10 ml solution of 1.11 g of 2-(5-bromo-3-chloropyridin-2-yl)-2-[[2-(trifluoromethyl)benzamide]methyl]malonic acid diethyl ester in N-methyl-2-pyrrolidone, 50 mg of potassium chloride, 10 ml of water and 274 mg of concentrated hydrochloric acid were added and stirred at 180° C. for 12 hours. After completion of the reaction, the reaction mixture was left to cool to room temperature, and after addition of water 30 ml, the mixture was extracted with ethyl acetate (50 ml×1). Organic layers were combined and washed with water (20 ml×1), whereupon it was dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 2:8 to 4:6), to obtain 0.40 g of the desired product as a colorless oily substance.

$^1$H NMR (CDCl$_3$, Me$_4$Si, 300 MHz) δ8.44 (d, J=2.1 Hz, 1H), 7.85 (d, J=2.1 Hz, 1H), 7.5-7.7 (m, 4H), 6.65 (bs, 1H), 3.95 (q, J=6.0 Hz, 2H), 3.19 (t, J=6.0 Hz, 2H).

Step 3: Production of N-[2-[3-chloro-5-(3,3-dimethyl-1-butynyl)pyridin-2-yl]ethyl]-2-(trifluoromethyl)benzamide To a 10 ml solution of 150 mg of N-[2-(5-bromo-3-chloropyridin-2-yl)ethyl]-2-(trifluoromethyl)benzamide, 45 mg of 3,3-dimethyl-1-butyne and 186 mg of triethylamine in N,N-dimethylformamide, 25 mg of copper(I) iodide and 86 mg of dichlorobis(triphenylphosphine)palladium(II) were added and stirred at 40° C. for 6 hours under a nitrogen atmosphere. After completion of the reaction, the reaction mixture was left to cool to room temperature, and after addition of 30 ml of water, the mixture was extracted with ethyl acetate (25 ml×2). Organic layers were combined and washed with water (20 ml×1), whereupon it was dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 4:6), to obtain 36 mg of the desired product as white crystals.

Melting point: 90.0 to 92.0° C.

$^1$H NMR (CDCl$_3$, Me$_4$Si, 300 MHz) δ8.33 (d, J=1.8 Hz, 1H), 7.65 (d, J=1.8 Hz, 1H), 7.45-7.65 (m, 4H), 6.76 (bs, 1H), 3.94 (q, J=6.0 Hz, 2H), 3.20 (t, J=6.0 Hz, 2H), 1.32 (s, 9H).

Synthesis Example 2

N-[2-[3-chloro-5-(1-propynyl)pyridin-2-yl]ethyl]-2-(trifluoromethyl)benzamide (compound No. 1-001 of the present invention)

To a 20 ml suspension of 467 mg of zinc(II) bromide in tetrahydrofuran under a nitrogen atmosphere, 3.76 ml of a 0.5M tetrahydrofuran solution of 1-propynylmagnesium bromide was added dropwisely under ice-cooling and stirring, followed by stirring at room temperature for 30 minutes. Then, to this reaction mixture, 192 mg of N-[2-(5-bromo-3-chloropyridin-2-yl)ethyl]-2-(trifluoromethyl) benzamide produced in Step 2 of Synthesis Example 1 and 20 mg of dichloro[1,1'-bis(diphenylphosphino)ferrocene] palladium(II) were added, and stirring was continued at room temperature for 12 hours. After completion of the reaction, 30 ml of water was added to the reaction mixture, followed by extraction with ethyl acetate (25 ml×2), and organic layers were combined and washed with water (20 ml×1), followed by dehydration and drying in the order of with saturated brine and then with anhydrous sodium sulfate, and the solvent was evaporated under reduced pressure. The residue was purified by silica gel column chromatography wherein it was eluded with ethyl acetate-hexane (gradient of from 1:4 to 2:3), to obtain 22 mg of the desired product as white crystals.

Melting point: 100.0 to 103.0° C.

$^1$H NMR (CDCl$_3$, Me$_4$Si, 300 MHz) δ8.35 (d, J=1.8 Hz, 1H), 7.45-7.7 (m, 5H), 6.70 (bs, 1H), 3.9-4.0 (m, 2H), 3.20 (t, J=6.3 Hz, 2H), 2.06 (s, 3H).

Synthesis Example 3

N-[2-[3-chloro-5-(cyclopropylethynyl)pyridin-2-yl] ethyl]-2-(difluoromethyl)nicotinamide (compound No. 3-001 of the present invention)

Step 1: Production of tert-butyl N-[2-(5-bromo-3-chloropyridin-2-yl)ethyl]carbamate To a 10 ml solution of 1.00 g of 2-(5-bromo-3-chloropyridin-2-yl)acetonitrile in dichloromethane under a nitrogen atmosphere, 12 ml of a 1.0M hexane solution of diisobutylaluminum hydride was added dropwisely under stirring at −40° C. over 30 minutes, and after completion of the dropwise addition, the mixture was stirred for 1 hour at the same temperature. Then, the reaction mixture was warmed to room temperature and dropped into 50 ml of a saturated aqueous solution of sodium potassium tartrate (Rochelle salt) under ice-cooling and stirring. After the completion of the dropping, stirring was further continued for one hour at room temperature. After completion of the reaction, the mixture was extracted with dichloromethane (50 ml×2), and organic layers were combined, and dehydrated and dried in the order of with saturated brine and then with anhydrous sodium sulfate, and the solvent was distilled off under reduced pressure.

The residue was dissolved in 20 ml of dichloromethane, and 1.41 g of di-tert-butyl dicarbonate and 0.66 g of triethylamine were added, followed by stirring at room temperature for 1 hour. After completion of the reaction, 20 ml of water was added to the reaction mixture, followed by extraction with chloroform (20 ml×1). The organic layer was washed with water (10 ml×1), and then dehydrated and dried in the order of with saturated brine and then with anhydrous sodium sulfate, and the solvent was distilled off under reduced pressure. The residue was purified by silica gel column chromatography wherein it was eluted with ethyl acetate-hexane (gradient of from 1:9 to 5:5), to obtain 615 mg of the desired product as a pale yellow oily substance.

$^1$H NMR (CDCl$_3$, Me$_4$Si, 300 MHz) δ8.49 (d, J=1.8 Hz, 1H), 7.82 (d, J=1.8 Hz, 1H), 5.08 (bs, 1H), 3.5-3.65 (m, 2H), 3.06 (t, J=6.0 Hz, 2H), 1.42 (s, 9H).

Step 2: Production of tert-butyl N-[2-[3-chloro-5-(cyclopropylethynyl)pyridin-2-yl]ethyl]carbamate To a 6 ml solution of 615 mg of tert-butyl N-[2-(5-bromo-3-chloropyridin-2-yl)ethyl]carbamate, in N,N-dimethylformamide, 742 mg of triethylamine, 45 mg of cyclopropylacetylene, 105 mg of copper(I) iodide and 128 mg of dichlorobis(triphenylphosphine)palladium(II) were added and stirred at room temperature for 18 hours under a nitrogen atmosphere. After completion of the reaction, 20 ml of a saturated aqueous ammonium chloride solution was added to the reaction mixture, followed by extraction with ethyl acetate (15 ml×2). Organic layers were combined and washed with 20 ml of a saturated aqueous ammonium chloride solution and then with 20 ml of water, and then dehydrated and dried in the order of with saturated brine and then with anhydrous sodium sulfate, and the solvent was distilled off under reduced pressure. The residue was purified by silica gel column chromatography wherein it was eluted with ethyl acetate-hexane (gradient of from 1:9 to 2:8), to obtain 233 mg of the desired product as a pale yellow oily substance.

$^1$H NMR (CDCl$_3$, Me$_4$Si, 300 MHz) δ8.36 (d, J=1.8 Hz, 1H), 7.58 (d, J=1.8 Hz, 1H), 5.08 (bs, 1H), 3.45-3.6 (m, 2H), 3.05 (t, J=6.0 Hz, 2H), 1.4-1.5 (m, 1H), 1.39 (s, 9H), 0.75-0.95 (m, 4H).

Step 3: Production of 2-[3-chloro-5-(cyclopropylethynyl)pyridin-2-yl]ethylamine

To a 5 ml solution of 233 mg of tert-butyl N-[2-[3-chloro-5-(cyclopropylethynyl)pyridin-2-yl]ethyl]carbamate in dichloromethane, 2 ml of trifluoroacetic acid was added, followed by stirring at room temperature for 2 hours.

After completion of the reaction, the solvent was distilled off under reduced pressure, and to the residue, 10 ml of a 10 wt % potassium carbonate solution was added, followed by extraction with ethyl acetate (10 ml×1). The organic layer was dehydrated and dried in the order of with saturated brine and then with anhydrous sodium sulfate, and the solvent was distilled off under reduced pressure to obtain 160 mg of the crude desired product as a brown oily substance. This compound was used directly in the next step without further purification.

$^1$H NMR (CDCl$_3$, Me$_4$Si, 300 MHz) δ8.40 (d, J=1.8 Hz, 1H), 7.62 (d, J=1.8 Hz, 1H), 3.0-3.2 (m, 4H), 1.4-1.5 (m, 1H), 0.75-0.9 (m, 4H).

Step 4: Production of N-[2-[3-chloro-5-(cyclopropylethynyl)pyridin-2-yl]ethyl]-2-(difluoromethyl)nicotinamide 80 mg of 2-[3-chloro-5-(cyclopropylethynyl)pyridin-2-yl]ethylamine was dissolved in 2 ml of a dichloromethane-N,N-dimethylformamide (1:1 (volume ratio)) mixed solvent, and 75 mg of 2-(difluoromethyl)nicotinic acid and 104 mg of 1-(3-dimethylaminopropyl)-3-ethylcarbodiimide hydrochloride were added, followed by stirring at room temperature for 12 hours. After completion of the reaction, 10 ml of water was added to the reaction mixture, followed by extraction with ethyl acetate (10 ml×2). Organic layers were combined and washed with water (5 ml×1), and dehydrated and dried in the order of with a saturated sodium chloride solution and then anhydrous sodium sulfate, and the solvent was distilled off under reduced pressure. The residue was purified by silica gel column chromatography wherein it was eluted with ethyl acetate-hexane (gradient of from 1:9 to 4:6), to obtain 70 mg of the desired product as white crystals.

Melting point: 114.0 to 117.0° C.

$^1$H NMR (CDCl$_3$, Me$_4$Si, 300 MHz) δ8.71 (dd, J=4.5, 1.8 Hz, 1H), 8.34 (d, J=1.8 Hz, 1H), 7.86 (d, J=7.8 Hz, 1H), 7.63 (d, J=1.8 Hz, 1H), 7.43 (dd, J=7.8, 1.8 Hz, 1H), 7.05 (bs, 1H), 6.94 (t, J=54.3 Hz, 1H), 3.9-4.0 (m, 2H), 3.19 (t, J=6.3 Hz, 2H), 1.35-1.5 (m, 1H), 0.75-0.95 (m, 4H).

Synthesis Example 4

N-[2-[3-chloro-5-(cyclopropylethynyl)pyridin-2-yl]propyl]-2-(trifluoromethyl)benzamide (compound No. 1-007 of the present invention)

Step 1: Production of 2-(5-bromo-3-chloropyridin-2-yl)propanenitrile

To a 20 ml solution of 1.50 g of 2-(5-bromo-3-chloropyridin-2-yl)acetonitrile in tetrahydrofuran, 7 ml of a 1.0M tetrahydrofuran solution of potassium tert-butoxide was added under stirring at −5° C., followed by stirring at room temperature for 2 hours. Then, 0.97 g of iodomethane was added to this reaction mixture, and stirring was further continued for 1 hour at room temperature. After completion of the reaction, 30 ml of water was added to the reaction mixture, followed by extraction with ethyl acetate (25 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 5:95 to 15:85), to obtain 1.38 g of the desired product as a colorless oily substance.

$^1$H NMR (CDCl$_3$, Me$_4$Si, 300 MHz) δ8.58 (d, J=2.1 Hz, 1H), 7.88 (d, J=2.1 Hz, 1H), 4.43 (q, J=7.2 Hz, 1H), 1.67 (d, J=7.2 Hz, 3H).

Step 2: Production of 2-(5-bromo-3-chloropyridin-2-yl)-1-propanamine

To a 20 ml solution of 1.38 g of 2-(5-bromo-3-chloropyridin-2-yl)propanenitrile in dichloromethane under a nitrogen atmosphere, 16 ml of a 1.0M hexane solution of diisobutylaluminum hydride was added dropwisely over 20 minutes under stirring at −40° C. After completion of the dropwise addition, the mixture was stirred for 1 hour at the same temperature. Then, the reaction mixture was warmed to room temperature and added dropwisely to 50 ml of a saturated aqueous solution of sodium potassium tartrate (Rochelle salt) under ice-cooling and stirring. After completion of the dropwise addition, stirring was further continued for one hour at room temperature. After completion of the reaction, the reaction mixture was extracted with dichloromethane (50 ml×2), and organic layers were combined and washed with water (20 ml×1), and then, the solvent was distilled off under reduced pressure. The residue was dissolved in 10 ml of ethyl acetate and extracted with 10 ml of a 1N aqueous hydrochloric acid solution, whereupon to the aqueous layer, a 10 wt % sodium hydroxide aqueous solution was added until the pH became 14, followed by back extraction with 30 ml of ethyl acetate. The organic layer was dehydrated and dried in the order of with a saturated sodium chloride solution and then with anhydrous sodium sulfate, and the solvent was distilled off under reduced pressure to obtain 1.04 g of the crude desired product as a reddish brown oily substance. This product was used directly in the next step without further purification.

$^1$H NMR (CDCl$_3$, Me$_4$Si, 300 MHz) δ8.50 (d, J=2.1 Hz, 1H), 7.80 (d, J=2.1 Hz, 1H), 3.35-3.45 (m, 1H), 3.05-3.15 (m, 1H), 2.85-2.95 (m, 1H), 1.20 (d, J=6.6 Hz, 3H).

Step 3: Production of tert-butyl N-[2-(5-bromo-3-chloropyridin-2-yl)propyl]carbamate To a 10 ml solution of 1.04 g of 2-(5-bromo-3-chloropyridin-2-yl)-1-propanamine and 0.63 g of triethylamine in dichloromethane, 1.08 g of di-tert-butyl dicarbonate was added, followed by stirring at room temperature for 1 hour. After completion of the reaction, the solvent was distilled off under reduced pressure, and the residue was purified by silica gel column chromatography wherein it was eluted with ethyl acetate-hexane (gradient of from 5:95 to 15:85) to obtain 1.05 g of the desired product as a colorless oily substance.

$^1$H NMR (CDCl$_3$, Me$_4$Si, 300 MHz) 8.51 (d, J=1.8 Hz, 1H), 7.82 (d, J=1.8 Hz, 1H), 4.86 (bs, 1H), 3.55-3.7 (m, 1H), 3.4-3.5 (m, 2H), 1.41 (s, 9H), 1.21 (d, J=7.2 Hz, 3H).

Step 4: Production of tert-butyl N-[2-[3-chloro-5-(cyclopropylethynyl)pyridin-2-yl]propyl]carbamate To a 5 ml solution of 1.05 g tert-butyl N-[2-(5-bromo-3-chloropyridin-2-yl)propyl]carbamate in N,N-dimethylformamide, 1.22 g of triethylamine, 238 mg of cyclopropylacetylene, 171 mg of copper(I) iodide and 211 mg of dichlorobis(triphenylphosphine)palladium(II) were added, followed by stirring at room temperature for 12 hours under a nitrogen atmosphere. After completion of the reaction, 30 ml of a saturated aqueous ammonium chloride solution was added to the reaction mixture, followed by extraction with ethyl acetate (20 ml×2). Organic layers were combined and washed with 20 ml of a saturated aqueous ammonium chloride solution and then with 20 ml of water, and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 2:8), to obtain 871 mg of the desired product as a brown oily substance.

$^1$H NMR (CDCl$_3$, Me$_4$Si, 300 MHz) 8.41 (d, J=1.8 Hz, 1H), 7.61 (d, J=1.8 Hz, 1H), 4.89 (bs, 1H), 3.55-3.7 (m, 1H), 3.45 (t, J=6.3 Hz, 2H), 1.35-1.5 (m, 10H), 1.21 (d, J=6.9 Hz, 3H), 0.75-0.95 (m, 4H).

Step 5: Production of 2-[3-chloro-5-(cyclopropylethynyl)pyridin-2-yl]-1-propanamine To a 5 ml solution of 871 mg of tert-butyl N-[2-[3-chloro-5-(cyclopropylethynyl)pyridin-2-yl]propyl]carbamate in dichloromethane, 3 ml of trifluoroacetic acid was added, followed by stirring at room temperature for 1 hour. After completion of the reaction, the solvent was distilled off under reduced pressure, and to the residue, 10 ml of a saturated aqueous potassium carbonate solution was added, followed by extraction with ethyl acetate (10 ml×2). Organic layers were combined and washed with 10 ml of a saturated aqueous potassium carbonate solution, and then dehydrated and dried in the order of with a saturated sodium chloride solution and then with anhydrous sodium sulfate, and the solvent was distilled off under reduced pressure to obtain 414 mg of the crude desired product as a brown oily substance. This product was used directly in the next step without further purification.

$^1$H NMR (CDCl$_3$, Me$_4$Si, 300 MHz) δ8.42 (d, J=1.8 Hz, 1H), 7.60 (d, J=1.8 Hz, 1H), 3.35-3.5 (m, 1H), 3.05-3.2 (m, 1H), 2.8-2.95 (m, 1H), 1.35-1.5 (m, 1H), 1.19 (d, J=6.6 Hz, 3H), 0.75-0.95 (m, 4H).

Step 6: Production of N-[2-[3-chloro-5-(cyclopropylethynyl)pyridin-2-yl]propyl]-2-(trifluoromethyl)benzamide To a 3 ml solution of 104 mg of 2-[3-chloro-5-(cyclopropylethynyl)pyridin-2-yl]-1-propanamine and 54 mg of triethylamine in dichloromethane, 92 mg of 2-(trifluoromethyl)benzoyl chloride was added under ice-cooling and stirring, followed by stirring at room temperature for 1 hour. After completion of the reaction, the solvent was distilled off under reduced pressure, and the residue was purified by silica gel column chromatography wherein it was eluted with ethyl acetate-hexane (gradient of from 1:4 to 2:3), to obtain 67 mg of the desired product as a colorless resinous substance.

$^1$H NMR (CDCl$_3$, Me$_4$Si, 300 MHz) δ8.32 (d, J=1.8 Hz, 1H), 7.4-7.65 (m, 5H), 6.49 (bs, 1H), 3.8-3.85 (m, 2H), 3.7-3.8 (m, 1H), 1.35-1.45 (m, 1H), 1.26 (d, J=6.6 Hz, 3H), 0.75-0.95 (m, 4H).

Synthesis Example 5

N-[[1-[3-chloro-5-(cyclopropylethynyl)pyridin-2-yl]cyclopropyl]methyl]-3-difluoromethyl-1-methyl-1H-pyrazole-4-carboxamide (compound No. 8-018 of the present invention)

Step 1: Production of tert-butyl N-[[1-(5-bromo-3-chloropyridin-2-yl)cyclopropyl]methyl]carbamate To a 5 ml solution of 462 mg of [1-(5-bromo-3-chloropyridin-2-yl)cyclopropyl]methylamine and 269 mg of triethylamine in dichloromethane, 578 mg of di-tert-butyl dicarbonate was added, followed by stirring at room temperature for 1 hour. After completion of the reaction, 10 ml of water was added to the reaction mixture, followed by extraction with dichloromethane (10 ml×2). Organic layers were combined, and dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 3:7), to obtain 498 mg of the desired product as white crystals.

Melting point: 81.0 to 82.0° C.

$^1$H NMR (CDCl$_3$, Me$_4$Si, 300 MHz) δ8.47 (d, J=2.1 Hz, 1H), 7.83 (d, J=2.1 Hz, 1H), 4.78 (bs, 1H), 3.38 (d, J=6.0 Hz, 2H), 1.33 (s, 9H), 0.9-1.05 (m, 4H).

Step 2: Production of tert-butyl N-[[1-[3-chloro-5-(cyclopropylethynyl)pyridin-2-yl]cyclopropyl]methyl]carbamate To a 3 ml solution of 498 mg of tert-butyl N-[[1-(5-bromo-3-chloropyridin-2-yl)cyclopropyl]methyl]carbamate in N,N-dimethylformamide, 557 mg of triethylamine, 110 mg of cyclopropylacetylene, 79 mg of copper(I) iodide and 97 mg of dichlorobis(triphenylphosphine)palladium(II) were added, followed by stirring at room temperature for 12 hours under a nitrogen atmosphere. After completion of the reaction, 15 ml of a saturated aqueous ammonium chloride solution was added to the reaction mixture, followed by extraction with ethyl acetate (15 ml×2). Organic layers were combined and washed with 10 ml of water, and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 2:8), to obtain 334 mg of the desired product as a pale yellow oily substance.

$^1$H NMR (CDCl$_3$, Me$_4$Si, 300 MHz) δ8.36 (d, J=1.8 Hz, 1H), 7.60 (d, J=1.8 Hz, 1H), 4.75 (bs, 1H), 3.36 (d, J=5.4 Hz, 1H), 1.4-1.5 (m, 1H), 1.32 (s, 9H), 0.75-1.05 (m, 8H).

Step 3: Production of [1-[3-chloro-5-(cyclopropylethynyl)pyridin-2-yl]cyclopropyl]methylamine To a 5 ml solution of 334 mg of tert-butyl N-[[1-[3-chloro-5-(cyclopropylethynyl)pyridin-2-yl]cyclopropyl]methyl]carbamate in dichloromethane, 2 ml of trifluoroacetic acid was added, followed by stirring for 2 hours at room temperature. After completion of the reaction, the solvent was distilled off under reduced pressure, and to the residue, 10 ml of a saturated aqueous potassium carbonate solution was added, followed by extraction with ethyl acetate (10 ml×1). The organic layer was washed with a saturated aqueous potassium carbonate solution (10 ml×2), and then dehydrated and dried in the order of with a saturated sodium chloride solution and then with anhydrous sodium sulfate, and the solvent was distilled off under reduced pressure, to obtain 230 mg of the crude desired product as a pale yellow oily substance. This product was used directly in the next step without further purification.

$^1$H NMR (CDCl$_3$, Me$_4$Si, 300 MHz) δ8.41 (d, J=1.8 Hz, 1H), 7.63 (d, J=1.8 Hz, 1H), 2.93 (bs, 2H), 1.3-1.5 (m, 1H), 1.33 (bs, 2H), 0.75-1.0 (m, 8H).

Step 4: Production of N-[[1-[3-chloro-5-(cyclopropylethynyl)pyridin-2-yl]cyclopropyl]methyl]-3-difluoromethyl-1-methyl-1H-pyrazole-4-carboxamide 115 mg of [1-[3-chloro-5-(cyclopropylethynyl)pyridin-2-yl]cyclopropyl]methylamine was dissolved in 3 ml of a dichloromethane-N,N-dimethylformamide (2:1) mixed solvent, and 99 mg of 3-difluoromethyl-1-methyl-1H-pyrazole-4-carboxylic acid and 135 mg of 1-(3-dimethylaminopropyl)-3-ethylcarbodiimide hydrochloride were added, followed by stirring at room temperature for 12 hours. After completion of the reaction, 10 ml of water was added to the reaction mixture, followed by extraction with ethyl acetate (10 ml×2). Organic layers were combined and washed with water (10 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 3:7), to obtain 23 mg of the desired product as a colorless resinous substance.

$^1$H NMR (CDCl$_3$, Me$_4$Si, 300 MHz) δ8.35 (d, J=1.8 Hz, 1H), 7.76 (s, 1H), 7.61 (d, J=1.8 Hz, 1H), 6.86 (t, J=54.3 Hz, 1H), 6.46 (bs, 1H), 3.89 (s, 3H), 3.63 (d, J=5.4 Hz, 2H), 1.35-1.5 (m, 1H), 1.0-1.1 (m, 4H), 0.75-0.95 (m, 4H).

Synthesis Example 6

N-[2-[3-chloro-5-(1-propynyl)pyridin-2-yl]-2-propenyl]-2-(trifluoromethyl)benzamide (compound No. 1-012 of the present invention)

Step 1: Production of 1-(5-bromo-3-chloropyridin-2-yl)ethanone

To a 15 ml solution of 3.0 g of 5-bromo-3-chloropyridine-2-carbonitrile in toluene, 4.8 ml of a 3M diethyl ether solution of methylmagnesium bromide was added dropwisely under ice-cooling and stirring, followed by stirring for 0.5 hours at the same temperature. After completion of the reaction, the reaction mixture was poured into 20 ml of 4N hydrochloric acid under ice-cooling and stirring, followed by extraction with toluene (30 ml×2). Organic layers were combined, and then dehydrated and dried in the order of with a saturated sodium chloride solution and then with anhydrous sodium sulfate, and the solvent was distilled off under reduced pressure to obtain 2.7 g of the crude desired product as brown crystals. This product was used directly in the next step without further purification.

Melting point: 78.0 to 79.0° C.

$^1$H NMR (CDCl$_3$, Me$_4$Si, 300 MHz) δ8.58 (d, J=1.8 Hz, 1H), 7.97 (d, J=1.8 Hz, 1H), 2.67 (s, 3H).

Step 2: Production of 2-bromo-1-(5-bromo-3-chloropyridin-2-yl)ethanone

To a 8 ml solution of 1.60 g of 1-(5-bromo-3-chloropyridin-2-yl)ethanone in toluene, 5.5 ml of a 30% hydrogen bromide acetic acid solution was added, and 1.28 g of bromine was added dropwisely under ice-cooling and stirring. After stirring 18 hours at room temperature, 0.62 g of bromine was added, and further 2.5 hours later, 0.31 g of bromine was added again, followed by continuously stirring for 3 hours. After completion of the reaction, 50 ml of water was added to the reaction mixture, followed by extraction with toluene (50 ml×2). Organic layers were combined and washed with 100 ml of water and then with 100 ml of a saturated aqueous sodium bisulfite solution, and then dehydrated and dried in the order of with a saturated sodium chloride solution and then with anhydrous sodium sulfate, and the solvent was distilled off under reduced pressure. To the residue, 20 ml of heptane was added, followed by stirring for 30 minutes under ice-cooling, whereupon the precipitated solid was filtered to obtain 1.7 g of the desired product as white crystals.

Melting point: 58.0 to 62.0° C.

$^1$H NMR (CDCl$_3$, Me$_4$Si, 300 MHz) δ8.60 (d, J=2.1 Hz, 1H), 8.02 (d, J=2.1 Hz, 1H), 4.76 (s, 2H).

Step 3: Production of N-[2-(5-bromo-3-chloropyridin-2-yl)-2-oxoethyl]phthalimide To a 30 ml solution of 3.0 g of potassium phthalimide in dimethyl sulfoxide, a 20 ml solution of 5.1 g of 2-bromo-1-(5-bromo-3-chloropyridin-2-yl)ethanone in dimethyl sulfoxide was added dropwisely. After completion of the reaction, 50 ml of water was added to the reaction mixture, followed by extraction with ethyl acetate (100 ml×2). Organic layers were combined and washed with water (100 ml×1), and then dehydrated and dried in the order of with a saturated sodium chloride solution and then with anhydrous sodium sulfate, and the solvent was distilled off under reduced pressure, to obtain 4.5 g of the crude desired product as yellow crystals. This product was used directly in the next step without further purification.

Melting point: 62.0 to 68.0° C.
$^1$H NMR (CDCl$_3$, Me$_4$Si, 300 MHz) δ8.67 (d, J=1.8 Hz, 1H), 8.03 (d, J=1.8 Hz, 1H), 7.7-7.95 (m, 4H), 5.28 (s, 2H).

Step 4: Production of N-[2-(5-bromo-3-chloropyridin-2-yl)-2-propenyl]phthalimide To a 100 ml solution of 2.20 g of N-[2-(5-bromo-3-chloropyridin-2-yl)-2-oxoethyl]phthalimide, 2.34 g of methyltriphenylphosphonium iodide and 0.01 g of crown ether (18-Crown-6) in toluene, 0.65 g of potassium tert-butoxide was added, followed by stirring under heating and refluxing. After 4 hours, 2.34 g of methyltriphenylphosphonium iodide and 0.65 g of potassium tert-butoxide were added to the reaction mixture, and stirring was further continued under heating and refluxing for one hour. After completion of the reaction, the solvent was distilled off under reduced pressure, and 200 ml of water and 200 ml of ethyl acetate were added to the residue, whereupon the organic layer was separated. The organic layer was washed with water (50 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 2:8), to obtain 0.83 g of the desired product as yellow crystals.

Melting point: 63.0 to 67.0° C.
$^1$H NMR (CDCl$_3$, Me$_4$Si, 300 MHz) 8.50 (d, J=2.1 Hz, 1H), 7.87 (d, J=2.1 Hz, 1H), 7.65-7.9 (m, 4H), 5.66 (s, 1H), 5.63 (s, 1H), 4.73 (s, 2H).

Step 5: Production of 2-(5-bromo-3-chloropyridin-2-yl)-2-propenylamine

To a 8 ml toluene/0.5 ml ethanol solution of 830 mg of N-[2-(5-bromo-3-chloropyridin-2-yl)-2-propenyl]phthalimide, 1.70 g of a 40 wt % aqueous methylamine solution was added under ice-cooling and stirring, followed by stirring at room temperature for 8 hours. After completion of the reaction, 10 ml of water was added to the reaction mixture, and concentrated hydrochloric acid was added dropwisely under ice-cooling and stirring until the pH became 1. Then, the aqueous layer was separated, and after addition of sodium carbonate until the pH became from 13 to 14, the mixture was extracted with ethyl acetate (50 ml×2). Organic layers were combined, and dehydrated and dried in the order of with a saturated sodium chloride solution and then with anhydrous sodium sulfate, and the solvent was distilled off under reduced pressure to obtain 280 mg of the crude desired product as a yellow oily substance. This product was used directly in the next step without further purification.

$^1$H NMR (CDCl$_3$, Me$_4$Si, 300 MHz) δ8.5-8.6 (m, 1H), 7.85-7.95 (m, 1H), 5.65 (s, 1H), 5.49 (s, 1H), 3.71 (s, 2H).

Step 6: Production of N-[2-(5-bromo-3-chloropyridin-2-yl)-2-propenyl]-2-(trifluoromethyl)benzamide To a 3 ml solution of 280 mg of 2-(5-bromo-3-chloropyridin-2-yl)-2-propenylamine and 228 mg of triethylamine in dichloromethane, 283 mg of 2-(trifluoromethyl)benzoyl chloride was added dropwisely under ice-cooling and stirring. After completion of the dropwise addition, stirring was continued at room temperature for additional 1.5 hours. After completion of the reaction, 15 ml of water was added to the reaction mixture, followed by extraction with dichloromethane (20 ml×1). Thereafter, the organic layer was dehydrated and dried in the order of with a saturated aqueous sodium chloride solution and then with anhydrous sodium sulfate, and the solvent was distilled off under reduced pressure. The residue was purified by silica gel column chromatography wherein it was eluted with ethyl acetate-hexane (1:9), to obtain 240 mg of the desired product as pale yellow crystals.

Melting point: 49.0 to 53.0° C.
$^1$H NMR (CDCl$_3$, Me$_4$Si, 300 MHz) δ8.50 (d, J=2.1 Hz, 1H), 7.93 (d, J=2.1 Hz, 1H), 7.45-7.7 (m, 4H), 6.43 (bs, 1H), 5.90 (s, 1H), 5.83 (s, 1H), 4.49 (d, J=5.7 Hz, 2H).

Step 7: Production of N-[2-[3-chloro-5-(1-propynyl)pyridin-2-yl]-2-propenyl]-2-(trifluoromethyl)benzamide To a 23 ml solution of 543 mg of zinc(II) bromide in tetrahydrofuran under a nitrogen atmosphere, 4.4 ml of a 0.5M tetrahydrofuran solution of 1-propynylmagnesium bromide was added dropwisely under ice-cooling and stirring, followed by stirring for 10 minutes at the same temperature. Then, to this reaction mixture, a 5 ml solution of 230 mg of N-[2-(5-bromo-3-chloropyridin-2-yl)-2-propenyl]-2-(trifluoromethyl)benzamide in tetrahydrofuran and 45 mg of dichloro[1,1'-bis(diphenylphosphino)ferrocene] palladium(II) were added, and stirring was continued at room temperature for 2.5 hours. After completion of the reaction, the reaction mixture was poured into 40 ml of a 1N aqueous hydrochloric acid solution under ice-cooling and stirring, followed by extraction with ethyl acetate (50 ml×2). Organic layers were combined, and dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 2:8), to obtain 180 mg of the desired product as a brown solid.

Melting point: 85.0 to 90.0° C.
$^1$H NMR (CDCl$_3$, Me$_4$Si, 300 MHz) δ8.41 (d, J=2.1 Hz, 1H), 7.72 (d, J=2.1 Hz, 1H), 7.4-7.7 (m, 4H), 6.53 (bs, 1H), 5.88 (s, 1H), 5.84 (s, 1H), 4.49 (d, J=5.7 Hz, 2H), 2.08 (s, 3H).

Synthesis Example 7

N-[2-[3-chloro-5-(cyclopropylethynyl)pyridin-2-yl]-2-propenyl]-3-difluoromethyl-1-methyl-1H-pyrazole-4-carboxamide (compound No. 8-011 of the present invention)

Step 1: Production of N-[2-[3-chloro-5-(cyclopropylethynyl)pyridin-2-yl]-2-oxoethyl]phthalimide To a 5 ml solution of 300 mg of N-[2-(3,5-dichloropyridin-2-yl)-2-oxoethyl]phthalimide in N,N-dimethylformamide, 181 mg of triethylamine, 70 mg of cyclopropylacetylene, 25 mg of copper(I) iodide and 31 mg of dichlorobis (triphenylphosphine)palladium(II) were added, followed by stirring at 50° C. for 8 hours under a nitrogen atmosphere.

After completion of the reaction, the reaction mixture was left to cool to room temperature, and 30 ml of water and 30 ml of ethyl acetate were added, followed by filtration through Celite, whereupon the organic layer was separated, and the aqueous layer was extracted with ethyl acetate (50 ml×2). Organic layers were combined and washed with water (30 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 2:8), to obtain 260 mg of the desired product as pale yellow crystals.

Melting point: 156.0 to 160.0° C.

$^1$H NMR (CDCl$_3$, Me$_4$Si, 300 MHz) δ8.53 (d, J=1.7 Hz, 1H), 7.85-7.95 (m, 2H), 7.7-7.8 (m, 3H), 5.32 (s, 2H), 1.45-1.6 (m, 1H), 0.85-1.05 (m, 4H).

Step 2: Production of N-[2-[3-chloro-5-(cyclopropylethynyl)pyridin-2-yl]-2-propenyl]phthalimide To a 60 ml solution of 1.03 g of N-[2-[3-chloro-5-(cyclopropylethynyl)pyridin-2-yl]-2-oxoethyl]phthalimide, 2.17 g of methyltriphenylphosphonium iodide and 0.071 g of crown ether (18-Crown-6) in toluene, 0.60 g of potassium tert-butoxide was added, followed by stirring for 2.5 hours under heating and refluxing. After completion of the reaction, the solvent was distilled off under reduced pressure, and to the residue, 100 ml of water and 100 ml of ethyl acetate were added, whereupon the organic layer was separated, and the aqueous layer was extracted with ethyl acetate (100 ml×2). Organic layers were combined, and dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 4:6), to obtain 0.30 g of the desired product as a brown resinous substance.

$^1$H NMR (CDCl$_3$, Me$_4$Si, 300 MHz) δ8.40 (d, J=1.5 Hz, 1H), 7.5-7.9 (m, 5H), 5.62 (s, 1H), 5.60 (s, 1H), 4.74 (s, 2H), 1.35-1.55 (m, 1H), 0.8-1.0 (m, 4H).

Step 3: Production of 2-[3-chloro-5-(cyclopropylethynyl)pyridin-2-yl]-2-propenylamine To a 3 ml solution of 300 mg N-[2-[3-chloro-5-(cyclopropylethynyl)pyridin-2-yl]-2-propenyl]phthalimide in toluene, 615 mg of a 40 wt % aqueous methylamine solution was added under ice-cooling and stirring, followed by stirring at room temperature for 19 hours. After completion of the reaction, 10 ml of water was added to the reaction mixture, and concentrated hydrochloric acid was added dropwisely until the pH became 1 under ice-cooling and stirring. The aqueous layer was separated, and after addition of sodium carbonate until the pH became from 13 to 14, it was extracted with ethyl acetate (40 ml×2). Organic layers were combined, and dehydrated and dried in the order of with a saturated sodium chloride solution and then with anhydrous sodium sulfate, and the solvent was distilled off under reduced pressure to obtain 90 mg of the crude desired product as a brown oily substance. This product was used directly in the next step without further purification.

$^1$H NMR (CDCl$_3$, Me$_4$Si, 300 MHz) δ8.43 (d, J=1.5 Hz, 1H), 7.68 (d, J=1.5 Hz, 1H), 5.61 (s, 1H), 5.47 (s, 1H), 3.70 (bs, 2H), 1.4-1.6 (m, 1H), 0.75-1.0 (m, 4H).

Step 4: Production of N-[2-[3-chloro-5-(cyclopropylethynyl)pyridin-2-yl]-2-propenyl]-3-difluoromethyl-1-methyl-1H-pyrazole-4-carboxamide To a 2 ml solution of 88 mg of 3-difluoromethyl-1-methyl-1H-pyrazole-4-carboxylic acid in dichloromethane, 10 mg of N,N-dimethylformamide and 76 mg of oxalyl chloride were added, followed by stirring at room temperature for 30 minutes. After completion of the reaction, the solvent was distilled off under reduced pressure, and the residue was dissolved in 1 ml of dichloromethane, and added dropwisely to a 2 ml solution of 90 mg of 2-[3-chloro-5-(cyclopropylethynyl)pyridin-2-yl]-2-propenylamine and 117 mg of triethylamine in dichloromethane under ice-cooling and stirring. After stirring at the same temperature for 30 minutes, 10 ml of water was added to the reaction mixture, followed by extraction with dichloromethane (20 ml×1). The organic layer was dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 4:6), to obtain 81 mg of the desired product as white crystals.

Melting point: 66.0 to 70.0° C.

$^1$H NMR (CDCl$_3$, Me$_4$Si, 300 MHz) δ8.43 (d, J=1.8 Hz, 1H), 7.87 (s, 1H), 7.68 (d, J=1.8 Hz, 1H), 6.93 (bs, 1H), 6.80 (t, J=54.6 Hz, 1H), 5.79 (s, 1H), 5.76 (s, 1H), 4.45 (d, J=6.0 Hz, 2H), 3.91 (s, 3H), 1.4-1.5 (m, 1H), 0.75-0.95 (m, 4H).

Synthesis Example 8

N-[2-[3-chloro-5-(cyclopropylethynyl)pyridin-2-yl]-2-methylpropyl]-2-(difluoromethyl)nicotinamide (compound No. 3-007 of the present invention)

Step 1: Production of 2-(5-bromo-3-chloropyridin-2-yl)-2-methylpropanenitrile

To a 20 ml solution of 1.50 g of 2-(5-bromo-3-chloropyridin-2-yl)acetonitrile in tetrahydrofuran, 13.6 ml of a 1.0M tetrahydrofuran solution of potassium tert-butoxide was added under stirring at −5° C., followed by stirring for 10 minutes at the same temperature. Then, 1.94 g of iodomethane was added to the reaction mixture, and stirring was continued at room temperature for 1 hour. After completion of the reaction, 30 ml of water was added to the reaction mixture, followed by extraction with ethyl acetate (25 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 1:9), to obtain 1.61 g of the desired product as a colorless oily substance.

$^1$H NMR (CDCl$_3$, Me$_4$Si, 300 MHz) δ8.45 (d, J=2.0 Hz, 1H), 7.84 (d, J=2.0 Hz, 1H), 1.76 (s, 6H).

Step 2: Production of 2-(5-bromo-3-chloropyridin-2-yl)-2-methyl-1-propanamine

To a 15 ml solution of 1.61 g of 2-(5-bromo-3-chloropyridin-2-yl)-2-methylpropanenitrile in dichloromethane under a nitrogen atmosphere, 18.5 ml of a 1.0M hexane solution of diisobutylaluminum hydride was added dropwisely under stirring at −40° C. over 20 minutes, and after completion of the dropwise addition, stirring was continued at the same temperature for 15 minutes. After completion of the reaction, to the reaction mixture, 30 ml of water was added dropwisely, followed by stirring at the same temperature for 30 minutes, and then, the temperature was raised to room temperature, whereupon 15 ml of dichloromethane and 6.70 g of sodium potassium tartrate (Rochelle salt) were added, and stirring was further continued at room temperature for 3 hours. The organic layer was separated, and the aqueous layer was extracted with dichloromethane (50 ml×2). Organic layers were combined and washed with water (20 ml×1), and then dehydrated and dried in the order of with a saturated sodium chloride solution and then with anhydrous sodium sulfate, and the solvent was distilled off under reduced pressure, to obtain 1.54 g of the crude desired product as a brown oily substance. This product was used directly in the next step without further purification.

$^1$H NMR (CDCl$_3$, Me$_4$Si, 300 MHz) δ8.44 (d, J=2.1 Hz, 1H), 7.74 (d, J=2.1 Hz, 1H), 3.90 (bs, 2H), 3.10 (s, 2H), 1.44 (s, 6H).

Step 3: Production of tert-butyl N-[2-(5-bromo-3-chloropyridin-2-yl)-2-methylpropyl]carbamate To a 15 ml solution of 1.54 g of 2-(5-bromo-3-chloropyridyn-2-yl)-2-methyl-1-propanamine and 1.60 ml of triethylamine in dichloromethane, 1.50 g of di-tert-butyl dicarbonate was added, followed by stirring at room temperature for 1 hour. After completion of the reaction, 10 ml of water was added to the reaction mixture, followed by extraction with ethyl acetate (20 ml×2). Organic layers were combined, and dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 3:7), to obtain 911 mg of the desired product as a yellow oily substance.

$^1$H NMR (CDCl$_3$, Me$_4$Si, 300 MHz) δ8.45 (d, J=2.0 Hz, 1H), 7.80 (d, J=2.0 Hz, 1H), 5.41 (bs, 1H), 3.54 (d, J=6.5 Hz, 2H), 1.47 (s, 6H), 1.42 (s, 9H).

Step 4: Production of tert-butyl N-[2-[3-chloro-5-(cyclopropylethynyl)pyridin-2-yl]-2-methylpropyl]carbamate To a 2.5 ml solution of 911 mg of tert-butyl N-[2-(5-bromo-3-chloropyridin-2-yl)-2-methylpropyl]carbamate in N,N-dimethylformamide, 1.7 ml of triethylamine, 248 mg of cyclopropylacetylene, 143 mg of copper(I) iodide and 175 mg of dichlorobis(triphenylphosphine)palladium(II) were added, followed by stirring at 50° C. for 1 hour under a nitrogen atmosphere. After completion of the reaction, 30 ml of a saturated aqueous ammonium chloride solution was added to the reaction mixture, followed by extraction with ethyl acetate (20 ml×2). Organic layers were combined and washed with 20 ml of water, and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 1:9), to obtain 770 mg of the desired product as a brown oily substance.

$^1$H NMR (CDCl$_3$, Me$_4$Si, 300 MHz) δ8.36 (d, J=1.8 Hz, 1H), 7.60 (d, J=1.8 Hz, 1H), 5.45 (bs, 1H), 3.53 (d, J=6.7 Hz, 2H), 1.35-1.5 (m, 1H), 1.45 (s, 6H), 1.42 (s, 9H), 0.75-1.0 (m, 4H).

Step 5: Production of 2-[3-chloro-5-(cyclopropylethynyl)pyridin-2-yl]-1-propanamine To a 1 ml solution of 770 mg of tert-butyl N-[2-[3-chloro-5-(cyclopropylethynyl)pyridin-2-yl]-2-methylpropyl]carbamate in chloroform, 1 ml of trifluoroacetic acid was added, followed by stirring at 40° C. for 2 hours. After completion of the reaction, the solvent was distilled off under reduced pressure, and to the residue, 10 ml of a saturated aqueous potassium carbonate solution was added, followed by extraction with ethyl acetate (10 ml×2). Organic layers were combined and washed with 10 ml of a saturated aqueous potassium carbonate solution, and then dehydrated and dried in the order of with a saturated sodium chloride solution and then with anhydrous sodium sulfate, and the solvent was distilled off under reduced pressure to obtain 593 mg of the crude desired product as a brown oily substance. This product was used directly in the next step without further purification.

$^1$H NMR (CDCl$_3$, Me$_4$Si, 300 MHz) δ8.37 (d, J=1.8 Hz, 1H), 7.61 (d, J=1.8 Hz, 1H), 3.32 (bs, 2H), 3.13 (bs, 2H), 1.35-1.5 (m, 1H), 1.47 (s, 6H), 0.75-1.0 (m, 4H).

Step 6: Production of N-[2-[3-chloro-5-(cyclopropylethynyl)pyridin-2-yl]-2-methylpropyl]-2-(difluoromethyl)nicotinamide To a 4 ml solution of 200 mg of 2-[3-chloro-5-(cyclopropylethynyl)pyridin-2-yl]-1-propanamine and 163 mg of triethylamine in dichloromethane, 185 mg of 2-(difluoromethyl)nicotinyl chloride was added under ice-cooling and stirring, followed by stirring at room temperature for 1 hour. After the completion of the reaction, 10 ml of water was added to the reaction mixture, followed by extraction with ethyl acetate (10 ml×2). Organic layers were combined, and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 4:6), to obtain 238 mg of the desired product as a colorless resinous substance.

$^1$H NMR (CDCl$_3$, Me$_4$Si, 300 MHz) δ8.71 (d, J=4.4 Hz, 1H), 8.31 (d, J=2.0 Hz, 1H), 7.86 (d, J=8.2 Hz, 1H), 7.63 (d, J=2.0 Hz, 1H), 7.43 (dd, J=7.8, 4.8 Hz, 1H), 7.35 (bs, 1H), 6.99 (t, J=58.2 Hz, 1H), 3.86 (d, J=6.5 Hz, 2H), 1.55 (s, 6H), 1.35-1.55 (m, 1H), 0.75-1.0 (m, 4H).

Synthesis Example 9

N-[2-[3-chloro-5-(cyclopropylethynyl)pyridin-2-yl]-2,2-difluoroethyl]-2-(difluoromethyl)nicotinamide (compound No. 3-003 of the present invention)

Step 1: Production of 2-(5-bromo-3-chloropyridin-2-yl)-2,2-difluoroacetonitrile

To a 40 ml solution of 2.00 g of 2-(5-bromo-3-chloropyridin-2-yl)acetonitrile in tetrahydrofuran, 16 ml of a 1.3M tetrahydrofuran solution of lithium bis(trimethylsilyl) amide was added dropwisely under stirring at −78° C., and after the completion of the addition, stirring was continued for 30 minutes at the same temperature. Then, to this reaction mixture, a 25 ml solution of 6.00 g of N-fluorobenzenesulfonimide in tetrahydrofuran was added dropwisely, and after completion of the addition, stirring was further continued at the same temperature for 3 hours. After completion of the reaction, 50 ml of water was added to the reaction mixture, followed by extraction with hexane (50 ml×3). Organic layers were combined and washed with water (50 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:100 to 5:95), to obtain 0.81 g of the desired product as a pale yellow oily substance.

$^1$H NMR (CDCl$_3$, Me$_4$Si, 300 MHz) δ8.66 (d, J=2.1 Hz, 1H), 8.08 (d, J=2.1 Hz, 1H).

Step 2: Production of 2-(5-bromo-3-chloropyridin-2-yl)-2,2-difluoroethanamine To a 20 ml solution of 810 mg of 2-(5-bromo-3-chloropyridin-2-yl)-2,2-difluoro acetonitrile in dichloromethane under a nitrogen atmosphere, 9 ml of a 1.0M hexane solution of diisobutylaluminum hydride was added dropwisely under stirring at −78° C., and after completion of the dropwise addition, stirring was continued for 2 hours at the same temperature. Then, to the reaction mixture, 20 ml of a saturated aqueous solution of sodium potassium tartrate (Rochelle salt) and 20 ml of dichloromethane were added, followed by further stirring at room temperature for 2 hours. After completion of the reaction, 30 ml of water was added to the reaction mixture, and the organic layer was separated and washed in the order of with a saturated Rochelle salt solution (20 ml×1) and then with water (20 ml×2), whereupon the solvent was distilled off under reduced pressure, to obtain 607 mg of the crude desired product as a brown oily substance. This product was used directly in the next step without further purification.

$^1$H NMR (CDCl$_3$, Me$_4$Si, 300 MHz) δ8.56 (d, J=2.1 Hz, 1H), 8.00 (d, J=2.1 Hz, 1H), 3.49 (t, J=13.8 Hz, 2H).

Step 3: Production of tert-butyl N-[2-(5-bromo-3-chloropyridin-2-yl)-2,2-difluoroethyl]carbamate To a 5 ml solution of 607 mg of 2-(5-bromo-3-chloropyridin-2-yl)-2,2-difluoroethanamine and 271 mg of triethylamine in dichloromethane, 584 mg of di-tert-butyl dicarbonate was added, followed by stirring at room temperature for 2 hours. After completion of the reaction, the solvent was distilled off under reduced pressure, and the residue was purified by silica gel column chromatography wherein it was eluted with ethyl acetate-hexane (gradient of from 0:10 to 1:9), to obtain 430 mg of the desired product as a pale yellow oily substance.

$^1$H NMR (CDCl$_3$, Me$_4$Si, 300 MHz) 8.55 (d, J=2.1 Hz, 1H), 8.00 (d, J=2.1 Hz, 1H), 5.05 (bs, 1H), 4.0-4.2 (m, 2H), 1.40 (s, 9H).

Step 4: Production of tert-butyl N-[2-[3-chloro-5-(cyclopropylethynyl)pyridin-2-yl]-2,2-difluoroethyl]carbamate To a 3 ml solution of 430 mg of tert-butyl N-[2-(5-bromo-3-chloropyridin-2-yl)-2,2-difluoroethyl]carbamate in N,N-dimethylformamide, 468 mg of triethylamine, 153 mg of cyclopropylacetylene, 66 mg of copper(I) iodide and 81 mg of dichlorobis(triphenylphosphine)palladium(II) were added, followed by stirring at 50° C. for 2 hours under a nitrogen atmosphere. After completion of the reaction, 20 ml of a saturated aqueous ammonium chloride solution was added to the reaction mixture, followed by extraction with ethyl acetate (15 ml×2). Organic layers were combined and washed with water (10 ml×2), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 3:97 to 10:90), to obtain 340 mg of the desired product as a pale yellow oily substance.

$^1$H NMR (CDCl$_3$, Me$_4$Si, 300 MHz) δ8.40 (d, J=1.8 Hz, 1H), 7.74 (d, J=1.8 Hz, 1H), 5.08 (bs, 1H), 3.95-4.15 (m, 2H), 1.4-1.5 (m, 1H), 1.40 (s, 9H), 0.9-1.0 (m, 2H), 0.8-0.9 (m, 2H).

Step 5: Production of 2-[3-chloro-5-(cyclopropylethynyl)pyridin-2-yl]-2,2-difluoroethanamine To a 2 ml solution of 340 mg of tert-butyl N-[2-[3-chloro-5-(cyclopropylethynyl)pyridin-2-yl]-2,2-difluoroethyl]carbamate in dichloromethane, 1 ml of trifluoroacetic acid was added, followed by stirring at room temperature for 1 hour. After completion of the reaction, the solvent was distilled off under reduced pressure, and to the residue, 10 ml of a 10 wt % aqueous potassium carbonate solution was added, followed by extraction with ethyl acetate (10 ml×2). Organic layers were combined and washed with water (10 ml×1), and then dehydrated and dried in the order of with a saturated sodium chloride solution and then with anhydrous sodium sulfate, and the solvent was distilled off under reduced pressure, to obtain 235 mg of the crude desired product as a pale yellow oily substance. This product was used directly in the next step without further purification.

$^1$H NMR (CDCl$_3$, Me$_4$Si, 300 MHz) δ8.42 (d, J=1.5 Hz, 1H), 7.74 (d, J=1.5 Hz, 1H), 3.48 (t, J=14.1 Hz, 2H), 1.4-1.5 (m, 1H), 0.9-1.0 (m, 2H), 0.8-0.9 (m, 2H).

Step 6: Production of N-[2-[3-chloro-5-(cyclopropylethynyl)pyridin-2-yl]-2,2-difluoroethyl]-2-(difluoromethyl)nicotinamide 78 mg of 2-[3-chloro-5-(cyclopropylethynyl)pyridin-2-yl]-2,2-difluoroethanamine was dissolved in 2 ml of a dichloromethane-N,N-dimethylformamide (1:1) mixed solvent, and 64 mg of 2-(difluoromethyl)nicotinic acid and 72 mg of 1-(3-dimethylaminopropyl)-3-ethylcarbodiimide hydrochloride were added, followed by stirring at room temperature for 12 hours. After completion of the reaction, 10 ml of water was added to the reaction mixture, followed by extraction with ethyl acetate (8 ml×2). Organic layers were combined and washed with water (10 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 3:7), to obtain 81 mg of the desired product as white crystals.

Melting point: 116.0 to 118.0° C.

$^1$H NMR (CDCl$_3$, Me$_4$Si, 300 MHz) δ8.74 (dd, J=4.8, 1.5 Hz, 1H), 8.38 (d, J=1.8 Hz, 1H), 7.91 (dd, J=7.8, 1.5 Hz, 1H), 7.78 (d, J=1.8 Hz, 1H), 7.46 (dd, J=7.8, 4.8 Hz, 1H), 6.89 (t, J=54.9 Hz, 1H), 6.81 (bs, 1H), 4.35-4.5 (m, 2H), 1.4-1.55 (m, 1H), 0.9-1.0 (m, 2H), 0.8-0.9 (m, 2H).

Synthesis Example 10

N-[2-[3-chloro-5-(3-fluoro-1-propynyl)pyridin-2-yl]-2,2-difluoroethyl]-3-difluoromethyl-1-methyl-1H-pyrazole-4-carboxamide (compound No. 8-005 of the present invention)

Step 1: Production of tert-butyl N-[2-[3-chloro-5-(3-hydroxy-1-propynyl)pyridin-2-yl]-2,2-difluoroethyl]carbamate To a 1 ml solution of 370 mg of tert-butyl N-[2-(5-bromo-3-chloropyridin-2-yl)-2,2-difluoroethyl]carbamate produced in Step 3 of Synthesis Example 9 in N,N-dimethylformamide, 313 mg of triethylamine, 60 mg of propargyl alcohol, 41 mg of copper(I) iodide and 43 mg of dichlorobis(triphenylphosphine)palladium(II) were added, followed by stirring under a nitrogen atmosphere at 50° C. for 30 minutes. After completion of the reaction, 10 ml of a saturated aqueous ammonium chloride solution was added to the reaction mixture, followed by extraction with ethyl acetate (15 ml×2). Organic layers were combined and washed with a saturated aqueous ammonium chloride solution (10 ml×1) and then with water (10 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 4:6), to obtain 350 mg of the desired product as pale yellow crystals.

Melting point: 45.0 to 47.0° C.

$^1$H NMR (CDCl$_3$, Me$_4$Si, 300 MHz) δ8.48 (d, J=1.5 Hz, 1H), 7.80 (d, J=1.5 Hz, 1H), 5.05 (bs, 1H), 4.45-4.55 (m, 2H), 3.9-4.15 (m, 2H), 1.38 (s, 9H).

Step 2: Production of tert-butyl N-[2-[3-chloro-5-(3-fluoro-1-propynyl)pyridin-2-yl]-2,2-difluoroethyl]carbamate To a 2 ml solution of 230 mg of tert-butyl N-[2-[3-chloro-5-(3-hydroxy-1-propynyl)pyridin-2-yl]-2,2-difluoroethyl]carbamate in dichloromethane, 128 mg of (N,N-diethylamino)sulfur trifluoride was added under ice-cooling and stirring, followed by stirring at room temperature for 45 minutes. After completion of the reaction, 10 ml of a saturated aqueous sodium bicarbonate solution was added to the reaction mixture under ice-cooling and stirring, followed by extraction with dichloromethane (10 ml×2). Organic layers were combined and washed with water (10 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:5 to 1:4), to obtain 115 mg of the desired product as white crystals.

Melting point: 84.0 to 86.0° C.

$^1$H NMR (CDCl$_3$, Me$_4$Si, 300 MHz) δ8.52 (d, J=1.5 Hz, 1H), 7.87 (d, J=1.5 Hz, 1H), 5.20 (d, J=47.4 Hz, 2H), 5.06 (bs, 1H), 3.95-4.15 (m, 2H), 1.40 (s, 9H).

Step 3: Production of 2-[3-chloro-5-(3-fluoro-1-propynyl)pyridin-2-yl]-2,2-difluoroethanamine To a 1 ml solution of 145 mg of tert-butyl N-[2-[3-chloro-5-(3-fluoro-1-propynyl)pyridin-2-yl]-2,2-difluoroethyl]carbamate in dichloromethane, 1 ml of trifluoroacetic acid was added, followed by stirring at room temperature for 1 hour. After completion of the reaction, 5 ml of water and 10 ml of a saturated aqueous sodium bicarbonate solution were added to the reaction mixture to adjust the pH to be from 10 to 11, followed by extraction with dichloromethane (15 ml×2). Organic layers were combined and washed with water (10 ml×1), and then dehydrated and dried in the order of with a saturated sodium chloride solution and then with anhydrous sodium sulfate, and the solvent was distilled off under reduced pressure, to obtain 90 mg of the crude desired product as a yellow oily substance. This product was used directly in the next step without further purification.

$^1$H NMR (CDCl$_3$, Me$_4$Si, 300 MHz) δ8.54 (d, J=1.5 Hz, 1H), 7.87 (d, J=1.5 Hz, 1H), 5.19 (d, J=47.4 Hz, 2H), 3.51 (t, J=14.4 Hz, 2H).

Step 4: Production of N-[2-[3-chloro-5-(3-fluoro-1-propynyl)pyridin-2-yl]-2,2-difluoroethyl]-3-difluoromethyl-1-methyl-1H-pyrazole-4-carboxamide To a 2 ml solution of 39 mg of 3-difluoromethyl-1-methyl-1H-pyrazole-4-carboxylic acid in dichloromethane, 10 mg of N,N-dimethylformamide and 34 mg of oxalyl chloride were added, followed by stirring at room temperature for 20 minutes. After completion of the reaction, the solvent was distilled off under reduced pressure, and the residue was dissolved in 1 ml ethyl acetate and added dropwisely to a mixture of a 1 ml ethyl acetate solution of 45 mg of 2-[3-chloro-5-(3-fluoro-1-propynyl)pyridin-2-yl]-2,2-difluoroethanamine and a 1 ml ethyl acetate solution of 50 mg of potassium carbonate under ice-cooling and stirring. Then, stirring was continued for 10 minutes at the same temperature, and then 10 ml of water was added to the reaction mixture, followed by extraction with ethyl acetate (10 ml×1). The organic layer was dehydrated and dried in the order with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 5:5) to obtain 60 mg of the desired product as white crystals.

Melting point: 110.0 to 111.0° C.

$^1$H NMR (CDCl$_3$, Me$_4$Si, 300 MHz) δ8.53 (d, J=1.5 Hz, 1H), 7.93 (s, 1H), 7.89 (d, J=1.5 Hz, 1H), 7.06 (bs, 1H), 6.75 (t, J=54.0 Hz, 1H), 5.20 (d, J=47.1 Hz, 2H), 4.3-4.5 (m, 2H), 3.91 (s, 3H).

Synthesis Example 11

N-[2-[3-chloro-5-(cyclopropylethynyl)pyridin-2-yl]-2-(methylthio)ethyl]-3-difluoromethyl-1-methyl-1H-pyrazole-4-carboxamide (compound No. 8-020 of the present invention)

Step 1: Production of 2-(5-bromo-3-chloropyridin-2-yl)]-2-(methylthio)acetonitrile To a 30 ml solution of 574 mg of 2-(methylthio)acetonitrile in tetrahydrofuran, 9.7 ml of a 1.03M tetrahydrofuran-n-hexane solution of lithium diisopropylamide was added dropwisely with stirring at −78° C., followed by stirring for 10 minutes at the same temperature. Then, to this reaction mixture, a 10 ml solution of 1.0 g of 5-bromo-2,3-dichloropyridine in tetrahydrofuran was added dropwisely under stirring at the same temperature. After completion of the dropwise addition, while raising the temperature to room temperature, stirring was further continued for 18 hours. After completion of the reaction, 50 ml of water was added to the reaction mixture, followed by extraction with ethyl acetate (50 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (3:97), to obtain 430 mg of the desired product as brown crystals.

Melting point: 46.0 to 51.0° C.
$^1$H NMR (CDCl$_3$, Me$_4$Si, 300 MHz) δ8.58 (d, J=1.8 Hz, 1H), 7.93 (d, J=1.8 Hz, 1H), 5.16 (s, 1H), 2.32 (s, 3H).

Step 2: Production of 2-(5-bromo-3-chloropyridin-2-yl)-2-(methylthio)ethanamine

To a 5 ml solution of 430 mg of 2-(5-bromo-3-chloropyridin-2-yl)]-2-(methylthio)acetonitrile in dichloromethane under a nitrogen atmosphere, 4.6 ml of a 1.0M hexane solution of diisobutylaluminum hydride was added dropwisely under stirring at −78° C., and after completion of the dropwise addition, the mixture was stirred for 2 hours at the same temperature. Then, the reaction mixture was warmed to room temperature and added dropwisely to 10 ml of a saturated aqueous solution of sodium potassium tartrate (Rochelle salt) under ice-cooling and stirring. After completion of the dropwise addition, stirring was further continued at room temperature for one hour. After completion of the reaction, the reaction mixture was extracted with dichloromethane (30 ml×1), and organic layers were combined and washed with water (20 ml×1), and the solvent was distilled off under reduced pressure to obtain 310 mg of the crude desired product as a brown oily substance. This product was used directly in the next step without further purification.
$^1$H NMR (CDCl$_3$, Me$_4$Si, 300 MHz) δ8.53 (d, J=1.8 Hz, 1H), 7.93 (d, J=1.8 Hz, 1H), 4.23 (t, J=7.2 Hz, 1H), 3.2-3.4 (m, 2H), 2.02 (s, 3H).

Step 3: Production of tert-butyl N-[2-(5-bromo-3-chloropyridin-2-yl)-2-(methylthio)ethyl]carbamate To a 2 ml solution of 303 mg of 2-(5-bromo-3-chloropyridin-2-yl)-2-(methylthio)ethanamine and 126 mg of pyridine in dichloromethane, 277 mg of di-tert-butyl dicarbonate was added, followed by stirring at room temperature for 1 hour. After completion of the reaction, to the reaction mixture, 10 ml of water was added, followed by extraction with dichloromethane (10 ml×2). Organic layers were combined and washed with water (10 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 1:9), to obtain 380 mg of the desired product as a yellow oily substance.
$^1$H NMR (CDCl$_3$, Me$_4$Si, 300 MHz) δ8.51 (d, J=1.8 Hz, 1H), 7.87 (d, J=1.8 Hz, 1H), 4.93 (bs, 1H), 4.41 (t, J=7.2 Hz, 1H), 3.6-3.85 (m, 2H), 2.09 (s, 3H), 1.42 (s, 9H).

Step 4: Production of tert-butyl N-[2-[3-chloro-5-(cyclopropylethynyl)pyridin-2-yl]-2-(methylthio)ethyl]carbamate To a 1 ml solution of 370 mg of tert-butyl N-[2-(5-bromo-3-chloropyridin-2-yl)-2-(methylthio)ethyl]carbamate in N,N-dimethylformamide, 490 mg of triethylamine, 128 mg of cyclopropylacetylene, 65 mg of copper(I) iodide and 68 mg of dichlorobis(triphenylphosphine)palladium(II) were added, followed by stirring under a nitrogen atmosphere at 65° C. for 3 hours. After completion of the reaction, the reaction mixture was left to cool to room temperature, 10 ml of a saturated aqueous solution of ammonium chloride was added, and the mixture was extracted with ethyl acetate (25 ml×2). Organic layers were combined and washed with water (50 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 1:9), to obtain 283 mg of the desired product as a brown oily substance.
$^1$H NMR (CDCl$_3$, Me$_4$Si, 300 MHz) 8.41 (d, J=1.8 Hz, 1H), 7.65 (d, J=1.8 Hz, 1H), 4.95 (bs, 1H), 4.43 (t, J=7.2 Hz, 1H), 3.65-3.8 (m, 2H), 2.07 (s, 3H), 1.4-1.5 (m, 1H), 1.42 (s, 9H), 0.75-0.95 (m, 4H).

Step 5: Production of 2-[3-chloro-5-(cyclopropylethynyl)pyridin-2-yl]-2-(methylthio)ethanamine To a 1.5 ml solution of 283 mg of tert-butyl N-[2-[3-chloro-5-(cyclopropylethynyl)pyridin-2-yl]-2-(methythio)ethyl]carbamate in dichloromethane, 1.5 ml of trifluoroacetic acid was added, followed by stirring for 2 hours at room temperature. After completion of the reaction, 10 ml of water and 5 ml of a 6M aqueous sodium hydroxide solution were added to the reaction mixture, followed by extraction with dichloromethane (15 ml×2). Organic layers were combined and washed with water (10 ml×1), and then dehydrated and dried in the order of with a saturated sodium chloride solution and then with anhydrous sodium sulfate, and the solvent was distilled off under reduced pressure, to obtain 196 mg of the crude desired product as a brown oily substance. This product was used directly in the next step without further purification.
$^1$H NMR (CDCl$_3$, Me$_4$Si, 300 MHz) δ8.35-8.45 (m, 1H), 7.6-7.7 (m, 1H), 4.15-4.35 (m, 1H), 3.1-3.4 (m, 2H), 2.04 (s, 3H), 1.4-1.5 (m, 1H), 0.75-0.9 (m, 4H).

Step 6: Production of N-[2-[3-chloro-5-(cyclopropylethynyl)pyridin-2-yl]-2-(methylthio)ethyl]-3-difluoromethyl-1-methyl-1H-pyrazole-4-carboxamide To a 2 ml solution of 47 mg of 3-difluoromethyl-1-methyl-1H-pyrazole-4-carboxylic acid in dichloromethane, 10 mg of N,N-dimethylformamide and 44 mg of oxalyl chloride were added, followed by stirring at room temperature for 20 minutes. After completion of the reaction, the solvent was distilled off under reduced pressure, and the residue was dissolved in 1 ml of dichloromethane, and added dropwisely to a 2 ml solution of 60 mg of 2-[3-chloro-5-(cyclopropylethynyl)pyridin-2-yl]-2-(methylthio)ethanamine and 45 mg of triethylamine in dichloromethane under ice-cooling and stirring. After stirring at the same temperature for 20 minutes, 10 ml of water was added to the reaction mixture, followed by extraction with dichloromethane (10 ml×1). The organic layer was dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 4:6), to obtain 60 mg of the desired product as a yellow resinous substance.

$^1$H NMR (CDCl$_3$, Me$_4$Si, 300 MHz) δ8.42 (d, J=1.8 Hz, 1H), 7.86 (s, 1H), 7.65 (d, J=1.8 Hz, 1H), 6.86 (bs, 1H), 6.74 (t, J=53.7 Hz, 1H), 4.57 (dd, J=8.4, 6.0 Hz, 1H), 4.0-4.2 (m, 2H), 3.90 (s, 3H), 2.09 (s, 3H), 1.4-1.55 (m, 1H), 0.8-1.0 (m, 4H).

Synthesis Example 12

N-[2-[3-chchloro-5-(cyclopropylethynyl)pyridin-2-yl]-2-cyanoethyl]-3-difluoromethyl-1-methyl-1H-pyrazole-4-carboxamide (compound No. 8-021 of the present invention)

Step 1: Production of N-[2-(5-bromo-3-chloropyridin-2-yl)-2-cyanoethyl]-3-difluoromethyl-1-methyl-1H-pyrazole-4-carboxamide To a 2 ml solution of 240 mg of 2-(5-bromo-3-chloropyridin-2-yl)acetonitrile in tetrahydrofuran, 1.1 ml of a 1.0M tetrahydrofuran solution of potassium tert-butoxide was added under ice-cooling and stirring, followed by stirring at room temperature for 1 hour. Then, to this reaction mixture, 276 mg of [3-difluoromethyl-1-methyl-1H-pyrazole-4-carboxamide]methyl acetate was added, and stirring was further continued at room temperature for 1 hour. After completion of the reaction, 10 ml of a saturated aqueous solution of ammonium chloride was added to the reaction mixture, followed by extraction with ethyl acetate (20 ml×1). The organic layer was dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 5:5), to obtain 150 mg of the desired product as brown crystals.

Melting point: 65.0 to 69.0° C.

$^1$H NMR (CDCl$_3$, Me$_4$Si, 300 MHz) δ8.60 (d, J=2.1 Hz, 1H), 7.93 (d, J=2.1 Hz, 1H), 7.92 (s, 1H), 6.83 (bs, 1H), 6.74 (t, J=54.6 Hz, 1H), 4.79 (t, J=6.6 Hz, 1H), 4.0-4.2 (m, 2H), 3.92 (s, 3H).

Step 2: Production of N-[2-[3-chloro-5-(cyclopropylethynyl)pyridin-2-yl]-2-cyanoethyl]-3-difluoromethyl-1-methyl-1H-pyrazole-4-carboxamide To a 1 ml solution of 135 mg of N-[2-(5-bromo-3-chloropyridin-2-yl)-2-cyanoethyl]-3-difluoromethyl-1-methyl-1H-pyrazole-4-carboxamide, 32 mg of cyclopropylacetylene and 163 mg of triethylamine in N,N-dimethylformamide, 21 mg of copper(I) iodide and 23 mg of dichlorobis(triphenylphosphine)palladium(II) were added, followed by stirring at 50° C. for 45 min under a nitrogen atmosphere. After completion of the reaction, the reaction mixture was left to cool to room temperature, and 10 ml of water was added, followed by extraction with ethyl acetate (20 ml×1). The organic layer was washed with a saturated aqueous ammonium chloride solution (10 ml) and then with water (10 ml), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 4:6), to obtain 125 mg of the desired product as brown crystals.

Melting point: 43.0 to 46.0° C.

$^1$H NMR (CDCl$_3$, Me$_4$Si, 300 MHz) δ8.47 (d, J=1.5 Hz, 1H), 7.91 (s, 1H), 7.69 (d, J=1.5 Hz, 1H), 6.93 (bs, 1H), 6.75 (t, J=54.6 Hz, 1H), 4.78 (t, J=6.9 Hz, 1H), 3.9-4.2 (m, 2H), 3.91 (s, 3H), 1.4-1.5 (m, 1H), 0.8-1.0 (m, 4H).

Synthesis Example 13

N-[2-[3-chloro-5-(cyclopropylethynyl)pyridin-2-yl]-2,2-dicyanoethyl]-2-(trifluoromethyl)benzamide (compound No. 1-023 of the present invention)

Step 1: Production of 2-(5-bromo-3-chloropyridin-2-yl)malononitrile

To a 30 ml solution of 2.0 g of 5-bromo-2,3-dichloropyridine and 1.2 g of malononitrile in dimethyl sulfoxide, 5.7 g of cesium carbonate was added, and the mixture was stirred for 5 hours at 100° C. After completion of the reaction, the reaction mixture was left to cool to room temperature, and 30 ml of a saturated aqueous ammonium chloride solution was added, followed by washing with ethyl acetate (30 ml×1). To the aqueous layer, 5 ml of a 1N aqueous hydrochloric acid solution was added to adjust the pH to 4, followed by extraction with ethyl acetate (100 ml×2). Organic layers were combined and washed with water (50 ml×1), and then dehydrated and dried in the order of with a saturated sodium chloride solution and then with anhydrous sodium sulfate, and the solvent was distilled off under reduced pressure to obtain 1.1 g of the desired product as brown crystals.

Melting point: 157.0 to 159.0° C.

$^1$H NMR (CDCl$_3$, Me$_4$Si, 300 MHz) δ8.01 (d, J=1.8 Hz, 1H), 7.61 (d, J=1.8 Hz, 1H), 4.43 (s, 1H).

Step 2: Production of N-[2-(5-bromo-3-chloropyridin-2-yl)-2,2-dicyanoethyl]-2-(trifluoromethyl)benzamide To a 4 ml solution of 150 mg of 2-(5-bromo-3-chloropyridin-2-yl)malononitrile in tetrahydrofuran, 75 mg of potassium tert-butoxide was added under ice-cooling and stirring, followed by stirring at 0° C. for 30 minutes. Then, to this reaction mixture, 150 mg of N-chloromethyl-2-(trifluoromethyl)benzamide was added, followed by further stirring at room temperature for 1 hour. After completion of the reaction, to the reaction mixture, 10 ml of a saturated aqueous ammonium chloride solution was added, followed by extraction with ethyl acetate (10 ml×2). Organic layers were combined and washed with water (50 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:100 to 5:95), to obtain 170 mg of the desired product as a colorless resinous substance.

$^1$H NMR (CDCl$_3$, Me$_4$Si, 300 MHz) δ8.59 (d, J=2.1 Hz, 1H), 8.11 (d, J=2.1 Hz, 1H), 7.5-7.65 (m, 4H), 6.66 (t, J=6.9 Hz, 1H), 4.71 (d, J=6.9 Hz, 2H).

Step 3: Production of N-[2-[3-chloro-5-(cyclopropylethynyl)pyridin-2-yl]-2,2-dicyanoethyl]-2-(trifluoromethyl)benzamide To a 1 ml solution of 150 mg of N-[2-(5-bromo-3-chloropyridin-2-yl)-2,2-dicyanoethyl]-2-(trifluoromethyl)

benzamide, 33 mg of cyclopropylacetylene and 167 mg of triethylamine in N,N-dimethylformamide, 22 mg of copper (I) iodide and 23 mg of dichlorobis(triphenylphosphine) palladium(II) were added, followed by stirring at 50° C. for 30 minutes under a nitrogen atmosphere. After completion of the reaction, the reaction mixture was left to cool to room temperature, and 10 ml of water was added, followed by extraction with ethyl acetate (10 ml×2). Organic layers were combined and washed with a saturated aqueous ammonium chloride solution (10 ml×1) and then with water (10 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 4:6), to obtain 12.1 mg of the desired product as brown crystals.

Melting point: 42.0 to 44.0° C.

$^1$H NMR (CDCl$_3$, Me$_4$Si, 300 MHz) δ8.42 (d, J=1.5 Hz, 1H), 7.84 (d, J=1.5 Hz, 1H), 7.5-7.75 (m, 4H), 6.66 (t, J=6.9 Hz, 1H), 4.71 (d, J=6.9 Hz, 2H), 1.4-1.55 (m, 1H), 0.8-1.0 (m, 4H).

Synthesis Example 14

2-[3-chloro-5-(cyclopropylethynyl)pyridin-2-yl]-2-[(3-difluoromethyl-1-methyl-1H-pyrazole-4-carboxamide)methyl]malonic acid diethyl ester (compound No. 8-023 of the present invention)

Step 1: Production of 2,3-dichloro-5-(cyclopropylethynyl)pyridine

To a 50 ml solution of 19.3 mg of dichlorobis(triphenylphosphine)palladium(II) and 52.5 mg of copper(I) iodide in dimethyl sulfoxide, 72.3 mg of triphenylphosphine was added, and the mixture was stirred at room temperature for 15 minutes. Then, to this reaction mixture, 5.00 g of 5-bromo-2,3-dichloropyridine, 9.50 g of cyclopropylacetylene and 22.30 g of triethylamine were added, followed by stirring under a nitrogen atmosphere at 100° C. for 6 hours. After completion of the reaction, the reaction mixture was left to cool to room temperature, and 50 ml of a saturated aqueous solution of ammonium chloride was added, followed by extraction with ethyl acetate (100 ml×2). Organic layers were combined and washed with water (100 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 1:9), to obtain 18.96 g of the desired product as a brown oily substance.

$^1$H NMR (CDCl$_3$, Me$_4$Si, 300 MHz) δ8.25 (d, J=1.8 Hz, 1H), 7.72 (d, J=1.8 Hz, 1H), 1.35-1.6 (m, 1H), 0.75-1.1 (m, 4H).

Step 2: Production of 2-[3-chloro-5-(cyclopropylethynyl)pyridin-2-yl]malonic acid diethyl ester To a 10 ml solution of 2.00 g of 2,3-dichloro-5-(cyclopropylethynyl)pyridine and 3.32 g of diethyl malonate in dimethyl sulfoxide, 6.74 g of cesium carbonate was added, followed by stirring at 90° C. for 5 hours. After completion of the reaction, the reaction mixture was left to cool to room temperature, and 30 ml of water was added, followed by extraction with ethyl acetate (20 ml×2). Organic layers were combined and washed with water (10 ml×2), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 6:4), to obtain 2.50 g of the desired product as a colorless oily substance.

$^1$H NMR (CDCl$_3$, Me$_4$Si, 300 MHz) δ8.44 (d, J=1.8 Hz, 1H), 7.67 (d, J=1.8 Hz, 1H), 5.18 (s, 1H), 4.31 (q, J=7.2 Hz, 4H), 1.4-1.55 (m, 1H), 1.29 (t, J=7.2 Hz, 6H), 0.8-1.0 (m, 4H).

Step 3: Production of 2-[3-chloro-5-(cyclopropylethynyl)pyridin-2-yl]-2-[(3-difluoromethyl-1-methyl-1H-pyrazole-4-carboxamide)methyl]malonic acid diethyl ester To a 15 ml solution of 2.48 g of 2-[3-chloro-5-(cyclopropylethynyl)pyridin-2-yl]malonic acid diethyl ester in N,N-dimethylacetamide, 2.02 g of [3-difluoromethyl-1-methyl-1H-pyrazole-4-carboxamide]methyl acetate and 0.67 g of sodium acetate were added under stirring at room temperature, followed by stirring at 80° C. for 9 hours. Then, after the completion of the reaction, the reaction mixture was cooled to 10° C., and 50 ml of water was added, followed by extraction with dichloromethane (30 ml×2). Organic layers were combined and washed with a saturated aqueous solution of ammonium chloride (30 ml×1) and then with water (30 ml×1). Then, dehydration and drying were carried out in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 5:5), to obtain 3.51 g of the desired product as white crystals.

Melting point: 87.0 to 88.0° C.

$^1$H NMR (CDCl$_3$, Me$_4$Si, 300 MHz) δ8.33 (d, J=1.8 Hz, 1H), 7.72 (s, 1H), 7.65 (d, J=1.8 Hz, 1H), 7.28 (bs, 1H), 6.81 (t, J=54.3 Hz, 1H), 4.50 (d, J=6.3 Hz, 2H), 4.2-4.35 (m, 4H), 3.90 (s, 3H), 1.4-1.55 (m, 1H), 1.25 (t, J=7.2 Hz, 6H), 0.8-1.0 (m, 4H).

Synthesis Example 15

2-[3-chloro-5-(cyclopropylethynyl)pyridin-2-yl]-3-(3-difluoromethyl-1-methyl-1H-pyrazole-4-carboxamide)propionic acid methyl ester (compound No. 8-022 of the present invention)

To a 5 ml solution of 440 mg of 2-[3-chloro-5-(cyclopropylethynyl)pyridin-2-yl]-2-[(3-difluoromethyl-1-methyl-1H-pyrazole-4-carboxamide)methyl]malonic acid diethyl ester in tetrahydrofuran, a 5.5 ml solution of 100 mg of sodium hydroxide in water was added, followed by stirring for 10 hours under heating and refluxing. After completion of the reaction, the reaction mixture was left to cool to room temperature, and 15 ml of water and 1ml of acetic acid were added, followed by extraction with dichloromethane (10 ml×2). Organic layers were combined and washed with water (10 ml×1), and then dehydrated and dried in the order of with a saturated sodium chloride solution and then with anhydrous sodium sulfate, and the solvent was distilled off under reduced pressure. The residue was dissolved in 4 ml of N,N-dimethylformamide, and 174 mg of potassium carbonate and 127 mg of dimethyl sulfate were added under stirring at room temperature, followed by stirring for 30 minutes at the same temperature. After completion of the reaction, 5 ml of water was added to the reaction mixture, followed by extraction with ethyl acetate (3 ml×2). Then, organic layers were combined and washed with water (5 ml×1), and then dehydrated and dried in the order of with a saturated aqueous sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 7:3), to obtain 152 mg of the desired product as a colorless resinous substance.

$^1$H NMR (CDCl$_3$, Me$_4$Si, 300 MHz) δ8.40 (d, J=1.8 Hz, 1H), 7.83 (s, 1H), 7.66 (d, J=1.8 Hz, 1H), 7.03 (bs, 1H), 6.82 (t, J=54.0 Hz, 1H), 4.57 (t, J=6.3 Hz, 1H), 4.05-4.2 (m, 1H), 3.95-4.05 (m, 1H), 3.91 (s, 3H), 3.71 (s, 3H), 1.4-1.55 (m, 1H), 0.8-1.0 (m, 4H).

Synthesis Example 16

N-[2-[3-chloro-5-(cyclopropylethynyl)pyridin-2-yl]-2-methoxy-1-methylethyl]-3-difluoromethyl-1-methyl-1H-pyrazole-4-carboxamide (compound No. 8-028 of the present invention)

Step 1: Production of 5-bromo-3-chloro-2-(2-nitro-1-propenyl)pyridine

A 10 ml solution of 2.06 g of 5-bromo-3-chloropicolyl aldehyde and 1.00 g of 1-butylamine in toluene, was heated and refluxed for 2 hours while azeotropically dried using a Dean-Stark tube. Then, the solvent was distilled off under reduced pressure, and to the residue, 10 ml of acetic acid and 1.05 g of nitroethane were added, followed by stirring at 100° C. for 40 minutes. After completion of the reaction, the reaction mixture was left to cool to room temperature, and after addition of 30 ml of water, the mixture was extracted with ethyl acetate (50 ml×2). Organic layers were combined, and dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (3:97), to obtain 0.76 g of the desired product as brown crystals.

Melting point: 44.0 to 50.0° C.

$^1$H NMR (CDCl$_3$, Me$_4$Si, 300 MHz) δ8.65 (d, J=1.8 Hz, 1H), 8.25 (s, 1H), 7.96 (d, J=1.8 Hz, 1H), 2.67 and 2.66 (s, 3H).

Step 2: Production of 5-bromo-3-chloro-2-(1-methoxy-2-nitropropyl)pyridine

To a 10 ml solution of 760 mg of 5-bromo-3-chloro-2-(2-nitro-1-propenyl)pyridine in toluene, 2.1 g of a 28% sodium methoxide methanol solution diluted by 3 ml of methanol, was added dropwisely with stirring under ice-cooling. After stirring for 30 minutes at the same temperature, 1.5 ml of acetic acid and 10 ml of water were added to the reaction mixture, followed by extraction with dichloromethane (30 ml×1). Then, organic layers were combined, and dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (3:97), to obtain 683 mg of the desired product as a red oily substance.

$^1$H NMR (CDCl$_3$, Me$_4$Si, 300 MHz) δ8.67 and 8.64 (d, J=2.1 Hz, 1H), 7.95 and 7.91 (d, J=2.1 Hz, 1H), 5.35 and 5.30 (d, J=6.3 and 9.6 Hz, 1H), 5.1-5.25 (m, 1H) and 5.04 (qui, J=6.6 Hz, 1H), 3.36 and 3.27 (s, 3H), 1.69 and 1.29 (d, J=6.9 Hz, 3H).

Step 3: Production of 2-(5-bromo-3-chloropyridin-2-yl)-2-methoxy-1-methylethylamine 340 mg of 5-bromo-3-chloro-2-(1-methoxy-2-nitropropyl)pyridine was dissolved in 4 ml of a methanol-water (1:1) mixed solvent, and 350 mg of ammonium chloride and 182 mg of reduced iron were added, followed by stirring for 30 minutes at room temperature and then for 1.5 hours at 65° C. After completion of the reaction, the reaction mixture was left to cool to room temperature, and after removing the insoluble matter by filtration by Celite, the solvent was distilled off under reduced pressure. The residue was dissolved in 30 ml of diethyl ether, and then extracted with 20 ml of a 1 wt % aqueous hydrochloric acid solution, whereupon 20 ml of a saturated aqueous sodium bicarbonate solution was added to the water layer so that the water layer was made basic, followed by back extraction with 100 ml of ethyl acetate. The organic layer was dehydrated and dried in the order of with a saturated sodium chloride solution and then with anhydrous sodium sulfate, and the solvent was distilled off under reduced pressure to obtain 200 mg of the crude desired product as a brown oily substance. This product was used directly in the next step without further purification.

$^1$H NMR (CDCl$_3$, Me$_4$Si, 300 MHz) δ8.66 and 8.65 (d, J=2.1 Hz, 1H), 7.88 and 7.87 (d, J=2.1 Hz, 1H), 4.58 and 4.46 (d, J=5.7 and 7.5 Hz, 1H), 3.30 and 3.27 (s, 3H), 3.25-3.45 (m, 1H), 1.12 and 0.93 (d, J=6.6 Hz, 3H).

Step 4: Production of tert-butyl N-[2-(5-bromo-3-chloropyridin-2-yl)-2-methoxy-1-methylethyl]carbamate To a 2 ml solution of 190 mg of 2-(5-bromo-3-chloropyridin-2-yl)-2-methoxy-1-methylethylamine and 80 mg of pyridine in dichloromethane, 178 mg of di-tert-butyl dicarbonate was added, followed by stirring at room temperature for 30 minutes. After completion of the reaction, 10 ml of water was added to the reaction mixture, followed by extraction with dichloromethane (10 ml×2). Organic layers were combined, and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 2:98 to 20:80), to obtain 200 mg of the desired product as a colorless oily substance.

$^1$H NMR (CDCl$_3$, Me$_4$Si, 300 MHz) δ8.65 and 8.59 (d, J=1.8 Hz, 1H), 7.87 and 7.85 (d, J=1.8 Hz, 1H), 5.31 and 4.85 (d, J=8.1 Hz, 1H), 4.75 and 4.67 (d, J=4.2 and 2.4 Hz, 1H), 4.0-4.3 (m, 1H), 3.53 (s, 3H), 1.42 and 1.26 (s, 9H), 1.32 and 1.05 (d, J=6.6 Hz, 3H).

Step 5: Production of tert-butyl N-[2-[3-chloro-5-(cyclopropylethynyl)pyridin-2-yl]-2-methoxy-1-methylethyl]carbamate To a 1 ml solution of 200 mg of tert-butyl N-[2-(5-bromo-3-chloropyridin-2-yl)-2-methoxy-1-methylethyl]carbamate in N,N-dimethylformamide, 267 mg of triethylamine, 52 mg of cyclopropylacetylene, 35 mg of copper(I) iodide and 37 mg of dichlorobis(triphenylphosphine)palladium(II) were added, followed by stirring under a nitrogen for 1.5 hours at room temperature, then for 1.5 hours at 45° C. and further at 60° C. for 3.5 hours. After completion of the reaction, the reaction mixture was left to cool to room temperature, and 10 ml of water was added, and after removing the insoluble materials by filtration by Celite, the mixture was extracted with ethyl acetate (10 ml×2). Organic layers were combined and washed with 20 ml of water, and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:19 to 2:18), to obtain 140 mg of the desired product as a yellow oily substance.

$^1$H NMR (CDCl$_3$, Me$_4$Si, 300 MHz) δ8.45-8.6 (m, 1H), 7.6-7.7 (m, 1H), 5.46 and 4.89 (d, J=7.5 Hz, 1H), 4.78 and 4.68 (d, J=4.5 and 3.0 Hz, 1H), 4.0-4.3 (m, 1H), 3.35 and 3.33 (s, 3H), 1.43 and 1.28 (s, 9H), 1.4-1.6 (m, 1H), 1.29 and 1.02 (d, J=9.3 and 6.9 Hz, 3H), 0.75-1.1 (m, 4H).

Step 6: Production of 2-[3-chloro-5-(cyclopropyl-ethynyl)pyridin-2-yl]-2-methoxy-1-methylethylamine To a 1.5 ml solution of 140 mg of tert-butyl N-[2-[3-chloro-5-(cyclopropylethynyl)pyridin-2-yl]-2-methoxy-1-methylethyl]carbamate in dichloromethane, 1 ml of trifluoroacetic acid was added with stirring under ice-cooling, followed by stirring at room temperature for 1.5 hours. After completion of the reaction, to the reaction mixture, 5 ml of water was added, and then, a 4M aqueous sodium hydroxide solution was added to adjust the pH to 13, followed by extraction with dichloromethane (10 ml×2). The organic layer was dehydrated and dried in the order of with a saturated sodium chloride solution and then with anhydrous sodium sulfate, and the solvent was distilled off under reduced pressure to obtain 90 mg of the crude desired product as a brown oily substance. This product was used directly in the next step without further purification.

$^1$H NMR (CDCl$_3$, Me$_4$Si, 300 MHz) δ8.45-8.6 (m, 1H), 7.65 and 7.6-7.7 (d and m, J=1.2 Hz, 1H), 4.55-4.65 and 4.46 (m and d, J=7.8 Hz, 1H), 3.26 (s, 3H), 3.2-3.35 (m, 1H), 1.4-1.6 (m, 1H), 1.05-1.2 and 0.9-1.0 (m, 3H), 0.8-1.0 (m, 4H).

Step 7: Production of N-[2-[3-chloro-5-(cyclopropylethynyl)pyridin-2-yl]-2-methoxy-1-methylethyl]-3-difluoromethyl-1-methyl-1H-pyrazole-4-carboxamide To a 2 ml solution of 72 mg of 3-difluoromethyl-1-methyl-1H-pyrazole-4-carboxylic acid in dichloromethane, 65 mg of oxalyl chloride and 10 mg of N,N-dimethylformamide were added, followed by stirring at room temperature for 20 minutes. Then, the solvent was distilled off under reduced pressure, and the residue was dissolved in 1 ml of dichloromethane, and added dropwisely to a 2 ml dichloromethane solution of 90 mg of 2-[3-chloro-5-(cyclopropylethynyl)pyridin-2-yl]-2-methoxy-1-methylethylamine and 101 mg of triethylamine with stirring under ice-cooling. After completion of the dropwise addition, the mixture was stirred for 20 minutes at the same temperature. After completion of the reaction, 10 ml of water was added to the reaction mixture, followed by extraction with dichloromethane (10 ml×1). The organic layer was dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 7:3), to obtain 140 mg of the desired product as a yellow resinous substance.

$^1$H NMR (CDCl$_3$, Me$_4$Si, 300 MHz) δ8.55 and 8.42 (d, J=1.8 Hz, 1H), 7.86 and 7.76 (s, 1H), 7.68 and 7.64 (d, J=1.8 Hz, 1H), 6.96 and 6.94 (t, J=54.3 Hz, 1H), 6.53 and 6.50 (bs, 1H), 4.86 and 4.79 (d, J=3.9 and 3.3 Hz, 1H), 4.4-4.6 (m, 1H), 3.93 and 3.92 (s, 3H), 3.37 and 3.35 (s, 3H), 1.35-1.55 (m, 1H), 1.38 and 1.07 (d, J=6.9 Hz, 3H), 0.75-1.0 (m, 4H).

Synthesis Example 17

N-[2-benzyloxy-2-[3-chloro-5-(cyclopropylethynyl)pyridin-2-yl]-1-methylethyl]-2-(trifluoromethyl)benzamide (compound No. 1-031 of the present invention)

Step 1: Production of tert-butyl N-[2-[3-chloro-5-(cyclopropylethynyl)pyridin-2-yl]-2-oxo-1-methylethyl]carbamate To a 34 ml solution of 927 mg of dichlorobis(triphenylphosphine)palladium(II) and 754 mg of copper(I) iodide in dimethyl sulfoxide, 1.5 g of triphenylphosphine was added, followed by stirring at room temperature for 15 minutes. Then, to this reaction mixture, 4.21 g of tert-butyl N-[2-(5-bromo-3-chloropyridin-2-yl)-2-oxo-1-methylethyl]carbamate, 9.2 ml of triethylamine and 1.1 g of cyclopropylacetylene were added, followed by stirring under a nitrogen atmosphere at 110° C. for 5 hours. After completion of the reaction, the reaction mixture was left to cool to room temperature, and 30 ml of a saturated aqueous solution of ammonium chloride was added, followed by extraction with ethyl acetate (50 ml×2). Organic layers were combined and washed with water (50 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:10 to 3:7), to obtain 3.04 g of the desired product as a yellow resinous substance.

$^1$H NMR (CDCl$_3$, Me$_4$Si, 300 MHz) δ8.47 (d, J=1.8 Hz, 1H), 7.73 (d, J=1.8 Hz, 1H), 7.32 (bs, 1H), 5.35-5.55 (m, 1H), 1.45-1.55 (m, 1H), 1.44 (s, 9H), 1.35 (d, J=7.4 Hz, 3H), 0.8-1.05 (m, 4H).

Step 2: Production of tert-butyl N-[2-[3-chloro-5-(cyclopropylethynyl)pyridin-2-yl]-2-hydroxy-1-methylethyl]carbamate 1.80 g of tert-butyl N-[2-[3-chloro-5-(cyclopropylethynyl)pyridin-2-yl]-2-oxo-1-methylethyl]carbamate is dissolved in 20 ml of a tetrahydrofuran-methanol (1:1) mixed solvent, and 0.74 g of sodium borohydride was added under stirring at −5° C., followed by stirring at the same temperature for 30 minutes. After completion of the reaction, 10 ml of a saturated aqueous ammonium chloride solution was added to the reaction mixture, followed by extraction with ethyl acetate (20 ml×2). Organic layers were combined, and then dehydrated and dried in the order of with a saturated sodium chloride solution and then with anhydrous sodium sulfate, and the solvent was distilled off under reduced pressure to obtain 1.85 g of the crude desired product as a yellow resinous substance. This product was used directly in the next step without further purification.

$^1$H NMR (CDCl$_3$, Me$_4$Si, 300 MHz) δ8.45 and 8.42 (d, J=1.7 Hz, 1H), 7.66 and 7.64 (d, J=1.7 Hz, 1H), 4.8-5.3 (m, 2H), 4.4-4.8 (m, 1H), 4.15-4.4 (m, 1H), 1.4-1.55 (m, 10H), 1.35 and 0.79 (d, J=6.8 Hz, 3H), 0.75-1.0 (m, 4H).

Step 3: Production of tert-butyl N-[2-benzyloxy-2-[3-chloro-5-(cyclopropylethynyl)pyridin-2-yl]-1-methylethyl]carbamate To a 1 ml solution of 100 mg of tert-butyl N-[2-[3-chloro-5-(cyclopropylethynyl)pyridin-2-yl]-2-hydroxy-1-methylethyl]carbamate in tetrahydrofuran, 25 mg of 60% oily sodium hydride was added under stirring at −5° C., followed by stirring for 1 hour at the same temperature. Then, 102 mg of benzyl bromide was added to this reaction mixture, and stirring was further continued at room temperature for 18 hours. After completion of the reaction, 1 ml of water was added to the reaction mixture, followed by extraction with ethyl acetate (10 ml×2). Organic layers were combined, and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:10 to 3:7), to obtain 63 mg of the desired product as a yellow resinous substance.

$^1$H NMR (CDCl$_3$, Me$_4$Si, 300 MHz) δ8.5-8.55 and 8.4-8.45 (m, 1H), 7.63 and 7.61 (d, J=1.8 Hz, 1H), 7.25-7.35 (m, 5H), 5.64 (d, J=9.5 Hz, 1H) and 5.50 (d, J=8.9 Hz, 1H), 4.90 (d, J=4.9 Hz, 1H) and 4.82 (d, J=3.4 Hz, 1H), 4.68 (d, J=12.3 Hz, 1H) and 4.60 (d, J=11.6 Hz, 1H), 4.49 (d, J=12.3 Hz, 1H) and 4.39 (d, J=11.6 Hz, 1H), 4.2-4.35 (m, 1H), 1.35-1.55 (m, 10H), 1.24 (d, J=6.7 Hz, 3H) and 1.07 (d, J=7.0 Hz, 3H), 0.75-1.0 (m, 4H).

Step 4: Production of N-[2-benzyloxy-2-[3-chloro-5-(cyclopropylethynyl)pyridin-2-yl]-1-methylethyl]-2-(trifluoromethyl)benzamide To a 1 ml solution of 63 mg of tert-butyl N-[2-benzyloxy-2-[3-chloro-5-(cyclopropylethynyl)pyridin-2-yl]-1-methylethyl]carbamate in dichloromethane, 1 ml of trifluoroacetic acid was added with stirring under ice-cooling, followed by stirring at room temperature for 1 hour. After completion of the reaction, 2 ml of toluene was added to the reaction mixture, and then, the solvent was distilled off under reduced pressure. The residue was dissolved in 1 ml of dichloromethane, and 0.2 ml of water, 59 mg of potassium carbonate and 36 mg of 2-(trifluoromethyl)benzoyl chloride were added with stirring under ice-cooling, followed by stirring at room temperature for 1 hour. After completion of the reaction, 1 ml of the water was added to the reaction mixture, followed by extraction with ethyl acetate (10 ml×2). Then, organic layers were combined, and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 4:6), to obtain 58 mg of the desired product as a colorless resinous substance.

$^1$H NMR (CDCl$_3$, Me$_4$Si, 300 MHz) δ8.51 and 8.45 (d, J=1.7 Hz, 1H), 7.2-7.7 (m, 10H), 6.47 (d, J=8.2 Hz, 1H), 5.05 (d, J=4.1 Hz, 1H) and 4.95 (d, J=2.7 Hz, 1H), 4.75-4.95 (m, 1H), 4.65 (d, J=11.9 Hz, 1H) and 4.60 (d, J=11.6 Hz, 1H), 4.47 (d, J=11.6 Hz, 1H) and 4.39 (d, J=11.9 Hz, 1H), 1.35-1.55 (m, 1H), 1.40 (d, J=6.5 Hz, 3H) and 1.12 (d, J=6.8 Hz, 3H), 0.75-1.0 (m, 4H).

Synthesis Example 18

N-[2-[3-chloro-5-(cyclopropylethynyl)pyridin-2-yl]-1-methylethyl]-3-difluoromethyl-1-methyl-1H-pyrazole-4-carboxamide (compound No. 8-024 of the present invention)

Step 1: Production of 3-difluoromethyl-1-methyl-N-[1-(4-methylphenylsulfonyl)ethyl]-1H-pyrazole-4-carboxamide To a 15 ml solution of 500 mg of 3-difluoromethyl-1-methyl-1H-pyrazole-4-carboxamide in formic acid-water (1:4), 151 mg of paraldehyde and 609 mg of sodium p-toluenesulfinate were added, followed by stirring for 2 hours at 90° C. After completion of the reaction, the reaction mixture was left to cool to room temperature and extracted with ethyl acetate (30 ml×1). The organic layer was washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 5:5), to obtain 573 mg of the desired product as white crystals.

Melting point: 116.0 to 118.0° C.

$^1$H NMR (CDCl$_3$, Me$_4$Si, 300 MHz) 57.83 (s, 1H), 7.76 (d, J=8.1 Hz, 2H), 7.28 (d, J=8.1 Hz, 2H), 6.82 (bs, 1H), 6.78 (t, J=54.6 Hz, 1H), 5.4-5.55 (m, 1H), 3.90 (s, 3H), 2.41 (s, 3H), 1.66 (d, J=6.9 Hz, 3H).

Step 2: Production of 2-(5-bromo-3-chloropyridin-2-yl)-3-(3-difluoromethyl-1-methyl-1H-pyrazole-4-carboxamide)butyric acid methyl ester To a 3 ml solution of 200 mg of 3-difluoromethyl-1-methyl-N-[1-(4-methylphenylsulfonyl)ethyl]-1H-pyrazole-4-carboxamide and 148 mg of 2-(5-bromo-3-chloropyridin-2-yl)acetic acid methyl ester in N,N-dimethylformamide, 365 mg of cesium carbonate was added, followed by stirring at room temperature for 12 hours. After completion of the reaction, 15 ml of water was added to the reaction mixture, followed by extraction with ethyl acetate (10 ml×2). Organic layers were combined and washed with water (10 ml×2), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 2:8 to 4:6), to obtain 98 mg of the desired product as a colorless resinous substance.

$^1$H NMR (CDCl$_3$, Me$_4$Si, 300 MHz) δ8.36 (d, J=2.1 Hz, 1H), 7.86 (d, J=2.1 Hz, 1H), 7.72 (s, 1H), 7.21 (d, J=7.2 Hz, 1H), 6.90 (t, J=54.6 Hz, 1H), 4.75-4.85 (m, 1H), 4.49 (d, J=3.3 Hz, 1H), 3.91 (s, 3H), 3.74 (s, 3H), 1.45 (d, J=7.2 Hz, 3H).

Step 3: Production of N-[2-(5-bromo-3-chloropyridin-2-yl)-1-methylethyl]-3-difluoromethyl-1-methyl-1H-pyrazole-4-carboxamide To a 10 ml solution of 2.50 g of 2-(5-bromo-3-chloropyridin-2-yl)-3-(3-difluoromethyl-1-methyl-1H-pyrazole-4- carboxamide)butyric acid methyl ester in methanol, a 5 ml solution of 0.43 g of sodium hydroxide in water was added, followed by stirring at room temperature for 4 hours. Then, to the reaction mixture, 1N aqueous hydrochloric acid was added until the pH became 2 or less, and stirring was continued at 90° C. for 2 hours. After completion of the reaction, the reaction mixture was left to cool to room temperature, and 40 ml of water was added, followed by extraction with ethyl acetate (50 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was crystallized by adding diisopropyl ether to obtain 2.2 g of the desired product as white crystals.

Melting point: 136.0 to 138.0° C.

$^1$H NMR (CDCl$_3$, Me$_4$Si, 300 MHz) δ8.47 (d, J=2.1 Hz, 1H), 7.83 (d, J=2.1 Hz, 1H), 7.82 (s, 1H), 6.89 (bs, 1H), 6.87 (t, J=54.3 Hz, 1H), 4.6-4.75 (m, 1H), 3.91 (s, 3H), 3.05-3.25 (m, 2H), 1.28 (d, J=6.6 Hz, 3H).

Step 4: Production of N-[2-[3-chloro-5-(cyclopropylethynyl)pyridin-2-yl]-1-methylethyl]-3-difluoromethyl-1-methyl-1H-pyrazole-4-carboxamide To a 2 ml solution of 200 mg of N-[2-(5-bromo-3-chloropyridin-2-yl)-1-methylethyl]-3-difluoromethyl-1-methyl-1H-pyrazole-4-carboxamide in N,N-dimethylformamide, 200 mg of triethylamine, 65 mg of cyclopropylacetylene, 28 mg of copper(I) iodide and 35 mg of dichlorobis(triphenylphosphine)palladium(II) were added, followed by stirring under a nitrogen atmosphere at 50° C. for 2 hours. After completion of the reaction, the reaction mixture was left to cool to room temperature, and 10 ml of a saturated aqueous solution of ammonium chloride was added, followed by extraction with ethyl acetate (10 ml×2). Organic layers were combined and washed with water (10 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of 2:8 to 5:5), to obtain 47 mg of the desired product as white crystals.

Melting point: 127.0 to 130.0° C.

$^1$H NMR (CDCl$_3$, Me$_4$Si, 300 MHz) δ8.38 (d, J=1.8 Hz, 1H), 7.79 (s, 1H), 7.62 (d, J=1.8 Hz, 1H), 7.00 (bs, 1H), 6.90 (t, J=54.6 Hz, 1H), 4.55-4.7 (m, 1H), 3.92 (s, 3H), 3.05-3.25 (m, 2H), 1.4-1.5 (m, 1H), 1.26 (d, J=6.3 Hz, 3H), 0.8-0.95 (m, 2H), 0.75-0.85 (m, 2H).

Synthesis Example 19

N-[2-[3-chloro-5-(cyclopropylethynyl)pyridin-2-yl]-2-methoxyethyl]-N-cyclopropyl-2-(trifluoromethyl) benzamide (compound No. 12-001 of the present invention)

Step 1: Production of 2-bromo-1-[3-chloro-5-(cyclopropylethynyl)pyridin-2-yl]ethanol To a 5 ml solution of 310 mg of 2-bromo-1-[3-chloro-5-(cyclopropylethynyl)pyridin-2-yl]ethanone in methanol, 39 mg of sodium borohydride was added with stirring under ice-cooling, followed by stirring at the same temperature for 1 hour. After completion of the reaction, 20 ml of a saturated aqueous ammonium chloride solution was added to the reaction mixture, followed by extraction with diethyl ether (25 ml×2). Organic layers were combined and washed with water (20 ml×1), and then dehydrated and dried in the order of with a saturated sodium chloride solution and then with anhydrous sodium sulfate, and the solvent was distilled off under reduced pressure, to obtain 300 mg of the crude desired product as a pale yellow oily substance. This product was used directly in the next step without further purification.

$^1$H NMR (CDCl$_3$, Me$_4$Si, 300 MHz) δ8.45 (d, J=1.8 Hz, 1H), 7.68 (d, J=1.8 Hz, 1H), 5.2-5.35 (m, 1H), 4.5-4.6 (m, 1H), 3.78 (dd, J=10.8, 3.6 Hz, 1H), 3.69 (dd, J=10.8, 5.7 Hz, 1H), 1.4-1.55 (m, 1H), 0.8-1.0 (m, 4H).

Step 2: Production of 1-[3-chloro-5-(cyclopropylethynyl)pyridin-2-yl]-2-(cyclopropylamino)ethanol To a 10 ml solution of 300 mg of 2-bromo-1-[3-chloro-5-(cyclopropylethynyl)pyridin-2-yl]ethanol in acetonitrile, 285 mg of cyclopropylamine and 431 mg of potassium carbonate were added, followed by stirring for 3 hours at 60° C. After completion of the reaction, the reaction mixture was left to cool to room temperature, and 20 ml of water was added, followed by extraction with diethyl ether (15 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 5:5), to obtain 70 mg of the desired product as a colorless oily substance.

$^1$H NMR (CDCl$_3$, Me$_4$Si, 300 MHz) δ8.43 (d, J=1.8 Hz, 1H), 7.65 (d, J=1.8 Hz, 1H), 5.1-5.2 (m, 1H), 4.0-4.2 (m, 1H), 3.05-3.15 (m, 1H), 2.7-2.8 (m, 1H), 2.15-2.25 (m, 1H), 1.55-1.9 (m, 1H), 1.4-1.5 (m, 1H), 0.8-1.0 (m, 4H), 0.3-0.45 (m, 4H).

Step 3: Production of N-[2-[3-chloro-5-(cyclopropylethynyl)pyridin-2-yl]-2-hydroxyethyl]-N-cyclopropyl-2-(trifluoromethyl)benzamide To a mixture of a 5 ml solution of 70 mg of 1-[3-chloro-5-(cyclopropylethynyl)pyridin-2-yl]-2-(cyclopropylamino) ethanol in ethyl acetate and a 5 ml solution of 105 mg of potassium carbonate in water, 57 mg of 2-(trifluoromethyl) benzoyl chloride was added dropwisely with stirring under ice-cooling. After completion of the dropwise addition, the mixture was stirred for 1 hour at the same temperature. After completion of the reaction, 10 ml of water and 10 ml of ethyl acetate were added to the reaction mixture, and then, the organic layer was separated and washed with water (10 ml×1). Then, dehydration and drying were carried out in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 1:9 to 3:7), to obtain 101 mg of the desired product as a colorless resinous substance.

$^1$H NMR (CDCl$_3$, Me$_4$Si, 300 MHz) δ8.47 (d, J=1.5 Hz, 1H), 7.67 (d, J=1.5 Hz, 1H), 7.4-7.65 (m, 4H), 5.35-5.6 (m,

1H), 4.2-4.45 (m, 2H), 3.2-3.65 (m, 1H), 2.7-3.0 (m, 1H), 1.4-1.55 (m, 1H), 0.8-1.0 (m, 4H), 0.3-0.7 (m, 4H).

Step 4: Production of N-[2-[3-chloro-5-(cyclopropylethynyl)pyridin-2-yl]-2-methoxyethyl]-N-cyclopropyl-2-(trifluoromethyl)benzamide To 12 mg of 55% oily sodium hydride in 15 ml of tetrahydrofuran, a 3 ml solution of 101 mg of N-[2-[3-chloro-5-(cyclopropylethynyl)pyridin-2-yl]-2-hydroxyethyl]-N-cyclopropyl-2-(trifluoromethyl)benzamide in tetrahydrofuran was added dropwisely with stirring under ice-cooling. After completion of the dropwise addition, the mixture was stirred for 30 minutes at the same temperature. Then, 49 mg of methyl iodide was added, and stirring was continued at room temperature for 2 hours. After completion of the reaction, 20 ml of water was added to the reaction mixture, followed by extraction with ethyl acetate (15 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 5:95 to 20:80), to obtain 55 mg of the desired product as a colorless resinous substance.

$^1$H NMR (CDCl$_3$, Me$_4$Si, 300 MHz) δ8.56 (d, J=1.5 Hz, 1H), 7.67 (d, J=1.5 Hz, 1H), 7.4-7.65 (m, 4H), 5.3-5.45 (m, 1H), 3.75-4.3 (m, 1H), 3.2-3.65 (m, 1H), 3.35 (s, 3H), 2.5-2.8 (m, 1H), 1.4-1.55 (m, 1H), 0.8-1.0 (m, 4H), 0.3-0.7 (m, 4H).

Synthesis Example 20 tert-butyl N-[2-[3-chloro-5-(cyclopropylethynyl) pyridin-2-yl]cyclopropyl]-N-[3-difluoromethyl-1-methyl-1H-pyrazole-4-carbonyl]carbamate (compound No. 12-002 of the present invention)

Step 1: Production of ethyl=2-[5-bromo-3-chloropyridin-2-yl]cyclopropanecarboxylate To a 5 ml solution of 1.56 g of 5-bromo-3-chloro-2-vinylpyridine in toluene, 5.43 g of a 15% toluene solution of ethyl diazoacetate was added dropwisely with stirring under heating at 110° C., and after completion of the dropwise addition, stirring was continued for one hour at the same temperature. After completion of the reaction, the reaction mixture was left to cool to room temperature, and the solvent was evaporated under reduced pressure. The residue was purified by silica gel column chromatography wherein it was eluted with ethyl acetate-hexane (gradient of from 0:100 to 15:85), to obtain 0.85 g of the desired product as a colorless oily substance.

$^1$H NMR (CDCl$_3$, Me$_4$Si, 300 MHz) δ8.37 (d, J=2.1 Hz, 1H), 7.79 (d, J=2.1 Hz, 1H), 4.18 (q, J=7.2 Hz, 2H), 2.95-3.05 (m, 1H), 2.2-2.3 (m, 1H), 1.55-1.7 (m, 2H), 1.28 (t, J=7.2 Hz, 3H).

Step 2: Production of 2-[5-bromo-3-chloropyridin-2-yl]cyclopropanecarboxylic acid To a 5 ml solution of 850 mg of ethyl=2-[5-bromo-3-chloropyridin-2-yl]cyclopropane carboxylate in ethanol, 5 ml of a 10 wt % sodium hydroxide aqueous solution was added, and the mixture was stirred at room temperature for 3 hours. After completion of the reaction, a 10 wt % aqueous solution of hydrochloric acid was added to the reaction mixture until the mixture became acidic, followed by extraction with ethyl acetate (15 ml×2). Organic layers were combined, and then dehydrated and dried in the order of with a saturated sodium chloride solution and then with anhydrous sodium sulfate, and the solvent was distilled off under reduced pressure to obtain 754 mg of the crude desired product as white crystals. This product was used directly in the next step without further purification.

Melting point: 170.0 to 172.0° C.

$^1$H NMR (CDCl$_3$, Me$_4$Si, 300 MHz) δ8.38 (d, J=1.8 Hz, 1H), 7.80 (d, J=1.8 Hz, 1H), 3.05-3.15 (m, 1H), 2.2-2.3 (m, 1H), 1.6-1.75 (m, 2H).

Step 3: Production of tert-butyl N-[2-[5-bromo-3-chloropyridin-2-yl]cyclopropyl]carbamate To a 10 ml suspension of 754 mg of 2-[5-bromo-3-chloropyridin-2-yl]cyclopropane carboxylic acid in tert-butanol, 304 mg of triethylamine and 902 mg of diphenylphosphate azide were added, and the mixture was stirred for 2 hours at 80° C. After completion of the reaction, the reaction mixture was left to cool to room temperature, and after addition of 20 ml of a saturated aqueous sodium bicarbonate solution, the mixture was extracted with ethyl acetate (15 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 5:95 to 15:85), to obtain 410 mg of the desired product as white crystals.

Melting point: 132.0 to 134.0° C.

$^1$H NMR (CDCl$_3$, Me$_4$Si, 300 MHz) δ8.34 (d, J=2.1 Hz, 1H), 7.75 (d, J=2.1 Hz, 1H), 4.80 (bs, 1H), 3.0-3.15 (m, 1H), 2.5-2.6 (m, 1H), 1.5-1.6 (m, 1H), 1.43 (s, 9H), 1.2-1.35 (m, 1H).

Step 4: Production of tert-butyl N-[2-[3-chloro-5-(cyclopropylethynyl)pyridin-2-yl]cyclopropyl]carbamate To a 3 ml solution of 573 mg of tert-butyl N-[2-[5-bromo-3-chloropyridin-2-yl]cyclopropyl]carbamate in N,N-dimethylformamide, 667 mg of triethylamine, 218 mg of cyclopropylacetylene, 94 mg of copper(I) iodide and 116 mg of dichlorobis(triphenylphosphine)palladium(II) were added, followed by stirring under a nitrogen atmosphere at 50° C. for 2 hours. After completion of the reaction, the reaction mixture was left to cool to room temperature, and after addition of 10 ml of a saturated aqueous solution of ammonium chloride, the mixture was extracted with ethyl acetate (10 ml×2). Organic layers were combined and washed with water (10 ml×1), then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate hexane (gradient of from 5:95 to 15:85), to obtain 438 mg of the desired product as white crystals.

Melting point: 137.0 to 139.0° C.

$^1$H NMR (CDCl$_3$, Me$_4$Si, 300 MHz) δ8.26 (d, J=1.8 Hz, 1H), 7.57 (d, J=1.8 Hz, 1H), 4.81 (bs, 1H), 3.0-3.15 (m, 1H), 2.5-2.6 (m, 1H), 1.5-1.6 (m, 1H), 1.4-1.5 (m, 1H), 1.44 (s, 9H), 1.2-1.3 (m, 1H), 0.85-0.95 (m, 2H), 0.75-0.85 (m, 2H).

Step 5: Production of tert-butyl N-[2-[3-chloro-5-(cyclopropylethynyl)pyridin-2-yl]cyclopropyl]-N-[3-difluoromethyl-1-methyl-1H-pyrazole-4-carbonyl]carbamate To a 3 ml solution of 256 mg of 3-difluoromethyl-1-methyl-1H-pyrazole-4-carboxylic acid in dichloromethane, 335 mg of oxalyl chloride and 5 mg of N,N-dimethylformamide were added, followed by stirring at room temperature for 2 hours. Then, the solvent was distilled off under reduced pressure, and the residue was dissolved in 3 ml of tetrahydrofuran.

To a 10 ml solution of 438 mg of tert-butyl N-[2-[3-chloro-5-(cyclopropylethynyl)pyridin-2-yl]cyclopropyl]carbamate in tetrahydrofuran, 0.73 ml of a n-butyl lithium hexane solution (2.65M) was added dropwisely with stirring at −78° C. After completion of the dropwise addition, stirring was further continued at the same temperature for 1 hour, and then, the above tetrahydrofuran solution of 3-difluoromethyl-1-methyl-1H-pyrazole-4-carbonyl chloride was added dropwisely, and while raising the temperature to room temperature, stirring was continued for 2 hours. After completion of the reaction, 20 ml of a saturated aqueous ammonium chloride solution was added to the reaction mixture, followed by extraction with ethyl acetate (20 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 5:95 to 50:50), to obtain 167 mg of the desired product as white crystals.

Melting point: 110.0 to 112.0° C.
$^1$H NMR (CDCl$_3$, Me$_4$Si, 300 MHz) δ8.31 (d, J=2.1 Hz, 1H), 7.74 (s, 1H), 7.59 (d, J=2.1 Hz, 1H), 6.86 (t, J=55.2 Hz, 1H), 3.93 (s, 3H), 3.3-3.4 (m, 1H), 2.7-2.8 (m, 1H), 1.7-1.8 (m, 1H), 1.35-1.45 (m, 2H), 1.34 (s, 9H), 0.8-0.95 (m, 4H).

Synthesis Example 21

N-[2-[3-chloro-5-(cyclopropylethynyl)pyridin-2-yl]cyclopropyl]-3-difluoromethyl-1-methyl-1H-pyrazole-4-carboxamide (compound No. 8-033 of the present invention)

To a 9 ml solution of 167 mg of tert-butyl N-[2-[3-chloro-5-(cyclopropylethynyl)pyridin-2-yl]cyclopropyl]-N-[3-difluoromethyl-1-methyl-1H-pyrazole-4-carbonyl]carbamate in dichloromethane, 1 ml of trifluoroacetic acid was added, followed by stirring at room temperature for 12 hours. After completion of the reaction, the solvent was distilled off under reduced pressure, and the residue was purified by silica gel column chromatography wherein it was eluted with ethyl acetate-hexane (gradient of from 1:4 to 2:3), to obtain 81 mg of the desired compound as white crystals.

Melting point: 176.0 to 178.0° C.
$^1$H NMR (CDCl$_3$, Me$_4$Si, 300 MHz) δ8.29 (d, J=2.1 Hz, 1H), 7.91 (s, 1H), 7.57 (d, J=2.1 Hz, 1H), 6.81 (t, J=54.9 Hz, 1H), 6.55 (bs, 1H), 3.91 (s, 3H), 3.35-3.45 (m, 1H), 2.6-2.7 (m, 1H), 1.65-1.75 (m, 1H), 1.4-1.5 (m, 1H), 1.3-1.4 (m, 1H), 0.75-0.95 (m, 4H).

Synthesis Example 22

N-[2-[3-chloro-5-(cyclopropylethynyl)pyridin-2-yl]-1-methylethyl]-4-difluoromethyl-2-methylthiazole-5-carboxamide (compound No. 9-007 of the present invention)

Step 1: Production of 5-bromo-3-chloro-2-(2-nitropropyl)pyridine

To a 1.5 ml solution of 156 mg of 5-bromo-3-chloro-2-(2-nitro-1-propenyl)pyridine produced in Step 1 of Synthesis Example 16 in methanol, 85 mg of sodium borohydride was added with stirring under ice-cooling, and the mixture was stirred for 6 hours at room temperature. After completion of the reaction, to the reaction mixture, 5 ml of water was added, followed by extraction with ethyl acetate (10 ml×2). Organic layers were combined, and then dehydrated and dried in the order of with a saturated sodium chloride solution and then with anhydrous sodium sulfate, and the solvent was distilled off under reduced pressure, to obtain 120 mg of the crude desired product as a yellow resinous substance. This product was used directly in the next step without further purification.

$^1$H NMR (CDCl$_3$, Me$_4$Si, 300 MHz) δ8.38 (d, J=2.1 Hz, 1H), 7.76 (d, J=2.1 Hz, 1H), 5.1-5.25 (m, 1H), 3.62 (dd, J=16.5, 8.6 Hz, 1H), 3.11 (dd, J=16.5, 5.2 Hz, 1H), 1.599 (d, J=7.0 Hz, 3H).

Step 2: Production of 2-(5-bromo-3-chloropyridin-2-yl)-1-methylethylamine 120 mg of 5-bromo-3-chloro-2-(2-nitropropyl)pyridine was dissolved in 3 ml of a methanol-water (2:1) mixed solvent, and 138 mg of ammonium chloride and 72 mg of reduced iron were added, followed by stirring at room 75° C. for 16 hours. After completion of the reaction, the reaction mixture was left to cool to room temperature, and after removing insoluble matters through Celite filtration, the solvent was distilled off under reduced pressure. The residue was dissolved in 10 ml of diethyl ether, and extracted with 10 ml of a 1N aqueous hydrochloric acid solution, and after addition of a 1N aqueous sodium hydroxide solution to the aqueous layer until the pH became 14, followed by back extraction with ethyl acetate (30 ml×2). Organic layers were combined, and then dehydrated and dried in the order of with a saturated sodium chloride solution and then with anhydrous sodium sulfate, and the solvent was distilled off under reduced pressure, to obtain 86 mg of the crude desired product as a yellow resinous substance. This product was used directly in the next step without further purification.

$^1$H NMR (CDCl$_3$, Me$_4$Si, 300 MHz) δ8.50 (d, J=2.1 Hz, 1H), 7.82 (d, J=2.1 Hz, 1H), 3.4-3.55 (m, 1H), 2.98 (dd, J=14.4, 4.9 Hz, 1H), 2.85 (dd, J=14.2, 8.1 Hz, 1H), 1.76 (bs, 2H), 1.18 (d, J=6.4 Hz, 3H).

Step 3: Production of tert-butyl N-[2-(5-bromo-3-chloropyridin-2-yl)-1-methylethyl]carbamate To a 1 ml solution of 86 mg of 2-(5-bromo-3-chloropyridin-2-yl)-1-methylethylamine and 42 mg of triethylamine in dichloromethane, 91 mg of di-tert-butyl dicarbonate was added, followed by stirring at room temperature for 1 hour. After completion of the reaction, the solvent was distilled off under reduced pressure, and the residue was purified by silica gel column chromatography wherein it was eluted with ethyl acetate-hexane (gradient of from 2:8 to 4:6), to obtain 74 mg of the desired product as a yellow resinous substance.

$^1$H NMR (CDCl$_3$, Me$_4$Si, 300 MHz) δ8.48 (d, J=2.0 Hz, 1H), 7.81 (d, J=1.7 Hz, 1H), 4.92 (bs, 1H), 4.0-4.3 (m, 1H), 2.9-3.2 (m, 2H), 1.36 (s, 9H), 1.21 (d, J=6.5 Hz, 3H).

Step 4: Production of tert-butyl N-[2-[3-chloro-5-(cyclopropylethynyl)pyridin-2-yl]-1-methylethyl]carbamate To a 3 ml solution of 74 mg of tert-butyl N-[2-(5-bromo-3-chloropyridin-2-yl)-1-methylethyl]carbamate in dimethyl sulfoxide, 107 mg of triethylamine, 28 mg of cyclopropylacetylene, 12 mg of copper(I) iodide and 15 mg of dichlorobis(triphenylphosphine)palladium(II) were added, followed by stirring under a nitrogen atmosphere at 50° C. for 1 hour. After completion of the reaction, the reaction mixture was left to cool to room temperature, and 10 ml of a saturated aqueous solution of ammonium chloride was added to the reaction mixture, followed by extraction with ethyl acetate (30 ml×2). Organic layers were combined and washed with water (20 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 15:85 to 35:65), to obtain 60 mg of the desired product as a brown resinous substance.

$^1$H NMR (CDCl$_3$, Me$_4$Si, 300 MHz) δ8.38 (d, J=1.7 Hz, 1H), 7.60 (d, J=2.0 Hz, 1H), 4.98 (bs, 1H), 4.05-4.2 (m, 1H), 3.04 (d, J=6.5 Hz, 2H), 1.4-1.55 (m, 1H), 1.37 (s, 9H), 1.18 (d, J=6.5 Hz, 3H), 0.75-1.0 (m, 4H).

Step 5: Production of 2-[3-chloro-5-(cyclopropylethynyl)pyridin-2-yl]-1-methylethylamine To a 5 ml solution of 335 mg tert-butyl N-[2-[3-chloro-5-(cyclopropylethynyl)pyridin-2-yl]-1-methylethyl]carbamate in dichloromethane, 5 ml of trifluoroacetic acid was added with stirring under ice-cooling, followed by stirring at room temperature for 1 hour. After completion of the reaction, 10 ml of toluene was added to the reaction mixture, and the solvent was distilled off under reduced pressure. The residue was dissolved in 20 ml of ethyl acetate and washed with 10 ml of a saturated aqueous sodium bicarbonate solution and then with 10 ml of water. The organic layer was dehydrated and dried in the order of with a saturated sodium chloride solution and then with anhydrous sodium sulfate, and the solvent was distilled off under reduced pressure to obtain 266 mg of the crude desired product as a yellow resinous substance. This product was used directly in the next step without further purification.

$^1$H NMR (CDCl$_3$, Me$_4$Si, 300 MHz) δ8.36 (s, 1H), 7.65 (d, J=1.5 Hz, 1H), 5.25 (bs, 2H), 3.5-3.75 (m, 1H), 2.95-3.2 (m, 2H), 1.4-1.55 (m, 1H), 1.37 (d, J=6.4 Hz, 3H), 0.75-1.0 (m, 4H).

Step 6: Production of N-[2-[3-chloro-5-(cyclopropylethynyl)pyridin-2-yl]-1-methylethyl]-4-difluoromethyl-2-methylthiazole-5-carboxamide 53 mg of 2-[3-chloro-5-(cyclopropylethynyl)pyridin-2-yl]-1-methylethylamine was dissolved in 2 ml of a dichloromethane-N,N-dimethylformamide (1:1) mixed solvent, and 52 mg of 4-difluoromethyl-2-methylthiazole-5-carboxylic acid, 2 mg of N,N-dimethyl-4-aminopyridine and 65 mg of 1-(3-dimethylaminopropyl)-3-ethylcarbodiimide hydrochloride were added, followed by stirring at room temperature for 16 hours. After completion of the reaction, 10 ml of water was added to the reaction mixture, followed by extraction with ethyl acetate (10 ml×2). Organic layers were combined and washed with water (10 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 3:7 to 6:4), to obtain 55 mg of the desired product as a colorless resinous substance.

$^1$H NMR (CDCl$_3$, Me$_4$Si, 300 MHz) δ8.41 (d, J=1.5 Hz, 1H), 7.66 (d, J=1.5 Hz, 1H), 7.51 (d, J=7.4 Hz, 1H), 7.26 (t, J=54.1 Hz, 1H), 4.45-4.7 (m, 1H), 3.21 (dd, J=14.7, 6.4 Hz, 1H), 3.13 (dd, J=14.5, 4.7 Hz, 1H), 2.75 (s, 3H), 1.4-1.55 (m, 1H), 1.28 (d, J=6.7 Hz, 3H), 0.75-1.0 (m, 4H).

Synthesis Example 23

N-[2-[3-chloro-5-(cyclopropylethynyl)pyridin-2-yl]-2-fluoropropyl]-2-(difluoromethyl)nicotinamide (compound No. 3-038 of the present invention)

Step 1: Production of 2-(5-bromo-3-chloropyridin-2-yl)-2-fluoropropanenitrile To a 20 ml solution of 1.40 g of 2-(5-bromo-3-chloropyridin-2-yl)propanenitrile produced in Step 1 of Synthesis Example 4 in tetrahydrofuran, 5.5 ml of a 1.3M tetrahydrofuran solution of lithium bis(trimethylsilyl)amide was added dropwisely with stirring at −78° C. After completion of the dropwise addition, stirring was continued at the same temperature for 30 minutes. Then, a 10 ml solution of 2.00 g of N-fluorobenzenesulfonimide in tetrahydrofuran was added dropwisely to this reaction mixture. After completion of the dropwise addition, stirring was continued for an additional 2 hours at the same temperature. After completion of the reaction, 30 ml of water was added to the reaction mixture, followed by extraction with ethyl acetate (25 ml×2). Organic layers were combined and washed with water (30 ml×1), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 0:10 to 1:9), to obtain 1.33 g of the desired product as a colorless oily substance.

$^1$H NMR (CDCl$_3$, Me$_4$Si, 300 MHz) δ8.59 (d, J=2.4 Hz, 1H), 8.02 (d, J=2.4 Hz, 1H), 2.23 (d, J=22.2 Hz, 3H).

Step 2: Production of tert-butyl N-[2-(5-bromo-3-chloropyridin-2-yl)-2-fluoropropyl]carbamate To a 20 ml solution of 1.33 g of 2-(5-bromo-3-chloropyridin-2-yl)-2-fluoropropanenitrile in dichloromethane under a nitrogen atmosphere, 11 ml of a 1.0M hexane solution of diisobutylaluminum hydride was added dropwisely with stirring at −78° C. After completion of the dropwise addition, stirring was continued at the same temperature for 1 hour. Then, 30 ml of dichloromethane was added to the reaction mixture, and the temperature was raised to room temperature, and 30 ml of a saturated aqueous solution of sodium potassium tartrate (Rochelle salt) was added. After continuing stirring for further 2 hours at the same temperature, 30 ml of water was added to the reaction mixture, and the organic layer was separated. The separated organic layer was washed with a saturated Rochelle salt solution (20 ml×1) and then with water (20 ml×2), and dehydrated and dried in the order of with a saturated sodium chloride solution and then with anhydrous sodium sulfate, and the solvent was distilled off under reduced pressure. The residue was dissolved in 10 ml of dichloromethane, and 0.57 g of triethylamine and 1.21 g of di-tert-butyl dicarbonate were added, followed by stirring at room temperature for 2 hours. After completion of the reaction, the solvent was distilled off under reduced pressure, and the residue was purified by silica gel column chromatography wherein it was eluted with ethyl acetate-hexane (gradient of from 0:100 to 5:95), to obtain 375 mg of the desired product as a colorless oily substance.

$^1$H NMR (CDCl$_3$, Me$_4$Si, 300 MHz) δ8.51 (d, J=2.1 Hz, 1H), 7.90 (d, J=2.1 Hz, 1H), 5.03 (bs, 1H), 3.87 (d, J=6.0 Hz, 1H), 3.81 (d, J=6.0 Hz, 1H), 1.78 (d, J=21.9 Hz, 3H), 1.41 (s, 9H).

Step 3: Production of tert-butyl N-[2-[3-chloro-5-(cyclopropylethynyl)pyridin-2-yl]-2-fluoropropyl]carbamate To a 3 ml solution of 375 mg of tert-butyl N-[2-(5-bromo-3-chloropyridin-2-yl)-2-fluoropropyl]carbamate in N,N-dimethylformamide, 413 mg of triethylamine, 135 mg of cyclopropylacetylene, 58 mg of copper(I) iodide and 70 mg of dichlorobis(triphenylphosphine)palladium(II) were added, followed by stirring under a nitrogen atmosphere at 50° C. for 2 hours. After completion of the reaction, the reaction mixture was left to cool to room temperature, and 20 ml of a saturated aqueous ammonium chloride solution was added, followed by extraction with ethyl acetate (15 ml×2). Organic layers were combined and washed with water (10 ml×2), and then dehydrated and dried in the order of with a saturated sodium chloride solution and then with anhydrous sodium sulfate, and the solvent was distilled off under reduced pressure. The residue was purified by silica gel column chromatography wherein it was eluted with ethyl acetate-hexane (gradient of from 5:95 to 15:85), to obtain 310 mg of the desired product as a colorless resinous substance.

$^1$H NMR (CDCl$_3$, Me$_4$Si, 300 MHz) δ8.38 (d, J=1.8 Hz, 1H), 7.68 (d, J=1.8 Hz, 1H), 5.08 (bs, 1H), 3.85-3.9 (m, 1H), 3.75-3.85 (m, 1H), 1.77 (d, J=21.6 Hz, 3H), 1.4-1.5 (m, 1H), 1.41 (s, 9H), 0.8-1.0 (m, 4H).

Step 4: Production of 2-[3-chloro-5-(cyclopropylethynyl)pyridin-2-yl]-2-fluoro-1-propanamine To a 2 ml solution of 310 mg of tert-butyl N-[2-[3-chloro-5-(cyclopropylethynyl)pyridin-2-yl]-2-fluoropropyl]carbamate in dichloromethane, 2 ml of trifluoroacetic acid was added, followed by stirring for 2 hours at room temperature. After completion of the reaction, the solvent was distilled off under reduced pressure, and 10 ml of a 10% aqueous potassium carbonate solution was added to the residue, followed by extraction with ethyl acetate (10 ml×2). Organic layers were combined and washed with 10 ml of water, and then dehydrated and dried in the order of with a saturated sodium chloride solution and then with anhydrous sodium sulfate, and the solvent was distilled off under reduced pressure to obtain 230 mg of the crude desired product as a brown oily substance. This product was used directly in the next step without further purification.

$^1$H NMR (CDCl$_3$, Me$_4$Si, 300 MHz) δ8.41 (d, J=1.5 Hz, 1H), 7.68 (d, J=1.5 Hz, 1H), 3.45-3.6 (m, 1H), 3.05-3.15 (m, 1H), 1.72 (d, J=21.6 Hz, 3H), 1.4-1.55 (m, 1H), 0.8-1.0 (m, 4H).

Step 5: Production of N-[2-[3-chloro-5-(cyclopropylethynyl)pyridin-2-yl]-2-fluoropropyl]-2-(difluoromethyl)nicotinamide To a 2 ml solution of 58 mg of 2-[3-chloro-5-(cyclopropylethynyl)pyridin-2-yl]-2-fluoro-1-propanamine in dichloromethane, 5 mg of N,N-dimethyl-4-aminopyridine, 44 mg of 2-(difluoromethyl)nicotinic acid and 66 mg of 1-(3-dimethylaminopropyl)-3-ethylcarbodiimide hydrochloride were added, followed by stirring at room temperature for 2 hours. After completion of the reaction, 3 ml of water was added to the reaction mixture, followed by extraction with dichloromethane (2 ml×1), and the organic layer was washed with water (10 ml×1) and then passed through a silica gel short path column eluting with ethyl acetate, whereupon the solvent was distilled off under reduced pressure. The residue was washed with hexane, to obtain 43 mg of the desired product as white crystals.

Melting point: 113.0 to 115.0° C.

$^1$H NMR (CDCl$_3$, Me$_4$Si, 300 MHz) δ8.73 (dd, J=4.8, 1.8 Hz, 1H), 8.36 (d, J=1.8 Hz, 1H), 7.87 (d, J=8.1 Hz, 1H), 7.71 (d, J=1.8 Hz, 1H), 7.45 (dd, J=8.1, 4.8 Hz, 1H), 6.90 (t, J=54.9 Hz, 1H), 6.74 (bs, 1H), 4.15-4.3 (m, 2H), 1.86 (d, J=21.3 Hz, 3H), 1.4-1.5 (m, 1H), 0.8-1.0 (m, 4H).

The compounds of the present invention can be produced according to the above-described production methods and Examples. Examples of alkynyl pyridine-substituted amide compounds which are encompassed by the present invention which were prepared in the same manner as in Synthesis Examples 1 to 23, are shown in Tables 3 to 14, but the alkynyl pyridine-substituted amide compounds encompassed by the present invention and their production intermediates are not limited thereto.

In the Tables, the symbol "*1" in the column for melting point means that the properties of the compounds are oily or resinous.

TABLE 3

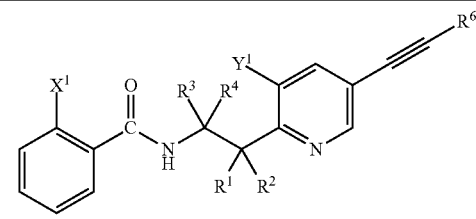

| No. | X$^1$ | R$^3$ | R$^4$ | R$^1$ | R$^2$ | Y$^1$ | R$^6$ | m.p. (° C.) |
|---|---|---|---|---|---|---|---|---|
| 1-001 | CF$_3$ | H | H | H | H | Cl | CH$_3$ | 100.0-103.0 |
| 1-002 | CF$_3$ | H | H | H | H | Cl | c-Pr | 105.0-108.0 |
| 1-003 | CF$_3$ | H | H | H | H | Cl | t-Bu | 90.0-92.0 |
| 1-004 | CF$_3$ | H | H | H | H | Cl | CH$_2$OCH$_3$ | 82.0-83.0 |
| 1-005 | CF$_3$ | H | H | F | F | Cl | c-Pr | 137.0-139.0 |
| 1-006 | CF$_3$ | H | H | F | F | Cl | CH$_2$OCH$_2$CF$_3$ | 105.0-106.0 |
| 1-007 | CF$_3$ | H | H | CH$_3$ | H | Cl | c-Pr | *1 |
| 1-008 | CF$_3$ | H | H | CH$_3$ | CH$_3$ | Cl | c-Pr | *1 |
| 1-009 | CF$_3$ | H | H | c-Pr | H | Cl | c-Pr | *1 |
| 1-010 | CF$_3$ | H | H | CH$_2$CF$_3$ | H | Cl | c-Pr | *1 |

TABLE 3-continued

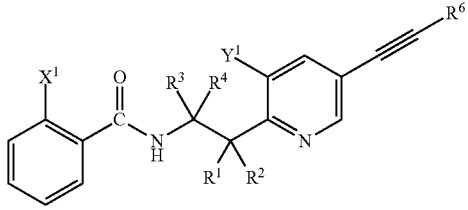

| No. | $X^1$ | $R^3$ | $R^4$ | $R^1$ | $R^2$ | $Y^1$ | $R^6$ | m.p. (° C.) |
|---|---|---|---|---|---|---|---|---|
| 1-011 | $CF_3$ | H | H | $CH_2$(Ph-3,4-$F_2$) | H | Cl | c-Pr | *1 |
| 1-012 | $CF_3$ | H | H | —$CH_2$— | | Cl | $CH_3$ | 85.0-90.0 |
| 1-013 | $CF_3$ | H | H | —$CH_2$— | | Cl | c-Pr | 50.0-55.0 |
| 1-014 | Cl | H | H | —$CH_2CH_2$— | | Cl | c-Pr | *1 |
| 1-015 | I | H | H | —$CH_2CH_2$— | | Cl | c-Pr | 125.0-126.0 |
| 1-016 | $CH_3$ | H | H | —$CH_2CH_2$— | | Cl | c-Pr | 96.0-97.0 |
| 1-017 | $CF_3$ | H | H | —$CH_2CH_2$— | | Cl | c-Pr | *1 |
| 1-018 | $NO_2$ | H | H | —$CH_2CH_2$— | | Cl | c-Pr | 98.0-99.0 |
| 1-019 | $CF_3$ | H | H | —$CH_2CH_2$— | | Cl | $CH_2OCH_2CF_3$ | 75.0-76.0 |
| 1-020 | $CF_3$ | H | H | —$OCH_2$— | | Cl | $CH_3$ | *1 |
| 1-021 | $CF_3$ | H | H | $SCH_3$ | H | Cl | c-Pr | *1 |
| 1-022 | $CF_3$ | H | H | CN | H | Cl | c-Pr | 132.0-134.0 |
| 1-023 | $CF_3$ | H | H | CN | CN | Cl | c-Pr | 42.0-44.0 |
| 1-024 | $CF_3$ | $CH_3$ | H | $OCH_3$ | H | Cl | c-Pr | *1 |
| 1-025 | $CF_3$ | $CH_3$ | H | $OCH_3$ | H | Cl | t-Bu | 36.0-38.0 |
| 1-026 | $CF_3$ | $CH_3$ | H | OEt | H | Cl | c-Pr | *1 |
| 1-027 | $CF_3$ | $CH_3$ | H | $OCH_2CF_3$ | H | Cl | c-Pr | *1 |
| 1-028 | $CF_3$ | $CH_3$ | H | $OCH_2CN$ | H | Cl | c-Pr | *1 |
| 1-029 | $CF_3$ | $CH_3$ | H | $OCH_2CH=CH_2$ | H | Cl | c-Pr | *1 |
| 1-030 | $CF_3$ | $CH_3$ | H | $OCH_2C\equiv CH$ | H | Cl | c-Pr | *1 |
| 1-031 | $CF_3$ | $CH_3$ | H | $OCH_2Ph$ | H | Cl | c-Pr | *1 |
| 1-032 | $CF_3$ | $CH_3$ | H | $SCH_2CF_3$ | H | Cl | c-Pr | *1 |
| 1-033 | $CF_3$ | —$CH_2CH_2$— | | H | H | Cl | c-Pr | 115.0-120.0 |
| 1-034 | $CF_3$ | $CH_3$ | H | H | H | Cl | c-Pr | 116.0-117.0 |
| 1-035 | $CF_3$ | H | H | $CH_3$ | F | Cl | c-Pr | 129.0 131.0 |

TABLE 4

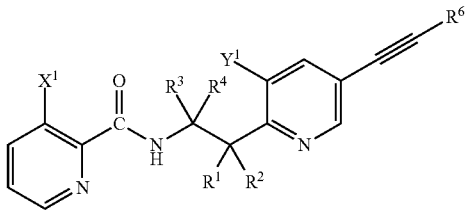

| No. | $X^1$ | $R^3$ | $R^4$ | $R^1$ | $R^2$ | $Y^1$ | $R^6$ | m.p. (° C.) |
|---|---|---|---|---|---|---|---|---|
| 2-001 | $CF_3$ | H | H | F | F | Cl | c-Pr | 157.0-158.0 |
| 2-002 | $CF_3$ | H | H | —$CH_2$— | | Cl | c-Pr | 107.0-109.0 |
| 2-003 | Cl | H | H | —$CH_2CH_2$— | | Cl | c-Pr | *1 |
| 2-004 | $CF_3$ | H | H | —$CH_2CH_2$— | | Cl | c-Pr | *1 |

TABLE 5

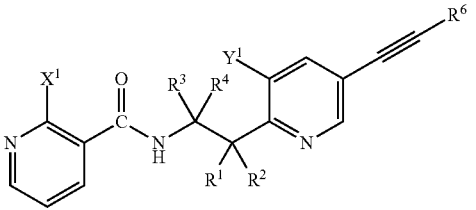

| No. | $X^1$ | $R^3$ | $R^4$ | $R^1$ | $R^2$ | $Y^1$ | $R^6$ | m.p. (° C.) |
|---|---|---|---|---|---|---|---|---|
| 3-001 | $CHF_2$ | H | H | H | H | Cl | c-Pr | 114.0-117.0 |
| 3-002 | $CHF_2$ | H | H | H | H | Cl | t-Bu | 144.0-146.0 |

TABLE 5-continued

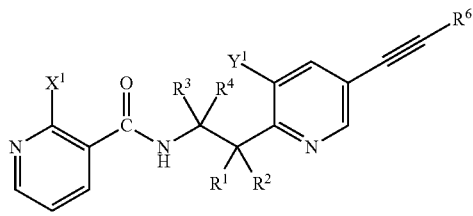

| No. | X¹ | R³ | R⁴ | R¹ | R² | Y¹ | R⁶ | m.p. (° C.) |
|---|---|---|---|---|---|---|---|---|
| 3-003 | CHF$_2$ | H | H | F | F | Cl | c-Pr | 116.0-118.0 |
| 3-004 | Cl | H | H | F | F | Cl | CH$_2$OCH$_2$CF$_3$ | 108.0-109.0 |
| 3-005 | Cl | H | H | CH$_3$ | H | Cl | c-Pr | *1 |
| 3-006 | CHF$_2$ | H | H | CH$_3$ | H | Cl | c-Pr | *1 |
| 3-007 | CHF$_2$ | H | H | CH$_3$ | CH$_3$ | Cl | c-Pr | *1 |
| 3-008 | CHF$_2$ | H | H | c-Pr | H | Cl | c-Pr | *1 |
| 3-009 | CHF$_2$ | H | H | CH$_2$(Ph-3,4-F$_2$) | H | Cl | c-Pr | *1 |
| 3-010 | Cl | H | H | —CH$_2$— | | Cl | c-Pr | 120.0-123.0 |
| 3-011 | CHF$_2$ | H | H | —CH$_2$— | | Cl | c-Pr | 114.0-116.0 |
| 3-012 | CF$_3$ | H | H | —CH$_2$— | | Cl | c-Pr | 125.0-129.0 |
| 3-013 | CHF$_2$ | H | H | —CH(Cl)—(E) | | Cl | c-Pr | *1 |
| 3-014 | CHF$_2$ | H | H | —CH(Cl)—(Z) | | Cl | c-Pr | *1 |
| 3-015 | Cl | H | H | —CH$_2$CH$_2$— | | Cl | c-Pr | *1 |
| 3-016 | CHF$_2$ | H | H | —CH$_2$CH$_2$— | | Cl | c-Pr | 94.0-95.0 |
| 3-017 | CF$_3$ | H | H | —CH$_2$CH$_2$— | | Cl | c-Pr | 140.0-140.5 |
| 3-018 | Cl | H | H | —CH$_2$CH$_2$— | | Cl | CH$_2$OCH$_2$CF$_3$ | *1 |
| 3-019 | CF$_3$ | H | H | —CH$_2$CH$_2$— | | Cl | CH$_2$OCH$_2$CF$_3$ | 107.0-108.5 |
| 3-020 | CHF$_2$ | H | H | SCH$_3$ | H | Cl | c-Pr | *1 |
| 3-021 | CHF$_2$ | CH$_3$ | H | OCH$_3$ | H | Cl | c-Pr | *1 |
| 3-022 | CHF$_2$ | CH$_3$ | H | OEt | H | Cl | c-Pr | *1 |
| 3-023 | Cl | CH$_3$ | H | OCH$_2$CF$_3$ | H | Cl | c-Pr | *1 |
| 3-024 | CHF$_2$ | CH$_3$ | H | OCH$_2$CF$_3$ | H | Cl | c-Pr | *1 |
| 3-025 | CHF$_2$ | CH$_3$ | H | OCH$_2$CN | H | Cl | c-Pr | *1 |
| 3-026 | Cl | CH$_3$ | H | OCH$_2$CH=CH$_2$ | H | Cl | c-Pr | 48.0-50.0 |
| 3-027 | CHF$_2$ | CH$_3$ | H | OCH$_2$CH=CH$_2$ | H | Cl | c-Pr | *1 |
| 3-028 | Cl | CH$_3$ | H | OCH$_2$C≡CH | H | Cl | c-Pr | *1 |
| 3-029 | CHF$_2$ | CH$_3$ | H | OCH$_2$C≡CH | H | Cl | c-Pr | *1 |
| 3-030 | Cl | CH$_3$ | H | OCH$_2$Ph | H | Cl | c-Pr | 50.0-52.0 |
| 3-031 | CHF$_2$ | CH$_3$ | H | OCH$_2$Ph | H | Cl | c-Pr | *1 |
| 3-032 | Cl | CH$_3$ | H | SCH$_2$CF$_3$ | H | Cl | c-Pr | *1 |
| 3-033a | CHF$_2$ | CH$_3$ | H | SCH$_2$CF$_3$ | H | Cl | c-Pr | 72.0-74.0 |
| 3-034 | CF$_3$ | CH$_3$ | H | SCH$_2$CF$_3$ | H | Cl | c-Pr | *1 |
| 3-034a | CF$_3$ | CH$_3$ | H | SCH$_2$CF$_3$ | H | Cl | c-Pr | 65.0-66.0 |
| 3-035 | Cl | CH$_3$ | H | H | H | Cl | c-Pr | 146.0-147.0 |
| 3-036 | CHF$_2$ | CH$_3$ | H | H | H | Cl | c-Pr | 149.0-150.0 |
| 3-037 | Cl | H | H | CH$_3$ | F | Cl | c-Pr | 83.0-85.0 |
| 3-038 | CHF$_2$ | H | H | CH$_3$ | F | Cl | c-Pr | 113.0-115.0 |

TABLE 6

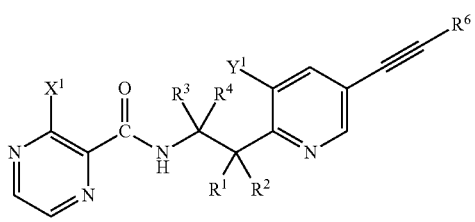

| No. | X¹ | R³ | R⁴ | R¹ | R² | Y¹ | R⁶ | m.p. (° C.) |
|---|---|---|---|---|---|---|---|---|
| 4-001 | CF$_3$ | H | H | F | F | Cl | c-Pr | 161.0-163.0 |
| 4-002 | CF$_3$ | H | H | —CH$_2$— | | Cl | c-Pr | 101.0-103.0 |
| 4-003 | CF$_3$ | H | H | —CH$_2$CH$_2$— | | Cl | c-Pr | 125.0-126.5 |
| 4-004 | CF$_3$ | CH$_3$ | H | OCH$_3$ | H | Cl | c-Pr | *1 |

TABLE 7

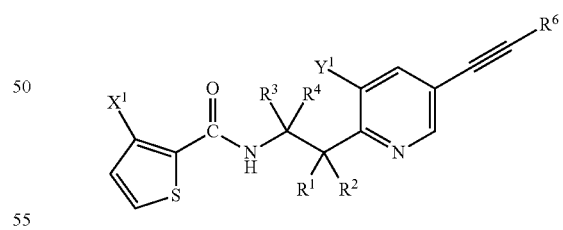

| No. | X¹ | R³ | R⁴ | R¹ | R² | Y¹ | R⁶ | m.p. (° C.) |
|---|---|---|---|---|---|---|---|---|
| 5-001 | CH$_3$ | H | H | F | F | Cl | c-Pr | 71.0-73.0 |
| 5-002 | CF$_3$ | H | H | —CH$_2$CH$_2$— | | Cl | c-Pr | *1 |

TABLE 8

| No. | X¹ | R³ | R⁴ | R¹ | R² | Y¹ | R⁶ | m.p. (° C.) |
|---|---|---|---|---|---|---|---|---|
| 6-001 | I | H | H | —CH$_2$CH$_2$— | | Cl | c-Pr | 64.0-65.0 |

TABLE 9

| No. | X¹ | R³ | R⁴ | R¹ | R² | Y¹ | R⁶ | m.p. (° C.) |
|---|---|---|---|---|---|---|---|---|
| 7-001 | CF$_3$ | H | H | F | F | Cl | c-Pr | 68.0-69.0 |

TABLE 10

| No. | X¹ | R³ | R⁴ | R¹ | R² | Y¹ | R⁶ | m.p. (° C.) |
|---|---|---|---|---|---|---|---|---|
| 8-001 | CHF$_2$ | H | H | H | H | Cl | c-Pr | 96.0-98.0 |
| 8-002 | CHF$_2$ | H | H | H | H | Cl | t-Bu | *1 |
| 8-003 | CHF$_2$ | H | H | F | F | Cl | c-Pr | 100.0-101.0 |
| 8-004 | CF$_3$ | H | H | F | F | Cl | c-Pr | 105.0-106.0 |
| 8-005 | CHF$_2$ | H | H | F | F | Cl | CH$_2$F | 110.0-111.0 |
| 8-006 | CHF$_2$ | H | H | F | F | Cl | CH$_2$OCH$_3$ | 135.0-138.0 |
| 8-007 | CHF$_2$ | H | H | CH$_3$ | H | Cl | c-Pr | *1 |
| 8-008 | CHF$_2$ | H | H | CH$_3$ | CH$_3$ | Cl | c-Pr | *1 |
| 8-009 | CHF$_2$ | H | H | c-Pr | H | Cl | c-Pr | *1 |
| 8-010 | CHF$_2$ | H | H | CH$_2$(Ph-3,4-F$_2$) | H | Cl | c-Pr | *1 |
| 8-011 | CHF$_2$ | H | H | —CH$_2$— | | Cl | c-Pr | 66.0-70.0 |
| 8-012 | CHF$_2$ | H | H | —CH(Cl)—(E) | | Cl | c-Pr | *1 |
| 8-013 | CHF$_2$ | H | H | —CH(Cl)—(Z) | | Cl | c-Pr | *1 |
| 8-014 | CHF$_2$ | H | H | —CH(CH$_3$)—(E) | | Cl | c-Pr | *1 |
| 8-015 | CHF$_2$ | H | H | —CH(CH$_3$)—(Z) | | Cl | c-Pr | *1 |
| 8-016 | CHF$_2$ | H | H | —CH(CH$_3$)—(E) | | Cl | t-Bu | *1 |
| 8-017 | CHF$_2$ | H | H | —CH(CH$_3$)—(Z) | | Cl | t-Bu | 103.0-105.0 |
| 8-018 | CHF$_2$ | H | H | —CH$_2$CH$_2$— | | Cl | c-Pr | *1 |
| 8-019 | CHF$_2$ | H | H | OCH$_3$ | H | Cl | c-Pr | 110.0-111.0 |
| 8-020 | CHF$_2$ | H | H | SCH$_3$ | H | Cl | c-Pr | *1 |
| 8-021 | CHF$_2$ | H | H | CN | H | Cl | c-Pr | 43.0-46.0 |
| 8-022 | CHF$_2$ | H | H | C(O)OCH$_3$ | H | Cl | c-Pr | *1 |
| 8-023 | CHF$_2$ | H | H | C(O)OEt | C(O)OEt | Cl | c-Pr | 87.0-88.0 |
| 8-024 | CHF$_2$ | CH$_3$ | H | H | H | Cl | c-Pr | 127.0-130.0 |
| 8-025 | CHF$_2$ | CH$_3$ | H | H | H | Cl | CH$_2$OH | *1 |
| 8-026 | CHF$_2$ | CH$_3$ | H | H | H | Cl | Si(CH$_3$)$_3$ | 125.0-126.0 |
| 8-027 | CHF$_2$ | CH$_3$ | H | H | H | Cl | Ph | *1 |
| 8-028 | CHF$_2$ | CH$_3$ | H | OCH$_3$ | H | Cl | c-Pr | *1 |
| 8-029 | CHF$_2$ | CH$_3$ | H | OEt | H | Cl | c-Pr | *1 |
| 8-030 | CHF$_2$ | CH$_3$ | H | OCH$_2$CF$_3$ | H | Cl | c-Pr | *1 |
| 8-031 | CHF$_2$ | CH$_3$ | H | OCH$_2$CH=CH$_2$ | H | Cl | c-Pr | *1 |
| 8-032 | CHF$_2$ | CH$_3$ | H | OCH$_2$Ph | H | Cl | c-Pr | *1 |
| 8-033 | CHF$_2$ | H | —CH$_2$-(trans) | | H | Cl | c-Pr | 176.0-178.0 |
| 8-034 | CF$_3$ | CH$_3$ | H | H | H | Cl | c-Pr | *1 |
| 8-035 | CHF$_2$ | H | H | CH$_3$ | F | Cl | c-Pr | 88.0-91.0 |

TABLE 11

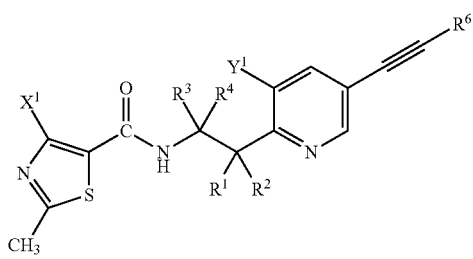

| No. | $X^1$ | $R^3$ | $R^4$ | $R^1$ | $R^2$ | $Y^1$ | $R^6$ | m.p. (° C.) |
|---|---|---|---|---|---|---|---|---|
| 9-001 | $CF_3$ | H | H | F | F | Cl | c-Pr | 129.0-131.0 |
| 9-002 | $CHF_2$ | H | H | $CH_3$ | H | Cl | c-Pr | *1 |
| 9-003 | $CHF_2$ | H | H | —$CH_2$— | | Cl | c-Pr | *1 |
| 9-004 | $CHF_2$ | H | H | —$CH_2CH_2$— | | Cl | c-Pr | *1 |
| 9-005 | $CF_3$ | H | H | —$CH_2CH_2$— | | Cl | c-Pr | 120.0-122.0 |
| 9-006a | $CHF_2$ | $CH_3$ | H | $OCH_3$ | H | Cl | c-Pr | *1 |
| 9-006b | $CHF_2$ | $CH_3$ | H | $OCH_3$ | H | Cl | c-Pr | *1 |
| 9-007 | $CHF_2$ | $CH_3$ | H | H | H | Cl | c-Pr | *1 |
| 9-008 | $CF_3$ | $CH_3$ | H | H | H | Cl | c-Pr | 122.0-123.0 |

TABLE 12

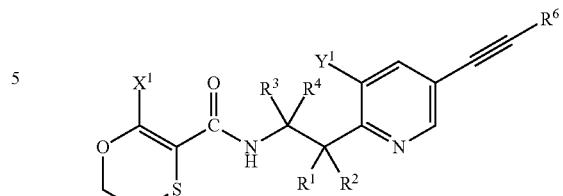

| No. | $X^1$ | $R^3$ | $R^4$ | $R^1$ | $R^2$ | $Y^1$ | $R^6$ | m.p. (° C.) |
|---|---|---|---|---|---|---|---|---|
| 10-001 | $CF_3$ | H | H | —$CH_2CH_2$— | | Cl | c-Pr | 117.0-120.0 |

TABLE 13

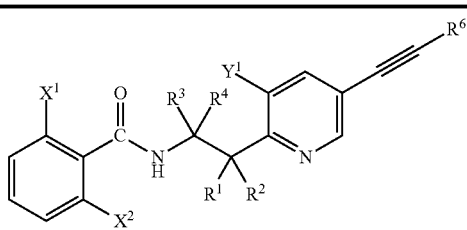

| No. | $X^1$ | $X^2$ | $R^3$ | $R^4$ | $R^1$ | $R^2$ | $Y^1$ | $R^6$ | m.p. (° C.) |
|---|---|---|---|---|---|---|---|---|---|
| 11-001 | F | F | H | H | —$CH_2CH_2$— | | Cl | c-Pr | 140.0-140.5 |

TABLE 14

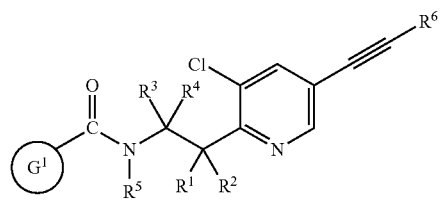

In the Table, symbols $G^1$-1a and $G^1$-27a in the column for substituent $G^1$, respectively, represent the following structural formulae.

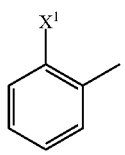

$G^1$-1a

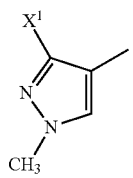

$G^1$-27a

| No. | $G^1$ | $X^1$ | $R^5$ | $R^3$ | $R^4$ | $R^1$ | $R^2$ | $R^6$ | m.p. (° C.) |
|---|---|---|---|---|---|---|---|---|---|
| 12-001 | $G^1$-1a | $CF_3$ | c-Pr | H | H | $OCH_3$ | H | c-Pr | *1 |
| 12-002 | $G^1$-27a | $CHF_2$ | COOBu-t | H | —$CH_2$-(trans)— | | H | c-Pr | 110.0-112.0 |

TABLE 15

| No. | R⁵ | R³ | R⁴ | R¹ | R² | Y¹ | R⁶ | m.p. (° C.) |
|---|---|---|---|---|---|---|---|---|
| 13-001 | H | H | H | H | H | Cl | c-Pr | *1 |
| 13-002 | H | H | H | F | F | Cl | c-Pr | *1 |
| 13-003 | H | H | H | F | F | Cl | CH₂F | *1 |
| 13-004 | H | H | H | F | F | Cl | CH₂OCH₃ | *1 |
| 13-005 | H | H | H | CH₃ | H | Cl | c-Pr | *1 |
| 13-006 | H | H | H | CH₃ | CH₃ | Cl | c-Pr | *1 |
| 13-007 | H | H | H | c-Pr | H | Cl | c-Pr | *1 |
| 13-008 | H | H | H | —CH₂— | | Cl | c-Pr | *1 |
| 13-009 | H | H | H | —CH(Cl)— | | Cl | c-Pr | *1 |
| 13-010 | H | H | H | —CH₂CH₂— | | Cl | c-Pr | *1 |
| 13-011 | c-Pr | H | H | OCH₃ | H | Cl | c-Pr | *1 |
| 13-012 | H | H | H | SCH₃ | H | Cl | c-Pr | *1 |
| 13-013 | H | CH₃ | H | OCH₃ | H | Cl | c-Pr | *1 |

TABLE 15-continued

| No. | R⁵ | R³ | R⁴ | R¹ | R² | Y¹ | R⁶ | m.p. (° C.) |
|---|---|---|---|---|---|---|---|---|
| 13-014 | H | CH₃ | H | H | H | Cl | c-Pr | *1 |
| 13-015 | H | H | H | CH₃ | F | Cl | c-Pr | *1 |

TABLE 16

| No. | R³ | R⁴ | R¹ | R² | Y¹ | R⁶ | m.p. (° C.) |
|---|---|---|---|---|---|---|---|
| 14-001 | H | H | —CH₂— | | Cl | c-Pr | *1 |

TABLE 17

| No. | R⁵ | R³ | R⁴ | R¹ | R² | Y¹ | R⁶ | m.p. (° C.) |
|---|---|---|---|---|---|---|---|---|
| 15-001 | H | H | H | H | H | Cl | c-Pr | *1 |
| 15-002 | H | H | H | F | F | Cl | c-Pr | *1 |
| 15-003 | H | H | H | F | F | Cl | CH₂F | 84.0-86.0 |
| 15-004 | H | H | H | F | F | Cl | CH₂OH | 45.0-47.0 |
| 15-005 | H | H | H | F | F | Cl | CH₂OCH₃ | *1 |
| 15-006 | H | H | H | CH₃ | H | Cl | c-Pr | *1 |
| 15-007 | H | H | H | CH₃ | CH₃ | Cl | c-Pr | *1 |
| 15-008 | H | H | H | c-Pr | H | Cl | c-Pr | *1 |
| 15-009 | H | H | H | —CH₂— | | Cl | c-Pr | *1 |
| 15-010 | H | H | H | —CH(Cl)— | | Cl | c-Pr | *1 |
| 15-011 | H | H | H | —CH₂CH₂— | | Cl | c-Pr | *1 |
| 15-012 | H | H | H | —CH₂CH₂— | | Cl | CH₂OCH₂CF₃ | *1 |
| 15-013 | H | H | H | SCH₃ | H | Cl | c-Pr | *1 |
| 15-011 | H | CH₃ | H | OCH₃ | H | Cl | c-Pr | *1 |
| 15-015 | H | CH₃ | H | OCH₂Ph | H | Cl | c-Pr | *1 |
| 15-016 | H | CH₃ | H | SCH₂CF₃ | H | Cl | c-Pr | *1 |
| 15-017 | H | H | —CH₂-(trans) | | H | Cl | c-Pr | 137.0-139.0 |
| 15-018 | H | CH₃ | H | H | H | Cl | c-Pr | *1 |
| 15-019 | H | H | H | CH₃ | F | Cl | c-Pr | *1 |

Among the compounds in Table 3 to Table 17, with respect to those, of which no melting points are indicated, $^1$H NMR data will be shown in Table 18.

TABLE 18

| No. | $^1$H NMR (CDCl$_3$, Me$_4$Si, 300 MHz) |
|---|---|
| 1-008 | δ 8.28 (d, J = 1.8 Hz, 1H), 7.45-7.8 (m, 6H), 3.86 (d, J = 3.2 Hz, 2H), 1.55 (s, 6H), 1.35-1.5 (m, 1H), 0.75-1.05 (m, 4H). |
| 1-009 | δ 8.39 (d, J = 1.8 Hz, 1H), 7.65 (d, J = 1.8 Hz, 1H), 7.45-7.65 (m, 4H), 6.41 (bs, 1H), 3.85-4.05 (m, 2H), 3.05-3.15 (m, 1H), 1.4-1.5 (m, 1H), 1.0-1.2 (m, 1H), 0.8-1.0 (m, 4H), 0.3-0.65 (m, 4H). |
| 1-010 | δ 8.39 (d, J = 1.8 Hz, 1H), 7.67 (d, J = 1.8 Hz, 1H), 7.65-7.7 (m, 1H), 7.4-7.6 (m, 3H), 6.33 (bs, 1H), 4.0-4.2 (m, 1H), 3.85-3.95 (m, 1H), 3.7-3.85 (m, 1H), 2.75-2.9 (m, 1H), 2.4-2.6 (m, 1H), 1.4-1.5 (m, 1H), 0.8-1.0 (m, 4H). |
| 1-011 | δ 8.39 (d, J = 1.8 Hz, 1H), 7.65 (dd, J = 7.8, 1.5 Hz, 1H), 7.59 (d, J = 1.8 Hz, 1H), 7.4-7.6 (m, 3H), 6.75-7.05 (m, 3H), 6.50 (bs, 1H), 3.75-4.0 (m, 3H), 2.85-3.05 (m, 2H), 1.4-1.5 (m, 1H), 0.8-0.95 (m, 4H). |
| 1-014 | δ 8.36 (d, J = 2.0 Hz, 1H), 7.64 (d, J = 2.0 Hz, 1H), 7.5-7.55 (m, 1H), 7.2-7.4 (m, 3H), 6.51 (bs, 1H), 3.71 (d, J = 5.1 Hz, 2H), 1.4-1.5 (m, 1H), 1.05-1.15 (m, 4H), 0.85-0.95 (m, 2H), 0.75-0.85 (m, 2H). |
| 1-017 | δ 8.32 (d, J = 1.8 Hz, 1H), 7.63 (d, J = 1.8 Hz, 1H), 7.35-7.65 (m, 4H), 6.14 (bs, 1H), 3.67 (d, J = 5.1 Hz, 2H), 1.4-1.5 (m, 1H), 1.0-1.1 (m, 4H), 0.75-0.95 (m, 4H). |
| 1-020 | δ 8.48 (d, J = 1.8 Hz, 1H), 7.70 (d, J = 1.8 Hz, 1H), 7.45-7.75 (m, 4H), 6.21 (d, J = 6.6 Hz, 1H), 4.17 (dd, J = 14.7, 6.0 Hz, 1H), 3.97 (dd, J = 14.7, 6.0 Hz, 1H), 3.26 (d, J = 4.5 Hz, 1H), 3.09 (d, J = 4.5 Hz, 1H), 2.08 (s, 3H). |
| 1-021 | δ 8.36 (d, J = 1.8 Hz, 1H), 7.68 (d, J = 1.8 Hz, 1H), 7.45-7.65 (m, 4H), 6.42 (bs, 1H), 4.56 (dd, J = 7.8, 6.0 Hz, 1H), 4.05-4.2 (m, 2H), 2.11 (s, 3H), 1.4-1.5 (m, 1H), 0.8-1.0 (m, 4H). |
| 1-024 | δ 8.50 and 8.47 (d, J = 2.1 Hz, 1H), 7.70 and 7.68 (d, J = 2.1 Hz, 1H), 7.4-7.7 (m, 3H), 7.25-7.35 (m, 1H), 6.39 and 6.36 (bs, 1H), 4.92 and 4.79 (d, J = 4.2 and 2.4 Hz, 1H), 4.5-4.65 (m, 1H), 3.38 and 3.35 (s, 3H), 1.46 and 1.16 (d, J = 7.2 Hz, 3H), 1.45-1.55 (m, 1H), 0.8-1.0 (m, 4H). |
| 1-026 | δ 8.47 (d, J = 2.0 Hz, 1H) and 8.43 (d, J = 1.7 Hz, 1H), 7.3-7.7 (m, 5H), 6.46 (d, J = 8.5 Hz, 1H), 5.00 (d, J = 4.1 Hz, 1H) and 4.90 (d, J = 2.7 Hz, 1H), 4.7-4.9 and 4.4-4.6 (m, 1H), 3.45-3.65 and 3.3-3.45 (m, 2H), 1.4-1.55 (m, 1H), 1.45 and 1.11 (d, J = 6.8 Hz, 3H), 1.20 and 1.19 (t, J = 7.0 Hz, 3H), 0.8-1.0 (m, 4H). |
| 1-027 | δ 8.47 (d, J = 1.5 Hz, 1H) and 8.46 (d, J = 1.8 Hz, 1H), 7.45-7.75 (m, 4H), 7.33 (d, J = 6.7 Hz, 1H) and 7.22 (d, J = 8.3 Hz, 1H), 6.31 (d, J = 8.9 Hz, 1H), 5.20 (d, J = 4.0 Hz, 1H) and 5.14 (d, J = 2.8 Hz, 1H), 4.75-4.95 and 4.55-4.8 (m, 1H), 3.5-4.2 (m, 2H), 1.46 (d, J = 6.7 Hz, 3H) and 1.14 (d, J = 7.0 Hz, 3H), 1.4-1.55 (m, 1H), 0.75-1.0 (m, 4H). |
| 1-028 | δ 8.47 (d, J = 1.5 Hz, 1H) and 8.45 (d, J = 1.8 Hz, 1H), 7.45-7.8 (m, 4H), 7.32 (d, J = 7.0 Hz, 1H) and 7.22 (d, J = 8.9 Hz, 1H), 6.20 (d, J = 8.9 Hz, 1H), 5.26 (d, J = 4.0 Hz, 1H) and 5.16 (d, J = 3.1 Hz, 1H), 4.8-5.0 and 4.45-4.7 (m, 1H), 4.45 and 4.44 (d, J = 16.2 Hz, 1H), 4.21 and 4.10 (d, J = 16.2 Hz, 1H), 1.4-1.55 (m, 1H), 1.14 (d, J = 6.7 Hz, 3H), 0.8-1.0 (m, 4H). |
| 1-029 | δ 8.48 (d, J = 1.7 Hz, 1H) and 8.44 (d, J = 2.0 Hz, 1H), 7.25-7.75 (m, 5H), 6.44 (d, J = 8.5 Hz, 1H), 5.75-6.0 (m, 1H), 5.1-5.3 (m, 2H), 5.06 (d, J = 4.1 Hz, 1H) and 4.97 (d, J = 2.4 Hz, 1H), 4.7-4.9 and 4.45-4.6 (m, 1H), 3.7-4.2 (m, 2H), 1.35-1.55 (m, 1H), 1.46 and 1.11 (d, J = 6.8 Hz, 3H), 0.75-1.0 (m, 4H). |
| 1-030 | δ 8.47 (d, J = 2.0 Hz, 1H) and 8.45 (d, J = 1.7 Hz, 1H), 7.71-7.44 (m, 4H), 7.32 (d, J = 6.5 Hz, 1H) and 7.23 (d, J = 8.5 Hz, 1H), 6.34 (d, J = 8.9 Hz, 1H), 5.34 (d, J = 4.1 Hz, 1H) and 5.23 (d, J = 2.4 Hz, 1H), 4.75-4.9 and 4.55-4.65 (m, 1H), 4.34 and 4.33 (dd, J = 16.2, 2.6 Hz, 1H), 4.07 and 3.97 (dd, J = 16.0, 2.4 Hz, 1H), 2.42 (t, J = 2.4 Hz, 1H), 1.4-1.55 (m, 1H), 1.47 (d, J = 5.1 Hz, 3H) and 1.12 (d, J = 6.8 Hz, 3H), 0.8-1.0 (m, 4H). |
| 1-032 | δ 8.45 (d, J = 2.1 Hz, 1H) and 8.33 (d, J = 1.7 Hz, 1H), 8.02 (d, J = 8.4 Hz, 1H) and 5.98 (d, J = 8.7 Hz, 1H), 7.5-7.75 (m, 5H), 4.6-4.95 (m, 2H), 3.0-3.45 (m, 2H), 1.4-1.55 (m, 1H), 1.28 (d, J = 6.9 Hz, 3H) and 1.18 (d, J = 6.3 Hz, 3H), 0.8-1.0 (m, 4H). |
| 2-003 | δ 8.43 (dd, J = 4.5, 1.5 Hz, 1H), 8.37 (d, J = 1.8 Hz, 1H), 7.98 (bs, 1H), 7.76 (dd, J = 8.0, 1.5 Hz, 1H), 7.63 (d, J = 1.8 Hz, 1H), 7.31 (dd, J = 8.0, 4.5 Hz, 1H), 3.72 (d, J = 5.7 Hz, 2H), 1.4-1.5 (m, 1H), 1.05-1.15 (m, 4H), 0.85-0.95 (m, 2H), 0.75-0.85 (m, 2H). |

TABLE 18-continued

| No. | $^1$H NMR (CDCl$_3$, Me$_4$Si, 300 MHz) |
|---|---|
| 2-004 | δ 8.70 (d, J = 4.2 Hz, 1H), 8.37 (d, J = 1.8 Hz, 1H), 8.11 (d, J = 8.1 Hz, 1H), 7.89 (bs, 1H), 7.64 (d, J = 1.8 Hz, 1H), 7.51 (dd, J = 8.1, 4.2 Hz, 1H), 3.73 (d, J = 5.7 Hz, 2H), 1.4-1.5 (m, 1H), 0.85-0.95 (m, 4H), 0.75-0.85 (m, 4H). |
| 3-005 | δ 8.42 (dd, J = 4.5, 1.8 Hz, 1H), 8.40 (d, J = 1.8 Hz, 1H), 8.06 (dd, J = 7.5, 1.8 Hz, 1H), 7.64 (d, J = 1.8 Hz, 1H), 7.31 (dd, J = 7.5, 4.5 Hz, 1H), 7.25-7.3 (m, 1H), 3.7-4.0 (m, 3H), 1.4-1.5 (m, 1H), 1.31 (d, J = 6.9 Hz, 3H), 0.75-0.95 (m, 4H). |
| 3-006 | δ 8.72 (dd, J = 5.1, 1.8 Hz, 1H), 8.37 (d, J = 1.8 Hz, 1H), 7.86 (dd, J = 7.8, 1.8 Hz, 1H), 7.64 (d, J = 1.8 Hz, 1H), 7.44 (dd, J = 7.8, 5.1 Hz, 1H), 6.91 (bs, 1H), 6.91 (t, J = 54.6 Hz, 1H), 3.7-4.0 (m, 3H), 1.4-1.5 (m, 1H), 1.30 (d, J = 6.9 Hz, 3H), 0.75-0.95 (m, 4H). |
| 3-008 | δ 8.73 (dd, J = 5.1, 1.5 Hz, 1H), 8.41 (d, J = 1.8 Hz, 1H), 7.84 (dd, J = 7.5, 1.5 Hz, 1H), 7.66 (d, J = 1.8 Hz, 1H), 7.45 (dd, J = 7.5, 5.1 Hz, 1H), 6.93 (t, J = 54.6 Hz, 1H), 6.83 (bs, 1H), 3.95-4.05 (m, 1H), 3.8-3.9 (m, 1H), 3.0-3.15 (m, 1H), 1.4-1.5 (m, 1H), 1.0-1.2 (m, 1H), 0.8-0.95 (m, 4H), 0.3-0.7 (m, 4H). |
| 3-009 | δ 8.72 (dd, J = 4.8, 1.5 Hz, 1H), 7.41 (d, J = 1.8 Hz, 1H), 7.84 (dd, J = 8.1, 1.5 Hz, 1H), 7.59 (d, J = 1.8 Hz, 1H), 7.45 (dd, J = 8.1, 4.8 Hz, 1H), 6.89 (t, J = 54.3 Hz, 1H), 6.75-7.1 (m, 4H), 3.6-4.0 (m, 3H), 2.85-3.05 (m, 2H), 1.4-1.5 (m, 1H), 0.8-0.95 (m, 4H). |
| 3-013 | δ 8.70 (dd, J = 4.8, 1.8 Hz, 1H), 8.37 (d, J = 1.8 Hz, 1H), 7.74 (d, J = 1.8 Hz, 1H), 7.66 (dd, J = 7.8, 1.8 Hz, 1H), 7.44 (dd, J = 7.8, 4.8 Hz, 1H), 6.89 (bs, 1H), 6.74 (t, J = 54.6 Hz, 1H), 6.71 (s, 1H), 4.71 (d, J = 6.6 Hz, 2H), 1.4-1.55 (m, 1H), 0.8-0.95 (m, 4H). |
| 3-014 | δ 8.75 (dd, J = 4.8, 1.8 Hz, 1H), 8.47 (d, J = 1.8 Hz, 1H), 7.8-7.9 (m, 1H), 7.74 (d, J = 1.8 Hz, 1H), 7.44 (dd, J = 7.8, 4.8 Hz, 1H), 6.95 (t, J = 54.6 Hz, 1H), 6.65 (s, 1H), 6.62 (bs, 1H), 4.42 (d, J = 6.6 Hz, 2H), 1.4-1.55 (m, 1H), 0.8-0.95 (m, 4H). |
| 3-015 | δ 8.41 (dd, J = 4.8, 2.1 Hz, 1H), 8.36 (d, J = 2.1 Hz, 1H), 7.94 (dd, J = 7.5, 2.1 Hz, 1H), 7.64 (d, J = 2.1 Hz, 1H), 7.28 (dd, J = 7.5, 4.8 Hz, 1H), 6.85 (bs, 1H), 3.71 (d, J = 4.8 Hz, 2H), 1.4-1.5 (m, 1H), 1.0-1.15 (m, 4H), 0.75-0.95 (m, 4H). |
| 3-018 | δ 8.46 (d, J = 1.5 Hz, 1H), 8.43 (dd, J = 4.8, 2.1 Hz, 1H), 7.98 (dd, J = 7.8, 2.1 Hz, 1H), 7.75 (d, J = 1.5 Hz, 1H), 7.30 (dd, J = 7.8, 4.8 Hz, 1H), 6.81 (bs, 1H), 4.54 (s, 2H), 3.97 (q, J = 8.7 Hz, 2H), 3.74 (d, J = 5.1 Hz, 2H), 1.05-1.2 (m, 4H). |
| 3-020 | δ 8.73 (dd, J = 5.1, 1.8 Hz, 1H), 8.37 (d, J = 1.8 Hz, 1H), 7.91 (dd, J = 7.8, 1.8 Hz, 1H), 7.68 (d, J = 1.8 Hz, 1H), 7.45 (dd, J = 7.8, 5.1 Hz, 1H), 6.92 (t, J = 54.3 Hz, 1H), 6.87 (bs, 1H), 4.57 (dd, J = 7.2, 5.7 Hz, 1H), 4.05-4.25 (m, 2H), 2.13 (s, 3H), 1.4-1.5 (m, 1H), 0.8-0.95 (m, 4H). |
| 3-021 | δ 8.76 and 8.73 (dd, J = 7.8, 1.8 Hz, 1H), 8.47 (d, J = 1.8 Hz, 1H), 7.95-8.05 (m, 1H), 7.79 and 6.57 (d, J = 8.1 Hz, 1H), 7.71 (d, J = 1.8 Hz, 1H), 7.49 and 7.43 (dd, J = 7.8, 4.8 Hz, 1H), 7.05 and 6.92 (t, J = 54.6 Hz, 1H), 4.92 (d, J = 4.2 Hz, 1H) and 4.80 (d, J = 2.4 Hz, 1H), 4.8-4.9 and 4.5-4.6 (m, 1H), 3.38 and 3.35 (s, 3H), 1.47 and 1.11 (d, J = 6.9 Hz, 3H), 1.4-1.55 (m, 1H), 0.8-1.0 (m, 4H). |
| 3-022 | δ 8.76 (dd, J = 4.8, 1.7 Hz, 1H) and 8.74 (dd, J = 3.4, 1.7 Hz, 1H), 8.47 and 8.44 (d, J = 1.7 Hz, 1H), 7.97 (d, J = 7.8 Hz, 1H) and 7.92 (d, J = 8.9 Hz, 1H), 7.83 and 6.64 (d, J = 8.2 Hz, 1H), 7.69 and 7.66 (d, J = 1.7 Hz, 1H), 7.47 (dd, J = 7.7, 4.6 Hz, 1H) and 7.43 (dd, J = 3.1, 1.5 Hz, 1H), 7.09 and 6.98 (t, J = 54.3 Hz, 1H), 5.00 (d, J = 4.1 Hz, 1H) and 4.91 (d, J = 2.4 Hz, 1H), 4.75-4.9 and 4.4-4.6 (m, 1H), 3.3-3.7 (m, 2H), 1.4-1.55 (m, 1H), 1.47 (d, J = 6.5 Hz, 3H) and 1.11 (d, J = 6.8 Hz, 3H), 1.21 and 1.20 (t, J = 7.0 Hz, 3H), 0.8-1.0 (m, 4H). |
| 3-023 | δ 8.4-8.55 (m, 2H), 8.07 and 7.80 (dd, J = 7.5, 2.0 Hz, 1H), 7.88 (d, J = 8.2 Hz, 1H) and 6.75 (d, J = 8.9 Hz, 1H), 7.72 (d, J = 2.0 Hz, 1H) and 7.68 (d, J = 1.7 Hz, 1H), 7.33 and 7.27 (dd, J = 7.8, 4.8 Hz, 1H), 5.22 (d, J = 4.4 Hz, 1H) and 5.15 (d, J = 3.1 Hz, 1H), 4.75-4.95 and 4.6-4.8 (m, 1H), 3.5-4.2 (m, 2H), 1.51 and 1.18 (d, J = 6.8 Hz, 3H), 1.4-1.55 (m, 1H), 0.75-1.0 (m, 4H). |
| 3-024 | δ 8.76 (dd, J = 3.1, 1.5 Hz, 1H) and 8.74 (dd, J = 4.8, 1.4 Hz, 1H), 8.47 (d, J = 2.0 Hz, 1H) and 8.43 (d, J = 1.7 Hz, 1H), 7.94 and 7.81 (d, J = 7.8 Hz, 1H), 7.72 and 7.68 (d, J = 1.7 Hz, 1H), 7.65 and 6.51 (d, J = 8.9 Hz, 1H), 7.4-7.55 (m, 1H), 7.03 (t, J = 54.3 Hz, 1H) and 6.94 (t, J = 54.5 Hz, 1H), 5.20 (d, J = 4.1 Hz, 1H) and 5.14 (d, J = 2.4 Hz, 1H), 4.8 4.95 and 4.6 4.7 (m, 1H), 3.5-4.15 (m, 2H), 1.50 and 1.14 (d, J = 6.8 Hz, 3H), 1.4-1.5 (m, 1H), 0.75-1.05 (m, 4H). |

TABLE 18-continued

| No. | $^1$H NMR (CDCl$_3$, Me$_4$Si, 300 MHz) |
|---|---|
| 3-025 | δ 8.75 (dd, J = 4.8, 1.4 Hz, 1H), 8.47 (d, J = 1.7 Hz, 1H), 7.98 (dt, J = 7.8, 0.7 Hz, 1H), 7.74 (d, J = 1.7 Hz, 1H), 7.60 (d, J = 8.5 Hz, 1H), 7.49 (dd, J = 7.8, 4.8 Hz, 1H), 7.01 (t, J = 54.5 Hz, 1H), 5.27 (d, J = 4.1 Hz, 1H), 4.8-5.0 (m, 1H), 4.44 (d, J = 16.3 Hz, 1H), 4.19 (d, J = 16.3 Hz, 1H), 1.4 1.55 (m, 1H), 1.15 (d, J = 6.8 Hz, 3H), 0.8-1.05 (m, 4H). |
| 3-027 | δ 8.76 (dd, J = 4.9, 1.5 Hz, 1H) and 8.73 (dd, J = 3.1, 1.5 Hz, 1H), 8.45 (d, J = 1.7 Hz, 1H), 7.96 (d, J = 7.8 Hz, 1H) and 7.90 (d, J = 8.2 Hz, 1H), 7.81 (d, J = 8.5 Hz, 1H) and 6.64 (d, J = 7.8 Hz, 1H), 7.69 and 7.66 (d, J = 2.0 Hz, 1H), 7.47 and 7.43 (dd, J = 7.7, 4.6 Hz, 1H), 7.07 (t, J = 54.8 Hz, 1H) and 6.95 (t, J = 54.5 Hz, 1H), 5.75-6.0 (m, 1H), 5.15-5.3 (m, 2H), 5.06 (d, J = 4.1 Hz, 1H) and 4.98 (d, J = 2.7 Hz, 1H), 4.75-4.9 and 4.5-4.6 (m, 1H), 3.75-4.2 (m, 2H), 1.4-1.55 (m, 1H), 1.48 and 1.11 (d, J = 6.8 Hz, 3H), 0.8-1.0 (m, 4H). |
| 3-028 | δ 8.53 (d, J = 2.0 Hz, 1H) and 8.51 (d, J = 1.7 Hz, 1H), 8.45 (dd, J = 4.8, 1.0 Hz, 1H) and 8.41 (dd, J = 4.8, 2.0 Hz, 1H), 8.09 (d, J = 9.5, 4.8 Hz, 1H) and 7.77 (dd, J = 7.7, 1.9 Hz, 1H), 7.90 and 6.72 (d, J = 8.5 Hz, 1H), 7.70 (d, J = 2.0 Hz, 1H) and 7.67 (d, J = 1.7 Hz, 1H), 7.33 and 7.26 (dd, J = 7.8, 4.8 Hz, 1H), 5.36 (d, J = 4.1 Hz, 1H) and 5.25 (d, J = 2.7 Hz, 1H), 4.75-4.9 and 4.55-4.7 (m, 1H), 4.36 (dd, J = 16.0, 2.4 Hz, 1H) and 4.33 (dd, J = 16.2, 2.6 Hz, 1H), 4.06 (dd, J = 16.0, 2.4 Hz, 1H) and 3.97 (dd, J = 16.2, 2.4 Hz, 1H), 2.44 and 2.43 (t, J = 2.4 Hz, 1H), 1.4-1.55 (m, 1H), 1.50 and 1.16 (d, J = 6.8 Hz, 3H), 0.8-1.0 (m, 4H). |
| 3-029 | δ 8.75 (dd, J = 4.8, 1.7 Hz, 1H) and 8.72 (dd, J = 4.8, 1.4 Hz, 1H), 8.47 and 8.44 (d, J = 1.7 Hz, 1H), 7.97 (d, J = 8.5 Hz, 1H) and 7.81 (d, J = 7.2 Hz, 1H), 7.71 (d, J = 2.0 Hz, 1H) and 7.68 (d, J = 1.7 Hz, 1H), 7.47 (dd, J = 7.8, 4.8 Hz, 1H) and 7.43 (dd, J = 8.2, 5.1 Hz, 1H), 7.08 and 6.93 (t, J = 54.3 Hz, 1H), 6.61 (d, J = 8.5 Hz, 1H), 5.34 (d, J = 4.1 Hz, 1H) and 5.24 (d, J = 2.7 Hz, 1H), 4.75-4.9 and 4.55-4.7 (m, 1H), 4.34 (dd, J = 16.2, 2.5 Hz, 1H) and 4.32 (dd, J = 16.0, 2.4 Hz, 1H), 4.07 (dd, J = 16.0, 2.4 Hz, 1H) and 3.97 (dd, J = 16.0, 2.5 Hz, 1H), 2.4-2.5 (m, 1H), 1.48 (d, J = 6.5 Hz, 3H) and 1.13 (d, J = 6.8 Hz, 3H), 1.4-1.55 (m, 1H), 0.75-1.0 (m, 4H). |
| 3-031 | δ 8.75 (dd, J = 4.6, 1.5 Hz, 1H) and 8.73 (dd, J = 6.1, 1.4 Hz, 1H), 8.48 and 8.47 (d, J = 1.7 Hz, 1H), 7.85 and 7.82 (d, J = 7.8 Hz, 1H), 7.69 (d, J = 2.0 Hz, 1H) and 7.66 (d, J = 1.7 Hz, 1H), 7.4-7.5 (m, 1H), 7.25-7.35 (m, 5H), 7.05 (t, J = 54.3 Hz, 1H) and 6.96 (t, J = 54.5 Hz, 1H), 6.68 (d, J = 8.5 Hz, 1H), 5.06 (d, J = 4.4 Hz, 1H) and 4.96 (d, J = 2.4 Hz, 1H), 4.75-4.95 (m, 1H), 4.65 (d, J = 11.9 Hz, 1H) and 4.59 (d, J = 11.6 Hz, 1H), 4.48 (d, J = 11.6 Hz, 1H) and 4.25 (d, J = 11.9 Hz, 1H), 1.4-1.55 (m, 1H), 1.42 and 1.12 (d, J = 6.8 Hz, 3H), 0.8-1.0 (m, 4H). |
| 3-032 | δ 8.62 (d, J = 7.8 Hz, 1H) and 6.60 (d, J = 8.4 Hz, 1H), 8.4-8.5 (m, 2H), 8.13 and 8.07 (dd, J = 7.5, 2.1 Hz, 1H), 7.71 (d, J = 2.1 Hz, 1H) and 7.68 (d, J = 1.8 Hz, 1H), 7.34 (dd, J = 7.5, 4.8 Hz, 1H), 4.7-4.95 (m, 2H), 3.0-3.4 (m, 2H), 1.4-1.55 (m, 1H), 1.34 and 1.21 (d, J = 6.6 Hz, 3H), 0.8-1.0 (m, 4H). |
| 3-034 | δ 8.7-8.8 (m, 1H), 8.45 (d, J = 1.7 Hz, 1H) and 8.32 (d, J = 1.8 Hz, 1H), 8.21 (d, J = 8.1 Hz, 1H) and 6.04 (d, J = 8.7 Hz, 1H), 8.0-8.05 and 7.9-8.0 (m, 1H), 7.71 (d, J = 1.8 Hz, 1H) and 7.69 (d, J = 1.7 Hz, 1H), 7.57 (dd, J = 7.8, 4.8 Hz, 1H), 4.6-4.95 (m, 2H), 3.0-3.4 (m, 2H), 1.4-1.55 (m, 1H), 1.30 and 1.18 (d, J = 6.6 Hz, 3H), 0.8-1.0 (m, 4H). |
| 4-004 | δ 8.7-8.8 (m, 2H), 8.54 and 8.40 (d, J = 1.8 Hz, 1H), 7.75 (d, J = 8.4 Hz, 1H) and 7.2-7.3 (m, 1H), 7.70 and 7.65 (d, J = 1.8 Hz, 1H), 4.93 (d, J = 4.2 Hz, 1H) and 4.84 (d, J = 2.4 Hz, 1H), 4.7-4.8 and 4.5-4.6 (m, 1H), 3.39 and 3.38 (s, 3H), 1.49 (d, J = 6.6 Hz, 3H) and 1.14 (d, J = 7.2 Hz, 3H), 1.4-1.5 (m, 1H), 0.8-1.0 (m, 4H). |
| 5-002 | δ 8.37 (d, J = 2.1 Hz, 1H), 7.63 (d, J = 2.1 Hz, 1H), 7.38 (d, J = 5.1 Hz, 1H), 7.20 (d, J = 5.1 Hz, 1H), 6.57 (bs, 1H), 3.66 (d, J = 5.1 Hz, 2H), 1.4-1.5 (m 1H), 1.0-1.15 (m, 4H), 0.75-0.95 (m, 4H). |
| 8-002 | δ 8.41 (d, J = 2.1 Hz, 1H), 7.84 (s, 1H), 7.64 (d, J = 2.1 Hz, 1H), 7.13 (bs, 1H), 6.83 (t, J = 54.6 Hz, 1H), 3.91 (s, 3H), 3.85-3.9 (m, 2H), 3.17 (t, J = 6.3 Hz, 2H), 1.32 (s, 9H). |
| 8-007 | δ 8.42 (d, J = 1.8 Hz, 1H), 7.85 (s, 1H), 7.61 (d, J = 1.8 Hz, 1H), 6.96 (bs, 1H), 6.74 (t, J = 54.0 Hz, 1H), 3.90 (s, 3H), 3.75-3.85 (m, 2H), 3.5-3.75 (m, 1H), 1.4-1.55 (m, 1H), 1.26 (d, J = 6.9 Hz, 3H), 0.8-0.95 (m, 4H). |

TABLE 18-continued

| No. | $^1$H NMR (CDCl$_3$, Me$_4$Si, 300 MHz) |
|---|---|
| 8-008 | δ 8.38 (d, J = 1.7 Hz, 1H), 7.87 (s, 1H), 7.62 (d, J = 2.4 Hz, 1H). 7.50 (bs, 1H), 6.74 (t, J = 54.1 Hz, 1H), 3.89 (s, 3H), 3.82 (d, J = 6.5 Hz, 2H), 1.50 (s, 6H), 1.4-1.5 (m, 1H), 0.8-1.0 (m, 4H). |
| 8-009 | δ 8.46 (d, J = 1.8 Hz, 1H), 7.83 (s, 1H), 7.62 (d, J = 1.8 Hz, 1H), 6.78 (bs, 1H), 6.74 (t, J = 54.0 Hz, 1H), 3.91 (s, 3H), 3.8-3.95 (m, 2H), 3.0-3.1 (m, 1H), 1.4-1.5 (m, 1H), 1.0-1.2 (m, 1H), 0.8-0.95 (m, 4H), 0.3-0.7 (m, 4H). |
| 8-010 | δ 8.46 (d, J = 1.8 Hz, 1H), 7.85 (s, 1H), 7.56 (d, J = 1.8 Hz, 1H), 6.7-7.0 (m, 4H), 6.72 (t, J = 54.6 Hz, 1H), 3.90 (s, 3H), 3.85-4.0 (m, 1H), 3.7-3.8 (m, 2H), 2.85-3.05 (m, 2H), 1.4-1.5 (m, 1H), 0.8-0.95 (m, 4H). |
| 8-012 | δ 8.42 (d, J = 1.8 Hz, 1H), 7.83 (s, 1H), 7.67 (d, J = 1.8 Hz, 1H), 6.80 (bs, 1H), 6.74 (s, 1H), 6.74 (t, J = 54.9 Hz, 1H), 4.67 (d, J = 6.0 Hz, 2H), 3.90 (s, 3H), 1.4-1.55 (m, 1H), 0.8 0.95 (m, 4H). |
| 8-013 | δ 8.48 (d, J = 1.8 Hz, 1H), 7.85 (s, 1H), 7.71 (d, J = 1.8 Hz, 1H), 6.81 (t, J = 54.9 Hz, 1H), 6.66 (bs, 1H), 6.57 (s, 1H), 4.37 (d, J = 5.4 Hz, 2H), 3.91 (s, 3H), 1.4-1.55 (m, 1H), 0.8-0.95 (m, 4H). |
| 8-014 | δ 8.40 (d, J = 1.8 Hz, 1H), 7.83 (s, 1H), 7.66 (d, J = 1.8 Hz, 1H), 6.93 (bs, 1H), 6.80 (t, J = 54.6 Hz, 1H), 6.24 (q, J = 7.2 Hz, 1H), 4.45 (d, J = 5.1 Hz, 2H), 3.90 (s, 3H), 1.98 (d, J = 7.2 Hz, 3H), 1.4-1.5 (m, 1H), 0.8-0.95 (m, 4H). |
| 8-015 | δ 8.48 (d, J = 1.8 Hz, 1H), 7.81 (s, 1H), 7.69 (d, J = 1.8 Hz, 1H), 6.84 (t, J = 54.3 Hz, 1H), 6.59 (bs, 1H), 6.01 (q, J = 7.2 Hz, 1H), 4.29 (d, J = 5.1 Hz, 2H), 3.91 (s, 3H), 1.52 (d, J = 7.2 Hz, 3H), 1.4-1.5 (m, 1H), 0.8-0.95 (m, 4H). |
| 8-016 | δ 8.41 (d, J = 2.1 Hz, 1H), 7.82 (s, 1H), 7.68 (d, J = 2.1 Hz, 1H), 6.95 (bs, 1H), 6.81 (t, J = 54.6 Hz, 1H), 6.23 (q, J = 7.2 Hz, 1H), 4.45 (d, J = 5.4 Hz, 2H), 3.90 (s, 3H), 1.98 (d, J = 7.2 Hz, 3H), 1.31 (s, 9H). |
| 8-025 | δ 8.46 (d, J = 1.8 Hz, 1H), 7.81 (s, 1H), 7.68 (d, J = 1.8 Hz, 1H), 6.93 (bs, 1H), 6.87 (t, J = 54.0 Hz, 1H), 4.6-4.7 (m, 1H), 4.50 (s, 2H), 3.91 (s, 3H), 3.23 (dd, J = 14.4, 6.9 Hz, 1H), 3.14 (dd, J = 14.4, 5.4 Hz, 1H), 1.28 (d, J = 6.6 Hz, 3H). |
| 8-027 | δ 8.55 (d, J = 1.8 Hz, 1H), 7.81 (s, 1H), 7.78 (d, J = 1.8 Hz, 1H), 7.45-7.6 (m, 2H), 7.3-7.4 (m, 3H), 7.01 (d, J = 7.8 Hz, 1H), 6.90 (t, J = 54.6 Hz, 1H), 4.6-4.75 (m, 1H), 3.92 (s, 3H), 3.26 (dd, J = 14.4, 6.9 Hz, 1H), 3.16 (dd, J = 14.4, 5.4 Hz, 1H), 1.30 (d, J = 6.6 Hz, 3H). |
| 8-029 | δ 8.5-8.55 and 8.4-8.45 (m, 1H), 7.87 and 7.78 (s, 1H), 7.65-7.7 and 7.6-7.65 (m, 1H), 7.51 and 6.65 (d, J = 7.7 Hz, 1H), 7.00 and 6.96 (t, J = 54.2 Hz, 1H), 4.96 (d, J = 4.3 Hz, 1H) and 4.90 (d, J = 3.4 Hz, 1H), 4.65-4.8 and 4.4-4.55 (m, 1H), 3.93 and 3.92 (s, 3H), 3.3-3.6 (m, 2H), 1.4-1.55 (m, 1H), 1.38 (d, J = 6.7 Hz, 3H) and 1.10 (d, J = 6.4 Hz, 3H), 1.22 (t, J = 6.9 Hz, 3H) and 1.20 (t, J = 7.0 Hz, 3H), 0.8-1.0 (m, 4H). |
| 8-030 | δ 8.53 and 8.38 (d, J = 1.7 Hz, 1H), 7.86 and 7.76 (s, 1H), 7.68 (d, J = 1.4 Hz, 1H) and 7.64 (d, J = 1.7 Hz, 1H), 7.30 and 6.61 (bs, 1H), 6.94 and 6.93 (t, J = 54.1 Hz, 1H), 5.16 (d, J = 4.1 Hz, 1H) and 5.12 (d, J = 3.1 Hz, 1H), 4.7-4.9 and 4.55-4.7 (m, 1H), 3.5-4.1 (m, 2H), 3.93 and 3.91 (s, 3H), 1.4-1.55 (m, 1H), 3.41 and 1.13 (d, J = 6.8 Hz, 3H), 0.75-1.0 (m, 4H). |
| 8-031 | δ 8.53 and 8.41 (d, J = 1.7 Hz, 1H), 7.84 and 7.75 (s, 1H), 7.66 and 7.61 (d, J = 1.7 Hz, 1H), 7.48 and 6.58 (d, J = 8.9 Hz, 1H), 6.97 and 6.94 (t, J = 54.1 Hz, 1H), 5.75-6.0 (m, 1H), 5.1-5.3 (m, 2H), 5.02 (d, J = 4.1 Hz, 1H) and 4.96 (d, J = 3.1 Hz, 1H), 4.65-4.8 and 4.4-4.55 (m, 1H), 3.75 4.2 (m, 2H), 3.93 and 3.92 (s, 3H). 1.4-1.55 (m, 1H), 1.39 (d, J = 6.5 Hz, 3H) and 1.09 (d, J = 6.8 Hz, 3H), 0.8-1.0 (m, 4H). |
| 8-032 | δ 8.54 (d, J = 1.7 Hz, 1H) and 8.43 (d, J = 2.0 Hz, 1H), 7.75 and 7.72 (s, 1H), 7.66 (d, J = 1.7 Hz, 1H) and 7.62 (d, J = 2.0 Hz, 1H), 7.49 (d, J = 8.2 Hz, 1H) and 6.63 (d, J = 7.8 Hz, 1H), 7.25-7.35 (m, 5H), 6.99 and 6.97 (t, J = 54.1 Hz, 1H), 5.02 (d, J = 4.4 Hz, 1H) and 4.95 (d, J = 3.1 Hz, 1H), 4.7-4.9 (m, 1H), 4.64 and 4.58 (d, J = 11.7 Hz, 1H), 4.45 and 4.28 (d, J = 11.7 Hz, 1H), 3.92 and 3.91 (s, 3H), 1.4-1.55 (m, 1H), 1.36 and 1.10 (d, J = 6.8 Hz, 3H), 0.8-1.0 (m, 4H). |
| 8-034 | δ 8.37 (d, J = 1.7 Hz, 1H), 7.84 (s, 1H), 7.62 (d, J = 1.7 Hz, 1H), 7.12 (d, J = 7.2 Hz, 1H), 4.55-4.75 (m, 1H), 3.25 (s, 3H), 3.22 (dd, J = 14.6, 6.8 Hz, 1H), 3.09 (dd, J = 14.6, 4.8 Hz, 1H), 1.4-1.55 (m, 1H), 1.25 (d, J = 6.8 Hz, 3H), 0.75-1.0 (m, 4H). |
| 9-002 | δ 8.42 (d, J = 1.8 Hz, 1H), 7.64 (d, J = 1.8 Hz, 1H), 7.25-7.3 (m, 1H), 7.16 (t, J = 54.3 Hz, 1H), 3.8-3.95 (m, 1H), 3.65-3.75 (m, 2H), 2.73 (s, 3H), 1.4-1.55 (m, 1H), 1.27 (d, J = 6.9 Hz, 3H), 0.8-1.0 (m, 4H). |

TABLE 18-continued

| No. | $^1$H NMR (CDCl$_3$, Me$_4$Si, 300 MHz) |
|---|---|
| 9-003 | δ 8.43 (d, J = 1.5 Hz, 1H), 7.71 (d, J = 1.5 Hz, 1H), 7.19 (bs, 1H), 7.18 (t, J = 54.3 Hz, 1H), 5.85 (s, 1H), 5.84 (s, 1H), 4.41 (d, J = 5.4 Hz, 2H), 2.73 (s, 3H), 1.4-1.5 (m, 1H), 0.8-1.0 (m, 4H). |
| 9-004 | δ 8.38 (d, J = 1.8 Hz, 1H), 7.64 (d, J = 1.8 Hz, 1H), 7.16 (t, J = 54.6 Hz, 1H), 6.53 (bs, 1H), 3.61 (d, J = 4.8 Hz, 2H), 2.73 (s, 3H), 1.4-1.5 (m, 1H), 1.0-1.15 (m, 4H), 0.75-0.95 (m, 4H). |
| 9-006a | δ 8.55 (d, J = 1.8 Hz, 1H), 8.06 (d, J = 7.5 Hz, 1H), 7.72 (d, J = 1.8 Hz, 1H), 7.30 (t, J = 54.0 Hz, 1H), 4.87 (d, J = 3.9 Hz, 1H), 4.7-4.8 (m, 1H), 3.36 (s, 3H), 2.76 (s, 3H), 1.45-1.55 (m, 1H), 1.07 (d, J = 6.6 Hz, 3H), 0.8-1.0 (m, 4H). |
| 9-006b | δ 8.43 (d, J = 1.8 Hz, 1H), 7.65 (d, J = 1.8 Hz, 1H), 7.15 (t, J = 54.0 Hz, 1H), 6.55 (d, J = 7.8 Hz, 1H), 4.79 (d, J = 2.4 Hz, 1H), 4.35-4.5 (m, 1H), 3.34 (s, 3H), 2.74 (s, 3H), 1.4 1.55 (m, 1H), 1.44 (d, J = 6.6 Hz, 3H), 0.8-1.0 (m, 4H). |
| 13-004 | δ 8.52 (d, J = 1.8 Hz, 1H), 7.84 (d, J = 1.8 Hz, 1H), 4.41 (s, 2H), 3.35-3.55 (m, 2H), 3.46 (s, 3H). |
| 13-007 | δ 8.4-8.5 (m, 1H), 7.63 (d, J = 1.8 Hz, 1H), 3.0-3.3 (m, 2H), 2.6-2.8 (m, 1H), 1.4-1.5 (m, 1H), 1.05-1.2 (m, 1H), 0.8-0.95 (m, 4H), 0.15 0.7 (m, 4H). |
| 13-009 | δ 8.50 and 8.44 (d, J = 1.8 Hz, 1H), 7.74 and 7.72 (d, J = 1.8 Hz, 1H), 6.4-6.5 (m, 1H), 3.65 (s, 2H), 1.4-1.5 (m, 1H), 0.8-1.0 (m, 4H). |
| 15-005 | δ 8.50 (d, J = 1.8 Hz, 1H), 7.84 (d, J = 1.8 Hz, 1H), 5.07 (bs, 1H), 4.34 (s, 2H), 3.95-4.15 (m, 2H), 3.46 (s, 3H), 1.40 (s, 9H). |
| 15-008 | δ 8.45 (d, J = 1.8 Hz, 1H), 7.62 (d, J = 1.8 Hz, 1H), 4.74 (bs, 1H), 3.4-3.7 (m, 2H), 2.85-3.05 (m, 1H), 1.4-1.5 (m, 1H), 1.39 (s, 9H), 1.0-1.15 (m, 1H), 0.8-0.95 (m, 4H), 0.2-0.6 (m, 4H). |
| 15-009 | δ 8.42 (d, J = 2.1 Hz, 1H), 7.67 (d, J = 2.1 Hz, 1H), 5.67 (s, 1H), 5.62 (s, 1H), 4.94 (bs, 1H), 4.1-4.2 (m, 2H), 1.4-1.5 (m, 1H), 1.42 (s, 9H), 0.8 0.95 (m, 4H). |
| 15-010 | δ 8.45-8.55 and 8.35-8.45 (m, 1H), 7.55-7.75 (m, 1H), 6.58 and 6.47 (s, 1H), 4.82 (bs, 1H), 4.0-4.2 (m, 2H), 1.4-1.5 (m, 1H), 1.39 and 1.38 (s, 9H), 0.8-1.0 (m, 4H). |
| 15-012 | δ 8.47 (d, J = 1.5 Hz, 1H), 7.72 (d, J = 1.5 Hz, 1H), 4.80 (bs, 1H), 4.54 (s, 2H), 3.97 (q, J = 8.4 Hz, 2H), 3.40 (d, J = 5.7 Hz, 2H), 1.33 (s, 9H), 0.95-1.1 (m, 4H). |
| 15-016 | δ 8.44 (d, J = 1.8 Hz, 1H), 7.65 (d, J = 1.8 Hz, 1H), 4.55-4.7 (m, 2H), 4.25-4.4 (m, 1H), 3.05-3.35 (m, 2H), 1.45-1.55 (m, 1H), 1.44 (s, 9H), 1.16 (d, J = 6.9 Hz, 3H), 0.8-1.0 (m, 4H). |

TEST EXAMPLES

Usefulness of the compounds of the present invention as pesticides will be described in detail by referring to the following the Test Examples, but the present invention is not limited thereto.

Preparation of the Test Solution A:

Compounds of the present invention were dissolved in a solvent for emulsion (a mixture of Sorpol (registered trademark) 3005XL (manufactured by Toho Chemical Industry Co., Ltd.): N-methylpyrrolidone: Solvesso (registered trademark) 200 (manufactured by ExxonMobil Chemical) in a ratio of 1:5:2) to prepare 20 wt % emulsifiable concentrates. Then, distilled water was added to dilute the emulsifiable concentrates to the prescribed concentration (500 ppm), and the obtained solutions were used in the following the Test Examples 1 to 8.

Preparation of the Test Solution B:

Compounds of the present invention were dissolved in dimethyl sulfoxide to prepare 1 wt % solutions. Then, distilled water was added to dilute the solutions to the prescribed concentration (100 ppm), and the obtained solutions were used in the following the Test Examples 9 to 12.

Test Example 1: Test on the Preventive Effect Against Cucumber Powdery Mildew

Cucumber (varieties: Sagami Hanjiro) was seeded in 90 cm$^3$ plastic pot, and at the cotyledon stage, 5 ml per pot of test solution A of the compounds of the present invention was sprayed. After drying in air, the pot was placed in an air-conditioned greenhouse (20° C.), and a suspension of conidium of *Erysiphe polygoni* (synonym: *Erysiphe betae*) was sprayed. After the pot were replaced at the same temperature for 9 days, the proportion of the formed lesion in the inoculated leaves were counted to calculate the control value in accordance with the following formula. The test was carried out in duplicate.

Control value=[1−(lesion area ratio in treated plot/lesion are a ratio in non-treated plot)]×100

As results of the compounds were tested, the following compounds showed a control value of at least 70%.

The compounds of the present invention: No. 1-001, 1-002, 1-003, 1-004, 1-005, 1-007, 1-008, 1-009, 1-010, 1-011, 1-012, 1-013, 1-016, 1-017, 1-018, 1-020, 1-021, 1-024, 1-025, 1-026, 1-027, 1-028, 1-029, 1-030, 1-031, 1-032, 2-004*, 3-001, 3-002, 3-003, 3-005, 3-006, 3-007, 3-008, 3-009, 3-010, 3-011, 3-012*, 3-013, 3-014, 3-015, 3-016, 3-020, 3-021, 3-022*, 3-025, 3-026, 3-027, 3-028, 3-029, 3-030, 3-031, 3-032, 3-033a, 3-034, 4-003, 4-004, 5-002, 6-001, 8-001, 8-002, 8-003, 8-007, 8-008, 8-009, 8-010, 8-011, 8-012, 8-013, 8-014, 8-015, 8-016, 8-017, 8-018, 8-019, 8-020, 8-022, 8-023, 8-024, 8-026, 8-027, 8-028, 8-031, 8-032, 9-002, 9-003, 9-004, 9-005, 9-006a, 9-006b, 10-001*.

The symbol * means that the test was carried out using a 100 ppm solution.

Test Example 2: Test on the Preventive Effect Against Cucumber Gray Mold (Spore Inoculation)

Cucumber (varieties: Sagami Hanjiro) was seeded in 90 cm$^3$ plastic pot, and at the cotyledon stage, 5 ml per pot of test solution A of the compounds of the present invention was applied. After drying in air, the treated leaves were cut and transferred in plastic containers. 30 μl of a mixture of a suspension of conidium of *Botrytis cinerea* and a dissolved PDA medium in a ratio of 1:1 was dropped on each treated leaf and inoculated. After the inoculation, the plastic containers were placed in 20° C. with humid conditions for 3 days, and the proportion of the formed lesion in the inoculated leaves were counted to calculate the control value in accordance with the same formula as in the Test Example 1. The test was carried out in duplicate.

As results of the compounds were tested, the following compounds showed a control value of at least 70%.
The compounds of the present invention: No. 1-001, 1-002, 1-003, 1-004, 1-005, 1-007, 1-008, 1-009, 1-010, 1-011, 1-012, 1-013, 1-016, 1-017, 1-018, 1-020, 1-021, 1-024, 1-025, 1-026, 1-027, 1-028, 1-029, 1-030, 1-031, 1-033, 2-004*, 3-001, 3-002, 3-003, 3-005, 3-006, 3-007, 3-008, 3-009, 3-010, 3-011, 3-012*, 3-013, 3-014, 3-015, 3-016, 3-020, 3-021, 3-022*, 3-025, 3-026, 3-027, 3-028, 3-029, 3-030, 3-031, 3-032, 3-033a, 3-034, 4-003, 4-004, 5-002, 6-001, 8-001, 8-002, 8-003, 8-007, 8-008, 8-009, 8-010, 8-011, 8-012, 8-013, 8-014, 8-015, 8-016, 8-017, 8-018, 8-019, 8-020, 8-022, 8-023, 8-024, 8-026, 8-027, 8-028, 8-031, 8-032, 8-033, 9-002, 9-003, 9-004, 9-005, 9-006a, 9-006b, 10-001*, 12-002.

The symbol * means that the test was carried out using a 100 ppm solution.

Test Example 3: Test on the Preventive Effect Against Cucumber Gray Mold (Mycelium Inoculation)

Cucumber (varieties: Sagami Hanjiro) was seeded in 90 cm$^3$ plastic pot, and at the cotyledon stage, 5 ml per pot of test solution A of the compounds of the present invention was applied. On the next day, the pot was transferred in a plastic container, and an agar blocks (diameter: 5 mm) containing *Botrytis cinerea* which was preliminarily cultivated in a PDA medium was inoculated on the cotyledon of the cucumber treated with the solution. After the inoculation, the plastic container was covered with a plastic sheet, then placed at 20° C. and humidified for 2 days. Thus the proportion of the formed lesion in the inoculated leaves were measured to calculate the control value in accordance with the same formula as in the Test Example 1. The test was carried out in duplicate.

As results of the compounds were tested, the following compounds showed a control value of at least 70%.
The compounds of the present invention: No. 1-001, 1-002, 1-003, 1-004, 1-005, 1-007, 1-008, 1-012, 1-013, 1-016, 1-017, 1-018, 1-020, 1-021, 1-024, 1-025, 1-026, 1-027, 1-028, 1-029, 1-030, 1-031, 1-033, 2-004*, 3-001, 3-002, 3-003, 3-005, 3-006, 3-007, 3-008, 3-009, 3-010, 3-011, 3-012*, 3-013, 3-014, 3-015, 3-016, 3-020, 3-021, 3-022*, 3-025, 3-026, 3-027, 3-028, 3-029, 3-030, 3-031, 3-034, 4-003, 4-004, 5-002, 6-001, 8-001, 8-002, 8-003, 8-007, 8-008, 8-009, 8-011, 8-012, 8-013, 8-014, 8-015, 8-016, 8-017, 8-018, 8-019, 8-020, 8-022, 8-024, 8-026, 8-027, 8-028, 8-031, 8-032, 8-033, 9-002, 9-003, 9-004, 9-005, 9-006a, 9-006b.

The symbol * means that the test was carried out using a 100 ppm solution.

Test Example 4: Test on the Preventive Effect Against Cucumber Stem Rot

Cucumber (varieties: Sagami Hanjiro) was seeded in 90 cm$^3$ plastic pot, and at the cotyledon stage, 5 ml per pot of test solution A of the compounds of the present invention was applied. After drying in air, the pot was transferred in a plastic container, and an agar blocks (diameter: 5 mm) containing *Sclerotinia sclerotiorum* which was preliminarily cultivated in a PDA medium was inoculated to the seed leaves of the cucumber treated with the solution. After the inoculation, the plastic container was covered with a plastic sheet, and placed at 20° C. and humidified for 2 days, thus the proportion of the formed lesion in the inoculated leaves were measured to calculate the control value in accordance with the same formula as in the Test Example 1. The test was carried out in duplicate.

As results of the compounds were tested, the following compounds showed a control value of at least 70%.
The compounds of the present invention: No. 1-001, 1-002, 1-003, 1-004, 1-005, 1-007, 1-008, 1-009, 1-010, 1-012, 1-013, 1-016, 1-017, 1-018, 1-020, 1-021, 1-024, 1-025, 1-026, 1-027, 1-028, 1-029, 1-030, 1-031, 1-033, 2-004*, 3-001, 3-002, 3-003, 3-005, 3-006, 3-007, 3-008, 3-009, 3-010, 3-011, 3-012*, 3-013, 3-014, 3-015, 3-016, 3-020, 3-021, 3-022*, 3-025, 3-026, 3-027, 3-028, 3-029, 3-030, 3-031, 3-032, 3-034, 4-003, 4-004, 5-002, 6-001, 8-001, 8-002, 8-003, 8-007, 8-008, 8-009, 8-010, 8-011, 8-012, 8-013, 8-014, 8-015, 8-016, 8-017, 8-018, 8-019, 8-020, 8-022, 8-024, 8-026, 8-027, 8-028, 8-031, 8-032, 8-033, 9-002, 9-003, 9-004, 9-005, 9-006a, 9-006b, 10-001*.

The symbol * means that the test was carried out using a 100 ppm solution.

Test Example 5: Test on the Preventive Effect Against Cucumber Anthracnose

Cucumber (varieties: Sagami Hanjiro) was seeded in 90 cm$^3$ plastic pot, and at the cotyledon stage, 5 ml per pot of test solution A of the compounds of the present invention was sprayed. One day later, a suspension of conidium of *Colletotrichum lagenarium* (Synonym: *Colletotrichum orbiculare*) was sprayed, and the pot was left for 2 days in the inoculation chamber at 25° C. under humidity of 100% RH. Thereafter, the pot was placed in an air-conditioned greenhouse (23° C.) and left at the same temperature for 7 days. Thereafter, the proportion of the formed lesion in the inoculated leaves were measured to calculate the control value in accordance with the same formula as in Test Example 1. The test was carried out in duplicate.

As results of the compounds were tested, the following compounds showed a control value of at least 70%.
The compounds of the present invention: No. 1-001, 1-002, 1-005, 1-013, 1-020, 3-002, 3-003, 3-006, 3-008, 3-016, 3-020, 3-033a, 6-001, 8-003, 8-009, 8-010, 8-016, 8-017, 8-020, 8-024, 8-025*, 8-026, 8-027, 8-032, 9-002.

The symbol * means that the test was carried out using a 100 ppm solution.

Test Example 6: Test on the Preventive Effect Against Wheat Powdery Mildew

Wheat (varieties: Norin 61) was seeded in 90 cm$^3$ plastic pot, and at the 1.3-leaf stage, 5 ml per pot of test solution A of the compounds of the present invention were applied. One day after treatment, the pot was placed in an air-conditioned greenhouse (20° C.), and conidium of *Blumeria graminis* f. sp. *tritici* was inoculated to the wheat. 7 days after, the proportion of the formed lesion in the inoculated leaves were measured to calculate the control value in accordance with the same formula as in the Test Example 1. The test was carried out in duplicate.

As results of the compounds were tested, the following compounds showed a control value of at least 70%.
The compounds of the present invention: No. 1-001, 1-002, 1-003, 1-004, 1-005, 1-007, 1-008, 1-009, 1-011, 1-012, 1-013, 1-016, 1-017, 1-018, 1-020, 1-021, 1-024, 1-025, 1-026, 1-027, 1-028, 1-029, 1-030, 1-031, 2-004*, 3-001, 3-002, 3-003, 3-005, 3-006, 3-007, 3-008, 3-010, 3-011, 3-012*, 3-013, 3-014, 3-015, 3-016, 3-020, 3-021, 3-022*, 3-025, 3-026, 3-027, 3-028, 3-029, 3-030, 3-031, 4-003, 4-004, 5-002, 6-001, 8-001, 8-002, 8-003, 8-007, 8-008, 8-009, 8-011, 8-012, 8-013, 8-014, 8-015, 8-016, 8-017, 8-018, 8-019, 8-020, 8-022, 8-023, 8-024, 8-026, 8-027, 8-028, 8-031, 8-032, 9-002, 9-003, 9-004, 9-006a, 9-006b.

The symbol * means that the test was carried out using a 100 ppm solution.

Test Example 7: Test on the Preventive Effect Against Wheat Glume Blotch

Wheat (varieties: Haruyutaka) was seeded in 90 cm$^3$ plastic pot, and at 1.3-leaf stage, 5 ml per pot of test solution A of the compounds of the present invention was applied. One day after treatment, a suspension of conidium of *Phaeosphaeria nodorum* (Synonym: *Septoria nodorum*) was sprayed to the wheat, and the pot was left in the inoculation chamber at 20° C. under humidity of 100% RH for 2 days. Then, the pot was placed in an air-conditioned greenhouse (20° C.) for 6 days. The proportion of the formed lesion in the inoculated leaves were measured to calculate the control value in accordance with the same formula as in the Test Example 1. The test was carried out in duplicate.

As results of the compounds were tested, the following compounds showed a control value of at least 70%.
The compounds of the present invention: No. 1-001, 1-002, 1-003, 1-004, 1-005, 1-007, 1-008, 1-009, 1-010, 1-012, 1-013, 1-017, 1-018, 1-020, 1-021, 1-023, 1-024, 1-025, 1-026, 1-027, 1-029, 1-030, 1-031, 1-032, 1-033, 3-001, 3-002, 3-003, 3-005, 3-006, 3-007, 3-008, 3-009, 3-010, 3-011, 3-012*, 3-013, 3-015, 3-016, 3-020, 3-021, 3-022*, 3-026, 3-027, 3-028, 3-029, 3-030, 3-031, 3-032, 3-033a, 3-034, 3-034a, 4-003, 4-004, 5-002, 6-001, 8-001, 8-002, 8-003, 8-007, 8-008, 8-009, 8-010, 8-011, 8-012, 8-013, 8-014, 8-015, 8-016, 8-017, 8-018, 8-019, 8-022, 8-023, 8-024, 8-026, 8-027, 8-028, 8-031, 8-032, 9-002, 9-003, 9-004, 9-005, 9-006a, 9-006b, 10-001, 11-001.

The symbol * means that the test was carried out using a 100 ppm solution.

Test Example 8: Test on the Preventive Effect Against Wheat Leaf Rust

Wheat (varieties: Norin 61) was seeded in 90 cm$^3$ plastic pot, and at 1.3-leaf stage, 5 ml per pot of test solution A of the compounds of the present invention was applied. One day after treatment, a suspension of spores of *Puccinia recondita* was sprayed to the wheat, and the pot was left in the inoculation chamber at 20° C. under humidity of 100% RH for 1 day. Thereafter, the pot was placed in an air-conditioned greenhouse (20° C.) for 8 days. The proportion of the formed lesion in the inoculated leaves were counted to calculate the control value in accordance with the same formula as in the Test Example 1. The test was carried out in duplicate.

As results of the compounds were tested, the following compounds showed a control value of at least 70%.
The compounds of the present invention: No. 1-016, 1-024, 1-025, 1-031, 3-001, 3-002, 3-003, 3-008, 3-009, 3-011, 3-013, 3-014, 3-016, 3-020, 3-021, 3-029, 4-004, 6-001, 8-001, 8-002, 8-007, 8-009, 8-011, 8-012, 8-014, 8-015, 8-016, 8-017, 8-022, 8-024, 8-026, 8-027, 8-033, 9-003, 9-006b.

Test Example 9: Test on the Antifungal Activity Against *Asperaillus niger*

60 μl of a potato dextrose 1% agar medium was added to each well of a 96 well plate, and 30 μl of sterilized water containing spores of *Asperaillus niger* (10 spores/3 μl) was added to each well. Further, 10 μl per well of test solution B of the compounds of the present invention was added, and the plate was left at rest at 25° C. under dark conditions. 2 days after treatment, the flora area ratio (%) was determined to calculate the efficacy (%) relative to the non-treated well in accordance with the following formula.

Efficacy (%)=[1−(flora area ratio in treated plot/flora area ratio in non-treated well)]×100

As results of the compounds were tested, the following compounds showed an efficacy of at least 50%.
The compounds of the present invention: No. 1-002, 1-003, 1-004, 1-005, 1-007, 1-008, 1-009, 1-011, 1-012, 1-013, 1-017, 1-021, 1-024, 1-025, 1-033, 3-001, 3-002, 3-003, 3-005, 3-006, 3-007, 3-008, 3-009, 3-015, 3-016, 3-020, 3-021, 8-001, 8-002, 8-003, 8-007, 8-008, 8-009, 8-010, 8-011, 8-019, 8-020, 8-028, 8-033, 9-002, 9-004, 9-006a.

Test Example 10: Insecticidal Test Against Southern Root-Knot Nematode

60 μl of a potato dextrose 1% agar medium was added to each well of a 96 well plate, and 30 μl of sterilized water containing eggs of Southern root-knot nematode (*Meloidogyne incoqnita*) (10 eggs/3 μl) was added to each well. Further, 10 μl per well of test solution B of the compounds of the present invention was added, and the plate was left at rest at 25° C. under dark conditions. 4 days after treatment, unhatched eggs and inactive larvae were counted, and calculated the efficacy (%) relative to the non-treated plot in accordance with the following formula.

Efficacy (%)=[(number of unhatched eggs+inactive larvae in treated well)/number of active larvae in non-treated well]×100

As results of the compounds were tested, the following compounds showed an efficacy of at least 50%.
The compounds of the present invention: No. 1-001, 1-002, 1-003, 1-004, 1-005, 1-007, 1-008, 1-009, 1-010, 1-011, 1-012, 1-013, 1-014, 1-015, 1-016, 1-017, 1-018, 1-021, 1-024, 1-025, 1-031, 1-033, 2-003, 2-004, 3-001, 3-002, 3-003, 3-005, 3-006, 3-007, 3-008, 3-009, 3-010, 3-011, 3-015, 3-016, 3-017, 3-020, 3-021, 5-002, 6-001, 8-001, 8-003, 8-007, 8-008, 8-010, 8-011, 8-018, 8-019, 8-028, 9-006a, 10-001.

Test Example 11: Test on the Preventive Effect Against Southern Root-Knot Nematode 1 ml per seedling of test solution B of the compounds of the present invention was treated to the bases of garden balsam seedlings (about 2 weeks after budding) planted in a cell tray of which each cell was filled with 10 g of soil. 1 hour after the application, 1 ml per cell of water containing Southern root-knot nematode (*Meloidogyne incognita*) 2 L larvae (100 larvae of 2 L/1 ml) was applied to the base. The tray was placed in a greenhouse for 3 weeks, and the degree of root knot on the root was determined in accordance with the following damage index and the damage degree to calculate the efficacy (%) relative to the non-treated plot in accordance with the following formula.

<Damage Index>
- 0: No knot formation was observed.
- 1: Knot formations were observed on parts of the root system.
- 2: Knot formations were observed on the entire root system.
- 3: Large knot formations were observed.
- 4: Large knot formations were observed on the entire root system.

[Damage degree]=[Σ(damage index×number of each damaged indexed seedling)/(4×number of seedlings investigated)]×100

Efficacy (%)=[1−(damage degree in treated plot/damage degree in non-treated plot)]×100

As results of the compounds were tested, the following compounds showed an efficacy of at least 50%.
The compounds of the present invention: No. 1-003, 1-005, 1-007, 1-009, 1-011, 1-012, 1-013, 1-017, 1-024, 1-025, 3-001, 3-002, 3-003, 3-005, 3-006, 3-008, 3-009, 3-016, 3-020, 3-021, 8-001, 8-002, 8-007, 8-009, 8-019, 8-028, 9-006a.

Test Example 12: Insecticidal Test Against Barber Pole Worm

60 μl of a potato dextrose 1% agar medium was added to each well of a 96 well plate, and 30 μl of sterilized water containing eggs of Barber pole worm (*Haemonchus contortus*) (10 eggs/3 μl) was added to each well. Further, 10 μl per well of test solution B of the compounds of the present invention was added, and the plate was left at rest at 25° C. under dark conditions. 4 days after treatment, unhatched eggs and inactive larvae were counted to calculate the efficacy (%) relative to the non-treated plot in accordance with the same formula as in the Test Example 9.

As results of the compounds were tested, the following compounds showed an efficacy of at least 50%.
The compounds of the present invention: No. 1-001, 1-002, 1-003, 1-004, 1-005, 1-007, 1-008, 1-009, 1-010, 1-011, 1-012, 1-013, 1-017, 1-021, 1-024, 1-025, 1-033, 3-001, 3-002, 3-003, 3-005, 3-006, 3-007, 3-008, 3-009, 3-015, 3-016, 3-020, 3-021, 4-004, 8-001, 8-002, 8-003, 8-007, 8-008, 8-009, 8-010, 8-011, 8-012, 8-013, 8-018, 8-019, 8-020, 8-028, 9-002, 9-004, 9-005, 9-006a.

INDUSTRIAL APPLICABILITY

The alkynyl pyridine-substituted amide compounds of the present invention are very useful compounds which are excellent in pesticidal activities, especially in fungicidal and nematocidal activities, and have little harmful effect on non-target organisms such as mammals, fishes and useful insects.

The entire disclosures of Japanese Patent Application No. 2014-028087 filed on Feb. 18, 2014, Japanese Patent Application No. 2014-082159 filed on Apr. 11, 2014, Japanese Patent Application No. 2014-088408 filed on Apr. 22, 2014 and Japanese Patent Application No. 2014-130395 filed on Jun. 25, 2014 including specifications, claims and summaries are incorporated herein by reference in their entireties.

The invention claimed is:
1. An alkynyl pyridine-substituted amide compound of the formula (I), its N-oxide or a salt thereof:

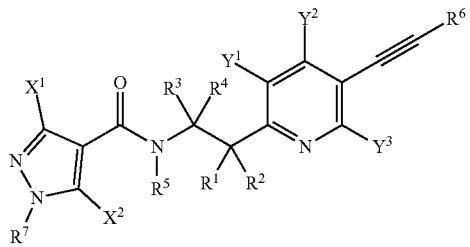

wherein:
$X^1$ is difluoromethyl,
$X^2$ is a hydrogen atom,
$R^7$ is methyl,
$Y^1$ is a hydrogen atom, a halogen atom, nitro, $C_1$-$C_4$ alkyl, $C_1$-$C_4$ haloalkyl, $C_1$-$C_4$ alkoxy, $C_1$-$C_4$ haloalkoxy or $C_1$-$C_4$ alkylthio,
$Y^2$ and $Y^3$ are each independently a hydrogen atom, a halogen atom or methyl,
$R^1$ and $R^2$ are each independently a hydrogen atom, a halogen atom, cyano, $C_1$-$C_4$ alkyl, $C_1$-$C_4$ haloalkyl, $C_3$-$C_6$ cycloalkyl, phenylmethyl, phenylmethyl substituted by $(Z)_m$, $C_1$-$C_4$ alkoxy, $C_1$-$C_4$ haloalkoxy, cyano $(C_1$-$C_4)$alkoxy, $C_3$-$C_6$ alkenyloxy, $C_3$-$C_6$ haloalkenyloxy, $C_3$-$C_6$ alkynyloxy, $C_3$-$C_6$ haloalkynyloxy, phenyl $(C_1$-$C_4)$alkoxy, $C_1$-$C_4$ alkylthio, $C_1$-$C_4$ alkoxyamino, $C_1$-$C_4$ alkoxycarbonyl, —C(O)NH$_2$, or —C(S)NH$_2$,
alternatively, $R^1$ and $R^2$ together form a $C_2$-$C_5$ alkylene chain thereby to form a 3-6 membered ring together with the carbon atom to which $R^1$ and $R^2$ are bonded, wherein the alkylene chain optionally contains one or two oxygen atoms, sulfur atoms or nitrogen atoms and is optionally substituted by a $C_1$-$C_3$ alkyl group, a $C_1$-$C_3$ haloalkyl group or an oxo group, or $R^1$ and $R^2$ together form $C_1$-$C_6$ alkylidene, $C_1$-$C_6$ haloalkylidene or $C_1$-$C_4$ alkoxy$(C_1$-$C_2)$alkylidene,
$R^3$ and $R^4$ are each independently a hydrogen atom, $C_1$-$C_4$ alkyl, $C_1$-$C_4$ haloalkyl, $C_1$-$C_4$ alkoxymethyl, $C_3$-$C_6$ cycloalkyl or phenyl,
alternatively, $R^3$ and $R^4$ together form an ethylene chain thereby to form a cyclopropyl ring together with the carbon atom to which $R^3$ and $R^4$ are bonded,
further alternatively, $R^1$ or $R^2$, and $R^3$ or $R^4$, together form a $C_1$-$C_4$ alkylene chain thereby to form a 3-6 membered ring together with the carbon atoms to which $R^1$ or $R^2$, and $R^3$ or $R^4$, are bonded, wherein the alkylene chain optionally contains one oxygen atom or sulfur atom,
$R^5$ is a hydrogen atom, $C_1$-$C_4$ alkyl, $C_1$-$C_4$ haloalkyl, $(C_1$-$C_2)$ alkyl substituted by $R^8$, $C_3$-$C_6$ cycloalkyl, $C_2$-$C_4$ alkenyl, $C_3$-$C_4$ alkynyl, —OH, $C_1$-$C_4$ alkoxy, $C_1$-$C_4$ haloalkoxy, $C_1$-$C_4$ haloalkylthio, —C(O)$R^9$ or $C_1$-$C_4$ alkoxycarbonyl,
$R^6$ is phenyl or phenyl substituted by (Z),
Z is halogen,
m is an integer of 1 to 5,
$R^8$ is cyano, —OR$^{14}$, $C_1$-$C_4$ alkylthio, $C_1$-$C_4$ alkoxycarbonyl, —C(O)NH$_2$, or —C(S)NH$_2$, $R^9$ is $C_1$-$C_4$ alkyl, $C_1$-$C_4$ alkoxymethyl, $C_3$-$C_4$ cycloalkyl or $C_2$-$C_4$ alkenyl, and $R^{14}$ is $C_1$-$C_4$ alkyl, $C_2$-$C_4$ haloalkyl, $C_1$-$C_4$ alkylcarbonyl, $C_3$-$C_6$ cycloalkylcarbonyl or $C_1$-$C_4$ alkoxycarbonyl.

2. The compound of claim 1, wherein:
$R^1$ and $R^2$ are H,
$R^3$ is $CH_3$,
$R^4$ is H,
$R^5$ is H,
$Y^1$ is Cl, and
$Y^2$ and $Y^3$ are H.

3. The compound of claim 2, wherein $R^6$ is phenyl.

4. A pesticidal composition comprising the alkynyl pyridine-substituted amide compound, its N-oxide or a salt thereof according to claim 1, as an active ingredient.

5. An agricultural fungicidal or nematicidal composition comprising the alkynyl pyridine-substituted amide compound, its N-oxide or a salt thereof of claim 1, as an active ingredient.

6. A method comprising applying the agricultural fungicidal or nematicidal composition of claim 5 to a plant by foliar treatment.

7. A method comprising applying the agricultural fungicidal or nematicidal composition of claim 5 to soil in which one or more plants grow.

8. A method comprising applying the agricultural fungicidal or nematicidal composition of claim 5 to a seed, a tuberous root or a rhizome of a plant.

9. An antifungal or endoparasiticidal composition suitable for mammals or birds, comprising the alkynyl pyridine-substituted amide compound, its N-oxide or a salt thereof of claim 1, as an active ingredient.

10. A method, comprising orally administering the antifungal or endoparasiticidal composition of claim 9 a mammal or a bird.

11. A method, comprising parenterally administering the antifungal or endoparasiticidal composition of claim 9 to a mammal or a bird.

12. The method of claim 11, wherein the parenteral administration is transdermal administration.

* * * * *

UNITED STATES PATENT AND TRADEMARK OFFICE
CERTIFICATE OF CORRECTION

PATENT NO. : 10,029,986 B2
APPLICATION NO. : 15/119660
DATED : July 24, 2018
INVENTOR(S) : Takeshi Mita et al.

Page 1 of 1

It is certified that error appears in the above-identified patent and that said Letters Patent is hereby corrected as shown below:

In the Claims

Claim 1,
Column 162, Line 63:
"$R^6$ is phenyl or phenyl substituted by (Z),"
Should read:
--$R^6$ is phenyl or phenyl substituted by $(Z)_m$,--

Signed and Sealed this
Second Day of October, 2018

Andrei Iancu
*Director of the United States Patent and Trademark Office*